(12) United States Patent
Tanaka et al.

(10) Patent No.: US 11,399,539 B2
(45) Date of Patent: Aug. 2, 2022

(54) HETEROCYCLIC COMPOUND AND HARMFUL ARTHROPOD CONTROLLING AGENT CONTAINING SAME

(71) Applicant: Sumitomo Chemical Company, Limited, Tokyo (JP)

(72) Inventors: Ayaka Tanaka, Takarazuka (JP); Masaru Shimomura, Tokyo (JP); Yoshihiko Nokura, Takarazuka (JP); Shinichiro Murakami, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 20 days.

(21) Appl. No.: 16/314,776

(22) PCT Filed: Jul. 6, 2017

(86) PCT No.: PCT/JP2017/024851
§ 371 (c)(1),
(2) Date: Jan. 2, 2019

(87) PCT Pub. No.: WO2018/008727
PCT Pub. Date: Jan. 11, 2018

(65) Prior Publication Data
US 2019/0327970 A1 Oct. 31, 2019

(30) Foreign Application Priority Data
Jul. 7, 2016 (JP) ............... JP2016-134793

(51) Int. Cl.
*A01N 43/40* (2006.01)
*A01N 43/54* (2006.01)
*A01N 43/58* (2006.01)
*C07D 403/04* (2006.01)
*C07D 403/14* (2006.01)

(52) U.S. Cl.
CPC ............. *A01N 43/40* (2013.01); *A01N 43/54* (2013.01); *A01N 43/58* (2013.01); *C07D 403/04* (2013.01); *C07D 403/14* (2013.01)

(58) Field of Classification Search
CPC ..................................................... A01N 43/40
See application file for complete search history.

(56) References Cited

U.S. PATENT DOCUMENTS

| | | |
|---|---|---|
| 4,941,911 A | 7/1990 | Freund et al. |
| 2003/0069242 A1 | 4/2003 | Toriyabe et al. |
| 2012/0053052 A1 | 3/2012 | Gross et al. |
| 2015/0181880 A1 | 7/2015 | Takahashi et al. |
| 2015/0239847 A1 | 8/2015 | Heilmann et al. |
| 2016/0251321 A1 | 9/2016 | Alig et al. |
| 2016/0316751 A1 | 11/2016 | Kohler et al. |
| 2017/0295787 A1 | 10/2017 | Tanabe et al. |
| 2017/0305896 A1 | 10/2017 | Tanabe et al. |
| 2018/0009778 A1 | 1/2018 | Tanabe et al. |
| 2018/0317485 A1 | 11/2018 | Orimoto et al. |

FOREIGN PATENT DOCUMENTS

| | | |
|---|---|---|
| CN | 104379567 A | 2/2015 |
| EP | 0272824 A2 | 6/1988 |
| EP | 336118 A1 | 10/1989 |
| EP | 0357201 A2 | 3/1990 |
| JP | S63170362 A | 7/1988 |
| JP | H0288570 A | 3/1990 |
| JP | 201775161 A | 4/2017 |
| JP | 201812664 A | 1/2018 |
| JP | 2019094335 A * | 6/2019 |
| RU | 2015116670 A | 11/2016 |
| WO | 9955668 A1 | 11/1999 |
| WO | 2010100189 A1 | 9/2010 |
| WO | 2013083774 A1 | 6/2013 |
| WO | 2013191113 A1 | 12/2013 |
| WO | 2015004028 A1 | 1/2015 |
| WO | 2015091267 A1 | 6/2015 |
| WO | 2016020286 A1 | 2/2016 |

(Continued)

OTHER PUBLICATIONS

Partial Supplementary European Search Report dated Feb. 3, 2020 in EP Application No. 17824330.9.
Int'l Preliminary Report on Patentability dated Jan. 8, 2019 in Int'l Application No. PCT/JP2017/024851.
Int'l Search Report dated Sep. 19, 2017 in Int'l Application No. PCT/JP2017/024851.
Office Action dated Sep. 15, 2020 in RU Application No. 2019103094.
Search Report dated Sep. 15, 2020 in RU Application No. 2019103094.
Extended European Search Report dated May 11, 2020 in EP Application No. 17824330.9.

(Continued)

*Primary Examiner* — John S Kenyon
(74) *Attorney, Agent, or Firm* — Panitch Schwarze Belisario & Nadel LLP

(57) ABSTRACT

A heterocyclic compound that exhibits superior control effects against harmful arthropods is provided. In particular, a heterocyclic compound of formula (I) is provided, wherein the variable groups are as defined in the specification. Also provided is a composition containing the heterocyclic compound of formula (I) and one or more types of components selected from the components described in the specification.

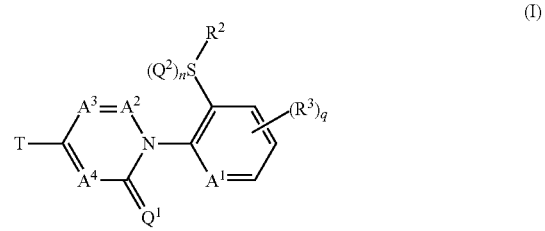

33 Claims, No Drawings

(56) References Cited

FOREIGN PATENT DOCUMENTS

| WO | 2016052247 A1 | 4/2016 | |
|---|---|---|---|
| WO | 2016052455 A1 | 4/2016 | |
| WO | 2016121969 A1 | 8/2016 | |
| WO | 2017077911 A1 | 5/2017 | |
| WO | 2017090655 A1 | 6/2017 | |
| WO | 2017134066 A1 | 8/2017 | |
| WO | WO-2017134066 A1 * | 8/2017 | ............. A01N 43/90 |

OTHER PUBLICATIONS

Office Action dated Aug. 31, 2020 in AU Application No. 2017293178.
Office Action dated Nov. 12, 2020 in IL Application No. 263723.
Office Action dated Dec. 29, 2020 in IN Application No. 201947003332.
Office Action dated Dec. 8, 2020 in ID Application No. P00201900264.
Office Action dated May 26, 2021 in EP Application No. 17824330.9.
Database Registry, RN 1346533-36-5; Retrieved from STN international [online] (Nov. 29, 2011); retrieved on May 14, 2021, 1 page.
Database Registry, RN 1346540-63-3; Retrieved from STN international [online] (Nov. 29, 2011); retrieved on May 14, 2021, 1 page.
Office Action dated May 25, 2021 in JP Application No. 2018526443.
Office Action dated Jul. 12, 2021 in CN Application No. 201780041682.2.
Examination Report dated Sep. 3, 2021 in AU Application No. 2021200550.
Office Action dated Dec. 2, 2021 in KR Application No. 20197003236.

* cited by examiner

HETEROCYCLIC COMPOUND AND HARMFUL ARTHROPOD CONTROLLING AGENT CONTAINING SAME

CROSS-REFERENCE TO RELATED APPLICATION

This application is a Section 371 of International Application No. PCT/JP2017/024851, filed Jul. 6, 2017, which was published in the Japanese language on Jan. 11, 2018, under International Publication No. WO 2018/008727 A1, which claims priority under 35 U.S.C. § 119(b) to Japanese Application No. 2016-134793 filed on Jul. 7, 2016, the disclosures of which are incorporated herein by reference in their entireties.

TECHNICAL FIELD

The present invention is related to a certain class of heterocyclic compound and an agent for controlling harmful arthropods comprising the same.

BACKGROUND ART

To date, in order to control harmful arthropods, some compounds have been developed and come into practical use.

Also, a certain class of compound has been known to have an effect on controlling pests (see Patent Documents 1 and 2).

CITATION LIST

Patent Document

Patent Document 1: JP S63-170362 A
Patent Document 2: JP H02-088570 A

SUMMARY OF THE INVENTION

Problems to be Solved by Invention

An object of the present invention is to provide a compound having an excellent efficacy for controlling harmful arthropods.

Means to Solve Problems

The present inventors have intensively studied to find compounds having an excellent efficacy for controlling harmful arthropods, and as a result, found that a compound represented by the below-mentioned formula (I) has an excellent efficacy for controlling plant diseases.

That is, the present invention includes the followings.
[1] A compound represented by formula (I):

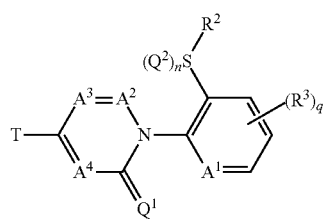

(I)

[wherein
$Q^1$ represents an oxygen atom or a sulfur atom;
n is 1 or 2;
$Q^2$ represents an oxygen atom, a N—CN, a N—NO$_2$, a NR$^5$, a N—C(O)R$^5$ or a N—C(O)OR$^{15}$, and when n is 2, said two $Q^2$ may be independently identical to or different from each other;
$R^5$ represents a C1-C6 alkyl group optionally having one or more halogen atoms, or a hydrogen atom;
$A^1$ represents a nitrogen atom or a CR$^6$;
$A^2$ represents a nitrogen atom or a CR$^{4a}$;
$A^3$ represents a nitrogen atom or a CR$^{4b}$;
$A^4$ represents a nitrogen atom or a CR$^{4c}$;
$R^{4a}$, $R^{4b}$ and $R^{4c}$ represent independently of each other a hydrogen atom, a C1-C6 chain hydrocarbon group optionally having one or more halogen atoms, a nitro group, a OR$^{18}$, a NR$^{18}$R$^{19}$, a cyano group, or a halogen atom;
$R^6$ represents a hydrogen atom or a halogen atom;
T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a OR$^1$, a S(O)$_v$R$^1$, a OS(O)$_2$R$^1$, a CH$_2$OR$^1$, a NR$^1$R$^{29}$, a C(O)R$^1$, a C(O)NR$^1$R$^{29}$, a NR$^{29}$C(O)R$^1$, a N=CR$^1$R$^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12,

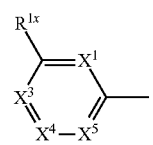

T-1

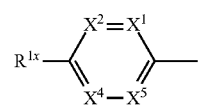

T-2

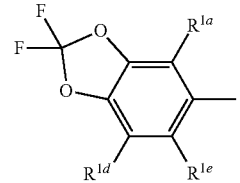

T-3

-continued

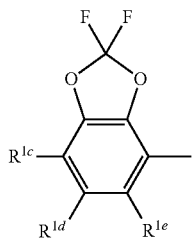

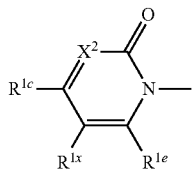

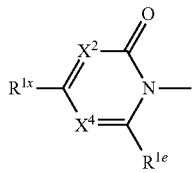

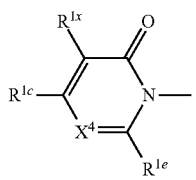

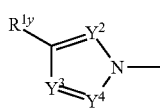

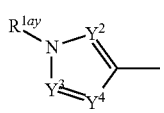

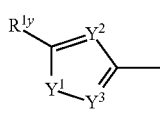

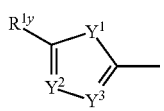

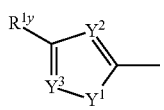

$X^1$ represents a nitrogen atom or a $CR^{1a}$;

$X^2$ represents a nitrogen atom or a $CR^{1b}$;

$X^3$ represents a nitrogen atom or a $CR^{1c}$;

$X^4$ represents a nitrogen atom or a $CR^{1d}$;

$X^5$ represents a nitrogen atom or a $CR^{1e}$;

$R^{1x}$ represents a $OR^7$, a $OS(O)_2R^7$, a $S(O)_mR^7$, a $NR^8S(O)_2R^7$, a C1-C5 chain hydrocarbon group having one or more halogen atoms, or a halogen atom;

q is 0, 1, 2, or 3;

$R^{1a}$, $R^{1b}$, $R^{1c}$, $R^{1d}$, and $R^{1e}$ represent independently of each other a hydrogen atom, a C1-C6 chain hydrocarbon group optionally having one or more halogen atoms, a C3-C6 cycloalkyl group optionally having one or more halogen atoms, or a halogen atom;

$Y^1$ represents a $NR^{25}$, an oxygen atom or a sulfur atom;

$Y^2$ represents a nitrogen atom or a $CR^{26}$;

$Y^3$ represents a nitrogen atom or a $CR^{27}$;

$Y^4$ represents a nitrogen atom or a $CR^{28}$;

$R^{25}$, $R^{26}$, $R^{27}$, and $R^{28}$ represent independently of each other a hydrogen atom, a C1-C6 chain hydrocarbon group optionally having one or more halogen atoms, a C3-C6 cycloalkyl group optionally having one or more halogen atoms, or a halogen atom;

$R^{1y}$ represents a $OR^7$, a $OS(O)_2R^7$, a $S(O)_mR^7$, a $NR^8S(O)_2R^7$, a cyano group, a C1-C5 chain hydrocarbon group having one or more halogen atoms, or a halogen atom;

$R^{1ay}$ and $R^7$ represent independently of each other a C1-C6 chain hydrocarbon group having one or more halogen atoms;

$R^8$ represents a hydrogen atom, or a C1-C6 chain hydrocarbon group optionally having one or more halogen atoms;

m and v are independently of each other 0, 1 or 2, $R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

$R^2$ represents a cyclopropyl group, a cyclopropylmethyl group, or a C1-C6 alkyl group optionally having one or more halogen atoms;

$R^3$ represents a C1-C6 chain hydrocarbon group optionally having one or more substituents selected from Group B, a C3-C7 cycloalkyl group optionally having one or more substituents selected from Group E, a C3-C7 cycloalkenyl group optionally having one or more substituents selected from Group J, a phenyl group optionally having one or more substituents selected from Group H, a five or six membered aromatic heterocyclic group optionally having one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15x}R^{16x}$, a $NR^{24}NR^{11}C(O)NR^{15x}R^{16x}$, a $N=CHNR^{15x}R^{16x}$, a $N=S(O)_xR^{15}R^{16}$, a $C(O)R^{17}$, a $C(O)OR^{17}$, a $C(O)NR^{15x}R^{16x}$, a $C(O)NR^{11}S(O)_2R^{23}$, a $CR^{24}=NOR^{17}$, a $NR^{11}CR^{24}=NOR^{17}$, a cyano group, a nitro group, or a halogen atom, and when q is 2 or 3, a plurality of $R^3$ may represent independently identical to or different from each other;

When two $R^3$ are adjacent to each other, said two $R^3$ may combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring {the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, or the pyrazine ring may optionally have one or more substituents selected from Group H};

$R^{17}$ represent independently of each other a hydrogen atom, a C1-C6 chain hydrocarbon group optionally having one or more substituents selected from Group F, or a C3-C7 cycloalkyl group optionally having one or more substituents selected from Group J;

$R^{11}$, $R^{19}$, $R^{24}$, and $R^{29}$ represent independently of each other a hydrogen atom, or a C1-C6 chain hydrocarbon group optionally having one or more halogen atoms;

$R^{30}$ represents a hydrogen atom, a halogen atom, a $OR^{35}$, a $NR^{36}R^{37}$, or a C1-C6 chain hydrocarbon group optionally having one or more halogen atoms;

$R^{18}$ and $R^{35}$ represent independently of each other a C1-C6 chain hydrocarbon group optionally having one or more halogen atoms;

$R^{36}$ and $R^{37}$ represent independently of each other a hydrogen atom, or a C1-C6 chain hydrocarbon group optionally having one or more halogen atoms;

$R^{12}$ represents a C1-C6 chain hydrocarbon group optionally having one or more halogen atoms, a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group, a six membered aromatic heterocyclic group {the phenyl group or the six membered aromatic heterocyclic group may optionally have one or more substituents selected from Group D}, a hydrogen atom, or a $S(O)_2R^{23}$;

$R^{23}$ represents a C1-C6 chain hydrocarbon group optionally having one or more halogen atoms, a C3-C7 cycloalkyl group optionally having one or more halogen atoms, or a phenyl group optionally having one or more substituents selected from Group D;

$R^{11a}$ and $R^{12a}$ combine together a nitrogen atom to which they are attached to form a three to seven membered nonaromatic heterocyclic group optionally having one or more substituents selected from Group E;

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {a phenyl moiety in the phenyl C1-C3 alkyl group may optionally have one or more substituents selected from group D};

$R^{15}$ and $R^{16}$ represent independently of each other a C1-C6 alkyl group optionally having one or more halogen atoms;

$R^{15x}$ represents a C1-C6 alkyl group optionally having one or more halogen atoms, or a hydrogen atom;

$R^{16x}$ represents a C1-C6 chain hydrocarbon group optionally having one or more substituents selected from Group F, a C3-C7 cycloalkyl group optionally having one or more substituents selected from Group J, or a hydrogen atom;

x is 0 or 1;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {the $R^{21}$ and the $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a five or six membered aromatic heterocyclic group optionally having one or more substituents selected from Group D, a C3-C7 cycloalkyl group optionally having one or more halogen atoms, and a three to seven nonaromatic heterocyclic group optionally having one or more substituents selected from Group C {the $R^{21}$ and the $R^{22}$ represent independently of each other a C1-C6 alkyl group optionally having one or more halogen atoms};

Group G: a group consisting of a halogen atom and a C1-C6 haloalkyl group;

Group H: a group consisting of a halogen atom, a nitro group, a cyano group, an amino group, a five or six membered aromatic heterocyclic group, a C1-C6 alkyl group optionally having one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$ {the $R^9$ represents a C1-C6 alkyl group optionally having one or more halogen atoms or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms};

Group J: a group consisting of a halogen atom, a cyano group, a triazolyl group, a C1-C6 alkyl group optionally having one or more halogen atoms, and a $NR^{10}C(O)R^9$ {the $R^9$ represents a C1-C6 alkyl group optionally having one or more halogen atoms or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms}] (hereinafter, the compound represented by formula (I) may be referred to as "Compound of the present invention" or "Present compound").

[2] The compound described in [1] wherein in the formula (I), $Q^1$ represents an oxygen atom or a sulfur atom;
n is 1 or 2,
$Q^2$ represents an oxygen atom, a N—CN, a N—NO$_2$, a $NR^5$, a N—C(O)R$^5$, or a N—C(O)OR$^{15}$, and when n is 2, the two $Q^2$ may be identical to or different from each other;
$R^5$ represents a C1-C6 alkyl group optionally having one or more halogen atoms or a hydrogen atom;
$A^1$ represents a nitrogen atom or a $CR^6$;
$A^2$ represents a nitrogen atom or a $CR^{4a}$;
$A^3$ represents a nitrogen atom or a $CR^{4b}$;
$A^4$ represents a nitrogen atom or a $CR^{4c}$;
$R^{4a}$, $R^{4b}$, and $R^{4c}$ represent independently of each other a hydrogen atom, a C1-C6 chain hydrocarbon group optionally having one or more halogen atoms, a nitro group, an $OR^{18}$, a $NR^{18}R^{19}$, a cyano group, or a halogen atom;
$R^6$ represents a hydrogen atom or a halogen atom;
T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_rR^1$, a $OS(O)_2R^1$, a $CH_2OR^1$, a $NR^1R^{29}$, a $C(O)R^1$, a $C(O)NR^1R^{29}$, a $NR^{29}C(O)R^1$, a $N=CR^1R^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12,

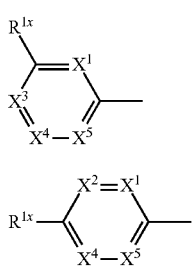

T-1

-continued

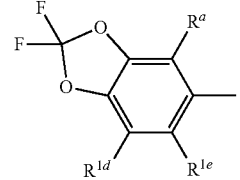

T-3

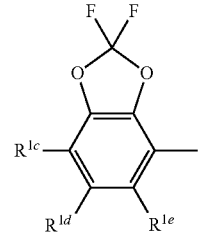

T-4

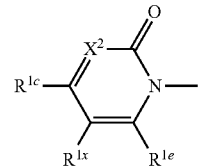

T-5

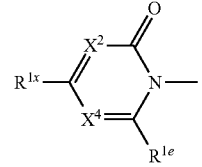

T-6

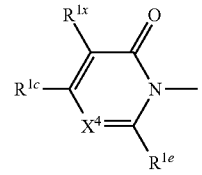

T-7

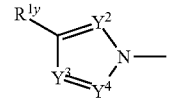

T-8

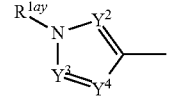

T-9

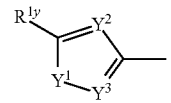

T-10

T-11

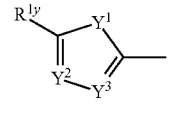

T-12 wherein, $X^1$ represents a nitrogen atom or a $CR^{1a}$;
$X^2$ represents a nitrogen atom or a $CR^{1b}$;
$X^3$ represents a nitrogen atom or a $CR^{1c}$;
$X^4$ represents a nitrogen atom or a $CR^{1d}$;
$X^5$ represents a nitrogen atom or a $CR^{1e}$;
$R^{1x}$ represents a $OR^7$, a $OS(O)_2R^7$, a $S(O)_mR^7$, a $NR^8S(O)_2R^7$, a C1-C5 chain hydrocarbon group having one or more halogen atoms, or a halogen atom;

q represents 0, 1, 2, or 3;

$R^{1a}$, $R^{1b}$, $R^{1c}$, $R^{1d}$, or $R^{1e}$ represent independently of each other a hydrogen atom, a C1-C6 chain hydrocarbon group optionally having one or more halogen atoms, a C3-C6 cycloalkyl group optionally having one or more halogen atoms, or a halogen atom;

$Y^1$ represents a $NR^{25}$, an oxygen atom, or a sulfur atom;
$Y^2$ represents a nitrogen atom or a $CR^{26}$;
$Y^3$ represents a nitrogen atom or a $CR^{27}$;
$Y^4$ represents a nitrogen atom or a $CR^{28}$;

$R^{25}$, $R^{26}$, $R^{27}$, and $R^{28}$ represent independently of each other a hydrogen atom, a C1-C6 chain hydrocarbon group optionally having one or more halogen atoms, a C3-C6 cycloalkyl group optionally having one or more halogen atoms, or a halogen atom;

$R^{1y}$ represents a $OR^7$, a $OS(O)_2R^7$, a $S(O)_mR^7$, a $NR^8S(O)_2R^7$, a cyano group, a C1-C5 chain hydrocarbon group having one or more halogen atoms, or a halogen atom;

$R^{1ay}$ and $R^7$ represent independently of each other a C1-C6 chain hydrocarbon group having one or more halogen atoms;

$R^8$ represents a hydrogen atom, or a C1-C6 chain hydrocarbon group optionally having one or more halogen atoms;

m and v are independently of each other 0, 1, or 2;

$R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;

$R^2$ represents a cyclopropyl group, a cyclopropylmethyl group, or a C1-C6 alkyl group optionally having one or more halogen atoms;

$R^3$ represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a N=$CHNR^{15}R^{16}$, a N=$S(O)_xR^{15}R^{16}$, a $C(O)OR^{17}$, a cyano group, a nitro group, or a halogen atom, and when q is 2 or 3, a plurality of the $R^3$ may be identical to or different from each other;

When q is 2 and two $R^3$ are adjacent to each other, said two $R^3$ may combine with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring {the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may optionally have one or more substituents selected from Group H};

$R^{11}$, $R^{17}$, $R^{19}$, $R^{24}$, and $R^{29}$ represent independently of each other a hydrogen atom, or a C1-C6 chain hydrocarbon group optionally having one or more halogen atoms;

$R^{30}$ represents a hydrogen atom, a halogen atom, a $OR^{35}$, a $NR^{36}R^{37}$, or a C1-C6 chain hydrocarbon group optionally having one or more halogen atoms;

$R^{18}$ and $R^{35}$ represent independently of each other a C1-C6 chain hydrocarbon group optionally having one or more halogen atoms;

$R^{36}$ and $R^{37}$ represent independently of each other a hydrogen atom, or a C1-C6 chain hydrocarbon group optionally having one or more halogen atoms;

$R^{12}$ represents a hydrogen atom, a $S(O)_2R^{23}$, a C1-C6 chain hydrocarbon group optionally having one or more halogen atoms, or a C1-C6 alkyl group having one or more substituents selected from Group F;

$R^{23}$ represents a C1-C6 chain hydrocarbon group optionally having one or more halogen atoms, or a phenyl group optionally having one or more substituents selected from Group D;

$R^{11a}$ and $R^{12a}$ combine together with a nitrogen atom to which they are attached to form a three to seven membered nonaromatic heterocyclic group optionally having one or more substituents selected from Group E;

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {a phenyl moiety in the phenyl C1-C3 alkyl group may optionally have one or more substituents selected from Group D}, $R^{15}$ and $R^{16}$ represent independently of each other a C1-C6 alkyl group optionally having one or more halogen atoms;

x represents 0 or 1;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {the $R^{21}$ and the $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a five or six membered aromatic heterocyclic group optionally having one or more substituents selected from Group D, a C3-C7 cycloalkyl group optionally having one or more halogen atoms, and a three to seven nonaromatic heterocyclic group optionally having one or more substituents selected from Group C {the $R^{21}$ and the $R^{22}$ represent independently of each other a C1-C6 alkyl group optionally having one or more halogen atoms};

Group G: a group consisting of a halogen atom and a C1-C6 haloalkyl group;

Group H: a group consisting of a halogen atom, a nitro group, a cyano group, an amino group, a five or six membered aromatic heterocyclic group, a C1-C6 alkyl group optionally having one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$ {the $R^9$ represents a C1-C6 alkyl group optionally having one or more halogen atoms, or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms}] (hereinafter, which may be referred to as "Compound A of the present invention" or "Present compound A");

[3] The compound described in [1] or [2] wherein $A^1$ represents a CH;

[4] The compound described in [1] or [2] wherein $A^1$ represents a nitrogen atom;

[5] The compound described in any one of [1] to [4] wherein $A^2$ represents a $CR^{4a}$, $A^3$ represents a $CR^{4b}$, and $A^4$ represents a $CR^{4c}$;

[6] The compound described in any one of [1] to [4] wherein $A^2$ represents a nitrogen atom, $A^3$ represents a $CR^{4b}$, and $A^4$ represents a $CR^{4c}$;

[7] The compound described in any one of [1] to [4] wherein $A^3$ represents a nitrogen atom, $A^2$ represents a $CR^{4a}$, and $A^4$ represents a $CR^{4c}$;

[8] The compound described in any one of [1] to [4] wherein $A^4$ represents a nitrogen atom, $A^2$ represents a $CR^{4a}$, and $A^3$ represents a $CR^{4b}$;

[9] The compound described in any one of [1] to [4] wherein $A^2$ and $A^4$ both represent a nitrogen atom, and $A^3$ represents a $CR^{4b}$;

[10] The compound described in any one of [1] to [9] wherein $Q^1$ represents an oxygen atom, and T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$, a $NR^1R^{29}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, or a group represented by the following formula T-9;

[11] The compound described in any one of [1] to [9] wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$, or a $NR^1R^{29}$;

[12] The compound described in any one of [1] to [9] wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[13] The compound described in any one of [1] to [9] wherein $Q^1$ represents an oxygen atom, and T represents a C1-C5 chain hydrocarbon group having one or more halogen atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, $R^1$, $R^{1x}$, $R^{1y}$, and $R^{1ay}$ represent independently of each other a C1-C5 chain hydrocarbon group having one or more halogen atoms, and q is 0 or 1;

[14] The compound described in any one of [1] to [9] wherein $Q^1$ represents an oxygen atom, T represents a C1-C5 chain hydrocarbon group having one or more halogen atoms, a $OR^1$, a $S(O)_vR^1$, a $OS(O)_2R^1$, a $NR^1R^{29}$, $R^1$ represents a C1-C5 chain hydrocarbon group having one or more halogen atoms, and q is 0 or 1;

[15] The compound described in any one of [1] to [9] wherein $Q^1$ represents an oxygen atom, T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, $R^{1a}$, $R^{1y}$, and $R^{1ay}$ represent independently of each other a C1-C5 chain hydrocarbon group having one or more halogen atoms, and q is 0 or 1;

[16] The compound described in any one of [1] to [15] wherein $R^3$ represents a C1-C6 alkyl group optionally having one or more halogen atoms, a phenyl group, a six membered aromatic heterocyclic group, a five membered aromatic heterocyclic group containing 1 to 4 nitrogen atoms {the phenyl group, the a six membered aromatic heterocyclic group, and the five membered aromatic heterocyclic group containing 1 to 4 nitrogen atoms may optionally have one or more substituents selected from Group J}, a $NR^{11}R^{12}$, a $NR^{11}C(O)OR^{14}$, or a halogen atom;

[17] The compound described in any one of [1] to [15] wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom;

[18] The compound described in any one of [1] to [17] wherein $R^2$ represents an ethyl group;

[19] The compound described in any one of [1] to [18] wherein $Q^2$ represents an oxygen atom;

[20] A method for controlling harmful arthropod which comprises applying an effective amount of the compound described in any one of [1] to [19] to a harmful arthropod or a habitat where a harmful arthropod lives;

[21] A method for controlling harmful arthropod which comprises applying an effective amount of the compound described in any one of [1] to [19] to a plant or soil where a plant grows;

[22] A method for controlling harmful arthropod which comprises applying an effective amount of the compound described in any one of [1] to [19] to a seed or bulb;

[23] A composition for controlling harmful arthropod comprising the compound described in any one of [1] to [19] and an inert carrier.

[24] A composition comprising the compound described in any one of [1] to [19] and one or more ingredients selected from the group consisting of the following Groups (a), (b), (c), and (d):

Group (a): one or more ingredients selected from the group consisting of insecticidal ingredients, miticidal ingredients, and nematicidal ingredients;

Group (b): fungicidal ingredients;

Group (c): plant growth modulating ingredients; and

Group (d): phytotoxicity-reducing ingredients (hereinafter, referred to as "Composition of the present invention" or "Present composition");

[25] A method for controlling harmful arthropod which comprises applying an effective amount of the composition according to claim 24 to a harmful arthropod or a habitat where a harmful arthropod lives.

[26] A method for controlling harmful arthropod which comprises applying an effective amount of the composition described in [24] to a plant or soil where a plant grows;

[27] A method for controlling harmful arthropod which comprises applying an effective amount of the composition described in [24] to a seed or bulb;

[28] A composition for controlling harmful arthropod comprising the composition described in [24] and an inert carrier.

[29] A seed or bulb carrying an effective amount of the compound described in any one of [1] to [19] or an effective amount of the composition described in [24];

[30] A compound represented by formula (II):

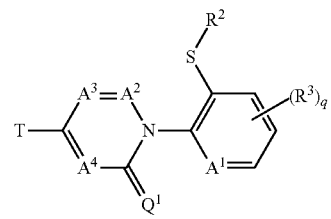

(II)

[wherein, $Q^1$ represents an oxygen atom or a sulfur atom;

$A^1$ represents a nitrogen atom or a $CR^6$;

A2 represents a nitrogen atom or a $CR^{4a}$;

A3 represents a nitrogen atom or a $CR^{4b}$;

A4 represents a nitrogen atom or a $CR^{4c}$;

$R^{4a}$, $R^{4b}$ and $R^{4c}$ represent independently of each other a hydrogen atom, a C1-C6 chain hydrocarbon group optionally having one or more halogen atoms, a nitro group, a $OR^{18}$, a $NR^{18}R^{19}$, a cyano group, or a halogen atom;

$R^6$ represents a hydrogen atom, or a halogen atom;

T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$, a $CH_2OR^1$, a $NR^1R^{29}$, a $C(O)R^1$, a $C(O)NR^1R^{29}$, a $NR^{29}C(O)R^1$, a $N{=}CR^1R^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12:

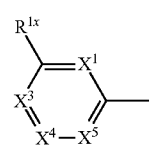

T-1

-continued

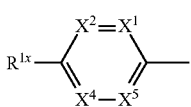
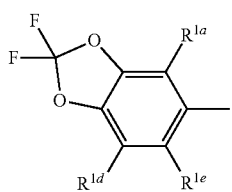
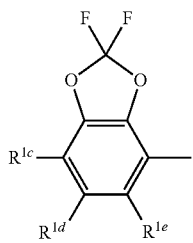
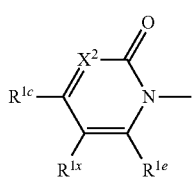
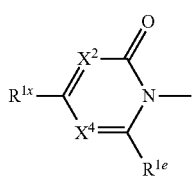
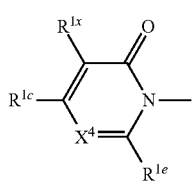
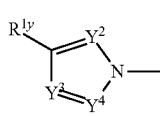
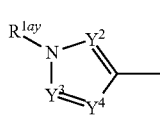
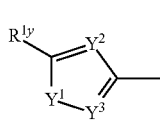
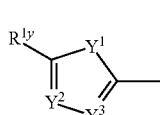

-continued

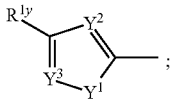

$X^1$ represents a nitrogen atom or a $CR^{1a}$;
$X^2$ represents a nitrogen atom or a $CR^{1b}$;
$X^3$ represents a nitrogen atom or a $CR^{1c}$;
$X^4$ represents a nitrogen atom or a $CR^{1d}$;
$X^5$ represents a nitrogen atom or a $CR^{1e}$;
$R^{1x}$ represents a $OR^7$, a $OS(O)_2R^7$, a $S(O)_mR^7$, a $NR^8S(O)_2R^7$, a C1-C5 chain hydrocarbon group having one or more halogen atoms, or a halogen atom;
q is 0, 1, 2, or 3;
$R^{1a}$, $R^{1b}$, $R^{1c}$, $R^{1d}$, and $R^{1e}$ represent independently of each other a hydrogen atom, a C1-C6 chain hydrocarbon group optionally having one or more halogen atoms, a C3-C6 cycloalkyl group optionally having one or more halogen atoms, or a halogen atom;
$Y^1$ represents a $NR^{25}$, an oxygen atom, or a sulfur atom;
$Y^2$ represents a nitrogen atom or a $CR^{26}$;
$Y^3$ represents a nitrogen atom or a $CR^{27}$;
$Y^4$ represents a nitrogen atom or a $CR^{28}$;
$R^{25}$, $R^{26}$, $R^{27}$, and $R^{28}$ represent independently of each other a hydrogen atom, a C1-C6 chain hydrocarbon group optionally having one or more halogen atoms, a C3-C6 cycloalkyl group optionally having one or more halogen atoms, or a halogen atom;
$R^{1y}$ represents a $OR^7$, a $OS(O)_2R^7$, a $S(O)_mR^7$, a $NR^8S(O)_2R^7$, a cyano group, a C1-C5 chain hydrocarbon group having one or more halogen atoms, or a halogen atom;
$R^{1ay}$ and $R^7$ represent independently of each other a C1-C6 chain hydrocarbon group having one or more halogen atoms;
$R^8$ represents a hydrogen atom, or a C1-C6 chain hydrocarbon group optionally having one or more halogen atoms;
m and v are independently of each other 0, 1 or 2;
$R^1$ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, or a C3-C7 cycloalkyl group having one or more substituents selected from Group G;
$R^2$ represents a cyclopropyl group, a cyclopropylmethyl group, or a C1-C6 alkyl group optionally having one or more halogen atoms;
$R^3$ represents a C1-C6 chain hydrocarbon group optionally having one or more substituents selected from Group B, a C3-C7 cycloalkyl group optionally having one or more substituents selected from Group E, a phenyl group optionally having one or more substituents selected from Group H, a five or six membered aromatic heterocyclic group optionally having one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $C(O)OR^{17}$, a cyano group, a nitro group, or a halogen atom, and when q is 2 or 3, a plurality of the $R^3$ may be identical to or different from each other;

When q is 2 and two $R^3$ are adjacent to each other, said two $R^3$ may combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring {the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may optionally have one or more substituents selected from Group H};

$R^{11}$, $R^{17}$, $R^{19}$, $R^{24}$, and $R^{29}$ represent independently of each other a hydrogen atom, or a C1-C6 chain hydrocarbon group optionally having one or more halogen atoms;

$R^{30}$ represents a hydrogen atom, a halogen atom, a $OR^{35}$, a $NR^{36}R^{37}$, or a C1-C6 chain hydrocarbon group optionally having one or more halogen atoms;

$R^{18}$ and $R^{35}$ represent independently of each other a C1-C6 chain hydrocarbon group optionally having one or more halogen atoms;

$R^{36}$ and $R^{37}$ represent independently of each other a hydrogen atom, or a C1-C6 chain hydrocarbon group optionally having one or more halogen atoms;

$R^{12}$ represents a hydrogen atom, a $S(O)_2R^{23}$, a C1-C6 chain hydrocarbon group optionally having one or more halogen atoms, or a C1-C6 alkyl group having one substituent selected from Group F;

$R^{23}$ represents a C1-C6 chain hydrocarbon group optionally having one or more halogen atoms, or a phenyl group optionally having one or more substituents selected from Group D;

$R^{11a}$ and $R^{12a}$ combine together a nitrogen atom to which they are attached to form a three to seven membered nonaromatic heterocyclic group optionally having one or more substituents selected from Group E;

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {a phenyl moiety in the phenyl C1-C3 alkyl group may optionally have one or more substituents selected from Group D};

$R^{15}$ and $R^{16}$ represent independently of each other a C1-C6 alkyl group optionally having one or more halogen atoms; and x is 0 or 1;

Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {the $R^{21}$ and the $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a five or six membered aromatic heterocyclic group optionally having one or more substituents selected from Group D, a C3-C7 cycloalkyl group optionally having one or more halogen atoms, and a three to seven nonaromatic heterocyclic group optionally having one or more substituents selected from Group C {the $R^{21}$ and the $R^{22}$ represent independently of each other a C1-C6 alkyl group optionally having one or more halogen atoms};

Group G: a group consisting of a halogen atom and a C1-C6 haloalkyl group;

Group H: a group consisting of a halogen atom, a nitro group, a cyano group, an amino group, a five or six membered aromatic heterocyclic group, a C1-C6 alkyl group optionally having one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$ {the $R^9$ represents a C1-C6 alkyl group optionally having one or more halogen atoms, or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms}];

[31] A compound represented by formula (II-1):

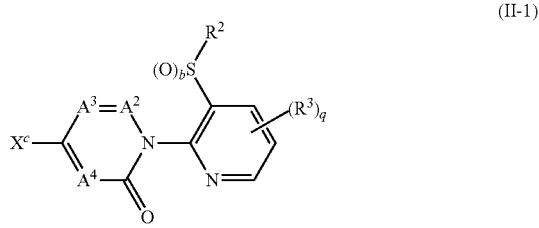

(II-1)

[wherein,
X represents a halogen atom;
b is 0, 1 or 2;
$A^2$ represents a nitrogen atom or a $CR^{4a}$;
$A^3$ represents a nitrogen atom or a $CR^{4b}$;
$A^4$ represents a nitrogen atom or a $CR^{4c}$;
$R^{4a}$, $R^{4b}$ and $R^{4c}$ represent independently of each other a hydrogen atom, a C1-C6 chain hydrocarbon group optionally having one or more halogen atoms, a nitro group, a $OR^{18}$, a $NR^{18}R^{19}$, a cyano group, or a halogen atom;
$R^2$ represents a cyclopropyl group, a cyclopropylmethyl group, or a C1-C6 alkyl group optionally having one or more halogen atoms;
q is 0, 1, 2, or 3;
$R^3$ represents a C1-C6 chain hydrocarbon group optionally having one or more substituents selected from Group B, a C3-C7 cycloalkyl group optionally having one or more substituents selected from Group E, a C3-C7 cycloalkenyl group optionally having one or more substituents selected from Group J, a phenyl group optionally having one or more substituents selected from Group H, a five or six membered aromatic heterocyclic group optionally having one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15x}R^{16x}$, a $NR^{24}NR^{11}C(O)NR^{15x}R^{16x}$, a N=CHNR^{15x}R^{16x}$, a N=S(O)_xR^{15}R^{16}$, a $C(O)R^{17}$, a $C(O)OR^{17}$, a $C(O)NR^{15x}R^{16x}$, a $C(O)NR^{11}S(O)_2R^{23}$, a $CR^{24}=NOR^{17}$, a $NR^{11}CR^{24}=NOR^{17}$, a cyano group, a nitro group, or a halogen atom, and when q is 2 or 3, a plurality of $R^3$ may be identical to or different from each other;
When two $R^3$ are adjacent to each other, said two $R^3$ combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring {the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may have optionally one or more substituents selected from Group H};
$R^{17}$ represents independently of each other a hydrogen atom, a C1-C6 chain hydrocarbon group optionally having one or more substituents selected from Group F, or a C3-C7 cycloalkyl group optionally having one or more substituents selected from Group J;
$R^{11}$, $R^{19}$, $R^{24}$, and $R^{29}$ represent independently of each other a hydrogen atom, or a C1-C6 chain hydrocarbon group optionally having one or more halogen atoms;
$R^{30}$ represents a hydrogen atom, a halogen atom, a $OR^{35}$, a $NR^{36}R^{37}$, or a C1-C6 chain hydrocarbon group optionally having one or more halogen atoms;
$R^{18}$ and $R^{35}$ represent independently of each other a C1-C6 chain hydrocarbon group optionally having one or more halogen atoms;
$R^{36}$ and $R^{37}$ represent independently of each other a hydrogen atom, or a C1-C6 chain hydrocarbon group optionally having one or more halogen atoms;
$R^{12}$ represents a C1-C6 chain hydrocarbon group optionally having one or more halogen atoms, a C1-C6 chain hydrocarbon group optionally having one or more substituents selected from Group F, a C3-C7 aliphatic hydrocarbon group optionally having one or more substituents selected from Group J, a phenyl group, a six membered aromatic heterocyclic group {the phenyl group, and the a six membered aromatic heterocyclic group may optionally have one or more substituents selected from Group D}, a hydrogen atom, or a $S(O)_2R^{23}$;
$R^{23}$ represents a C1-C6 chain hydrocarbon group optionally having one or more halogen atoms, a C3-C7 cycloalkyl group optionally having one or more halogen atoms, or a phenyl group optionally having one or more substituents selected from Group D;
$R^{11a}$ and $R^{12a}$ combine together a nitrogen atom to which they are attached to form a three to seven membered nonaromatic heterocyclic group optionally having one or more substituents selected from Group E;
$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D;
$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may optionally have one or more substituents selected from Group D};
$R^{15}$ and $R^{16}$ represent independently of each other a C1-C6 alkyl group optionally having one or more halogen atoms;
$R^{15x}$ represents a C1-C6 alkyl group optionally having one or more halogen atoms, or a hydrogen atom;
$R^{16x}$ represents a C1-C6 chain hydrocarbon group optionally having one or more substituents selected from Group F, a C3-C7 cycloalkyl group optionally having one or more substituents selected from Group J, or a hydrogen atom; and
x is 0 or 1;
Group B: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom;
Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {the $R^{21}$ and the $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a five or six membered aromatic heterocyclic group optionally having one or more substituents selected from Group D, a C3-C7 cycloalkyl group optionally having one or more halogen atoms, and a three to seven nonaromatic heterocyclic group optionally having one or more substituents selected from Group C {the $R^{21}$ and the $R^{22}$ represent independently of each other a C1-C6 alkyl group optionally having one or more halogen atoms};

Group H: a group consisting of a halogen atom, a nitro group, a cyano group, an amino group, a five or six membered aromatic heterocyclic group, a C1-C6 alkyl group optionally having one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$ {the $R^9$ represents a C1-C6 alkyl group optionally having one or more halogen atoms or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms};

Group J: a group consisting of a halogen atom, a cyano group, a triazolyl group, a C1-C6 alkyl group optionally having one or more halogen atoms, and a $NR^{10}C(O)R^9$ {the $R^9$ represents a C1-C6 alkyl group optionally having one or more halogen atoms, or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms}](hereinafter, the compound represented by formula (II-1) may be referred to as "Compound B");

[32] A compound represented by formula (II-2):

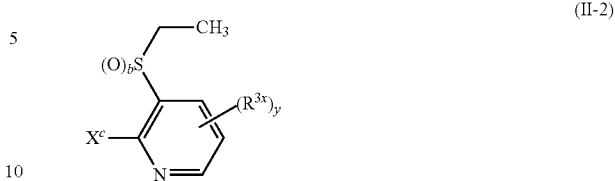

[wherein,
$X^c$ represents a halogen atom;
b is 0, 1, or 2;
y is 1, 2, or 3;
$R^{3x}$ represents a C1-C6 chain hydrocarbon group optionally having one or more substituents selected from group K, a C3-C7 cycloalkyl group optionally having one or more substituents selected from Group E, a C3-C7 cycloalkenyl group optionally having one or more substituents selected from Group J, a phenyl group optionally having one or more substituents selected from Group H, a five or six membered aromatic heterocyclic group optionally having one or more substituents selected from Group H, a $OR^{12}$, a $NR^{11b}R^{12b}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15x}R^{16x}$, a $NR^{24}NR^{11}C(O)NR^{15x}R^{16x}$, a $N=CHNR^{15x}R^{16x}$, a $N=S(O)_xR^{15}R^{16}$, a $C(O)R^{17}$, a $C(O)OR^{17a}$, a $C(O)NR^{15x}R^{16x}$, a $C(O)NR^{11}S(O)_2R^{23}$, a $CR^{24}=NOR^{17}$, a $NR^{11}CR^{24}=NOR^{17}$, a cyano group, or a nitro group, and when q is 2 or 3, a plurality of $R^{3x}$ may be identical to or different from each other;

When two $R^{3x}$ are adjacent to each other, said two $R^{3x}$-combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring {the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may optionally have one or more substituents selected from Group H};

$R^{17}$ represents independently of each other a hydrogen atom, a C1-C6 chain hydrocarbon group optionally having one or more substituents selected from Group F, or a C3-C7 cycloalkyl group optionally having one or more substituents selected from Group J;

$R^{17a}$ represents independently of each other a C1-C6 chain hydrocarbon group optionally having one or more substituents selected from Group F, or a C3-C7 cycloalkyl group optionally having one or more substituents selected from Group J;

$R^{11}$, $R^{19}$, $R^{24}$, and $R^{29}$ represent independently of each other a hydrogen atom, or a C1-C6 chain hydrocarbon group optionally having one or more halogen atoms;

$R^{11b}$ represents a C1-C6 chain hydrocarbon group optionally having one or more halogen atoms;

$R^{30}$ represents a hydrogen atom, a halogen atom, a $OR^{35}$, a $NR^{36}R^{37}$, or a C1-C6 chain hydrocarbon group optionally having one or more halogen atoms;

$R^{18}$ and $R^{35}$ represent independently of each other a C1-C6 chain hydrocarbon group optionally having one or more halogen atoms;

$R^{36}$ and $R^{37}$ represent independently of each other a hydrogen atom, or a C1-C6 chain hydrocarbon group optionally having one or more halogen atoms;

$R^{12}$ represents a C1-C6 chain hydrocarbon group optionally having one or more halogen atoms, a C1-C6 chain hydrocarbon group optionally having one or more substituents selected from Group F, a C3-C7 cycloalkyl group optionally having one or more substituents selected from Group J, a C3-C7 cycloalkenyl group optionally having one or more substituents selected from Group J, a phenyl group, a six membered aromatic heterocyclic group {the phenyl group or the a six membered aromatic heterocyclic group may optionally have one or more substituents selected from Group D}, a hydrogen atom, or a $S(O)_2R^{23}$;

$R^{12b}$ represents a C1-C6 chain hydrocarbon group optionally having one or more halogen atoms, a C1-C6 chain hydrocarbon group optionally having one or more substituents selected from Group F, a C3-C7 aliphatic hydrocarbon group optionally having one or more substituents selected from Group J, a phenyl group, a six membered aromatic heterocyclic group {the phenyl group or the six membered aromatic heterocyclic group may optionally have one or more substituents selected from Group D}, or a $S(O)_2R^{23}$;

$R^{23}$ represents a C1-C6 chain hydrocarbon group optionally having one or more halogen atoms, a C3-C7 cycloalkyl group optionally having one or more halogen atoms, or a phenyl group optionally having one or more substituents selected from Group D;

$R^{11a}$ and $R^{12a}$ combine together a nitrogen atom to which they are attached to form a three to seven membered nonaromatic heterocyclic group optionally having one or more substituents selected from Group E;

$R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a five or six membered aromatic heterocyclic group optionally having one or more substituents selected from Group D;

$R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group {the phenyl moiety in the phenyl C1-C3 alkyl group may optionally have one or more substituents selected from Group D};

$R^{15}$ and $R^{16}$ represent independently of each other a C1-C6 alkyl group optionally having one or more halogen atoms;

$R^{15x}$ represents a C1-C6 alkyl group optionally having one or more halogen atoms, or a hydrogen atom;

$R^{16x}$ represents a C1-C6 chain hydrocarbon group optionally having one or more substituents selected from Group F, a C3-C7 cycloalkyl group optionally having one or more substituents selected from Group J, or a hydrogen atom; and x is 0 or 1;

Group C: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom;

Group D: a group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom {the $R^{21}$ and the $R^{22}$ represent independently of each other a C1-C6 alkyl group optionally having one or more halogen atoms};

Group E: a group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group;

Group F: a group consisting of a C1-C6 alkoxy group optionally having one or more halogen atoms, an amino group, a $NHR^{21}$, a $NR^{21}R^{22}$, a cyano group, a phenyl group optionally having one or more substituents selected from Group D, a five or six membered aromatic heterocyclic group optionally having one or more substituents selected from Group D, a C3-C7 cycloalkyl group optionally having one or more halogen atoms, and a three to seven nonaromatic heterocyclic group optionally having one or more substituents selected from Group C {the $R^{21}$ and the $R^{22}$ represent independently of each other a C1-C6 alkyl group optionally having one or more halogen atoms};

Group H: a group consisting of a halogen atom, a nitro group, a cyano group, an amino group, a five or six membered aromatic heterocyclic group, a C1-C6 alkyl group optionally having one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$ {the $R^9$ represents a C1-C6 alkyl group optionally having one or more halogen atoms, or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms};

Group J: a group consisting of a halogen atom, a cyano group, a triazolyl group, a C1-C6 alkyl group optionally having one or more halogen atoms, and a $NR^{10}C(O)R^9$ {the $R^9$ represents a C1-C6 alkyl group optionally having one or more halogen atoms, or a C3-C6 cycloalkyl group optionally having one or more halogen atoms, and the $R^{10}$ represents a hydrogen atom, a C1-C6 alkyl group optionally having one or more halogen atoms, or a C3-C6 cycloalkyl group optionally having one or more halogen atoms};

Group K: a group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, and a hydroxy group](hereinafter, the compound represented by formula (II-2) may be referred to as "Compound C").

Effect of Invention

The compound of the present invention has an excellent control efficacy against harmful arthropods, and is thus useful as an active ingredient of a composition for controlling harmful arthropods.

MODE FOR CARRYING OUT THE INVENTION

The substituent(s) as described herein is/are explained.

The term of "optionally having one or more halogen atoms" represents that when two or more halogen atoms are present, these halogen atoms may be identical to or different from each other.

The expression of "CX-CY" as used herein represents that the number of carbon atom is from X to Y. For example, the expression of "C1-C6" represents that the number of carbon atom is from 1 to 6.

The term "halogen atom" represents fluorine atom, chlorine atom, bromine atom, or iodine atom.

The term of "chain hydrocarbon group" represents an alkyl group, an alkenyl group, or an alkynyl group.

Example of the term of "alkyl group" include methyl group, ethyl group, propyl group, isopropyl group, 1,1-dimethylpropyl group, 1,2-dimethylpropyl group, 1-ethyl-propyl group, butyl group, tert-butyl group, pentyl group, and hexyl group.

Example of the term of "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 1-ethyl-1-propenyl group, 1-ethyl-2-propenyl group, 3-butenyl group, 4-pentenyl group, and 5-hexenyl group.

Example of the term of "alkynyl group" includes ethynyl group, 1-propynyl group, 2-propynyl group, 1-methyl-2-propynyl group, 1,1-dimethyl-2-propynyl group, 1-ethyl-2-propynyl group, 2-butynyl group, 4-pentynyl group, and 5-hexynyl group.

Example of the term of "C1-C6 haloalkyl group" include trifluoromethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

Example of the term of "cycloalkyl group" includes cyclopropyl group, cyclobutyl group, cyclopentyl group, cyclohexyl group, and cycloheptyl group.

Example of the term of "cycloalkenyl group" includes cyclopropenyl group, cyclobutenyl group, cyclopentenyl group, cyclohexenyl group, and cycloheptenyl group.

Example of the term of "alkoxy group" includes methoxy group, ethoxy group, propoxy group, butoxy group, pentoxy group, and hexyloxy group.

The term of "C1-C6 haloalkoxy group" represents a group wherein one or more hydrogen atoms of the C1-C6 alkoxy group is/are substituted with halogen atom(s), and includes for example, trifluoromethoxy group, difluoromethoxy group, 2,2,2-trichloroethoxy group, and 2,2,2-trifluoroethoxy group.

The term of "C3-C6 haloalkenyloxy group" represents a group wherein one or more hydrogen atoms of C3-C6 alkenyloxy group is/are substituted with halogen atom(s), and includes for example, 3,3,3-trifluoro-1-propenyloxy group, 3,3,3-trichloro-1-propenyloxy group, and 2,3,3,3-tetrafluoro-1-propenyloxy group.

The term of "C3-C6 haloalkynyloxy group" represents a group wherein one or more hydrogen atoms of C3-C6 alkynyloxy group is/are substituted with halogen atom(s), and includes for example, 3,3,3-trifluoro-1-propynyloxy group, and 3,3,3-trichloro-1-propynyloxy group.

The terms of "alkylsulfanyl", "alkylsulfinyl", and "alkylsulfonyl" represent an alkyl group containing a $S(O)_z$ moiety, respectively.

For example, examples of the "alkylsulfanyl" when z is 0 include methylsulfanyl group, ethylsulfanyl group, propylsulfanyl group, and isopropylsulfanyl group.

For example, examples of the "alkylsulfinyl" when z is 1 include methylsulfinyl group, ethylsulfinyl group, propylsulfinyl group, and isopropylsulfinyl group.

For example, examples of the "alkylsulfonyl" when z is 2 include methylsulfonyl group, ethylsulfonyl group, propylsulfonyl group, and isopropylsulfonyl group.

Examples of the term of "three (3) to seven (7) membered nonaromatic heterocyclic group" include aziridine, azetidine, pyrrolidine, imidazoline, imidazolidine, piperidine, tetrahydropyrimidine, hexahydropyrimidine, piperazine, azepane, oxazolidine, isoxazolidine, 1,3-oxazinane, morpholine, 1,4-oxazepane, thiazolidine, isothiazolidine, 1,3-thiazinane, thiomorpholine, and 1,4-thiazepane. Examples of the three to seven membered nonaromatic heterocyclic group optionally having one or more substituents selected from Group E include the followings:

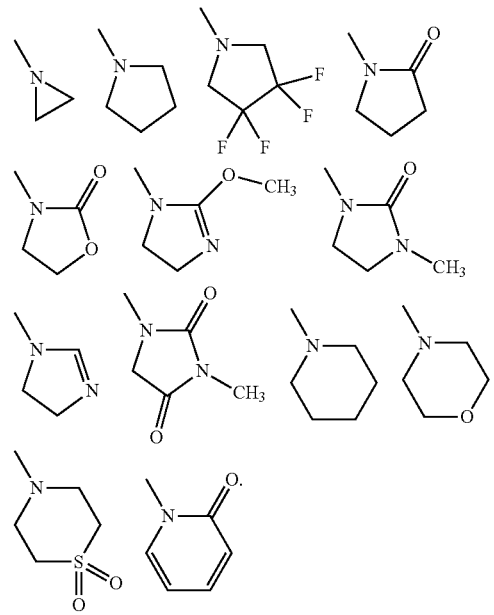

The term of "(C1-C5 alkoxy)C2-C5 alkyl group having one or more halogen atoms" represents a group wherein the (C1-C5 alkoxy) and/or the (C2-C5 alkyl) has/have one or more halogen atoms, and includes for example, 2-(trifluoromethoxy)ethyl group, 2,2-difluoro-3-methoxypropyl group, 2,2-difluoro-3-(2,2,2-trifluoroethoxy)propyl group, and 3-(2-chloroethoxy)propyl group.

The term of "(C1-C5 alkylsulfanyl)C2-C5 alkyl group having one or more halogen atoms" represents a group wherein the (C1-C5 alkylsulfanyl) and/or the (C2-C5 alkyl) has/have one or more halogen atoms, and includes for example, 2,2-difluoro-2-(trifluoromethylthio)ethyl group.

The term of "(C1-C5 alkylsulfinyl)C2-C5 alkyl group having one or more halogen atoms" represents a group wherein the (C1-C5 alkylsulfinyl) and/or the (C2-C5 alkyl)

has/have one or more halogen atoms, and includes for example, 2,2-difluoro-2-(trifluoromethansulfinyl)ethyl group.

The term of "(C1-C5 alkylsulfonyl)C2-C5 alkyl group having one or more halogen atoms" represents a group wherein the (C1-C5 alkylsulfonyl) and/or the (C2-C5 alkyl) has/have one or more halogen atoms, and includes for example, 2,2-difluoro-2-(trifluoromethansulfonyl)ethyl group.

The term of "(C3-C6 cycloalkyl)C1-C3 alkyl group optionally having one or more halogen atoms" represents the (C3-C6 cycloalkyl) and/or the (C1-C3 alkyl) optionally has/have one or more halogen atoms, and includes for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term of "(C3-C7 cycloalkyl)C1-C3 alkyl group having one or more substituents selected from Group G" represents a group wherein the (C3-C7 cycloalkyl) and/or the (C1-C3 alkyl) has/have one or more substituents selected from Group G, and includes for example, (2,2-difluorocyclopropyl)methyl group, [1-(trifluoromethyl)cyclopropyl]methyl group, [2-(trifluoromethyl)cyclopropyl]methyl group, 2-cyclopropyl-1,1,2,2-tetrafluoroethyl group, 2-cyclopropyl-3,3,3-trifluoropropyl group, and 1,1,2,2-tetrafluoro-2-[2-(trifluoromethyl)cyclopropyl]ethyl group.

Examples of the term of "C3-C7 cycloalkyl group having one or more substituents selected from Group G" include 2,2-difluorocyclopropyl group, 1-(2,2,2-trifluoroethyl)cyclopropyl group, and 4-(trifluoromethyl)cyclohexyl group.

Examples of the term of "phenyl C1-C3 alkyl group {the phenyl moiety in the phenyl C1-C3 alkyl group may optionally have one or more substituents selected from Group D}" include benzyl group, 2-fluorobenzyl group, 4-chlorobenzyl group, 4-(trifluoromethyl)benzyl group, and 2-[4-(trifluoromethyl)phenyl]ethyl group.

The term of "five (5) or six (6) membered aromatic heterocyclic group" represents a five membered aromatic heterocyclic group or a six membered aromatic heterocyclic group, and examples of the five membered aromatic heterocyclic group include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, and thiadiazolyl group. As the five membered aromatic heterocyclic group, a five membered aromatic heterocyclic group containing 1 to 4 nitrogen atoms, that is, pyrrolyl group, pyrazolyl group, imidazolyl group, 1,2,4-triazolyl group, 1,2,3-triazolyl group, or tetrazolyl group is preferably included. Examples of the six membered aromatic heterocyclic group include pyridyl group, pyridazinyl group, pyrimidinyl group, and pyrazinyl group.

The term of "when q is 2 and two $R^3$ are adjacent to each other, said two $R^3$ combine together with a carbon atom to which they are attached to form benzene ring, pyrrole ring, furan ring, thiophene ring, pyrazole ring, imidazole ring, triazole ring, oxazole ring, isoxazole ring, thiazole ring, oxadiazole ring, thiadiazole ring, pyridine ring, pyridazine ring, pyrimidine ring, or pyrazine ring" represents, for example, the following compounds when pyrrole ring is formed.

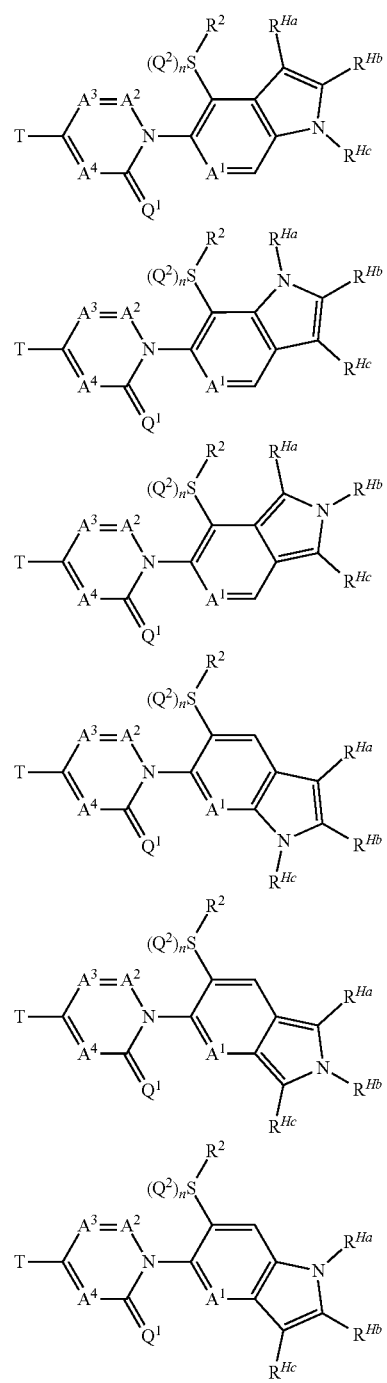

[wherein, $R^{Ha}$, $R^{Hb}$, and $R^{Hc}$ represent independently of each other a hydrogen atom, a halogen atom, a nitro group, a cyano group, an amino group, a five or six membered aromatic heterocyclic group, a C1-C6 alkyl group optionally having one or more halogen atoms, a $OR^{10}$, a $N^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, or a $C(O)OR^{10}$, and the other symbols are the same as defined above].

Examples of the embodiment of the compound of the present invention include the followings.

[Embodiment 1] a compound A of the present invention wherein $R^3$ represents a phenyl group optionally having one or more substituents selected from Group H, one of six membered aromatic heterocyclic group selected from Group V, or one of five membered aromatic heterocyclic group selected from Group W (the six membered aromatic heterocyclic group may optionally have one or more substituents selected from Group H), or one of five membered aromatic heterocyclic group selected from Group W (the five membered aromatic heterocyclic group may optionally have one or more substituents selected from Group H);

Group V:

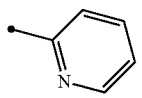 V-1

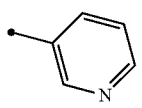 V-2

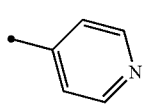 V-3

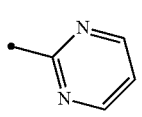 V-4

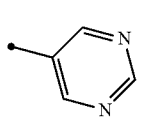 V-5

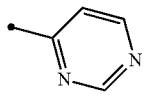 V-6

 V-7

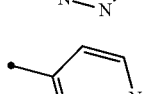 V-8

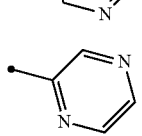 V-9

Group W:

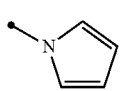 W-1

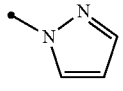 W-2

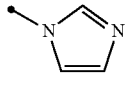 W-3

-continued

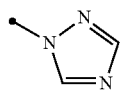 W-4

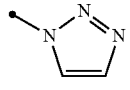 W-5

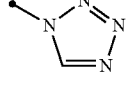 W-6

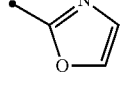 W-7

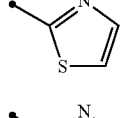 W-8

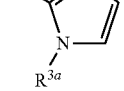 W-9

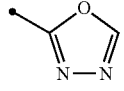 W-10

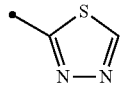 W-11

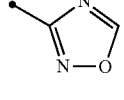 W-12

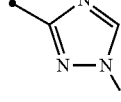 W-13

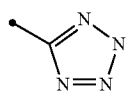 W-14

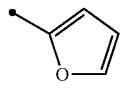 W-15

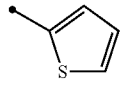 W-16

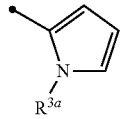 W-17

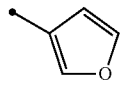 W-18

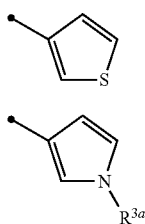

W-19

W-20

{in the above formulae, $R^{3a}$ represents a C1-C6 alkyl group optionally having one or more halogen atoms};

[Embodiment 2] a compound A of the present invention wherein $A^2$ represents a $CR^{4a}$, $A^3$ represents a $CR^{4b}$, and $A^4$ represents a $CR^{4c}$;

[Embodiment 3] a compound A of the embodiment 2 wherein $A^1$ represents a nitrogen atom or a CH, $R^2$ represents a C1-C6 alkyl group, $R^3$ represents a C1-C6 alkyl group optionally having one or more halogen atoms, a phenyl group, a six membered aromatic heterocyclic group, or a five membered aromatic heterocyclic group containing 1 to 4 nitrogen atoms {the phenyl group, the six membered aromatic heterocyclic group, and the five membered aromatic heterocyclic group containing 1 to 4 nitrogen atoms may optionally have one or more substituents selected from Group J}, a $NR^{11}R^{12}$, a $NR^{11}C(O)OR^{14}$, or a halogen atom, Q1 represents an oxygen atom, and $Q^2$ represents an oxygen atom, a N—CN, a $NR^5$, a NH, a or N—C(O)$R^5$;

[Embodiment 4] a compound of embodiment 3 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$ and $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 5] a compound of the embodiment 3 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$ and $R^{4c}$ represent independently of each other a hydrogen atom, $Q^2$ represents an oxygen atom, a N—CN, a $NR^5$, or a N—C(O)$R^5$, and q is 0 or 1;

[Embodiment 6] a compound of the embodiment 3 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$ and $R^{4c}$ represent independently of each other a hydrogen atom, $Q^2$ represents an oxygen atom, and q is 0 or 1;

[Embodiment 7] a compound of the embodiment 3 wherein $A^1$ represents a nitrogen atom;

[embodiment 8] a compound of the embodiment 7 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, and $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 9] a compound of the embodiment 7 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a NR11C(O)OR14, or a halogen atom, $R^{4a}$, $R^{4b}$, and $R^{4c}$ represent independently of each other a hydrogen atom, $Q^2$ represents an oxygen atom, a N—CN, a $NR^5$, or a N—C(O)$R^5$, and q is 0 or 1;

[Embodiment 10] a compound of the embodiment 7 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, and $R^{4c}$ represent independently of each other a hydrogen atom, $Q^2$ represents an oxygen atom, and q is 0 or 1;

[Embodiment 11] a compound of the embodiment 2 wherein $A^1$ represents a CH;

[Embodiment 12] a compound of the embodiment 11 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, and $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 13] a compound of the embodiment 11 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, and $R^{4c}$ represent independently of each other a hydrogen atom, $Q^2$ represents an oxygen atom, a N—CN, a $NR^5$, or a N—C(O)$R^5$, and q is 0 or 1;

[Embodiment 14] a compound of the embodiment 11 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, and $R^{4c}$ represent independently of each other a hydrogen atom, $Q^2$ represents an oxygen atom, and q is 0 or 1;

[Embodiment 15] a compound of any of the embodiments 1 to 14 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[Embodiment 16] a compound of any of the embodiments 1 to 14 wherein T represents a C1-C5 chain hydrocarbon group having one or more halogen atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C1-C5 chain hydrocarbon group having one or more halogen atoms;

[Embodiment 17] a compound of any of the embodiments 1 to 14 wherein T represents a C1-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the following formula T-7, a group represented by the formula T-8, or a group represented by the formula T-9, and $R^1$, $R^{1x}$, $R^{1y}$, and $R^{1ay}$ represents independently of each other a C1-C5 alkyl group having three or more fluorine atoms;

[Embodiment 18] a compound of any of the embodiments 1 to 14 wherein T represents a C2-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C2-C5 alkyl group having three or more fluorine atoms;

[Embodiment 19] a compound of any of the embodiments 1 to 14 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$ or a $NR^1R^{29}$;

[Embodiment 20] a compound of any one of the embodiments 1 to 14 wherein T represents a C1-C5 chain hydrocarbon group having one or more halogen atoms, a $OR^1$, a $S(O)_vR^1$, a $OS(O)_2R^1$, or a $NR^1R^{29}$, and $R^1$ represents a C1-C5 chain hydrocarbon group having one or more halogen atoms;

[Embodiment 21] a compound of any one of the embodiments 1 to 14 wherein T represents a C1-C5 alkyl group having three or more fluorine atoms, a $OR^1$, a $S(O)_vR^1$, a $OS(O)_2R^1$, or a $NR^1R^{29}$, and $R^1$ represents a C1-C5 alkyl group having three or more fluorine atoms;

[Embodiment 22] a compound of any one of the embodiments 1 to 14 wherein T represents a C2-C5 alkyl group having three or more fluorine atoms, a $OR^1$, a $S(O)_vR^1$, a $OS(O)_2R^1$, or a $NR^1R^{29}$, and $R^1$ represents a C2-C5 alkyl group having three or more fluorine atoms;

[Embodiment 23] a compound of any one of the embodiments 1 to 14 wherein T represents a $OR^1$;

[Embodiment 24] a compound of any one of the embodiments 1 to 14 wherein T represents a $OR^1$, and $R^1$ represents a C1-C5 chain hydrocarbon group having one or more halogen atoms;

[Embodiment 25] a compound of any one of the embodiments 1 to 14 wherein T represents a $OR^1$, and $R^1$ represents a C1-C5 alkyl group having three or more fluorine atoms;

[Embodiment 26] a compound of any one of the embodiments 1 to 14 wherein T represents a $OR^1$, and $R^1$ represents a C2-C5 alkyl group having three or more fluorine atoms;

[Embodiment 27] a compound of any one of the embodiments 1 to 14 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[Embodiment 28] a compound of any one of the embodiments 1 to 14 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 chain hydrocarbon group having one or more halogen atoms;

[Embodiment 29] a compound of any one of the embodiments 1 to 14 wherein a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 alkyl group having three or more fluorine atoms;

[Embodiment 30] a compound of any one of the embodiments 1 to 14 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C2-C5 alkyl group having three or more fluorine atoms;

[Embodiment 31] a compound A of the present invention wherein $A^2$ represents a nitrogen atom, $A^3$ represents a $CR^{4b}$, and $A^4$ represents a $CR^{4c}$;

[Embodiment 32] a compound of the embodiment 31 wherein $A^1$ represents a nitrogen atom or a CH, $R^2$ represents a C1-C6 alkyl group, $R^3$ represents a C1-C6 alkyl group optionally having one or more halogen atoms, a phenyl group, a six membered aromatic heterocyclic group, or a five membered aromatic heterocyclic group containing 1 to 4 nitrogen atoms {the phenyl group, the a six membered aromatic heterocyclic group, and the five membered aromatic heterocyclic group containing 1 to 4 nitrogen atoms may optionally have one or more substituents selected from Group J}, a $NR^{11}R^{12}$, a $NR^{11}C(O)OR^{14}$, or a halogen atom, $Q^1$ represents an oxygen atom, and $Q^2$ represents an oxygen atom, a N—CN, a $NR^5$, a NH, or a N—C(O)$R^5$;

[Embodiment 33] a compound of the embodiment 32 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, or a halogen atom, $Q^2$ represents an oxygen atom, a N—CN, a $NR^5$, or a N—C(O)$R^5$, and q is 0 or 1;

[Embodiment 34] a compound of the embodiment 32 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 35] a compound of the embodiment 32 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 36] a compound of the embodiment 31 wherein $A^1$ represents a nitrogen atom;

[Embodiment 37] a compound of the embodiment 36 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 38] a compound of the embodiment 36 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 39] a compound of the embodiment 36 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, and q is 0 or 1;

[Embodiment 40] a compound of the embodiment 31 wherein $A^1$ represents a CH;

[Embodiment 41] a compound of the embodiment 40 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 42] a compound of the embodiment 40 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 43] a compound of the embodiment 40 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 44] a compound of any one of embodiments 31 to 43 wherein T represents a C1-C10 chain hydrocarbon group having one or more halogen atoms, a (C1-C5 alkoxy) C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)

C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$, a $NR^1R^{29}$, a group represented by the formula T-1, a group represented by the following formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[Embodiment 45] a compound of any one of embodiments 31 to 43 wherein T represents a C1-C5 chain hydrocarbon group having one or more halogen atoms, a $OR^1$, a $S(O)_vR^1$, a $OS(O)_2R^1$, a $NR^1R^{29}$, a group represented by the formula T-1, a group represented by the g formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, $R^1$, $R^{1x}$, $R^{1y}$, and $R^{1ay}$ represents independently of each other a C1-C5 chain hydrocarbon group having one or more halogen atoms;

[Embodiment 46] a compound of any one of embodiments 31 to 43 wherein T represents a C1-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, $R^1$, $R^{1x}$, $R^{1y}$, and $R^{1ay}$ represents independently of each other a C1-C5 alkyl group having three or more fluorine atoms;

[Embodiment 47] a compound of any one of embodiments 31 to 43 wherein T represents a C2-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, $R^1$, $R^{1x}$, $R^{1y}$, and $R^{1ay}$ represents independently of each other a C2-C5 alkyl group having three or more fluorine atoms;

[Embodiment 48] a compound of any one of embodiments 31 to 43 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl) C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$ or a $NR^1R^{29}$.

[Embodiment 49] a compound of any one of embodiments 31 to 43 wherein T represents a C1-C5 chain hydrocarbon group having one or more halogen atoms, a $OR^1$, a $S(O)_vR^1$, $OS(O)_2R^1$ or a $NR^1R^{29}$, and $R^1$ represents a C1-C5 chain hydrocarbon group having one or more halogen atoms;

[Embodiment 50] a compound of any one of embodiments 31 to 43 wherein T represents a C1-C5 alkyl group having three or more fluorine atoms, a $OR^1$, a $S(O)_vR^1$, a $OS(O)_2R^1$ or a $NR^1R^{29}$, and $R^1$ represents a C1-C5 alkyl group having three or more fluorine atoms;

[Embodiment 51] a compound of any one of embodiments 31 to 43 wherein T represents a C2-C5 alkyl group having three or more fluorine atoms, a $OR^1$, a $S(O)_vR^1$, a $OS(O)_2R^1$ or a $NR^1R^{29}$, and $R^1$ represents a C2-C5 alkyl group having three or more fluorine atoms;

[Embodiment 52] a compound of any one of embodiments 31 to 43 wherein T represents a $OR^1$;

[Embodiment 53] a compound of any one of embodiments 31 to 43 wherein T represents a $OR^1$, and $R^1$ represents a C1-C5 chain hydrocarbon group having one or more halogen atoms;

[Embodiment 54] a compound of any one of embodiments 31 to 43 wherein T represents a $OR^1$, and $R^1$ represents a C1-C5 alkyl group having three or more fluorine atoms;

[Embodiment 55] a compound of any one of embodiments 31 to 43 wherein T represents a $OR^1$, and $R^1$ represents a C2-C5 alkyl group having three or more fluorine atoms;

[Embodiment 56] a compound of any one of embodiments 31 to 43 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[Embodiment 57] a compound of any one of embodiments 31 to 43 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 chain hydrocarbon group having one or more halogen atoms;

[Embodiment 58] a compound of any one of embodiments 31 to 43 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 alkyl group having three or more fluorine atoms;

[Embodiment 59] a compound of any one of embodiments 31 to 43 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C2-C5 alkyl group having three or more fluorine atoms;

[Embodiment 60] a compound A of the present invention wherein $A^3$ represents a nitrogen atom, $A^2$ represents a $CR^{4a}$, and $A^4$ represents a $CR^4C$;

[Embodiment 61] a compound of the embodiment 60 wherein $A^1$ represents a nitrogen atom or a CH, $R^2$ represents a C1-C6 alkyl group, $R^3$ represents a C1-C6 alkyl group optionally having one or more halogen atoms, a phenyl group, a six membered aromatic heterocyclic group, a five membered aromatic heterocyclic group containing 1 to 4 nitrogen atoms {the phenyl group, the a six membered aromatic heterocyclic group, and the five membered aromatic heterocyclic group containing 1 to 4 nitrogen atoms may optionally have one or more substituents selected from Group J}, a $NR^{11}R^{12}$, a $NR^{11}C(O)OR^{14}$, or a halogen atom, $Q^1$ represents an oxygen atom, $Q^2$ represents an oxygen atom, a N—CN, a $NR^5$, a NH, or a N—C(O)$R^5$;

[Embodiment 62] a compound of the embodiment 61 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 63] a compound of the embodiment 61 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 64] a compound of the embodiment 61 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 65] a compound of the embodiment 61 wherein $A^1$ represents a nitrogen atom;

[Embodiment 66] a compound of the embodiment 65 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 67] a compound of the embodiment 65 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 68] a compound of the embodiment 65 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 69] a compound of the embodiment 65 wherein $A^1$ represents a CH;

[Embodiment 70] a compound of the embodiment of 69 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 71] a compound of the embodiment 69 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 72] a compound of the embodiment 69 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 73] a compound of any one of embodiments 60 to 72 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[Embodiment 74] a compound of any one of embodiments 60 to 72 wherein T represents a C1-C5 chain hydrocarbon group having one or more halogen atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C1-C5 chain hydrocarbon group having one or more halogen atoms;

[Embodiment 75] a compound of any one of embodiments 60 to 72 wherein T represents a C1-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other or a C1-C5 alkyl group having three or more fluorine atoms;

[Embodiment 76] a compound of any one of embodiments 60 to 72 wherein T represents a C2-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other or a C2-C5 alkyl group having three or more fluorine atoms;

[Embodiment 77] a compound of any one of embodiments 60 to 72 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$ or a $NR^1R^{29}$;

[Embodiment 78] a compound of any one of embodiments 60 to 72 wherein T represents a C1-C5 chain hydrocarbon group having one or more halogen atoms, a $OR^1$, a $S(O)_vR^1$, a $OS(O)_2R^1$ or a $NR^1R^{29}$, and $R^1$ represents a C1-C5 chain hydrocarbon group having one or more halogen atoms;

[Embodiment 79] a compound of any one of embodiments 60 to 72 wherein T represents a C1-C5 alkyl group having three or more fluorine atoms, a $OR^1$, a $S(O)_vR^1$, a $OS(O)_2R^1$ or a $NR^1R^{29}$, and $R^1$ represents a C1-C5 alkyl group having three or more fluorine atoms;

[Embodiment 80] a compound of any one of embodiments 60 to 72 wherein T represents a C2-C5 alkyl group having three or more fluorine atoms, a $OR^1$, a $S(O)_vR^1$, a $OS(O)_2R^1$ or a $NR^1R^{29}$, and $R^1$ represents a C2-C5 alkyl group having three or more fluorine atoms;

[Embodiment 81] a compound of any one of embodiments 60 to 72 wherein T represents a $OR^1$;

[embodiment 82] a compound of any one of embodiments 60 to 72 wherein T represents a $OR^1$, and $R^1$ represents a C1-C5 chain hydrocarbon group having one or more halogen atoms;

[Embodiment 83] a compound of any one of embodiments 60 to 72 wherein T represents a $OR^1$, and $R^1$ represents a C1-C5 alkyl group having three or more fluorine atoms;

[embodiment 84] a compound of any one of embodiments 60 to 72 wherein T represents $OR^1$, and $R^1$ represents a C2-C5 alkyl group having three or more fluorine atoms;

[Embodiment 85] a compound of any one of embodiments 60 to 72 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[embodiment 86] a compound of any one of embodiments 60 to 72 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 chain hydrocarbon group having one or more halogen atoms;

[Embodiment 87] a compound of any one of embodiments 60 to 72 wherein T represents a group represented by the formula T-1, a group represented by the formula T-2, a group represented by the formula T-3, a group represented by the following formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 alkyl group having three or more fluorine atoms;

[Embodiment 88] a compound of any one of embodiments 60 to 72 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C2-C5 alkyl group having three or more fluorine atoms;

[Embodiment 89] a compound A of the present invention wherein $A^4$ represents a nitrogen atom, $A^2$ represents a $CR^{4a}$, and $A^3$ represents a $CR^{4b}$;

[Embodiment 90] a compound of the embodiment 89 wherein $A^1$ represents a nitrogen atom or a CH, $R^2$ represents a C1-C6 alkyl group, $R^3$ represents a C1-C6 alkyl group optionally having one or more halogen atoms, a phenyl group, a six membered aromatic heterocyclic group, a five membered aromatic heterocyclic group containing 1 to 4 nitrogen atoms {the phenyl group, the a six membered aromatic heterocyclic group, and the five membered aromatic heterocyclic group containing 1 to 4 nitrogen atoms may optionally have one or more substituents selected from Group J}, a $NR^{11}R^{12}$, a $NR^{11}C(O)OR^{14}$, or a halogen atom, $Q^1$ represents an oxygen atom, and $Q^2$ represents an oxygen atom, a N—CN, a $NR^5$, a NH, or a N—C(O)$R^5$;

[Embodiment 91] a compound of the embodiment 90 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 92] a compound of the embodiment 90 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 93] a compound of the embodiment 90 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 94] a compound of the embodiment 89 wherein $A^1$ represents a nitrogen atom;

[Embodiment 95] a compound of the embodiment 94 wherein $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, or a halogen atom, $Q^2$ represents an oxygen atom, a N—CN, a $NR^5$, or a N—C(O)$R^5$, and q is 0 or 1;

[Embodiment 96] a compound of the embodiment 94 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 97] a compound of the embodiment 94 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 98] a compound of the embodiment 89 wherein $A^1$ represents a CH;

[Embodiment 99] a compound of the embodiment 98 wherein $R^3$ represents a C1-C6 alkyl group optionally having one or more halogen atoms, phenyl group, pyridyl group, pyrimidinyl group, pyrazolyl group, or triazolyl group{the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom or a halogen atom, $Q^2$ represents an oxygen atom, a N—CN, a $NR^5$, or a N—C(O)$R^5$, and q is 0 or 1;

[Embodiment 100] a compound of the embodiment 98 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, a N—CN, a $NR^5$, or a N—C(O)$R^5$, and q is 0 or 1;

[Embodiment 101] a compound of the embodiment 98 wherein $R^2$ represents an ethyl group, $R^3$ represents a C1-C6 alkyl group optionally having one or more halogen atoms, a phenyl group, a pyridyl group, a pyrimidinyl group, a pyrazolyl group, or a triazolyl group {the phenyl group, the pyridyl group, the pyrimidinyl group, the pyrazolyl group, and the triazolyl group may optionally have one or more substituents selected from Group J}, an amino group, a $NR^{11}C(O)OR^{14}$, or a halogen atom, $R^{4a}$, $R^{4b}$, or $R^{4c}$ represent independently of each other a hydrogen atom, $Q^2$ represents an oxygen atom, and q is 0 or 1;

[Embodiment 102] a compound of any one of embodiments 89 to 101 wherein T represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[Embodiment 103] a compound of any one of embodiments 89 to 101 wherein T represents a C1-C5 chain hydrocarbon group having one or more halogen atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C1-C5 chain hydrocarbon group having one or more halogen atoms;

[Embodiment 104] a compound of any one of embodiments 89 to 101 wherein T represents a C1-C5 alkyl group having three or more fluorine atoms, a OR1, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C1-C5 alkyl group having three or more fluorine atoms;

[Embodiment 105] a compound of any one of embodiments 89 to 101 wherein T represents a C2-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C2-C5 alkyl group having three or more fluorine atoms;

[Embodiment 106] a compound of any one of embodiments 89 to 101 wherein T represents a C1-C10 chain hydrocarbon group having one or more halogen atoms, a (C1-C5 alkoxy) C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl) C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, a $OR^1$, a $S(O)_vR^1$, a $OS(O)_2R^1$ or a $NR^1R^{29}$;

[embodiment 107] a compound of any one of embodiments 89 to 101 wherein T represents a C1-C5 chain hydrocarbon group having one or more halogen atoms, a $OR^1$, a $S(O)_vR^1$, a $OS(O)_2R^1$ or a $NR^1R^{29}$, and $R^1$ represents a C1-C5 chain hydrocarbon group having one or more halogen atoms;

[Embodiment 108] a compound of any one of embodiments 89 to 101 wherein T represents a C1-C5 alkyl group having three or more fluorine atoms, a $OR^1$, a $S(O)_vR^1$, a $OS(O)_2R^1$ or a $NR^1R^{29}$, and $R^1$ represents a C1-C5 alkyl group having three or more fluorine atoms;

[Embodiment 109] a compound of any one of embodiments 89 to 101 wherein T represents a C2-C5 alkyl group having three or more fluorine atoms, a $OR^1$, a $S(O)_vR^1$, a $OS(O)_2R^1$ or a $NR^1R^{29}$, and $R^1$ represents a C2-C5 alkyl group having three or more fluorine atoms;

[Embodiment 110] a compound of any one of embodiments 89 to 101 wherein T represents a $OR^1$;

[Embodiment 111] a compound of any one of embodiments 89 to 101 wherein T represents a $OR^1$, and $R^1$ represents a C1-C5 chain hydrocarbon group having one or more halogen atoms;

[Embodiment 112] a compound of any one of embodiments 89 to 101 wherein T represents a $OR^1$, and $R^1$ represents a C1-C5 alkyl group having three or more fluorine atoms;

[Embodiment 113] a compound of any one of embodiments 89 to 101 wherein T represents a $OR^1$, and $R^1$ represents a C2-C5 alkyl group having three or more fluorine atoms;

[Embodiment 114] a compound of any one of embodiments 89 to 101 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9;

[Embodiment 115] a compound of any one of embodiments 89 to 101 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 chain hydrocarbon group having one or more halogen atoms;

[Embodiment 116] a compound of any one of embodiments 89 to 101 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C1-C5 alkyl group having three or more fluorine atoms;

[Embodiment 117] a compound of any one of embodiments 89 to 101 wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^{1x}$, $R^{1y}$, and $R^{1ay}$ represent independently of each other a C2-C5 alkyl group having three or more fluorine atoms;

[Embodiment 118] a compound A of the present invention wherein $R^2$ represents a C1-C6 alkyl group, q is 0 or 1, $R^3$ represents a C1-C6 alkyl group optionally having one or more halogen atoms, $Q^1$ represents an oxygen atom, T represents a $OR^1$, and $R^1$ represents the following formula:

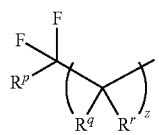

[wherein RP, $R^q$ and R represent independently of each other a hydrogen atom or a fluorine atom, and z is 1, 2, 3 or 4];

[Embodiment 119] a compound A of the present invention wherein $A^2$, $A^3$ and $A^4$ represent independently of each other a CH, $R^2$ represents a C1-C6 alkyl group, q is 0 or 1, $R^3$ represents a C1-C6 alkyl group optionally having one or more halogen atoms, $Q^1$ represents an oxygen atom, T represents a $OR^1$, and $R^1$ represents the following formula:

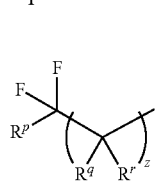

[wherein RP, $R^q$ and R represent independently of each other a hydrogen atom or a fluorine atom, and z represents 1, 2, 3 or 4];

[Embodiment 120] a compound A of the present invention wherein $A^2$ represents a nitrogen atom, $A^3$ represents a CH, $A^4$ represents a $CR^4c$, $R^{4c}$ represents a hydrogen atom or a halogen atom, $R^2$ represents a C1-C6 alkyl group, q is 0 or 1, $R^3$ represents a C1-C6 alkyl group optionally having one or more halogen atoms, $Q^1$ represents an oxygen atom, T represents a $OR^1$, and $R^1$ represents the following formula:

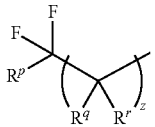

[wherein RP, $R^q$ and $R^z$ represent independently of each other a hydrogen atom or a fluorine atom, and z is 1, 2, 3 or 4]

[Embodiment 121] a compound A of the present invention wherein $A^2$ and $A^4$ represent a CH, $A^3$ represents a nitrogen atom, $R^2$ represents a C1-C6 alkyl group, q is 0 or 1, $R^3$ represents a C1-C6 alkyl group optionally having one or more halogen atoms, $Q^1$ represents an oxygen atom, T represents a $OR^1$, and $R^1$ represents the following formula:

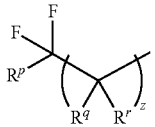

[wherein RP, $R^q$ and $R^r$ represent independently of each other represent a hydrogen atom or a fluorine atom, and z is 1, 2, 3 or 4];

[Embodiment 122] a compound A of the present invention wherein $A^2$ and $A^3$ represent a CH, $A^4$ represents a nitrogen atom, $R^2$ represents a C1-C6 alkyl group, q is 0 or 1, $R^3$ represents a C1-C6 alkyl group optionally having one or more halogen atoms, $Q^1$ represents an oxygen atom, T represents a $OR^1$, and $R^1$ represents the following formula:

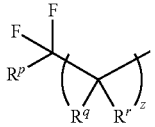

[wherein RP, $R^q$ and R represent independently of each other a hydrogen atom or a fluorine atom, and z is 1, 2, 3 or 4];

[Embodiment 123] a compound A of the present invention wherein $A^2$, $A^3$ and $A^4$ represent a CH, $R^2$ represents a C1-C6 alkyl group, q is 0 or 1, $R^3$ represents a C1-C6 alkyl group optionally having one or more halogen atoms, $Q^1$ represents an oxygen atom, T represents a group represented by the formula T-8, $Y^2$ represents a nitrogen atom, and $Y^3$ and $Y^4$ represent a CH;

[Embodiment 124] a compound of the present invention wherein $A^2$ represents a $CR^{4a}$, $A^3$ represents a nitrogen atom, A4 represents a $CR^4C$, $R^2$ represents a C1-C6 alkyl group, q is 0 or 1, $R^3$ represents a C1-C6 alkyl group optionally having one or more halogen atoms, $Q^1$ represents an oxygen atom, T represents a group represented by the formula T-1, a group represented by the formula T-2, a group represented by the formula T-3, a group represented by the formula T-4, or a group represented by the formula T-8, $X^1$ represents a $CR^{1a}$, $X^2$ represents a $CR^{1b}$, $X^3$ represents a $CR^{1c}$, and $R^{1x}$ and $R^{1y}$ represent independently of each other a C1-C5 chain hydrocarbon group having one or more halogen atoms;

[Embodiment 125] a compound of the present invention wherein $A^1$ represents a nitrogen atom or a CH, $A^2$ represents a $CR^{4a}$, $A^3$ represents a nitrogen atom, A4 represents a $CR^4C$, $R^2$ represents an ethyl group, $Q^1$ and $Q^2$ represent an oxygen atom, and q is 0 or 1:

[Embodiment 126] a compound of the embodiment 125 wherein $R^3$ represents a C1-C6 chain hydrocarbon group optionally having one or more substituents selected from Group F, a C3-C7 cycloalkyl group optionally having one or more substituents selected from Group J, a phenyl group, or a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom, $R^{4a}$, $R^{4b}$, or $R^{4c}$ represent independently of each other a hydrogen atom or a halogen atom;

[embodiment 127] a compound of the embodiment 125 wherein $R^3$ represents a C1-C6 chain hydrocarbon group optionally having one or more substituents selected from Group F, a C3-C7 cycloalkyl group optionally having one or more substituents selected from Group J, a phenyl group, a pyridyl group, a pyrimidinyl group, a furyl group, a thienyl group {the phenyl group, the pyridyl group, the pyrimidinyl group, the a furyl group, and the a thienyl group may optionally have one or more substituents selected from Group H}, a $OR^{12}$, or a halogen atom;

[Embodiment 128] a compound of the embodiment 127 wherein $R^{4a}$, $R^{4b}$, or $R^{4c}$ represent independently of each other a hydrogen atom or a halogen atom;

[Embodiment 129] a compound of the embodiment 127 wherein $R^{4a}$, $R^{4b}$, or $R^{4c}$ represent independently of each other a hydrogen atom;

[Embodiment 130] a compound of the present invention wherein $A^1$ represents a nitrogen atom, $A^2$ represents a $CR^{4a}$, $A^3$ represents a nitrogen atom, A4 represents a $CR^4C$, $R^2$ represents an ethyl group, $Q^1$ and $Q^2$ represent an oxygen atom, and q is 0 or 1;

[Embodiment 131] a compound of the embodiment 130 wherein $R^3$ represents a C1-C6 chain hydrocarbon group optionally having one or more substituents selected from Group F, a C3-C7 cycloalkyl group optionally having one or more substituents selected from Group J, a phenyl group, a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom, $R^{4a}$, $R^{4b}$, or $R^{4c}$ represent independently of each other a hydrogen atom, or a halogen atom;

[Embodiment 132] a compound of the embodiment 130 wherein $R^3$ represents a C1-C6 chain hydrocarbon group optionally having one or more substituents selected from Group F, a C3-C7 cycloalkyl group optionally having one or more substituents selected from Group J, a phenyl group, a pyridyl group, a pyrimidinyl group, a furyl group, a thienyl group {the phenyl group, the pyridyl group, the pyrimidinyl group, the a furyl group, and the a thienyl group may optionally have one or more substituents selected from Group H}, a $OR^{12}$, or a halogen atom;

[Embodiment 133] a compound of the embodiment 132 wherein $R^{4a}$, $R^{4b}$, or $R^{4c}$ represent independently of each other a hydrogen atom, or a halogen atom;

[Embodiment 134] a compound of the embodiment 132 wherein $R^{4a}$, $R^{4b}$, or $R^{4c}$ represent independently of each other a hydrogen atom;

[Embodiment 135] a compound of the embodiment 130 wherein $R^3$ represents a C1-C6 chain hydrocarbon group optionally having one or more substituents selected from Group F, a C3-C7 cycloalkyl group optionally having one or more substituents selected from Group J, a $OR^{12}$, or a halogen atom;

[Embodiment 136] a compound of the embodiment 135 wherein $R^{4a}$, $R^{4b}$, or $R^{4c}$ represent independently of each other a hydrogen atom;

[Embodiment 137] a compound of the embodiment 130 wherein $R^3$ represents a phenyl group, a pyridyl group, a pyrimidinyl group, a furyl group, or a thienyl group {the phenyl group, the pyridyl group, the pyrimidinyl group, the a furyl group, and the a thienyl group may optionally have one or more substituents selected from Group H}, or a halogen atom;

[Embodiment 138] a compound of the embodiment 137 wherein $R^{4a}$, $R^{4b}$, or $R^{4c}$ represent independently of each other a hydrogen atom;

[Embodiment 139] a compound of the present invention wherein $A^1$ represents a nitrogen atom or a CH, $A^2$ represents a $CR^{4a}$, $A^3$ represents a $CR^{4b}$, $A^4$ represents a $CR^{4c}$, $R^2$ represents an ethyl group, $Q^1$ and $Q^2$ represent an oxygen atom, and q is 0 or 1;

[Embodiment 140] a compound of the embodiment 139 wherein $R^3$ represents a C1-C6 chain hydrocarbon group optionally having one or more substituents selected from Group F, a C3-C7 cycloalkyl group optionally having one or more substituents selected from Group J, a phenyl group, a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom, and $R^{4a}$, $R^{4b}$, or $R^{4c}$ represent independently of each other a hydrogen atom or a halogen atom;

[Embodiment 141] a compound of the embodiment 139 wherein $R^3$ represents a C1-C6 chain hydrocarbon group optionally having one or more substituents selected from Group F, a C3-C7 cycloalkyl group optionally having one or more substituents selected from Group J, a phenyl group, a pyridyl group, a pyrimidinyl group, a furyl group, or a thienyl group {the phenyl group, the pyridyl group, the pyrimidinyl group, the a furyl group, and the a thienyl group may optionally have one or more substituents selected from Group H}, a $OR^{12}$, or a halogen atom;

[Embodiment 142] a compound of the embodiment 141 wherein $R^{4a}$, $R^{4b}$, or $R^{4c}$ represent independently of each other a hydrogen atom or a halogen atom;

[Embodiment 143] a compound of the embodiment 141 wherein $R^{4a}$, $R^{4b}$, or $R^{4c}$ represent independently of each other a hydrogen atom;

[Embodiment 144] a compound of the present invention wherein $A^1$ represents a nitrogen atom, $A^2$ represents a $CR^{4a}$, $A^3$ represents a $CR^{4b}$, $A^4$ represents a $CR^{4c}$, $R^2$ represents an ethyl group, $Q^1$ and $Q^2$ represent an oxygen atom, and q is 0 or 1;

[Embodiment 145] a compound of the embodiment 144 wherein $R^3$ represents a C1-C6 chain hydrocarbon group optionally having one or more substituents selected from Group F, a C3-C7 cycloalkyl group optionally having one or more substituents selected from Group J, a phenyl group, or a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom, and $R^{4a}$, $R^{4b}$, or $R^{4c}$ represent independently of each other a hydrogen atom or a halogen atom;

[Embodiment 146] a compound of the embodiment 144 wherein $R^3$ represents a C1-C6 chain hydrocarbon group optionally having one or more substituents selected from Group F, a C3-C7 cycloalkyl group optionally having one or more substituents selected from Group J, a phenyl group, a pyridyl group, a pyrimidinyl group, a furyl group, or a thienyl group {the phenyl group, the pyridyl group, the pyrimidinyl group, the a furyl group, and the a thienyl group may optionally have one or more substituents selected from Group H}, a $OR^{12}$, or a halogen atom;

[Embodiment 147] a compound of the embodiment 146 wherein $R^{4a}$, $R^{4b}$, or $R^{4c}$ represent independently of each other a hydrogen atom or a halogen atom;

[Embodiment 148] a compound of the embodiment 146 wherein $R^{4a}$, $R^{4b}$, or $R^{4c}$ represent independently of each other a hydrogen atom;

[Embodiment 149] a compound of the embodiment 144 wherein $R^3$ represents a C1-C6 chain hydrocarbon group optionally having one or more substituents selected from Group F, a C3-C7 cycloalkyl group optionally having one or more substituents selected from Group J, a $OR^{12}$, or a halogen atom;

[Embodiment 150] a compound of the embodiment 149 wherein $R^{4a}$, $R^{4b}$, or $R^{4c}$ represent independently of each other a hydrogen atom;

[Embodiment 151] a compound of the embodiment 144 wherein $R^3$ represents a phenyl group, a pyridyl group, a pyrimidinyl group, a furyl group, or a thienyl group {the phenyl group, the pyridyl group, the pyrimidinyl group, the a furyl group, and the thienyl group may optionally have one or more substituents selected from Group H}, or a halogen atom;

[Embodiment 152] a compound of the embodiment 151 wherein $R^{4a}$, $R^{4b}$, or $R^{4c}$ represent independently of each other a hydrogen atom;

[embodiment 153] a compound of the present invention wherein $A^1$ represents a nitrogen atom or a CH, and $R^2$ represents a C1-C6 alkyl group];

[Embodiment 154] a compound of the present invention wherein $A^1$ represents a nitrogen atom or a CH, and $R^2$ represents a C1-C6 alkyl group, $R^3$ represents a C1-C6 chain hydrocarbon group optionally having one or more substituents selected from Group F, a C3-C7 cycloalkyl group optionally having one or more substituents selected from Group J, a phenyl group, a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom, $Q^1$ and $Q^2$ represent an oxygen atom, and q is 0 or 1;

[Embodiment 155] a compound of the present invention wherein $A^1$ represents a nitrogen atom or a CH, $R^2$ represents an ethyl group, $R^3$ represents a C1-C6 chain hydrocarbon group optionally having one or more substituents selected from Group F, a C3-C7 cycloalkyl group optionally having one or more substituents selected from Group J, a phenyl group, a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom, $Q^1$ and $Q^2$ represent an oxygen atom, and q is 0 or 1;

[Embodiment 156] a compound of the present invention wherein $A^1$ represents a nitrogen atom, $R^2$ represents an ethyl group, $R^3$ represents a C1-C6 chain hydrocarbon group optionally having one or more substituents selected from Group F, a C3-C7 cycloalkyl group optionally having one or more substituents selected from Group J, a phenyl group, a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom, $Q^1$ and $Q^2$ represent an oxygen atom, and q is 0 or 1;

[Embodiment 157] a compound of the present invention wherein $A^1$ represents a nitrogen atom or a CH, $A^2$ represents a $CR^{4a}$, $A^4$ represents a $CR^4C$, $R^{4a}$, $R^{4b}$, or $R^{4c}$ represent independently of each other a methyl group, a halogen atom, or a hydrogen atom, q is 0 or 1, and $Q^1$ and $Q^2$ represent an oxygen atom;

[Embodiment 158] a compound of the embodiment 157 wherein $R^2$ represents a C1-C6 alkyl group, $R^3$ represents a C1-C6 chain hydrocarbon group optionally having one or more substituents selected from Group F, a C3-C7 cycloalkyl group optionally having one or more substituents selected from Group J, a phenyl group, or a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom;

[Embodiment 159] a compound of the embodiment 157 wherein $R^2$ represents an ethyl group, $R^3$ represents a C1-C6 chain hydrocarbon group optionally having one or more substituents selected from Group F, a C3-C7 cycloalkyl group optionally having one or more substituents selected from Group J, a phenyl group, or a five or six membered aromatic heterocyclic group {the phenyl group and the five or six membered aromatic heterocyclic group may optionally have one or more substituents selected from Group H}, a $OR^{12}$, a $NR^{11}R^{12}$, a $NR^{11}C(O)OR^{14}$, or a halogen atom;

[Embodiment 160] a compound of the embodiment 157 wherein $R^2$ represents an ethyl group, $R^3$ represents a C1-C6 chain hydrocarbon group optionally having one or more substituents selected from Group F, a C3-C7 cycloalkyl group optionally having one or more substituents selected from Group J, a phenyl group, a pyridyl group, a pyrimidinyl group, a furyl group, a thienyl group {the phenyl group, the pyridyl group, the pyrimidinyl group, the a furyl group, and the a thienyl group may optionally have one or more substituents selected from Group H}, a $OR^{12}$, or a halogen atom;

[Embodiment 161] a compound of the embodiment 158 wherein $A^1$ represents a nitrogen atom;

[Embodiment 162] a compound of the embodiment 159 wherein $A^1$ represents a nitrogen atom;

[Embodiment 163] a compound of the embodiment 160 wherein $A^1$ represents a nitrogen atom;

[embodiment 164] a compound of the present invention wherein T represents a C3-C5 alkyl group having three or more fluorine atoms, a $OR^1$, a $S(O)_vR^1$, a $OS(O)_2R^1$, a $CH_2OR'$, a $NR^1R^{29}$, a $C(O)R^1$, a $C(O)NR^1R^{29}$, a $NR^{29}C(O)R^1$, a $N=CR^1R^{30}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, a group represented by the formula T-9, a group represented by the formula T-10, a group represented by the formula T-11, or a group represented by the formula T-12, and $R^1$, $R^{1x}$, $R^{1y}$, and $R^{1ay}$ represents independently of each other a C3-C5 alkyl group having three or more fluorine atoms;

[Embodiment 165] a compound of the present invention wherein T represents a C3-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C3-C5 alkyl group having three or more fluorine atoms;

[Embodiment 166] a compound of the present invention wherein T represents a C3-C5 alkyl group having three or more fluorine atoms, a $OR^1$, a $S(O)_vR^1$, a $OS(O)_2R^1$ or a $NR^1R^{29}$ and $R^1$ represents a C3-C5 alkyl group having three or more fluorine atoms;

[Embodiment 167] a compound of the present invention wherein T represents a $OR^1$, and $R^1$ represents a C2-C5 alkyl group having three or more fluorine atoms;

[Embodiment 168] a compound of the present invention wherein T represents a $OR^1$, and $R^1$ represents a C3-C5 alkyl group having three or more fluorine atoms;

[Embodiment 169] a compound of the present invention wherein T represent a group represented by the formula T-1, a group represented by the formula T-2, a group represented by the formula T-3, a group represented by the formula T-4, or a group represented by the formula T-8, $X^1$ represents a $CR^{1a}$, $X^2$ represents a $CR^{1b}$, $X^3$ represents a $CR^{1c}$, and $R^{1x}$ and $R^{1y}$ represent independently of each other a C3-C5 alkyl group having three or more fluorine atoms;

[Embodiment 170] a compound of any one of the embodiments 2, 31, 60, 89, and 125 to 163 wherein T represents a C3-C5 alkyl group having three or more fluorine atoms, a $OR^1$, a $S(O)_vR^1$, a $OS(O)_2R^1$, a $CH_2OR^1$, a $NR^1R^{29}$, a $C(O)R^1$, a $C(O)NR^1R^{29}$, a $NR^{29}C(O)R^1$, a $N=CR^1R^{30}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, a group represented by the formula T-9, a group represented by the formula T-10, a group represented by the formula T-11, or a group represented by the formula T-12, and $R^1$, $R^{1x}$, $R^{1y}$, and $R^{1ay}$ represents independently of each other a C3-C5 alkyl group having three or more fluorine atoms;

[Embodiment 171] a compound of any one of the embodiments 2, 31, 60, 89, and 125 to 163 wherein T represents a C3-C5 alkyl group having three or more fluorine atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, and $R^1$, $R^{1x}$, $R^{1y}$, and $R^{1ay}$ represents independently of each other a C3-C5 alkyl group having three or more fluorine atoms;

[Embodiment 172] a compound of any one of the embodiments 2, 31, 60, 89, and 125 to 163 wherein T represents a C3-C5 alkyl group having three or more fluorine atoms, a $OR^1$, a $S(O)_rR^1$, a $OS(O)_2R^1$ or a $NR^1R^{29}$, and $R^1$ represents a C3-C5 alkyl group having three or more fluorine atoms;

[Embodiment 173] a compound of any one of the embodiments 2, 31, 60, 89, and 125 to 163 wherein T represents a $OR^1$, and $R^1$ represents a C2-C5 alkyl group having three or more fluorine atoms;

[Embodiment 174] a compound of any one of the embodiments 2, 31, 60, 89, and 125 to 163 wherein T represents a $OR^1$, and $R^1$ represents a C3-C5 alkyl group having three or more fluorine atoms;

[Embodiment 175] a compound of any one of the embodiments 2, 31, 60, 89, and 125 to 163 wherein T represents a group represented by the formula T-1, a group represented by the formula T-2, a group represented by the formula T-3, a group represented by the formula T-4, or a group represented by the formula T-8, $X^1$ represents a $CR^{1a}$, $X^2$ represents a $CR^{1b}$, $X^3$ represents a $CR^{1c}$, $R^{1x}$ and $R^{1y}$ represent independently of each other a C3-C5 alkyl group having three or more fluorine atoms;

Examples of the embodiment of Compound B include the followings.

[Embodiment 176] a compound B wherein $R^2$ represents an ethyl group, q is 0 or 1, and b is 2;

[embodiment 177] a compound of the embodiment 176 wherein $R^3$ represents a C1-C6 alkyl group, a C3-C7 cycloalkyl group {the C1-C6 alkyl group and the C3-C7 cycloalkyl group may optionally have one or more substituents selected from a group consisting of a halogen atom and a cyano group}, a phenyl group, or a five or six membered aromatic heterocyclic group {the phenyl group, and a five or six membered aromatic heterocyclic group may optionally have one or more substituents selected from Group H}, and $R^{4a}$, $R^{4b}$, or $R^{4c}$ represent independently of each other a methyl group, a halogen atom, or a hydrogen atom;

[Embodiment 178] a compound of the embodiment 176 wherein $R^3$ represents a C1-C6 alkyl group, a C3-C7 cycloalkyl group {the C1-C6 alkyl group and the C3-C7 cycloalkyl group may optionally have one or more substituents selected from a group consisting of a halogen atom and a cyano group}, a phenyl group, or a five or six membered aromatic heterocyclic group {the phenyl group, and the five or six membered aromatic heterocyclic group may optionally have one or more substituents selected from Group H}, and $R^{4a}$, $R^{4b}$, or $R^{4c}$ represent independently of each other a hydrogen atom;

[Embodiment 179] a compound of the embodiment 176 wherein $R^3$ represents a C1-C6 alkyl group optionally having one or more halogen atoms, or a halogen atom, and $R^{4a}$, $R^{4b}$, or $R^{4c}$ represent independently of each other a hydrogen atom;

[Embodiment 180] a compound of the embodiment 177 wherein $A^2$ represents a $CR^{4a}$, and $A^4$ represents a $CR^{4c}$;

[Embodiment 181] a compound of the embodiment 178 wherein $A^2$ represents a $CR^{4a}$, and $A^4$ represents a $CR^{4c}$;

[Embodiment 182] a compound of the embodiment 179 wherein $A^2$ represents a $CR^{4a}$, and $A^4$ represents a $CR^{4c}$;

[Embodiment 183] a compound of the embodiment 177 wherein $A^2$ represents a $CR^{4a}$, $A^3$ represents a $CR^{4b}$, and $A^4$ represents a $CR^{4c}$;

[Embodiment 184] a compound of the embodiment 178 wherein $A^2$ represents a $CR^{4a}$, $A^3$ represents a $CR^{4b}$, and $A^4$ represents a $CR^{4c}$;

[Embodiment 185] a compound of the embodiment 179 wherein $A^2$ represents a $CR^{4a}$, $A^3$ represents a $CR^{4b}$, and $A^4$ represents a $CR^{4c}$;

[Embodiment 186] a compound of the embodiment 177 wherein $A^2$ represents a nitrogen atom, $R^{4a}$ is not present, $A^3$ represents a $CR^{4b}$, and $A^4$ represents a $CR^{4c}$;

[Embodiment 187] a compound of the embodiment 178 wherein $A^2$ represents a nitrogen atom, $R^{4a}$ is not present, $A^3$ represents a $CR^{4b}$, and $A^4$ represents a $CR^{4c}$;

[Embodiment 188] a compound of the embodiment 179 wherein $A^2$ represents a nitrogen atom, $R^{4a}$ is not present, $A^3$ represents a $CR^{4b}$, and $A^4$ represents a $CR^{4c}$;

[Embodiment 189] a compound of the embodiment 177 wherein $A^2$ represents a $CR^{4a}$, $A^3$ represents a nitrogen atom, $R^{4b}$ is not present, and $A^4$ represents a $CR^{4c}$;

[Embodiment 190] a compound of the embodiment 178 wherein $A^2$ represents a $CR^{4a}$, $A^3$ represents a nitrogen atom, $R^{4b}$ is not present, and $A^4$ represents a $CR^{4c}$;

[Embodiment 191] a compound of the embodiment 179 wherein $A^2$ represents a $CR^{4a}$, $A^3$ represents a nitrogen atom, $R^{4b}$ is not present, and $A^4$ represents a $CR^{4c}$;

[Embodiment 192] a compound of the embodiment 177 wherein $A^4$ represents a nitrogen atom, $R^{4c}$ is not present, $A^2$ represents a $CR^{4a}$, and $A^3$ represents a $CR^{4b}$;

[Embodiment 193] a compound of the embodiment 178 wherein $A^4$ represents a nitrogen atom, $R^{4c}$ is not present, $A^2$ represents a $CR^{4a}$, and $A^3$ represents a $CR^{4b}$;

[Embodiment 194] a compound of the embodiment 179 wherein $A^4$ represents a nitrogen atom, $R^{4c}$ is not present, $A^2$ represents a $CR^{4a}$, and $A^3$ represents a $CR^{4b}$;

Examples of the embodiment of Compound C include the followings.

[Embodiment 195] a Compound C wherein y is 1, and b is 2;

[Embodiment 196] a compound of the embodiment 195 wherein $R^{3x}$ represents a C1-C6 alkyl group or a C3-C7 cycloalkyl group {the C1-C6 alkyl group and the C3-C7 cycloalkyl group may optionally have one or more cyano groups}, a phenyl group, or a five or six membered aromatic heterocyclic group {the phenyl group and the five or six membered aromatic heterocyclic group may optionally have one or more substituents selected from Group H};

[Embodiment 197] a compound of the embodiment 195 wherein $R^{3x}$ represents a C1-C6 alkyl group optionally having one or more cyano groups, a C3-C7 cycloalkyl group optionally having one or more cyano groups, or a phenyl group optionally having one or more halogen atoms;

Next, a process for preparing the compound of the present invention, and the compound represented by formula (II) as an intermediate compound for preparing the compound of the present invention (hereinafter, referred to as Compound (II)) is explained.

Process 1

In the compound of the present invention, a compound represented by formula (Ib) (hereinafter, referred to as Compound (Ib)) or a compound represented by formula (Ic) (hereinafter, referred to as Compound (Ic)) may prepared by oxidizing the compound (II).

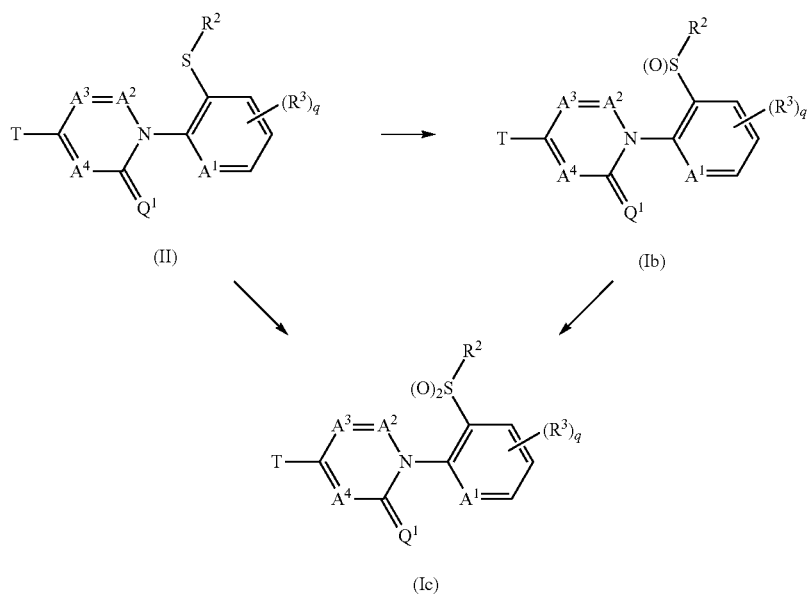

[wherein the symbols are the same as defined above]

First, a process for preparing the Compound (Ib) from the compound (II) is described.

The reaction is usually carried out in a solvent.

Examples of the solvent to be used in the reaction include halogenated hydrocarbons such as dichloromethane and chloroform (hereinafter, collectively referred to as halogenated hydrocarbons); nitriles such as acetonitrile (hereinafter collectively referred to nitriles); alcohols such as methanol and ethanol (hereinafter, collectively referred to as alcohols); acetic acid; water; and mixed solvents thereof.

Examples of the oxidizing agent to be used in the reaction include sodium periodate, m-chloroperoxybenzoic acid (hereinafter, referred to as mCPA) and hydrogen peroxide. When hydrogen peroxide is used as an oxidizing agent, sodium carbonate or a catalyst may be added as needed.

Examples of the catalyst to be used in the reaction include tungstic acid, and sodium tungstate.

In the reaction, the oxidizing agent is used usually within a range of 1 to 1.2 molar ratio(s), the base is used usually within a range of 0.01 to 1 molar ratio(s), and the catalyst is used usually within a range of 0.01 to 0.5 molar ratios, as opposed to 1 mole of the compound (II).

The reaction temperature of the reaction is usually within a range of −20 to 80° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give the compound (Ib).

Next, a process for preparing the compound (Ic) from the compound (Ib) is described.

The reaction is usually carried out in a solvent.

Examples of the solvent to be used in the reaction include halogenated hydrocarbons, nitriles, alcohols, acetic acid, water, and mixed solvents thereof.

Examples of the oxidizing agent to be used in the reaction include mCPBA and peroxide hydrogen. When peroxide hydrogen is used an oxidizing agent, a base or a catalyst may be added as needed.

Examples of the base to be used in the reaction include sodium carbonate.

Examples of the catalyst to be used in the reaction include sodium tungstate.

In the reaction, the oxidizing agent is used usually within a range of 1 to 2 molar ratio(s), the base is used usually within a range of 0.01 to 1 molar ratio(s), and the catalyst is used usually within a range of 0.01 to 0.5 molar ratios, as opposed to 1 mole of the compound (Ib).

The reaction temperature of the reaction is usually within a range of −20 to 120° C. The reaction period of the reaction is usually within a range of 0.1 to 12 hours.

When the reaction is completed, water is added to reaction mixtures, and the reaction mixtures are extracted with organic solvent(s), and if necessary, the organic layers are washed with an aqueous solution of a reducing agent (such as sodium sulfite, and sodium thiosulfate) and an aqueous solution of a base (such as sodium hydrogen carbonate). The resulting organic layers are worked up (for example, drying and concentration) to give the compound (Ic).

Also, the compound (Ic) may be prepared by reacting the compound (II) with an oxidizing agent in one step (one-pot).

The reaction may be conducted by using the oxidizing agent in a ratio of usually 2 to 5 molar ratios as opposed to 1 mole of the compound (II) according to a method for preparing the compound (Ic) from the compound (Ib).

Process 2

The compound (II) may be prepared by reacting a compound represented by formula (M-1) (hereinafter, referred to as Compound (M-1)) with a compound represented by formula (R-1) (hereinafter, referred to as Compound (R-1)) in the presence of a base.

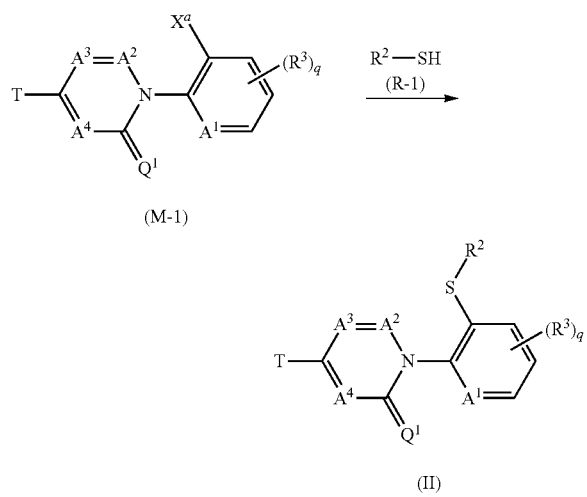

(M-1)

(II)

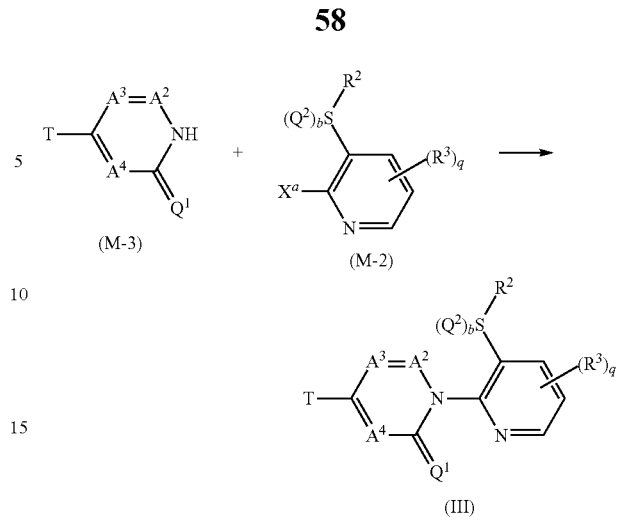

(M-3)

(M-2)

(III)

[wherein $X^a$ represents a fluorine atom or a chlorine atom, and the other symbols are the same as defined above]

This reaction is usually carried out in the presence of a solvent. Examples of the solvents to be used in the reaction include ethers such as tetrahydrofuran (hereinafter, sometimes referred to as THF), ethylene glycol dimethyl ether (hereinafter, referred to as DME), methyl tert-butyl ether (hereinafter, referred to as MTBE), and 1,4-dioxane (hereinafter, collectively referred to as ethers); aromatic hydrocarbons such as toluene and xylene (hereinafter, allectivily referred to as aromatic hydrocarbons); nitriles; and polar aprotic solvents such as dimethylformamide (hereinafter, referred to as DMF), N-methyl pyrrolidone (hereinafter, referred to as NMP), and dimethyl sulfoxide (hereinafter, referred to DMSO) (hereinafter, collectively referred to as polar aprotic solvent); and mixed solvents thereof.

Examples of the base to be used in the reaction include alkali metal carbonates (such as sodium carbonate, and potassium carbonate) (hereinafter, collectively referred to as alkali metal carbonates); and alkali metal hydrides such as sodium hydride (hereinafter, collectively referred to as alkali metal hydrides).

In the reaction, the compound (R-1) is used usually within a range of 1 to 10 molar ratio(s), and the base is used usually within a range of 1 to 10 molar ratio(s), as opposed to 1 mole of the compound (M-1).

The reaction temperature of the reaction is usually within a range of −20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (for example, drying and concentration) to give the compound (II).

Process 3

The compound represented by formula (III) (hereinafter, referred to as Compound (III)) may be prepared by reacting a compound represented by formula (M-3) (hereinafter, referred to as Compound (M-3)) with a compound represented by formula (M-2) (hereinafter, referred to as Compound (M-2) in the presence of a base.

[wherein b is 0, 1 or 2, and the other symbols are the same as defined above]

The reaction is usually carried out in the presence of a solvent.

Examples of the solvent to be used in the reaction include ethers, aromatic hydrocarbons, nitriles, polar aprotic solvents, and mixed solvents thereof.

Examples of the base to be used in the reaction include alkali metal carbonates and alkali metal hydrides.

In the reaction, the compound (M-2) is used usually within a range of 1 to 2 molar ratio(s), and the base is used usually within a range of 1 to 10 molar ratio(s), as opposed to 1 mole of the compound (M-3).

The reaction temperature is usually within a range of −20 to 150° C. The reaction period of the reaction is usually within a range of 0.5 to 24 hours.

When the reaction is completed, water is added to reaction mixtures, and the reaction mixtures are extracted with organic solvent(s), and the organic layers are worked up (for example, drying and concentration) to give the compound (III).

The compound (M-2) is a publically known compound, or may be prepared according to the similar method to that described in Journal of Organic Chemistry, 68(12), 4918, 2003 or WO 2013/086397 A1.

The compound (M-3) is a publically known compound, or may be prepared according to the similar method to that described in WO2005/018557 A1, WO2009/149188 A1, WO2010/104818 A1, or WO2015/153304 A1 and the others.

Process 4

A compound represented by formula (IV) (hereinafter, referred to as Compound (IV)) may be prepared by reacting a compound represented by formula (M-3) (hereinafter, referred to Compound (M-3)) with a compound represented by formula (M-4) (hereinafter, referred to as Compound M-4) in the presence of a metal catalyst and a base.

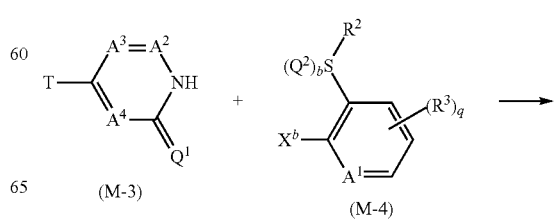

(M-3)

(M-4)

-continued

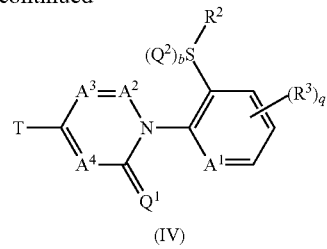

(IV)

[wherein $X^b$ represents a chlorine atom, a bromine atom, or an iodine atom; and the other symbols are the same defined as above]

This reaction is usually carried out in the presence of a solvent. Examples of the solvent to be used in the reaction include ethers, aromatic hydrocarbons, aprotic polar solvents, water, and mixed solvents thereof.

Examples of the metal catalyst to be used in the reaction include copper catalyst such as copper(I) iodide, copper(I) bromide, copper(I) chloride, copper(I) oxide, trifluoromethanesulfonic acid copper(I) salt benzene complex, tetrakis(acetonitrile)copper(I) hexafluorophosphate, and 2-thiophenecarboxylic acid copper(I) salt; and nickel catalyst such as bis(cyclooctadiene)nickel(0) and nickel(II) chloride.

A ligand, a base and/or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis(diphenylphosphino)ethane, 2,2'-bipyridine, 2-aminoethanol, 8-hydroquinoline, 1,10-phenanthroline, trans-1,2-cyclohexanediamine, trans-1,2-bis(methylamino)cyclohexane, and N,N'-dimethylethylenediamine.

Examples of the base to be used in the reaction include organic bases such as triethylamine, diisopropylethylamine, pyridine, 4-(dimethylamino)pyridine; alkali metal hydrides; and alkali metal carbonates.

Examples of the inorganic halogenated compounds to be used in the reaction include alkali metal fluorides such as potassium fluoride, and sodium fluoride; and alkali metal chlorides such as lithium chloride and sodium chloride.

In the reaction, the compound (M-4) is usually used within a range of 1 to 10 molar ratio(s), the metal catalyst is usually used within a range of 0.01 to 2 molar ratio(s), the ligand is usually used within a range of 0.01 to 1 molar ratio(s), abase is usually used within a range of 0.1 to 5 molar ratio(s), and the inorganic halogenated compound is usually used within a range of 0.1 to 5 molar ratio(s), as opposed to 1 mole of the compound (M-3).

The reaction temperature is usually within a range of −20 to 200° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (IV).

The compound (M-4) is a publically known compound, or can be prepared according to the similar method to that described in Synthesis, 45(11), 1489, 2013 or WO 2012/122011 A1.

Process 5

The compound represented by formula (IVa) (hereinafter, referred to as Compound (IVa)) may be prepared by reacting a compound represented by formula (M-5) (hereinafter, referred to as Compound (M-5)) with a compound represented by formula (R-2)) (hereinafter, referred to as Compound (R-2)) in the presence of a base.

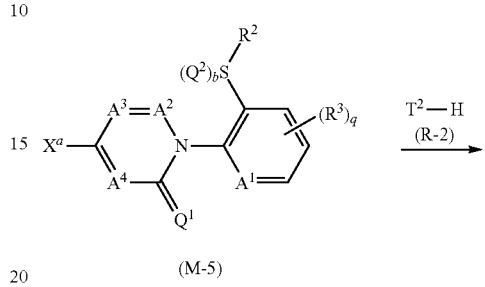

(M-5)

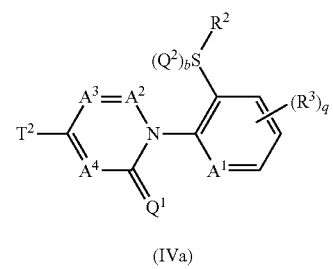

(IVa)

[wherein, $T^2$ represents a $OR^1$, a $NR^1R^{29}$, a group represented by the formula T-5, a group represented by the formula T-6, a group represented by the formula T-7, or a group represented by the formula T-8; and the other symbols are the same as defined above]

This reaction is usually carried out in the presence of a solvent. Examples of the solvent to be used in the reaction include ethers, aromatic hydrocarbons, nitriles, aprotic polar solvents, and mixed solvents thereof.

Examples of the base to be used in the reaction include alkali metal carbonates, and alkali metal hydrides.

In the reaction, the compound (R-2) is usually used within a range of 1 to 2 molar ratio(s), and the base is usually used within a range of 1 to 10 molar ratio(s), as opposed to 1 mole of the compound (M-5)).

The reaction temperature is usually within a range of −20 to 150° C. The reaction period of the reaction is usually within a range of 0.5 to 24 hours.

When the reaction is completed, water is added to the reaction mixtures, and the reaction mixtures are extracted with organic solvent(s), and the organic solvents are worked up (for example, drying and concentration) to give the compound (IVa).

Process 6

The compound represented by formula (IVb) (hereinafter, referred to as Compound (IVb)) may be prepared by reacting a compound represented by formula (M-6) (hereinafter, referred to as Compound M-6) with a compound represented by formula (R-3) (hereinafter, referred to as Compound (R-3)) in the presence of a metal catalyst.

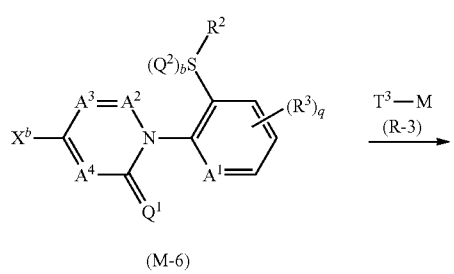

(M-6)

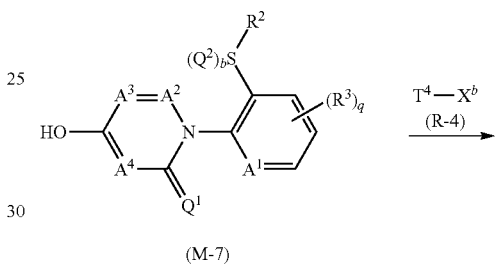

(IVb)

[wherein, T³ represents a group represented by the formula T-1, a group represented by the formula T-2, a group represented by the formula T-3, a group represented by the formula T-4, a group represented by the formula T-9, a group represented by the formula T-10, a group represented by the formula T-11, or the group represented by the formula T-12, each of which being described herein; M represents 9-borabiclo[3.3.1]nonan-9-yl, a boron group, 4,4,5,5,-tetramethyl-1,3,2-dioxaborolan-2-yl, tributylstannyl, ZnCl, MgCl, or MgBr; and the other symbols are the same as defined above]

This reaction is usually carried out in the presence of a solvent. Examples of the solvent to be used in the reaction include ethers, aromatic hydrocarbons, aprotic polar solvents, water, and mixed solvents thereof.

Examples of the metal catalyst to be used in the reaction include palladium catalysts such as tetrakis(triphenylphosphine)palladium(0), 1,1'-bis(diphenylphoshino)ferrocene palladium(II) dichloride, tris(dibenzylideneacetone)dipalladium(0), and palladium(II) acetate; nickel catalysts such as bis(cyclooctadiene)nickel(0) and nickel(II) chloride; and copper catalyst such as copper(I) iodide and copper(I) chloride.

A ligand, a base and/or an inorganic halogenated compound may be added to the reaction as needed.

Examples of the ligand to be used in the reaction include triphenylphosphine, Xantphos, 2,2'-bis(diphenylphoshino)-1,1'-binaphthyl, 1,1'-bis(diphenylphoshino)ferrocene, 2-(dicyclohexylphosphino)-2',4',6'-triisopropyl-1,1'-biphenyl, 2-dicyclohexylphosphino-2',6'-dimethoxybiphenyl, 1,2-bis(diphenylphosphino)ethane, 2,2'-bipyridine, 2-aminoethanol, 8-hydroquinoline, and 1,10-phenanthroline.

Examples of the base to be used in the reaction include alkali metal hydrides, alkali metal carbonates, and organic bases.

Examples of the inorganic halogenated compounds include alkali metal fluorides such as potassium fluoride, and sodium fluoride; and alkali metal chlorides such as lithium chloride, and sodium chloride.

In the reaction, the compound (R-3) is usually used within a range of 1 to 10 molar ratio(s), the metal catalyst is usually used within a range of 0.01 to 0.5 molar ratios, the ligand is usually used within a range of 0.01 to 1 molar ratio(s), the base is usually used within a range of 0.1 to 5 molar ratios, and the inorganic halogenated compound is usually used within a range of 0.1 to 5 molar ratios, as opposed to 1 mole of the compound (M-6).

The reaction temperature is usually within a range of −20 to 200° C. The reaction period of the reaction is usually within a range of 0.1 to 24 hours.

When the reaction is completed, water is added to the reaction mixtures, and the reaction mixtures are extracted with organic solvent(s), and the organic solvents are worked up (for example, drying and concentration) to give the compound (IVb).

The compound (R-3) is a commercially available compound, or can be prepared by using a known method.

Process 7

A compound represented by formula (IVc) may be prepared by reacting a compound represented by formula (M-7) (hereinafter, referred to as Compound (M-7)) with a compound represented by formula (R-4) (hereinafter, referred to as Compound (R-4)) in the presence of a base.

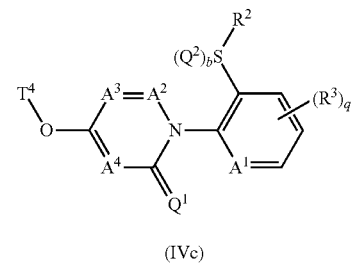

(M-7)

(IVc)

[wherein T⁴ represents a C1-C10 chain hydrocarbon group having one or more halogen atoms, a (C1-C5 alkoxy)C2-C5 alkyl group having one or more halogen atoms, a (C1-C5 alkylsulfanyl)C2-C5 alkyl group having one or more halogen atoms, a (C1-C5 alkylsulfinyl)C2-C5 alkyl group having one or more halogen atoms, a (C1-C5 alkylsulfonyl)C2-C5 alkyl group having one or more halogen atoms, a (C3-C7 cycloalkyl)C1-C3 alkyl group having one or more substituents selected from Group G, a C3-C7 cycloalkyl group having one or more substituents selected from Group G, or a S(O)ᵥR¹; and the other symbols are the same as defined above]

The reaction may be conducted by using the compound (M-7) instead of the compound (R-2), and the compound (R-4) instead of the compound (M-5) according the similar method to that described in Process 5

The compound (R-4) is a commercially available compound, or may be prepared according to a known method.

Process 8

The compound represented by formula (Id) (hereinafter, referred to as Compound (Id)) and the compound represented by formula (Ie) (hereinafter, referred to as Compound (Ie)) may be prepared according to the following scheme.

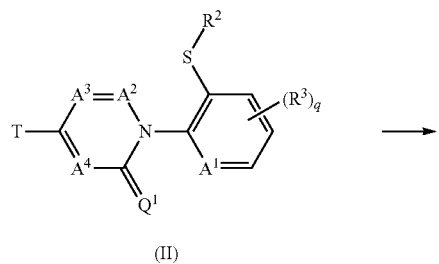

(II)

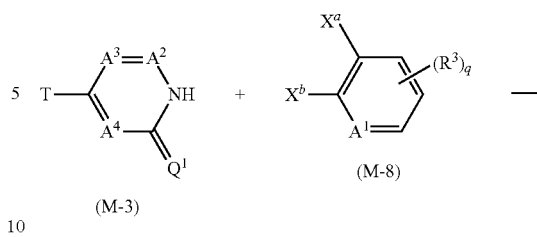

(M-3)　　(M-8)

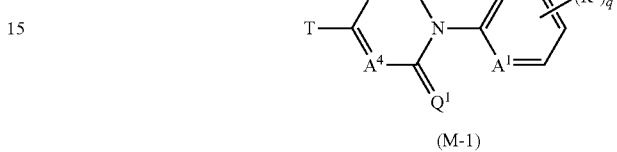

(M-1)

[wherein, the symbols are the same as defined above]

The reaction may be conducted by using the compound (M-8) instead of the compound (M-4) according to the similar method to that described in Process 4.

The compound (M-8) is a publically known compound, or may be prepared according to the similar method to that described in WO 2015/187845.

Reference Process 2

The compound represented by formula (M-10) (hereinafter, referred to as Compound (M-10)) may be prepared by reacting a compound represented by formula (M-9) (hereinafter, referred to as Compound (M-9)) with a compound (M-4) in the presence of a metal catalyst and a base.

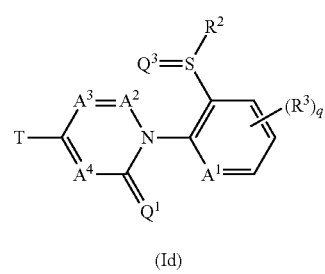

(Id)

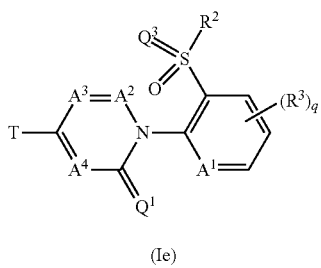

(Ie)

[wherein, $Q^3$ represents a N—CN, a N—NO$_2$, a NR$^5$, a N—C(O)R$^5$ or a N—C(O)OR$^{15}$; and the other symbols are the same as defined above]

The compound (Id) may be prepared by using the compound (II) according to the similar method to that described in Organic Letters, 9(19), 3809, 2007.

The compound (Ie) may be prepared by using the compound (Id) according to the similar method to that described in Process 1 for preparing the compound (Ib) from the compound (II).

A method for preparing an intermediate compound in the preparation is described.

Reference Process 1

The compound (M-1) may be prepared by reacting a compound (M-3) with a compound represented by formula (M-8) (hereinafter, referred to as Compound (M-8)) in the presence of a metal catalyst and a base.

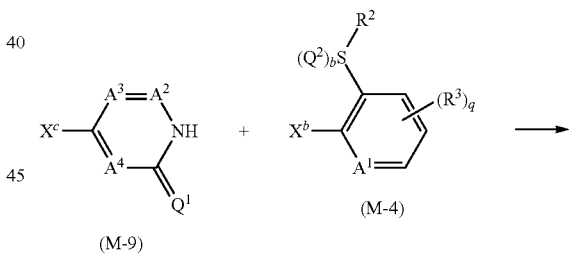

(M-9)　　(M-4)

(M-10)

[wherein, $X^c$ represents a halogen atom; and the other symbols are the same as defined above]

The reaction may be conducted by using the compound (M-9) instead of the compound (M-3) according to the similar method to that described in Process 4.

The compound (M-9) is a publically known compound, or may be prepared according to the similar method to that described in Synlett, 27(1), 67, 2016.
Reference Process 3

The compound (M-7) may be prepared according to the following scheme.

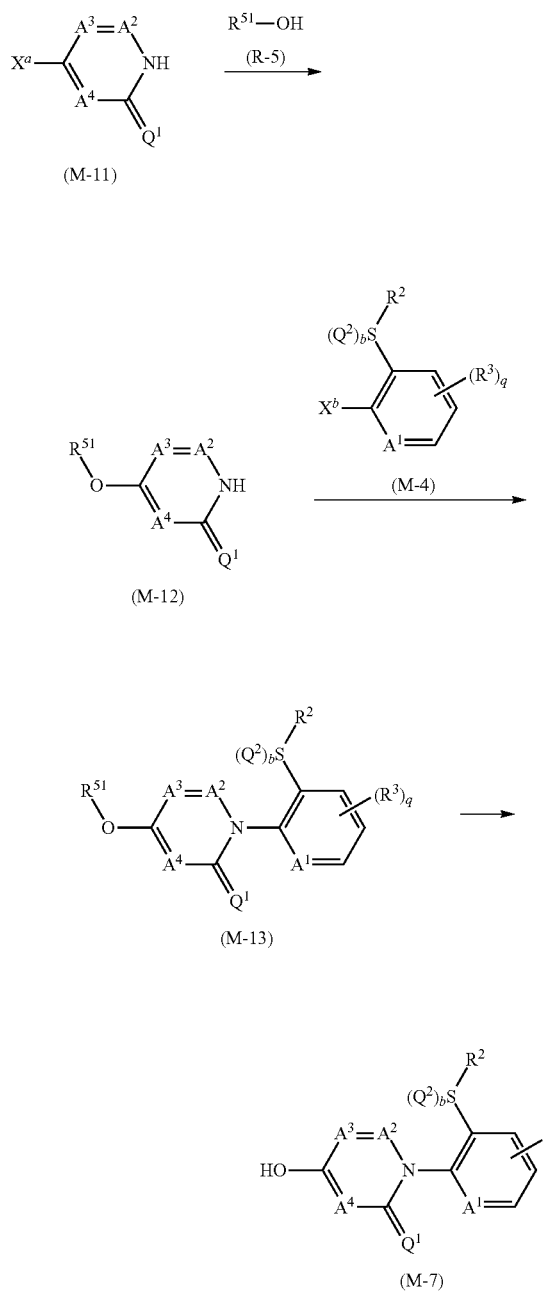

(M-11)

(M-12)

(M-13)

(M-7)

[wherein, $R^{51}$ represents a methyl group or an ethyl group; and the other symbols are the same as defined above]

The compound represented by formula (M-12) (hereinafter, referred to as Compound (M-12)) may be prepared by using the compound represented by formula (M-11) (hereinafter, referred to as Compound (M-11)) and a compound represented by formula (R-5) (hereinafter, referred to as Compound (R-5)) according to the similar method to that described in Process 5.

The compound represented by formula (M-13) (hereinafter, referred to Compound (M-13)) may be prepared by using the compound (M-12) and the compound (M-4) according to the similar method to that described in Process 4.

The compound (M-7) may be prepared by reacting the compound (M-13) with an acid. The reaction may be conducted according to the similar method to that described in WO 2016/052455 A1.

Reference Process 4

The compound represented by formula (M-15) and a compound represented by formula (M-16) may be prepared according to the following scheme.

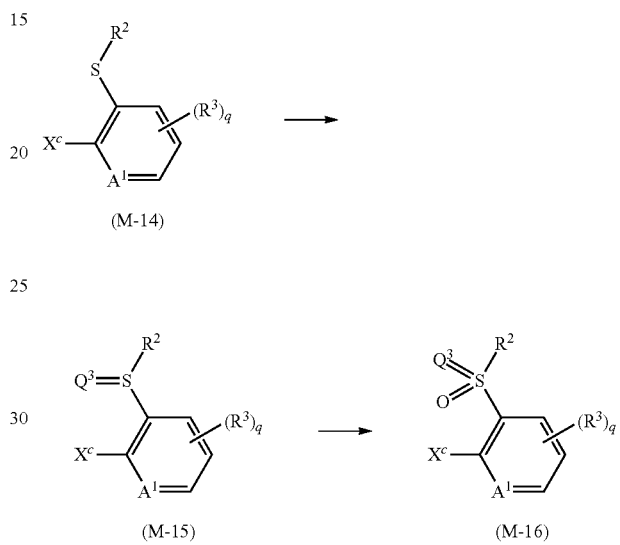

(M-14)

(M-15)   (M-16)

[wherein, the symbols are the same as defined above]

The reaction may be conducted by using a compound represented by formula (M-14) (hereinafter, referred to Compound (M-14)) according to the similar method to that described in Process 8.

Reference Process 5

The compound (M-14) may be prepared by reacting a compound represented by formula (M-17) (hereinafter, referred to as Compound (M-17)) and the compound (R-1) in the presence of a base.

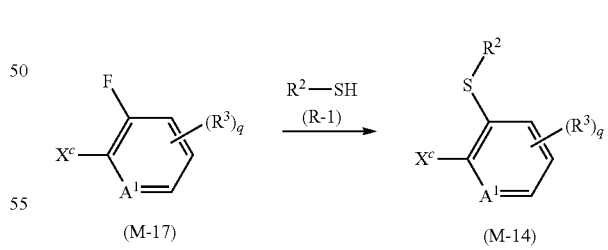

(M-17)   (M-14)

[wherein the symbols are the same as defined above]

The reaction may be conducted according to the similar method to that described in Process 2.

The compound (M-17) is a commercially available compound, or may be prepared according to a known method.

Reference Process 6

The compound represented by formula (M-18) or the compound represented by formula (M-19) may be prepared by oxidizing the compound (M-14).

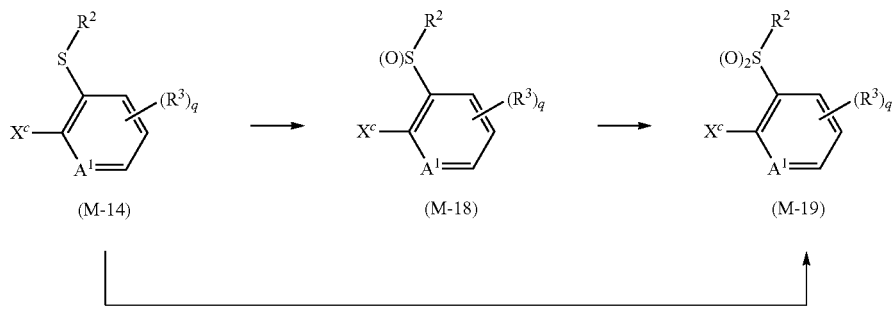

[wherein, the symbols are the same as defined above]

The reaction may be conducted according to the similar method to that described in Process 1.

Reference Process 7

The compound represented by formula (M-21) may be prepared by reacting a compound represented by formula (M-20) (hereinafter, referred to as Compound (M-20)) with a compound represented by formula (R-6) (hereinafter, referred to as Compound (R-6)) in the presence of a metal catalyst.

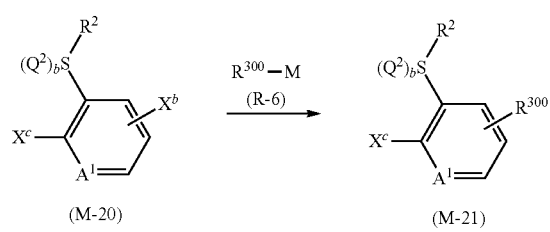

[wherein, $R^{300}$ represents a C1-C6 chain hydrocarbon group optionally having a cyano group, a C3-C7 cycloalkyl group, a phenyl group optionally having one or more substituents selected from Group H, a five or six membered aromatic heterocyclic group optionally having one or more substituents selected from Group H, a $NR^{11b}R^{12b}$, a $NR^{11a}R^{12a}$, a $NR^{29}NR^{11}R^{12}$, a $NR^{11}C(O)R^{13}$, a $C(O)OR^{17a}$, or a cyano group; and the other symbols are the same as defined above]

The reaction may be conducted by using the compound (M-20) instead of the compound (M-6), and the compound (R-6) instead of the compound (R-3) according to the similar method to that described in Process 6.

The compound (R-6) is a commercially available compound, or may be prepared according to a known method.

Reference Process 8

The compound (M-23) may be prepared by reacting a compound represented by formula (M-22) (hereinafter, referred to as Compound (M-22)) with a compound represented by formula (R-7) (hereinafter, referred to as Compound (R-7)) in the presence of a base.

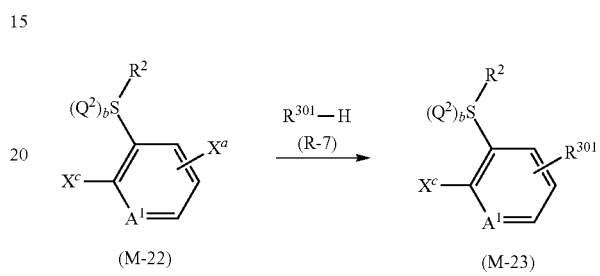

[wherein, $R^{301}$ represents a $OR^{12}$, a $NR^{11b}R^{12b}$, a $NR^{11a}R^{12a}$, or a $NR^{29}OR^{11}$; and the other symbols are the same as defined above]

The reaction may be conducted by using the compound (M-22) instead of the compound (M-5) and the compound (R-7) instead of the compound (R-2) according to the similar method to that described in Process 5.

The compound (R-7) is a commercially available compound, or may be prepared according to a known method.

Next, specific examples of the compound of the present invention are indicated below.

Herein, Me represents a methyl group, Et represents an ethyl group, Pr represents a propyl group, i-Pr represents an isopropyl group, c-Pr represents a cyclopropyl group, c-Bu represents a cyclobutyl group, c-Pen represents a cyclopentyl group, c-Hex represents a cyclohexyl group, Ph represents a phenyl group, Py2 represents a 2-pyridyl group, Py3 represents a 3-pyridyl group, and Py4 represents a 4-pyridyl group. When the c-py, c-Pr, c-Bu, c-Pen, c-Hex, Ph, Py2, Py3, and Py4 have any substituent(s), the substituent(s) is described together with a substitution position before the symbol. For example, 1-CN-c-Pr represents a 1-cyano-cyclopropyl group, 4-$CF_3$-Py2 represents a 4-(trifluoromethyl)-2-pyridyl group, and 3,5-$(CF_3)_2$-Ph represents a 3,5-bis(trifluoromethyl)phenyl group.

a compound represented by formula (L-1):

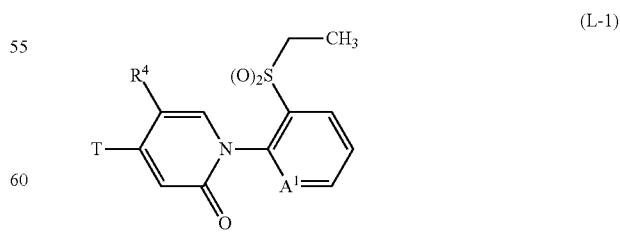

(hereinafter, referred to as Compound (L-1)) wherein $A^1$ represents a CH, $R^4$ represents a hydrogen atom, and T represents any substituents indicated in Table 1 to Table 6 (hereinafter, referred to as Compound Class $SX_1$).

TABLE 1

CF$_3$
CHF$_2$
CH$_2$CF$_3$
CF$_2$CF$_3$
CH$_2$CF$_2$CF$_3$
CF$_2$CF$_2$CF$_3$
CF$_2$CF$_2$CF$_2$CF$_3$
CF$_2$CF$_2$CF$_2$CF$_2$CF$_3$
OCF$_3$
OCHF$_2$
OCH$_2$CF$_3$
OCH$_2$CHF$_2$
OCF$_2$CF$_3$
OCH(CH$_3$)CF$_3$
OCH$_2$CF$_2$CHF$_2$
OCH$_2$CF$_2$CF$_3$
OCF$_2$CF$_2$CF$_3$
OCH$_2$CF$_2$CHFCF$_3$
OCH$_2$CF$_2$CF$_2$CF$_3$
OCF$_2$CF$_2$CF$_2$CF$_3$
OCH$_2$CF$_2$CF$_2$CF$_2$CF$_3$

TABLE 2

SCF$_3$
SCH$_2$CF$_3$
SCF$_2$CF$_3$
SCH$_2$CF$_2$CF$_3$
SCF$_2$CF$_2$CF$_3$
SCH$_2$CF$_2$CF$_2$CF$_3$
SCF$_2$CF$_2$CF$_2$CF$_3$
S(O)CF$_3$
S(O)CH$_2$CF$_3$
S(O)CF$_2$CF$_3$
S(O)CH$_2$CF$_2$CF$_3$
S(O)CF$_2$CF$_2$CF$_3$
S(O)CH$_2$CF$_2$CF$_2$CF$_3$
S(O)CF$_2$CF$_2$CF$_2$CF$_3$
S(O)$_2$CF$_3$
S(O)$_2$CH$_2$CF$_3$
S(O)$_2$CF$_2$CF$_3$
S(O)$_2$CH$_2$CF$_2$CF$_3$
S(O)$_2$CF$_2$CF$_2$CF$_3$
S(O)$_2$CH$_2$CF$_2$CF$_2$CF$_3$
S(O)$_2$CF$_2$CF$_2$CF$_2$CF$_3$

TABLE 3

NHCH$_2$CF$_3$
NHCH$_2$CF$_2$CF$_3$
NHCH$_2$CF$_2$CF$_2$CF$_3$
NMeCH$_2$CF$_3$
NMeCH$_2$CF$_2$CF$_3$
NMeCH$_2$CF$_2$CF$_2$CF$_3$
NEtCH$_2$CF$_3$
NEtCH$_2$CF$_2$CF$_3$
NEtCH$_2$CF$_2$CF$_2$CF$_3$
OS(O)$_2$CF$_3$
OS(O)$_2$CF$_2$CF$_3$
OS(O)$_2$CF$_2$CF$_2$CF$_3$
CH$_2$OCF$_3$
CH$_2$OCH$_2$CF$_3$
CH$_2$OCF$_2$CF$_3$
C(O)CF$_3$
C(O)CF$_2$CF$_3$
C(O)CF$_2$CF$_2$CF$_3$
C(O)NMeCH$_2$CF$_3$
NMeC(O)CF$_3$
N=CEtCH$_2$CF$_3$

TABLE 4

3-CF$_3$—Ph
4-CF$_3$—Ph
3,5-(CF$_3$)$_2$—Ph
3-SCF$_3$—Ph
3-S(O)CF$_3$—Ph
3-S(O)$_2$CF$_3$—Ph
4-SCF$_3$—Ph
4-S(O)CF$_3$—Ph
4-S(O)$_2$CF$_3$—Ph

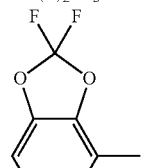

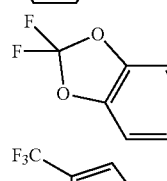

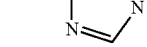

TABLE 5

4-CF$_3$—Py2
5-CF$_3$—Py2
4-SCF$_3$—Py2
4-S(O)CF$_3$—Py2
4-S(O)$_2$CF$_3$—Py2
5-SCF$_3$—Py2
5-S(O)CF$_3$—Py2
5-S(O)$_2$CF$_3$—Py2
5-NMeCH$_2$CF$_3$—Py2

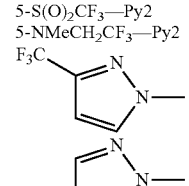

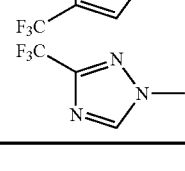

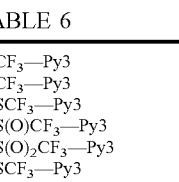

TABLE 6

5-CF$_3$—Py3
6-CF$_3$—Py3
5-SCF$_3$—Py3
5-S(O)CF$_3$—Py3
5-S(O)$_2$CF$_3$—Py3
6-SCF$_3$—Py3
6-S(O)CF$_3$—Py3
6-S(O)$_2$CF$_3$—Py3
6-NMeCH$_2$CF$_3$—Py3

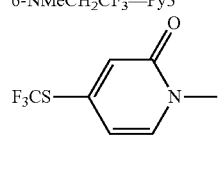

TABLE 6-continued

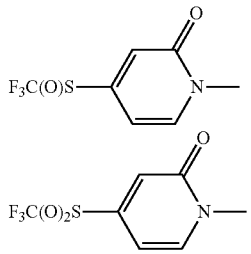

a compound (L-1) wherein $A^1$ represents a CH, $R^4$ represents a chlorine atom, and T represents any substituent indicated in Table 1 to Table 6 (hereinafter, referred to as Compound Class $SX_2$).

a compound (L-1) wherein $A^1$ represents a CH, $R^4$ represents a methyl group, and T represents any substituent indicated in Table 1 to Table 6 (hereinafter, referred to as Compound Class $SX_3$).

a compound (L-1) wherein $A^1$ represents a CH, $R^4$ represents a methoxy group, and T represents any substituent indicated in Table 1 to Table 6 (hereinafter, referred to as Compound Class $SX_4$).

a compound (L-1) wherein $A^1$ represents a nitrogen atom, $R^4$ represents a hydrogen atom, and T represents any substituent indicated in Table 1 to Table 6 (hereinafter, referred to as Compound Class $SX_5$).

a compound (L-1) wherein $A^1$ represents a nitrogen atom, $R^4$ represents a chorine atom, and T represents any substituent indicated in Table 1 to Table 6 (hereinafter, referred to as Compound Class $SX_6$).

a compound (L-1) wherein $A^1$ represents a nitrogen atom, $R^4$ represents a methyl group, and T represents any substituent indicated in Table 1 to Table 6 (hereinafter, referred to as Compound Class $SX_7$).

a compound (L-1) wherein $A^1$ represents a nitrogen atom, $R^4$ represents a methoxy group, and T represents any substituent indicated in Table 1 to Table 6 (hereinafter, referred to as Compound Class $SX_8$).

a compound represented by formula (L-2):

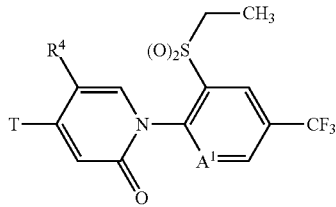

(hereinafter, referred to as Compound (L-2)) wherein $A^1$ represents a CH, $R^4$ represents a hydrogen atom, and T represents any substituent indicated in Table 1 to Table 6 (hereinafter, referred to as Compound Class $SX_9$).

a compound (L-2) wherein $A^1$ represents a CH, $R^4$ represents a chlorine atom, and T represents any substituent indicated in Table 1 to Table 6 (hereinafter, referred to as Compound Class $SX_{10}$).

a compound (L-2) wherein $A^1$ represents a CH, $R^4$ represents a methyl group, and T represents any substituent indicated in Table 1 to Table 6 (hereinafter, referred to as Compound Class $SX_{11}$).

a compound (L-2) wherein $A^1$ represents a CH, $R^4$ represents a methoxy group, and T represents any substituent indicated in Table 1 to Table 6 (hereinafter, referred to as Compound Class $SX_{12}$).

a compound (L-2) wherein $A^1$ represents a nitrogen atom, $R^4$ represents a hydrogen atom, and T represents any substituent indicated in Table 1 to Table 6 (hereinafter, referred to as Compound Class $SX_{13}$).

a compound (L-2) wherein $A^1$ represents a nitrogen atom, $R^4$ represents a chlorine atom, and T represents any substituent indicated in Table 1 to Table 6 (hereinafter, referred to as Compound Class $SX_{14}$).

a compound (L-2) wherein $A^1$ represents a nitrogen atom, $R^4$ represents a methyl group, and T represents any substituent indicated in Table 1 to Table 6 (hereinafter, referred to as Compound Class $SX_{15}$).

a compound (L-2) wherein $A^1$ represents a nitrogen atom, $R^4$ represents a methoxy group, and T represents any substituent indicated in Table 1 to Table 6 (hereinafter, referred to as Compound Class $SX_{16}$).

a compound represented by formula (L-3):

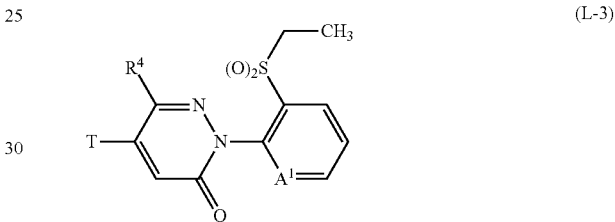

(hereinafter, referred to Compound (L-3)) wherein $A^1$ represents a CH, $R^4$ represents a hydrogen atom, and T represents any substituents indicated in Table 1 to Table 6 (hereinafter, referred to as Compound Class $SX_{17}$).

a compound (L-3) wherein $A^1$ represents a CH, $R^4$ represents a chlorine atom, and T represents any substituent indicated in Table 1 to Table 6 (hereinafter, referred to as Compound Class $SX_{18}$).

a compound (L-3) wherein $A^1$ represents a CH, $R^4$ represents a methyl group, and T represents any substituent indicated in Table 1 to Table 6 (hereinafter, referred to as Compound Class $SX_{19}$).

a compound (L-3) wherein $A^1$ represents a CH, $R^4$ represents a methoxy group, and T represents any substituent indicated in Table 1 to Table 6 (hereinafter, referred to as Compound Class $SX_{20}$).

a compound (L-3) wherein $A^1$ represents a nitrogen atom, $R^4$ represents a hydrogen atom, and T represents any substituent indicated in Table 1 to Table 6 (hereinafter, referred to as Compound Class $SX_{21}$).

a compound (L-3) wherein $A^1$ represents a nitrogen atom, $R^4$ represents a chlorine atom, and T represents any substituent indicated in Table 1 to Table 6 (hereinafter, referred to as Compound Class $SX_{22}$).

a compound (L-3) wherein $A^1$ represents a nitrogen atom, $R^4$ represents a methyl group, and T represents any substituent indicated in Table 1 to Table 6 (hereinafter, referred to as Compound Class $SX_{23}$).

a compound (L-3) wherein $A^1$ represents a nitrogen atom, $R^4$ represents a methoxy group, and T represents any substituent indicated in Table 1 to Table 6 (hereinafter, referred to as Compound Class $SX_{24}$).

a compound represented by formula (L-4):

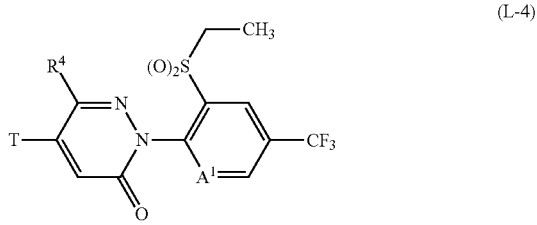

(hereinafter, referred to Compound (L-4)) wherein $A^1$ represents a CH, $R^4$ represents a hydrogen atom, and T represents any substituent indicated in Table 1 to Table 6 (hereinafter, referred to as Compound Class $SX_{25}$).

a compound (L-4) wherein $A^1$ represents a CH, $R^4$ represents a chlorine atom, and T represents any substituent indicated in Table 1 to Table 6 (hereinafter, referred to as Compound Class $SX_{26}$).

a compound (L-4) wherein $A^1$ represents a CH, $R^4$ represents a methyl group, and T represents any substituent indicated in Table 1 to Table 6 (hereinafter, referred to as Compound Class $SX_{27}$).

a compound (L-4) wherein $A^1$ represents a CH, $R^4$ represents a methoxy group, and T represents any substituent indicated in Table 1 to Table 6 (hereinafter, referred to as Compound Class $SX_{28}$).

a compound (L-4) wherein $A^1$ represents a nitrogen atom, $R^4$ represents a hydrogen atom, and T represents any substituent indicated in Table 1 to Table 6 (hereinafter, referred to as Compound Class $SX_{29}$).

a compound (L-4) wherein $A^1$ represents a nitrogen atom, $R^4$ represents a chlorine atom, and T represents any substituent indicated in Table 1 to Table 6 (hereinafter, referred to as Compound Class $SX_{30}$).

a compound (L-4) wherein $A^1$ represents a nitrogen atom, $R^4$ represents a methyl group, and T represents any substituent indicated in Table 1 to Table 6 (hereinafter, referred to as Compound Class $SX_{31}$).

a compound (L-4) wherein $A^1$ represents a nitrogen atom, $R^4$ represents a methoxy group, and T represents any substituent indicated in Table 1 to Table 6 (hereinafter, referred to as Compound Class $SX_{32}$).

a compound represented by formula (L-5):

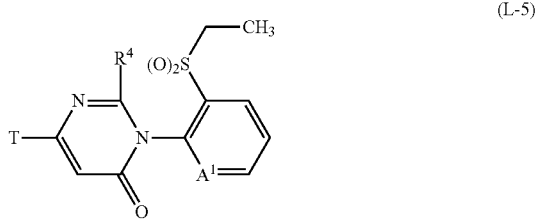

(hereinafter, referred to Compound (L-5)) wherein $A^1$ represents a CH, $R^4$ represents a hydrogen atom, and T represents any substituent indicated in Table 1 to Table 6 (hereinafter, referred to as Compound Class $SX_{33}$).

a compound (L-5) wherein $A^1$ represents a CH, $R^4$ represents a chlorine atom, and T represents any substituent indicated in Table 1 to Table 6 (hereinafter, referred to as Compound Class $SX_{34}$).

a compound (L-5) wherein $A^1$ represents a CH, $R^4$ represents a methyl group, and T represents any substituent indicated in Table 1 to Table 6 (hereinafter, referred to as Compound Class $SX_{35}$).

a compound (L-5) wherein $A^1$ represents a CH, $R^4$ represents a methoxy group, and T represents any substituent indicated in Table 1 to Table 6 (hereinafter, referred to as Compound Class $SX_{36}$).

a compound (L-5) wherein $A^1$ represents a nitrogen atom, $R^4$ represents a hydrogen atom, and T represents any substituent indicated in Table 1 to Table 6 (hereinafter, referred to as Compound Class $SX_{37}$).

a compound (L-5) wherein $A^1$ represents a nitrogen atom, $R^4$ represents a chlorine atom, and T represents any substituent indicated in Table 1 to Table 6 (hereinafter, referred to as Compound Class $SX_{38}$).

a compound (L-5) wherein $A^1$ represents a nitrogen atom, $R^4$ represents a methyl group, and T represents any substituent indicated in Table 1 to Table 6 (hereinafter, referred to as Compound Class $SX_{39}$).

a compound (L-5) wherein $A^1$ represents a nitrogen atom, $R^4$ represents a methoxy group, and T represents any substituent indicated in Table 1 to Table 6 (hereinafter, referred to as Compound Class $SX_{40}$).

a compound represented by formula (L-6):

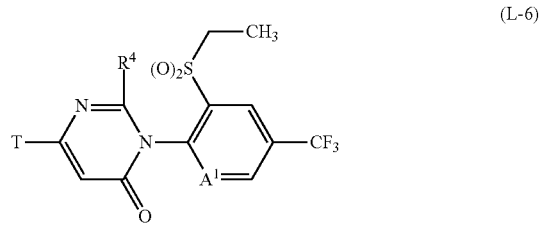

(hereinafter, referred to Compound (L-6)) wherein $A^1$ represents a CH, $R^4$ represents a hydrogen atom, and T represents any substituent indicated in Table 1 to Table 6 (hereinafter, referred to as Compound Class $SX_{41}$).

a compound (L-6) wherein $A^1$ represents a CH, $R^4$ represents a chlorine atom, and T represents any substituent indicated in Table 1 to Table 6 (hereinafter, referred to as Compound Class $SX_{42}$).

a compound (L-6) wherein $A^1$ represents a CH, $R^4$ represents a methyl group, and T represents any substituent indicated in Table 1 to Table 6 (hereinafter, referred to as Compound Class $SX_{43}$).

a compound (L-6) wherein $A^1$ represents a CH, $R^4$ represents a methoxy group, and T represents any substituent indicated in Table 1 to Table 6 (hereinafter, referred to as Compound Class $SX_{44}$).

a compound (L-6) wherein $A^1$ represents a nitrogen atom, $R^4$ represents a hydrogen atom, and T represents any substituent indicated in Table 1 to Table 6 (hereinafter, referred to as Compound Class $SX_{45}$).

a compound (L-6) wherein $A^1$ represents a nitrogen atom, $R^4$ represents a chlorine atom, and T represents any substituent indicated in Table 1 to Table 6 (hereinafter, referred to as Compound Class $SX_{46}$).

a compound (L-6) wherein $A^1$ represents a nitrogen atom, $R^4$ represents a methyl group, and T represents any substituent indicated in Table 1 to Table 6 (hereinafter, referred to as Compound Class $SX_{47}$).

a compound (L-6) wherein $A^1$ represents a nitrogen atom, $R^4$ represents a methoxy group, and T represents any substituent indicated in Table 1 to Table 6 (hereinafter, referred to as Compound Class $SX_{48}$).

a compound represented by formula (L-7):

(L-7)

(hereinafter, referred to Compound (L-7)) wherein $A^1$ represents a CH, $R^4$ represents a hydrogen atom, and T represents any substituent indicated in Table 1 to Table 6 (hereinafter, referred to as Compound Class $SX_{49}$).

a compound (L-7) wherein $A^1$ represents a CH, $R^4$ represents a chlorine atom, and T represents any substituent indicated in Table 1 to Table 6 (hereinafter, referred to as Compound Class $SX_{50}$).

a compound (L-7) wherein $A^1$ represents a CH, $R^4$ represents a methyl group, and T represents any substituent indicated in Table 1 to Table 6 (hereinafter, referred to as Compound Class $SX_{51}$).

a compound (L-7) wherein $A^1$ represents a CH, $R^4$ represents a methoxy group, and T represents any substituent indicated in Table 1 to Table 6 (hereinafter, referred to as Compound Class $SX_{52}$).

a compound (L-7) wherein $A^1$ represents a nitrogen atom, $R^4$ represents a hydrogen atom, and T represents any substituent indicated in Table 1 to Table 6 (hereinafter, referred to as Compound Class $SX_{53}$).

a compound (L-7) wherein $A^1$ represents a nitrogen atom, $R^4$ represents a chlorine atom, and T represents any substituent indicated in Table 1 to Table 6 (hereinafter, referred to as Compound Class $SX_{54}$).

a compound (L-7) wherein $A^1$ represents a nitrogen atom, $R^4$ represents a methyl group, and T represents any substituent indicated in Table 1 to Table 6 (hereinafter, referred to as Compound Class $SX_{55}$).

a compound (L-7) wherein $A^1$ represents a nitrogen atom, $R^4$ represents a methoxy group, and T represents any substituent indicated in Table 1 to Table 6 (hereinafter, referred to as Compound Class $SX_{56}$).

a compound represented by formula (L-8):

(L-8)

(hereinafter, referred to Compound (L-8)) wherein $A^1$ represents a CH, $R^4$ represents a hydrogen atom, and T represents any substituent indicated in Table 1 to Table 6 (hereinafter, referred to as Compound Class $SX_{57}$).

a compound (L-8) wherein $A^1$ represents a CH, $R^4$ represents a chlorine atom, and T represents any substituent indicated in Table 1 to Table 6 (hereinafter, referred to as Compound Class $SX_{58}$).

a compound (L-8) wherein $A^1$ represents a CH, $R^4$ represents a methyl group, and T represents any substituent indicated in Table 1 to Table 6 (hereinafter, referred to as Compound Class $SX_{59}$).

a compound (L-8) wherein $A^1$ represents a CH, $R^4$ represents a methoxy group, and T represents any substituent indicated in Table 1 to Table 6 (hereinafter, referred to as Compound Class $SX_{60}$).

a compound (L-8) wherein $A^1$ represents a nitrogen atom, $R^4$ represents a hydrogen atom, and T represents any substituent indicated in Table 1 to Table 6 (hereinafter, referred to as Compound Class $SX_{61}$).

a compound (L-8) wherein $A^1$ represents a nitrogen atom, $R^4$ represents a chlorine atom, and T represents any substituent indicated in Table 1 to Table 6 (hereinafter, referred to as Compound Class $SX_{62}$).

a compound (L-8) wherein $A^1$ represents a nitrogen atom, $R^4$ represents a methyl group, and T represents any substituent indicated in Table 1 to Table 6 (hereinafter, referred to as Compound Class $SX_{63}$).

a compound (L-8) wherein $A^1$ represents a nitrogen atom, $R^4$ represents a methoxy group, and T represents any substituent indicated in Table 1 to Table 6 (hereinafter, referred to as Compound Class $SX_{64}$).

a compound represented by formula (L-9):

(L-9)

(hereinafter, referred to Compound (L-9)) wherein $A^1$ represents a CH, $R^4$ represents a hydrogen atom, and T represents any substituent indicated in Table 1 to Table 6 (hereinafter, referred to as Compound Class $SX_{65}$).

a compound (L-9) wherein $A^1$ represents a CH, $R^4$ represents a chlorine atom, and T represents any substituent indicated in Table 1 to Table 6 (hereinafter, referred to as Compound Class $SX_{66}$).

a compound (L-9) wherein $A^1$ represents a CH, $R^4$ represents a methyl group, and T represents any substituent indicated in Table 1 to Table 6 (hereinafter, referred to as Compound Class $SX_{67}$).

a compound (L-9) wherein $A^1$ represents a CH, $R^4$ represents a methoxy group, and T represents any substituent indicated in Table 1 to Table 6 (hereinafter, referred to as Compound Class $SX_{68}$).

a compound (L-9) wherein $A^1$ represents a nitrogen atom, $R^4$ represents a hydrogen atom, and T represents any substituent indicated in Table 1 to Table 6 (hereinafter, referred to as Compound Class $SX_{69}$).

a compound (L-9) wherein $A^1$ represents a nitrogen atom, $R^4$ represents a chlorine atom, and T represents any substituent indicated in Table 1 to Table 6 (hereinafter, referred to as Compound Class $SX_{70}$).

a compound (L-9) wherein $A^1$ represents a nitrogen atom, $R^4$ represents a methyl group, and T represents any substituent indicated in Table 1 to Table 6 (hereinafter, referred to as Compound Class $SX_{71}$).

a compound (L-9) wherein $A^1$ represents a nitrogen atom, $R^4$ represents a methoxy group, and T represents any substituent indicated in Table 1 to Table 6 (hereinafter, referred to as Compound Class $SX_{72}$).

a compound represented by formula (L-10):

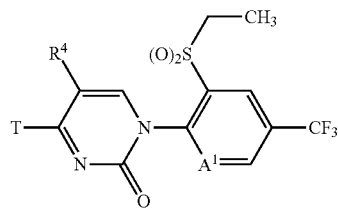

(L-10)

(hereinafter, referred to Compound (L-10)) wherein $A^1$ represents a CH, $R^4$ represents a hydrogen atom, and T represents any substituent indicated in Table 1 to Table 6 (hereinafter, referred to as Compound Class $SX_{73}$).

a compound (L-10) wherein $A^1$ represents a CH, $R^4$ represents a chlorine atom, and T represents any substituent indicated in Table 1 to Table 6 (hereinafter, referred to as Compound Class $SX_{74}$).

a compound (L-10) wherein $A^1$ represents a CH, $R^4$ represents a methyl group, and T represents any substituent indicated in Table 1 to Table 6 (hereinafter, referred to as Compound Class $SX_{75}$).

a compound (L-10) wherein $A^1$ represents a CH, $R^4$ represents a methoxy group, and T represents any substituent indicated in Table 1 to Table 6 (hereinafter, referred to as Compound Class $SX_{76}$).

a compound (L-10) wherein $A^1$ represents a nitrogen atom, $R^4$ represents a hydrogen atom, and T represents any substituent indicated in Table 1 to Table 6 (hereinafter, referred to as Compound Class $SX_{77}$).

a compound (L-10) wherein $A^1$ represents a nitrogen atom, $R^4$ represents a chlorine atom, and T represents any substituent indicated in Table 1 to Table 6 (hereinafter, referred to as Compound Class $SX_{78}$).

a compound (L-10) wherein $A^1$ represents a nitrogen atom, $R^4$ represents a methyl group, and T represents any substituent indicated in Table 1 to Table 6 (hereinafter, referred to as Compound Class $SX_{79}$).

a compound (L-10) wherein $A^1$ represents a nitrogen atom, $R^4$ represents a methoxy group, and T represents any substituent indicated in Table 1 to Table 6 (hereinafter, referred to as Compound Class $SX_{80}$).

a compound represented by formula (L-11):

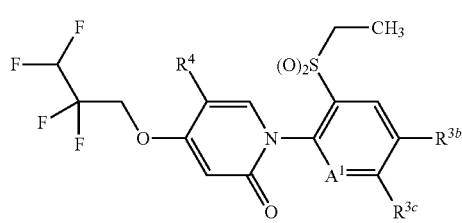

(L-11)

(hereinafter, referred to Compound (L-11)) wherein $A^1$ represents a CH, $R^{3b}$ represents a hydrogen atom, $R^4$ represents a hydrogen atom, and $R^{3'}$ represents any substituent indicated in Table 7 to Table 15 (hereinafter, referred to as Compound Class $SX_{81}$).

[Table 3]

TABLE 7

F
Cl
Br
Me
Et
Pr
i-Pr
c-Pr
1-CN—c-Pr
OMe
OEt
OPr
Oi-Pr
$CF_3$
$NH_2$
$NHCH_2CF_3$
CN
C(O)OEt
NHC(O)c-Pr
NMeC(O)c-Pr
1-F—c-Pr
1-$NH_2$—c-Pr
1-$CF_3$—c-Pr
1-C(O)OMe—c-Pr
1-OH—c-Pr
1-$CH_3$—c-Pr
$NHCH_2CH_2CN$
NHC(O)Pr
NMePr

TABLE 8

Ph
3-F—Ph
4-F—Ph
3-Cl—Ph
4-Cl—Ph
3-$CF_3$—Ph
4-$CF_3$—Ph
3-$NMe_2$—Ph
4-$NMe_2$—Ph
3-CN—Ph
4-CN—Ph
4-C(O)$NMe_2$—Ph
4-NHC(O)Me—Ph
3,4-$F_2$—Ph
3,5-$F_2$—Ph
2,4-$F_2$—Ph
3,4,5-$F_3$—Ph
3,4-$Cl_2$—Ph
3,5-$Cl_2$—Ph
3,5-$Cl_2$-4-F—Ph
OPh
O-2-F—Ph
1-C(O)O$C_2H_5$—c-Pr
1-OMe—c-Pr
CH=N—OH
CH=N—OMe
$NHCH_2CN$
C(O)NHPr
N=CHPr

TABLE 9

Py2
4-F—Py2
5-F—Py2
4-Cl—Py2
5-Cl—Py2
4-$CF_3$—Py2
5-$CF_3$—Py2
3-Me—Py2
4-Me—Py2

TABLE 9-continued
5-Me—Py2
6-Me—Py2
5-CN—Py2
5-OCH$_2$CF$_2$CF$_3$—Py2
3,5-F$_2$—Py2
Py3
6-CF$_3$—Py3
5-CF$_3$—Py3
6-F—Py3
6-Cl—Py3
Py4
OPy2
OPy3
C(O)NMe$_2$
CH=CH$_2$
CMe=CH$_2$
CMe$_3$
NMeCH$_2$CN
C(O)Me
NHCH=NMe
[Table 4]
TABLE 10
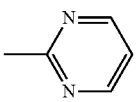
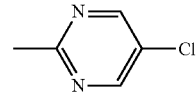
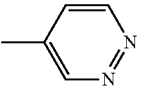
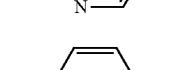
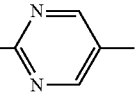
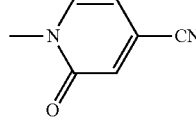
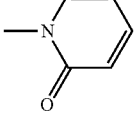
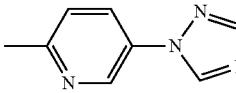
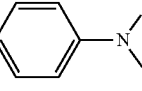
TABLE 10-continued
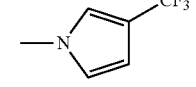
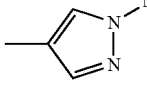
TABLE 11
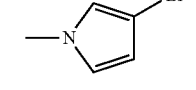
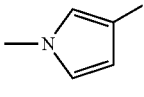
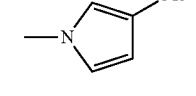
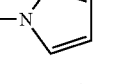
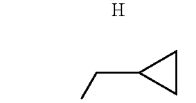
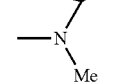
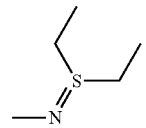
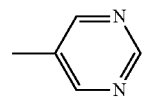
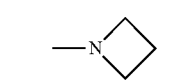

TABLE 12
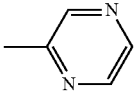
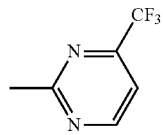
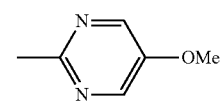
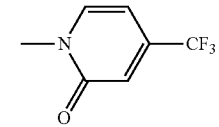
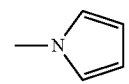
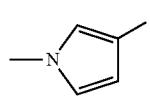
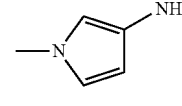
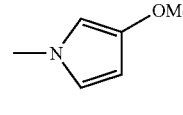
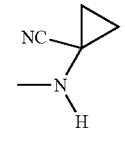
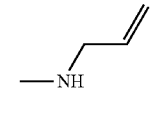
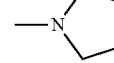
TABLE 13
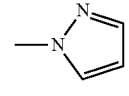
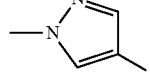
TABLE 13-continued
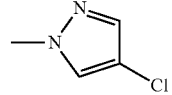
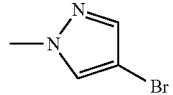
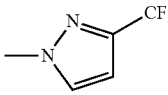
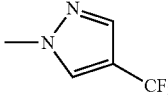
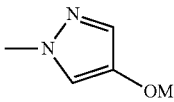
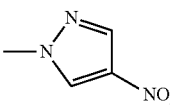
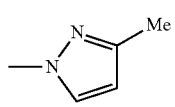
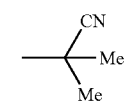
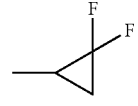
TABLE 14
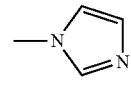
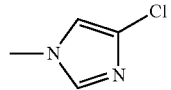
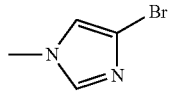
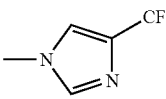
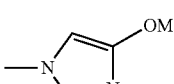

TABLE 14-continued

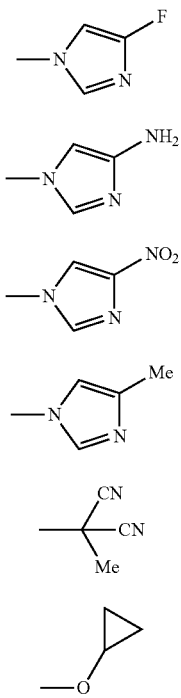

TABLE 15

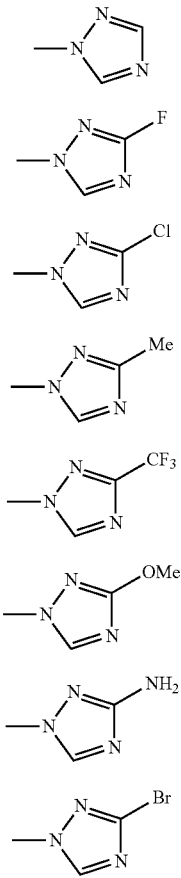

TABLE 15-continued

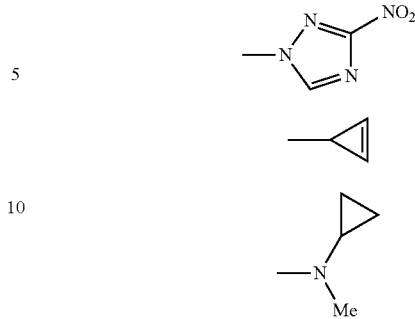

a compound (L-11) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{82}$).

a compound (L-11) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{83}$).

a compound (L-11) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{84}$).

a compound (L-11) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{85}$).

a compound (L-11) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{86}$).

a compound (L-11) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{87}$).

a compound (L-11) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{88}$).

a compound (L-11) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{89}$).

a compound (L-11) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{90}$).

a compound (L-11) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{91}$).

a compound (L-11) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{92}$).

a compound (L-11) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{93}$).

a compound (L-11) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{94}$).

a compound (L-11) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{95}$).

a compound (L-11) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{96}$).

a compound represented by formula (L-12):

(hereinafter, referred to Compound (L-12)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{97}$).

a compound (L-12) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{98}$).

a compound (L-12) wherein $A^1$ represents a nitrogen atom, $R^{3c}$ represents a hydrogen atom, $R^4$ represents a hydrogen atom, and $R^{3c}$ represents any substituent indicated in Table 7 to Table 15 (hereinafter, referred to as Compound Class $SX_{99}$).

a compound (L-12) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{100}$).

a compound (L-12) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{101}$).

a compound (L-12) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{102}$).

a compound (L-12) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{103}$).

a compound (L-12) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{104}$).

a compound (L-12) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{105}$).

a compound (L-12) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{106}$).

a compound (L-12) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{107}$).

a compound (L-12) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{108}$).

a compound (L-12) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{109}$).

a compound (L-12) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{110}$).

a compound (L-12) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{111}$).

a compound (L-12) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{112}$).

a compound represented by formula (L-13):

(hereinafter, referred to Compound (L-13)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{113}$).

a compound (L-13) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{114}$).

a compound (L-13) wherein A¹ represents a nitrogen atom, R³ᵇ represents a hydrogen atom, R⁴ represents a hydrogen atom, and R³ᶜ represents any substituent indicated in Table 7 to Table 15 (hereinafter, referred to as Compound Class $SX_{115}$).

a compound (L-13) wherein A¹ represents a nitrogen atom, R³ᶜ represents a hydrogen atom, R⁴ represents a hydrogen atom, and R³ᵇ represents any substituent indicated in Table 7 to Table 15 (hereinafter, referred to as Compound Class $SX_{116}$).

a compound (L-13) wherein A¹ represents a CH, R³ᵇ represents a hydrogen atom, R⁴ represents a chlorine atom, and R³ᶜ represents any substituent indicated in Table 7 to Table 15 (hereinafter, referred to as Compound Class $SX_{117}$).

a compound (L-13) wherein A¹ represents a CH, R³ᶜ represents a hydrogen atom, R⁴ represents a chlorine atom, and R³ᵇ represents any substituent indicated in Table 7 to Table 15 (hereinafter, referred to as Compound Class $SX_{118}$).

a compound (L-13) wherein A¹ represents a nitrogen atom, R³ᵇ represents a hydrogen atom, R⁴ represents a chlorine atom, and R³ᶜ represents any substituent indicated in Table 7 to Table 15 (hereinafter, referred to as Compound Class $SX_{119}$).

a compound (L-13) wherein A¹ represents a nitrogen atom, R³ᶜ represents a hydrogen atom, R⁴ represents a chlorine atom, and R³ᵇ represents any substituent indicated in Table 7 to Table 15 (hereinafter, referred to as Compound Class $SX_{120}$).

a compound (L-13) wherein A¹ represents a CH, R³ᵇ represents a hydrogen atom, R⁴ represents a methyl group, and R³ᶜ represents any substituent indicated in Table 7 to Table 15 (hereinafter, referred to as Compound Class $SX_{121}$).

a compound (L-13) wherein A¹ represents a CH, R³ᶜ represents a hydrogen atom, R⁴ represents a methyl group, and R³ᵇ represents any substituent indicated in Table 7 to Table 15 (hereinafter, referred to as Compound Class $SX_{122}$).

a compound (L-13) wherein A¹ represents a nitrogen atom, R³ᵇ represents a hydrogen atom, R⁴ represents a methyl group, and R³ᶜ represents any substituent indicated in Table 7 to Table 15 (hereinafter, referred to as Compound Class $SX_{123}$).

a compound (L-13) wherein A¹ represents a nitrogen atom, R³ᶜ represents a hydrogen atom, R⁴ represents a methyl group, and R³ᵇ represents any substituent indicated in Table 7 to Table 15 (hereinafter, referred to as Compound Class $SX_{124}$).

a compound (L-13) wherein A¹ represents a CH, R³ᵇ represents a hydrogen atom, R⁴ represents a methoxy group, and R³ᶜ represents any substituent indicated in Table 7 to Table 15 (hereinafter, referred to as Compound Class $SX_{125}$).

a compound (L-13) wherein A¹ represents a CH, R³ᶜ represents a hydrogen atom, R⁴ represents a methoxy group, and R³ᵇ represents any substituent indicated in Table 7 to Table 15 (hereinafter, referred to as Compound Class $SX_{126}$).

a compound (L-13) wherein A¹ represents a nitrogen atom, R³ᵇ represents a hydrogen atom, R⁴ represents a methoxy group, and R³ᶜ represents any substituent indicated in Table 7 to Table 15 (hereinafter, referred to as Compound Class $SX_{127}$).

a compound (L-13) wherein A¹ represents a nitrogen atom, R³ᶜ represents a hydrogen atom, R⁴ represents a methoxy group, and R³ᵇ represents any substituent indicated in Table 7 to Table 15 (hereinafter, referred to as Compound Class $SX_{128}$).

a compound represented by formula (L-14):

(hereinafter, referred to Compound (L-14)) wherein A¹ represents a CH, R³ᵇ represents a hydrogen atom, R⁴ represents a hydrogen atom, and R³ᶜ represents any substituent indicated in Table 7 to Table 15 (hereinafter, referred to as Compound Class $SX_{129}$).

a compound (L-14) wherein A¹ represents a CH, R³ᶜ represents a hydrogen atom, R⁴ represents a hydrogen atom, and R³ᵇ represents any substituent indicated in Table 7 to Table 15 (hereinafter, referred to as Compound Class $SX_{130}$).

a compound (L-14) wherein A¹ represents a nitrogen atom, R³ᵇ represents a hydrogen atom, R⁴ represents a hydrogen atom, and R³' represents any substituent indicated in Table 7 to Table 15 (hereinafter, referred to as Compound Class $SX_{131}$).

a compound (L-14) wherein A¹ represents a nitrogen atom, R³ᶜ represents a hydrogen atom, R⁴ represents a hydrogen atom, and R³ᵇ represents any substituent indicated in Table 7 to Table 15 (hereinafter, referred to as Compound Class $SX_{132}$).

a compound (L-14) wherein A¹ represents a CH, R³ᵇ represents a hydrogen atom, R⁴ represents a chlorine atom, and R³' represents any substituent indicated in Table 7 to Table 15 (hereinafter, referred to as Compound Class $SX_{133}$).

a compound (L-14) wherein A¹ represents a CH, R³ᶜ represents a hydrogen atom, R⁴ represents a chlorine atom, and R³ᵇ represents any substituent indicated in Table 7 to Table 15 (hereinafter, referred to as Compound Class $SX_{134}$).

a compound (L-14) wherein A¹ represents a nitrogen atom, R³ᵇ represents a hydrogen atom, R⁴ represents a chlorine atom, and R³' represents any substituent indicated in Table 7 to Table 15 (hereinafter, referred to as Compound Class $SX_{135}$).

a compound (L-14) wherein A¹ represents a nitrogen atom, R³' represents a hydrogen atom, R⁴ represents a chlorine atom, and R³ᵇ represents any substituent indicated in Table 7 to Table 15 (hereinafter, referred to as Compound Class $SX_{136}$).

a compound (L-14) wherein A¹ represents a CH, R³ᵇ represents a hydrogen atom, R⁴ represents a methyl group, and R³' represents any substituent indicated in Table 7 to Table 15 (hereinafter, referred to as Compound Class $SX_{137}$).

a compound (L-14) wherein A¹ represents a CH, R³ᶜ represents a hydrogen atom, R⁴ represents a methyl group, and R³ᵇ represents any substituent indicated in Table 7 to Table 15 (hereinafter, referred to as Compound Class $SX_{138}$).

a compound (L-14) wherein $A^1$ represents a nitrogen atom, $R^{3b}$ represents a hydrogen atom, $R^4$ represents a methyl group, and $R^{3'}$ represents any substituent indicated in Table 7 to Table 15 (hereinafter, referred to as Compound Class $SX_{139}$).

a compound (L-14) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{140}$).

a compound (L-14) wherein $A^1$ represents a CH, $R^{3b}$ represents a hydrogen atom, $R^4$ represents a methoxy group, and $R^{3'}$ represents any substituent indicated in Table 7 to Table 15 (hereinafter, referred to as Compound Class $SX_{141}$).

a compound (L-14) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{142}$).

a compound (L-14) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{143}$).

a compound (L-14) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{144}$).

a compound represented by formula (L-15):

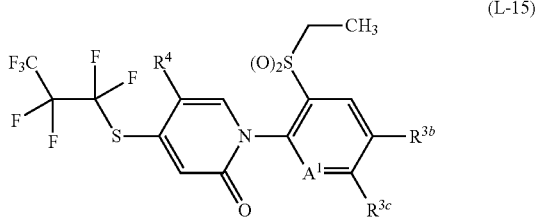

(L-15)

(hereinafter, referred to Compound (L-15)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{145}$).

a compound (L-15) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{146}$).

a compound (L-15) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{147}$).

a compound (L-15) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{148}$).

a compound (L-15) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{149}$).

a compound (L-15) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{150}$).

a compound (L-15) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{151}$).

a compound (L-15) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{152}$).

a compound (L-15) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{153}$).

a compound (L-15) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{154}$).

a compound (L-15) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{155}$).

a compound (L-15) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{156}$).

a compound (L-15) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{157}$).

a compound (L-15) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{158}$).

a compound (L-15) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{159}$).

a compound (L-15) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{160}$).

a compound represented by formula (L-16):

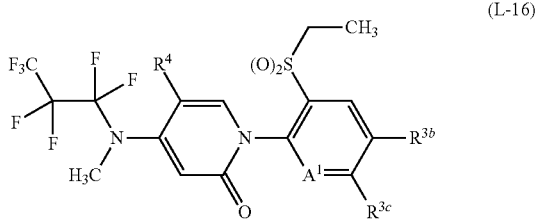

(L-16)

(hereinafter, referred to Compound (L-16)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{11}$).

a compound (L-16) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{162}$).

a compound (L-16) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{163}$).

a compound (L-16) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{164}$).

a compound (L-16) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{165}$).

a compound (L-16) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{166}$).

a compound (L-16) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{167}$).

a compound (L-16) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{168}$).

a compound (L-16) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{169}$).

a compound (L-16) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{170}$).

a compound (L-16) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{171}$).

a compound (L-16) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{172}$).

a compound (L-16) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{173}$).

a compound (L-16) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{174}$).

a compound (L-16) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{175}$).

a compound (L-16) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{176}$).

a compound represented by formula (L-17):

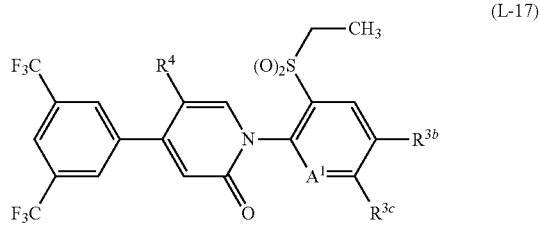

(L-17)

(hereinafter, referred to Compound (L-17)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{177}$).

a compound (L-17) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{178}$).

a compound (L-17) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{179}$).

a compound (L-17) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{180}$).

a compound (L-17) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{181}$).

a compound (L-17) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{182}$).

a compound (L-17) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{183}$).

a compound (L-17) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{184}$).

a compound (L-17) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{185}$).

a compound (L-17) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{186}$).

a compound (L-17) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{187}$).

a compound (L-17) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{188}$).

a compound (L-17) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{189}$).

a compound (L-17) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{190}$).

a compound (L-17) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{191}$).

a compound (L-17) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{192}$).

a compound represented by formula (L-18):

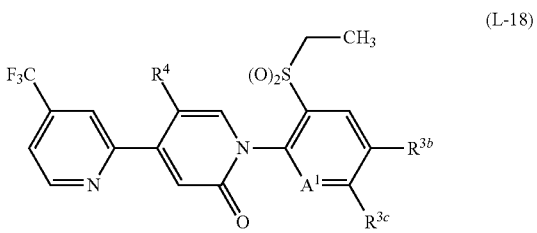

(hereinafter, referred to Compound (L-18)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{193}$).

a compound (L-18) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{194}$).

a compound (L-18) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{195}$).

a compound (L-18) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{196}$).

a compound (L-18) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{197}$).

a compound (L-18) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{198}$).

a compound (L-18) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{199}$).

a compound (L-18) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{200}$).

a compound (L-18) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{201}$).

a compound (L-18) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{202}$).

a compound (L-18) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{203}$).

a compound (L-18) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{204}$).

a compound (L-18) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{205}$).

a compound (L-18) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{206}$).

a compound (L-18) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{207}$).

a compound (L-18) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{208}$).

a compound represented by formula (L-19):

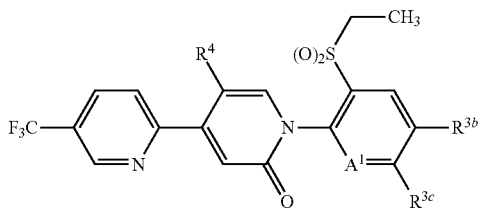

(L-19)

(hereinafter, referred to Compound (L-19)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{209}$).

a compound (L-19) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{210}$).

a compound (L-19) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{211}$).

a compound (L-19) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{212}$).

a compound (L-19) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{213}$).

a compound (L-19) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{214}$).

a compound (L-19) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{215}$).

a compound (L-19) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{216}$).

a compound (L-19) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{217}$).

a compound (L-19) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{218}$).

a compound (L-19) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{219}$).

a compound (L-19) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{220}$).

a compound (L-19) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{221}$).

a compound (L-19) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{222}$).

a compound (L-19) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{223}$).

a compound (L-19) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{224}$).

a compound represented by formula (L-20):

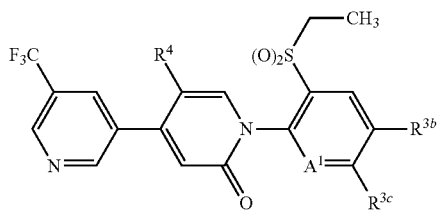

(L-20)

(hereinafter, referred to Compound (L-20)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{225}$).

a compound (L-20) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{226}$).

a compound (L-20) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{227}$).

a compound (L-20) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{228}$).

a compound (L-20) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{229}$).

a compound (L-20) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{230}$).

a compound (L-20) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{231}$).

a compound (L-20) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{232}$).

a compound (L-20) wherein $A^1$ represents a CH, $R^{3b}$ represents a hydrogen atom, $R^4$ represents a methyl group, and $R^{3'}$ represents any substituent indicated in Table 7 to Table 15 (hereinafter, referred to as Compound Class $SX_{233}$).

a compound (L-20) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{234}$).

a compound (L-20) wherein $A^1$ represents a nitrogen atom, $R^{3b}$ represents a hydrogen atom, $R^4$ represents a methyl group, and $R^{3'}$ represents any substituent indicated in Table 7 to Table 15 (hereinafter, referred to as Compound Class $SX_{235}$).

a compound (L-20) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{236}$).

a compound (L-20) wherein $A^1$ represents a CH, $R^{3b}$ represents a hydrogen atom, $R^4$ represents a methoxy group, and $R^{3'}$ represents any substituent indicated in Table 7 to Table 15 (hereinafter, referred to as Compound Class $SX_{237}$).

a compound (L-20) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{238}$).

a compound (L-20) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{239}$).

a compound (L-20) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{240}$).

a compound represented by formula (L-21):

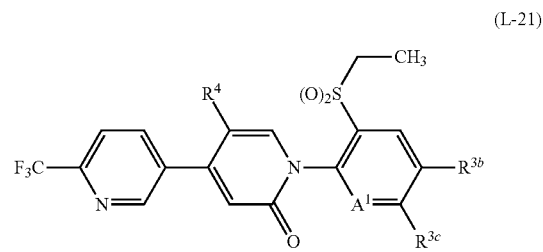

(L-21)

(hereinafter, referred to Compound (L-21)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{241}$).

a compound (L-21) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{242}$).

a compound (L-21) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{243}$).

a compound (L-21) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{244}$).

a compound (L-21) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{245}$).

a compound (L-21) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{246}$).

a compound (L-21) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{247}$).

a compound (L-21) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{248}$).

a compound (L-21) wherein $A^1$ represents a CH, $R^{3b}$ represents a hydrogen atom, $R^4$ represents a methy group, and $R^{3c}$ represents any substituent indicated in Table 7 to Table 15 (hereinafter, referred to as Compound Class $SX_{249}$).

a compound (L-21) wherein $A^1$ represents a CH, $R^{3c}$ represents a hydrogen atom, $R^4$ represents a methy group, and $R^{3b}$ represents any substituent indicated in Table 7 to Table 15 (hereinafter, referred to as Compound Class $SX_{250}$).

a compound (L-21) wherein $A^1$ represents a nitrogen atom, $R^{3b}$ represents a hydrogen atom, $R^4$ represents a methy group, and $R^{3c}$ represents any substituent indicated in Table 7 to Table 15 (hereinafter, referred to as Compound Class $SX_{251}$).

a compound (L-21) wherein $A^1$ represents a nitrogen atom, $R^{3c}$ represents a hydrogen atom, $R^4$ represents a methy group, and $R^{3b}$ represents any substituent indicated in Table 7 to Table 15 (hereinafter, referred to as Compound Class $SX_{252}$).

a compound (L-21) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{253}$).

a compound (L-21) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{254}$).

a compound (L-21) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{255}$).

a compound (L-21) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{256}$).

a compound represented by formula (L-22):

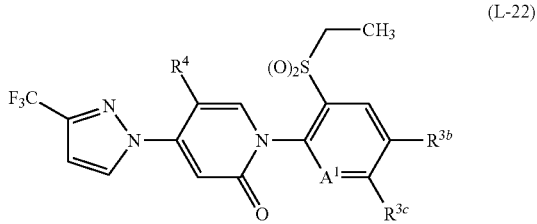

(L-22)

(hereinafter, referred to Compound (L-22)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{257}$).

a compound (L-22) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{258}$).

a compound (L-22) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{259}$).

a compound (L-22) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{260}$).

a compound (L-22) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{261}$).

a compound (L-22) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{262}$).

a compound (L-22) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{263}$).

a compound (L-22) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{264}$).

a compound (L-22) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{265}$).

a compound (L-22) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{266}$).

a compound (L-22) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{267}$).

a compound (L-22) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{268}$).

a compound (L-22) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{269}$).

a compound (L-22) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{270}$).

a compound (L-22) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{271}$).

a compound (L-22) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{272}$).

a compound represented by formula (L-23):

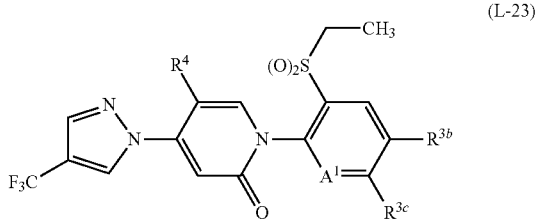

(L-23)

(hereinafter, referred to Compound (L-23)) wherein $A^1$ represents a CH, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{273}$).

a compound (L-23) wherein $A^1$ represents a CH, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{274}$).

a compound (L-23) wherein $A^1$ represents a nitrogen atom, $R^{3b}$ represents a hydrogen atom, $R^4$ represents a hydrogen atom, and $R^{3c}$ represents any substituent indicated in Table 7 to Table 15 (hereinafter, referred to as Compound Class $SX_{275}$).

a compound (L-23) wherein $A^1$ represents a nitrogen atom, $R^{3c}$ represents a hydrogen atom, $R^4$ represents a hydrogen atom, and $R^{3b}$ represents any substituent indicated in Table 7 to Table 15 (hereinafter, referred to as Compound Class $SX_{276}$).

a compound (L-23) wherein $A^1$ represents a CH, $R^{3b}$ represents a hydrogen atom, $R^4$ represents a chlorine atom, and $R^{3c}$ represents any substituent indicated in Table 7 to Table 15 (hereinafter, referred to as Compound Class $SX_{277}$).

a compound (L-23) wherein $A^1$ represents a CH, $R^{3c}$ represents a hydrogen atom, $R^4$ represents a chlorine atom, and $R^{3b}$ represents any substituent indicated in Table 7 to Table 15 (hereinafter, referred to as Compound Class $SX_{278}$).

a compound (L-23) wherein $A^1$ represents a nitrogen atom, $R^{3b}$ represents a hydrogen atom, $R^4$ represents a chlorine atom, and $R^{3c}$ represents any substituent indicated in Table 7 to Table 15 (hereinafter, referred to as Compound Class $SX_{279}$).

a compound (L-23) wherein $A^1$ represents a nitrogen atom, $R^{3c}$ represents a hydrogen atom, $R^4$ represents a chlorine atom, and $R^{3b}$ represents any substituent indicated in Table 7 to Table 15 (hereinafter, referred to as Compound Class $SX_{280}$).

a compound (L-23) wherein $A^1$ represents a CH, $R^{3b}$ represents a hydrogen atom, $R^4$ represents a methyl group, and $R^{3c}$ represents any substituent indicated in Table 7 to Table 15 (hereinafter, referred to as Compound Class $SX_{281}$).

a compound (L-23) wherein $A^1$ represents a CH, $R^{3c}$ represents a hydrogen atom, $R^4$ represents a methyl group, and $R^{3b}$ represents any substituent indicated in Table 7 to Table 15 (hereinafter, referred to as Compound Class $SX_{282}$).

a compound (L-23) wherein $A^1$ represents a nitrogen atom, $R^{3b}$ represents a hydrogen atom, $R^4$ represents a methyl group, and $R^{3c}$ represents any substituent indicated in Table 7 to Table 15 (hereinafter, referred to as Compound Class $SX_{283}$).

a compound (L-23) wherein $A^1$ represents a nitrogen atom, $R^{3c}$ represents a hydrogen atom, $R^4$ represents a methyl group, and $R^{3b}$ represents any substituent indicated in Table 7 to Table 15 (hereinafter, referred to as Compound Class $SX_{284}$).

a compound (L-23) wherein $A^1$ represents a CH, $R^{3b}$ represents a hydrogen atom, $R^4$ represents a methoxy group, and $R^{3c}$ represents any substituent indicated in Table 7 to Table 15 (hereinafter, referred to as Compound Class $SX_{285}$).

a compound (L-23) wherein $A^1$ represents a CH, $R^{3c}$ represents a hydrogen atom, $R^4$ represents a methoxy group, and $R^{3b}$ represents any substituent indicated in Table 7 to Table 15 (hereinafter, referred to as Compound Class $SX_{286}$).

a compound (L-23) wherein $A^1$ represents a nitrogen atom, $R^{3b}$ represents a hydrogen atom, $R^4$ represents a methoxy group, and $R^{3c}$ represents any substituent indicated in Table 7 to Table 15 (hereinafter, referred to as Compound Class $SX_{287}$).

a compound (L-23) wherein $A^1$ represents a nitrogen atom, $R^{3c}$ represents a hydrogen atom, $R^4$ represents a methoxy group, and $R^{3b}$ represents any substituent indicated in Table 7 to Table 15 (hereinafter, referred to as Compound Class $SX_{288}$).

a compound represented by formula (L-24):

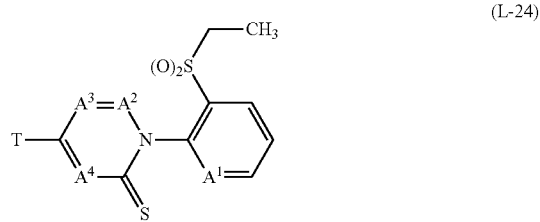

(L-24)

(hereinafter, referred to Compound (L-24)) wherein $A^1$, $A^2$, $A^3$, and $A^4$ represent each a CH, and T represents any substituent indicated in Table 1 to Table 6 (hereinafter, referred to as Compound Class $SX_{289}$).

a compound (L-24) wherein $A^1$ represents a nitrogen atom, $A^2$, $A^3$, and $A^4$ represent each a CH, and T represents any substituent indicated in Table 1 to Table 6 (hereinafter, referred to as Compound Class $SX_{290}$).

a compound (L-24) wherein $A^2$ represents a nitrogen atom, $A^1$, $A^3$, and $A^4$ represent each a CH, and T represents any substituent indicated in Table 1 to Table 6 (hereinafter, referred to as Compound Class $SX_{291}$).

a compound (L-24) wherein $A^1$ and $A^2$ represent each a nitrogen atom, $A^3$ and $A^4$ represent each a CH, and T represents any substituent indicated in Table 1 to Table 6 (hereinafter, referred to as Compound Class $SX_{292}$).

a compound (L-24) wherein $A^3$ represents a nitrogen atom, $A^1$, $A^2$, and $A^4$ represent each a CH, and T represents any substituent indicated in Table 1 to Table 6 (hereinafter, referred to as Compound Class $SX_{293}$).

a compound (L-24) wherein $A^1$ and $A^3$ represent each a nitrogen atom, $A^2$ and $A^4$ represent each a CH, and T represents any substituent indicated in Table 1 to Table 6 (hereinafter, referred to as Compound Class $SX_{294}$).

a compound (L-24) wherein $A^4$ represents a nitrogen atom, $A^1$, $A^2$ and $A^3$ represent each a CH, and T represents any substituent indicated in Table 1 to Table 6 (hereinafter, referred to as Compound Class $SX_{295}$).

a compound (L-24) wherein $A^1$ and $A^4$ represent each a nitrogen atom, $A^2$ and $A^3$ represent each a CH, and T represents any substituent indicated in Table 1 to Table 6 (hereinafter, referred to as Compound Class $SX_{296}$).

a compound represented by formula (L-25):

(hereinafter, referred to Compound (L-25)) wherein $A^1$, $A^2$, $A^3$, and $A^4$ represent each a CH, and T represents any substituent indicated in Table 1 to Table 6 (hereinafter, referred to as Compound Class $SX_{297}$).

a compound (L-25) wherein $A^1$ represents a nitrogen atom, $A^2$, $A^3$ and $A^4$ represent each a CH, and T represents any substituent indicated in Table 1 to Table 6 (hereinafter, referred to as Compound Class $SX_{298}$).

a compound (L-25) wherein $A^2$ represents a nitrogen atom, $A^1$, $A^3$ and $A^4$ represent each a CH, and T represents any substituent indicated in Table 1 to Table 6 (hereinafter, referred to as Compound Class $SX_{299}$).

a compound (L-25) wherein $A^1$ and $A^2$ represent each a nitrogen atom, $A^3$ and $A^4$ represent each a CH, and T represents any substituent indicated in Table 1 to Table 6 (hereinafter, referred to as Compound Class $SX_{300}$).

a compound (L-25) wherein $A^3$ represents a nitrogen atom, $A^1$, $A^2$ and $A^4$ represent each a CH, and T represents any substituent indicated in Table 1 to Table 6 (hereinafter, referred to as Compound Class $SX_{301}$).

a compound (L-25) wherein $A^1$ and $A^3$ represent each a nitrogen atom, and $A^2$ and $A^4$ represents each a CH, and T represents any substituents indicated in Table 1 to Table 6 (hereinafter, referred to as Compound Class $SX_{302}$).

a compound (L-25) wherein $A^4$ represent a nitrogen atom, and $A^1$, $A^2$ and $A^3$ represents each a CH, and T represents any substituents indicated in Table 1 to Table 6 (hereinafter, referred to as Compound Class $SX_{303}$).

a compound (L-25) wherein $A^1$ and $A^4$ represent each a nitrogen atom, and $A^2$ and $A^3$ represents each a CH, and T represents any substituents indicated in Table 1 to Table 6 (hereinafter, referred to as Compound Class $SX_{304}$).

a compound represented by formula (L-26):

(hereinafter, referred to Compound (L-26)) wherein $A^1$, $A^2$, $A^3$, and $A^4$ represent each a CH, and T represents any substituent indicated in Table 1 to Table 6 (hereinafter, referred to as Compound Class $SX_{305}$).

a compound (L-26) wherein $A^1$ represents a nitrogen atom, and $A^2$, $A^3$ and $A^4$ represent each a CH, and T represents any substituents indicated in Table 1 to Table 6 (hereinafter, referred to as Compound Class $SX_{306}$).

a compound (L-26) wherein $A^2$ represents a nitrogen atom, and $A^1$, $A^3$ and $A^4$ represent each a CH, and T represents any substituents indicated in Table 1 to Table 6 (hereinafter, referred to as Compound Class $SX_{307}$).

a compound (L-26) wherein $A^1$ and $A^2$ represent each a nitrogen atom, and $A^3$ and $A^4$ represent each a CH, and T represents any substituents indicated in Table 1 to Table 6 (hereinafter, referred to as Compound Class $SX_{308}$).

a compound (L-26) wherein $A^3$ represents a nitrogen atom, and $A^1$, $A^2$ and $A^4$ represent each a CH, and T represents any substituents indicated in Table 1 to Table 6 (hereinafter, referred to as Compound Class $SX_{309}$).

a compound (L-26) wherein $A^1$ and $A^3$ represent each a nitrogen atom, and $A^2$ and $A^4$ represent each a CH, and T represents any substituents indicated in Table 1 to Table 6 (hereinafter, referred to as Compound Class $SX_{310}$).

a compound (L-26) wherein $A^4$ represents a nitrogen atom, and $A^1$, $A^2$ and $A^3$ represent each a CH, and T represents any substituents indicated in Table 1 to Table 6 (hereinafter, referred to as Compound Class $SX_{311}$).

a compound (L-26) wherein $A^1$ and $A^4$ represent each a nitrogen atom, and $A^2$ and $A^3$ represent each a CH, and T represents any substituents indicated in Table 1 to Table 6 (hereinafter, referred to as Compound Class $SX_{312}$).

a compound represented by formula (L-27):

(hereinafter, referred to Compound (L-27)) wherein $A^1$, $A^2$, $A^3$, and $A^4$ represent each a CH, and T represents any substituent indicated in Table 1 to Table 6 (hereinafter, referred to as Compound Class $SX_{313}$).

a compound (L-27) wherein $A^1$ represents a nitrogen atom, and $A^2$, $A^3$ and $A^4$ represent each a CH, and T represents any substituents indicated in Table 1 to Table 6 (hereinafter, referred to as Compound Class $SX_{314}$).

a compound (L-27) wherein $A^2$ represents a nitrogen atom, and $A^1$, $A^3$ and $A^4$ represent each a CH, and T represents any substituents indicated in Table 1 to Table 6 (hereinafter, referred to as Compound Class $SX_{315}$).

a compound (L-27) wherein $A^1$ and $A^2$ represent each a nitrogen atom, and $A^3$ and $A^4$ represent each a CH, and T represents any substituents indicated in Table 1 to Table 6 (hereinafter, referred to as Compound Class $SX_{316}$).

a compound (L-27) wherein $A^3$ represents a nitrogen atom, and $A^1$, $A^2$ and $A^4$ represent each a CH, and T represents any substituents indicated in Table 1 to Table 6 (hereinafter, referred to as Compound Class $SX_{317}$).

a compound (L-27) wherein $A^1$ and $A^3$ represent each a nitrogen atom, and $A^2$ and $A^4$ represent each a CH, and T represents any substituents indicated in Table 1 to Table 6 (hereinafter, referred to as Compound Class $SX_{318}$).

a compound (L-27) wherein $A^4$ represents a nitrogen atom, and $A^1$, $A^2$ and $A^3$ represent each a CH, and T represents any substituents indicated in Table 1 to Table 6 (hereinafter, referred to as Compound Class $SX_{319}$).

a compound (L-27) wherein $A^1$ and $A^4$ represent each a nitrogen atom, and $A^2$ and $A^3$ represent each a CH, and T represents any substituents indicated in Table 1 to Table 6 (hereinafter, referred to as Compound Class $SX_{320}$).

a compound represented by formula (L-28):

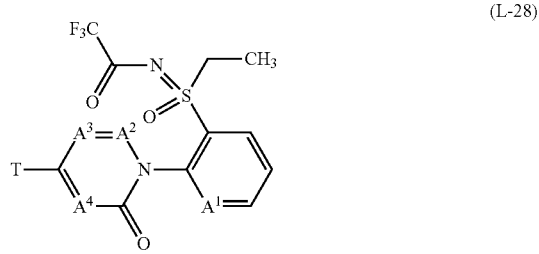

(L-28)

(hereinafter, referred to Compound (L-28)) wherein $A^1$, $A^2$, $A^3$, and $A^4$ represent each a CH, and T represents any substituent indicated in Table 1 to Table 6 (hereinafter, referred to as Compound Class $SX_{321}$).

a compound (L-28) wherein $A^1$ represents a nitrogen atom, and $A^2$, $A^3$ and $A^4$ represent each a CH, and T represents any substituents indicated in Table 1 to Table 6 (hereinafter, referred to as Compound Class $SX_{322}$).

a compound (L-28) wherein $A^2$ represents a nitrogen atom, and $A^1$, $A^3$ and $A^4$ represent each a CH, and T represents any substituents indicated in Table 1 to Table 6 (hereinafter, referred to as Compound Class $SX_{323}$).

a compound (L-28) wherein $A^1$ and $A^2$ represent each a nitrogen atom, and $A^3$ and $A^4$ represent each a CH, and T represents any substituents indicated in Table 1 to Table 6 (hereinafter, referred to as Compound Class $SX_{324}$).

a compound (L-28) wherein $A^3$ represents a nitrogen atom, and $A^1$, $A^2$ and $A^4$ represent each a CH, and T represents any substituents indicated in Table 1 to Table 6 (hereinafter, referred to as Compound Class $SX_{325}$).

a compound (L-28) wherein $A^1$ and $A^3$ represent each a nitrogen atom, and $A^2$ and $A^4$ represent each a CH, and T represents any substituents indicated in Table 1 to Table 6 (hereinafter, referred to as Compound Class $SX_{326}$).

a compound (L-28) wherein $A^4$ represents a nitrogen atom, and $A^1$, $A^2$ and $A^3$ represent each a CH, and T represents any substituents indicated in Table 1 to Table 6 (hereinafter, referred to as Compound Class $SX_{327}$).

a compound (L-28) wherein $A^1$ and $A^4$ represent each a nitrogen atom, and $A^2$ and $A^3$ represent each a CH, and T represents any substituents indicated in Table 1 to Table 6 (hereinafter, referred to as Compound Class $SX_{328}$).

a compound represented by formula (L-29):

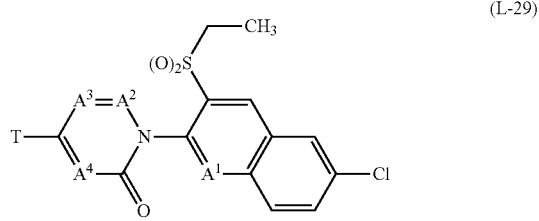

(L-29)

(hereinafter, referred to Compound (L-29)) wherein $A^1$, $A^2$, $A^3$, and $A^4$ represent each a CH, and T represents any substituent indicated in Table 1 to Table 6 (hereinafter, referred to as Compound Class $SX_{329}$).

a compound (L-29) wherein $A^1$ represents a nitrogen atom, and $A^2$, $A^3$ and $A^4$ represent each a CH, and T represents any substituents indicated in Table 1 to Table 6 (hereinafter, referred to as Compound Class $SX_{330}$).

a compound (L-29) wherein $A^2$ represents a nitrogen atom, and $A^1$, $A^3$ and $A^4$ represent each a CH, and T represents any substituents indicated in Table 1 to Table 6 (hereinafter, referred to as Compound Class $SX_{331}$).

a compound (L-29) wherein $A^1$ and $A^2$ represent each a nitrogen atom, and $A^3$ and $A^4$ represent each a CH, and T represents any substituents indicated in Table 1 to Table 6 (hereinafter, referred to as Compound Class $SX_{332}$).

a compound (L-29) wherein $A^3$ represents a nitrogen atom, and $A^1$, $A^2$ and $A^4$ represent each a CH, and T represents any substituents indicated in Table 1 to Table 6 (hereinafter, referred to as Compound Class $SX_{333}$).

a compound (L-29) wherein $A^1$ and $A^3$ represent each a nitrogen atom, and $A^2$ and $A^4$ represent each a CH, and T represents any substituents indicated in Table 1 to Table 6 (hereinafter, referred to as Compound Class $SX_{334}$).

a compound (L-29) wherein $A^4$ represents a nitrogen atom, and $A^1$, $A^2$ and $A^3$ represent each a CH, and T represents any substituents indicated in Table 1 to Table 6 (hereinafter, referred to as Compound Class $SX_{335}$).

a compound (L-29) wherein $A^1$ and $A^4$ represent each a nitrogen atom, and $A^2$ and $A^3$ represent each a CH, and T represents any substituents indicated in Table 1 to Table 6 (hereinafter, referred to as Compound Class $SX_{336}$).

a compound represented by formula (L-30):

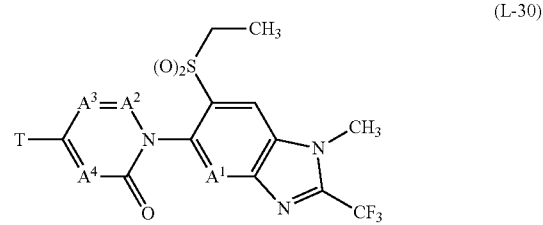

(L-30)

(hereinafter, referred to Compound (L-30)) wherein $A^1$, $A^2$, $A^3$, and $A^4$ represent each a CH, and T represents any substituent indicated in Table 1 to Table 6 (hereinafter, referred to as Compound Class $SX_{337}$).

a compound (L-30) wherein $A^1$ represents a nitrogen atom, and $A^2$, $A^3$ and $A^4$ represent each a CH, and T represents any substituents indicated in Table 1 to Table 6 (hereinafter, referred to as Compound Class $SX_{338}$).

a compound (L-30) wherein $A^2$ represents a nitrogen atom, and $A^1$, $A^3$ and $A^4$ represent each a CH, and T represents any substituents indicated in Table 1 to Table 6 (hereinafter, referred to as Compound Class $SX_{339}$).

a compound (L-30) wherein $A^1$ and $A^2$ represent each a nitrogen atom, and $A^3$ and $A^4$ represent each a CH, and T represents any substituents indicated in Table 1 to Table 6 (hereinafter, referred to as Compound Class $SX_{340}$).

a compound (L-30) wherein $A^3$ represents a nitrogen atom, and $A^1$, $A^2$ and $A^4$ represent each a CH, and T represents any substituents indicated in Table 1 to Table 6 (hereinafter, referred to as Compound Class $SX_{341}$).

a compound (L-30) wherein $A^1$ and $A^3$ represent each a nitrogen atom, and $A^2$ and $A^4$ represent each a CH, and T represents any substituents indicated in Table 1 to Table 6 (hereinafter, referred to as Compound Class $SX_{342}$).

a compound (L-30) wherein $A^4$ represents a nitrogen atom, and $A^1$, $A^2$ and $A^3$ represent each a CH, and T represents any substituents indicated in Table 1 to Table 6 (hereinafter, referred to as Compound Class $SX_{343}$).

a compound (L-30) wherein $A^1$ and $A^4$ represent each a nitrogen atom, and $A^2$ and $A^3$ represent each a CH, and T represents any substituents indicated in Table 1 to Table 6 (hereinafter, referred to as Compound Class $SX_{344}$).

a compound represented by formula (L-3).

(L-31)

[Chemical structure]

(hereinafter, referred to Compound (L-31)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{345}$).

a compound (L-31) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{346}$).

a compound (L-31) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{347}$).

a compound (L-31) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{348}$).

a compound (L-31) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{349}$).

a compound (L-31) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{350}$).

a compound (L-31) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{351}$).

a compound (L-31) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{352}$).

a compound (L-31) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{353}$).

a compound (L-31) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{354}$).

a compound (L-31) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{355}$).

a compound (L-31) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{356}$).

a compound (L-31) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{357}$).

a compound (L-31) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{358}$).

a compound (L-31) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{359}$).

a compound (L-31) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{360}$).

a compound (L-31) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{361}$).

a compound (L-31) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{362}$).

a compound (L-31) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{363}$).

a compound (L-31) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{364}$).

a compound (L-31) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{365}$).

a compound (L-31) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{366}$).

a compound (L-31) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{367}$).

a compound (L-31) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{368}$).

a compound (L-31) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{369}$).

a compound (L-31) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{370}$).

a compound (L-31) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{371}$).

a compound (L-31) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{372}$).

a compound represented by formula (L-32):

(L-32)

(hereinafter, referred to Compound (L-32)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{373}$).

a compound (L-32) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{374}$).

a compound (L-32) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{375}$).

a compound (L-32) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{376}$).

a compound (L-32) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{377}$).

a compound (L-32) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{378}$).

a compound (L-32) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{379}$).

a compound (L-32) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{380}$).

a compound (L-32) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{381}$).

a compound (L-32) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{382}$).

a compound (L-32) wherein $A^1$ represents a nitrogen atom, $R^{4a}$ represents a hydrogen atom, $R^{4c}$ represents a chlorine atom. $R^{3b}$ represents a hydrogen atom, and $R^{3c}$ represents any substituents indicated in Table 7 to Table 15 (hereinafter, referred to as Compound Class $SX_{383}$).

a compound (L-32) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{384}$).

a compound (L-32) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{385}$).

a compound (L-32) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{386}$).

a compound (L-32) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{387}$).

a compound (L-32) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{388}$).

a compound (L-32) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{389}$).

a compound (L-32) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{390}$).

a compound (L-32) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{391}$).

a compound (L-32) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{392}$).

a compound (L-32) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $S_{X393}$).

a compound (L-32) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{394}$).

a compound (L-32) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{395}$).

a compound (L-32) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{396}$).

a compound (L-32) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{397}$).

a compound (L-32) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{398}$).

a compound (L-32) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{399}$).

a compound (L-32) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{400}$).

a compound represented by formula (L-33):

(L-33)

a compound (L-33)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{401}$).

a compound (L-33) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{402}$).

a compound (L-33) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{403}$).

a compound (L-33) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{404}$).

a compound (L-33) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{405}$).

a compound (L-33) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{406}$).

a compound (L-33) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{40}$).

a compound (L-33) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{408}$).

a compound (L-33) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{409}$).

a compound (L-33) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{410}$).

a compound (L-33) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{411}$).

a compound (L-33) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{412}$).

a compound (L-33) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{413}$).

a compound (L-33) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{414}$).

a compound (L-33) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{415}$).

a compound (L-33) wherein $A^1$ represents a nitrogen atom, $R^{4a}$ represents a methyl group, $R^{4c}$ represents a hydrogen atom. $R^{3c}$ represents a hydrogen atom, and $R^{3b}$ represents any substituents indicated in Table 7 to Table 15 (hereinafter, referred to as Compound Class $SX_{416}$).

a compound (L-33) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{417}$).

a compound (L-33) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{418}$).

a compound (L-33) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{419}$).

a compound (L-33) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{420}$).

a compound (L-33) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{421}$).

a compound (L-33) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{422}$).

a compound (L-33) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{423}$).

a compound (L-33) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{424}$).

a compound (L-33) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{425}$).

a compound (L-33) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{426}$).

a compound (L-33) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{427}$).

a compound (L-33) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{428}$).

a compound represented by formula (L-34):

(hereinafter, referred to Compound (L-34)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{429}$).

a compound (L-34) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{430}$).

a compound (L-34) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{431}$).

a compound (L-34) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{432}$).

a compound (L-34) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{433}$).

a compound (L-34) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{434}$).

a compound (L-34) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{435}$).

a compound (L-34) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{436}$).

a compound (L-34) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{437}$).

a compound (L-34) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{438}$).

a compound (L-34) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{439}$).

a compound (L-34) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{440}$).

a compound (L-34) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{441}$).

a compound (L-34) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{442}$).

a compound (L-34) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{443}$).

a compound (L-34) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{444}$).

a compound (L-34) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{445}$).

a compound (L-34) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{446}$).

a compound (L-34) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{447}$).

a compound (L-34) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{448}$).

a compound (L-34) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{449}$).

a compound (L-34) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{450}$).

a compound (L-34) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{451}$).

a compound (L-34) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{452}$).

a compound (L-34) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{453}$).

a compound (L-34) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{454}$).

a compound (L-34) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{455}$).

a compound (L-34) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{456}$).

a compound represented by formula (L-35):

(L-35)

(hereinafter, referred to Compound (L-35)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{457}$).

a compound (L-35) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{458}$).

a compound (L-35) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{459}$).

a compound (L-35) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{460}$).

a compound (L-35) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{461}$).

a compound (L-35) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{462}$).

a compound (L-35) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{463}$).

a compound (L-35) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{464}$).

a compound (L-35) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{465}$).

a compound (L-35) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{466}$).

a compound (L-35) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{467}$).

a compound (L-35) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{468}$).

a compound (L-35) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{469}$).

a compound (L-35) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{470}$).

a compound (L-35) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{471}$).

a compound (L-35) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{472}$).

a compound (L-35) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{473}$).

a compound (L-35) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{474}$).

a compound (L-35) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{475}$).

a compound (L-35) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{476}$).

a compound (L-35) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{477}$).

a compound (L-35) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{478}$).

a compound (L-35) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{479}$).

a compound (L-35) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{480}$).

a compound (L-35) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{481}$).

a compound (L-35) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{482}$).

a compound (L-35) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{483}$).

a compound (L-35) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{484}$).

a compound represented by formula (L-36):

(L-36)

(hereinafter, referred to Compound (L-36)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{485}$).

a compound (L-36) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{486}$).

a compound (L-36) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{487}$).

a compound (L-36) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{488}$).

a compound (L-36) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{489}$).

a compound (L-36) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{490}$).

a compound (L-36) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{491}$).

a compound (L-36) wherein $A^1$ represents a nitrogen atom, $R^{4a}$ represents a chlorine atom, $R^{4c}$ represents a hydrogen atom. $R^{3c}$ represents a hydrogen atom, and $R^{3b}$ represents any substituents indicated in Table 7 to Table 15 (hereinafter, referred to as Compound Class $SX_{492}$).

a compound (L-36) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{493}$).

a compound (L-36) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{494}$).

a compound (L-36) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{495}$).

a compound (L-36) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{496}$).

a compound (L-36) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{497}$).

a compound (L-36) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{498}$).

a compound (L-36) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{499}$).

a compound (L-36) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{500}$).

a compound (L-36) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{501}$).

a compound (L-36) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{502}$).

a compound (L-36) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{503}$).

a compound (L-36) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{504}$).

a compound (L-36) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{505}$).

a compound (L-36) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{506}$).

a compound (L-36) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{507}$).

a compound (L-36) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{508}$).

a compound (L-36) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{509}$).

a compound (L-36) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{510}$).

a compound (L-36) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{511}$).

a compound (L-36) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{512}$).

a compound represented by formula (L-37):

$$\text{(L-37)}$$

[Chemical structure showing a pyrimidinone compound with F$_3$C groups on a phenyl ring, and an (O)$_2$S-CH$_3$ group, with substituents $R^{4a}$, $R^{4c}$, $R^{3b}$, $R^{3c}$, and $A^1$]

(hereinafter, referred to Compound (L-37)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{513}$).

a compound (L-37) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{514}$).

a compound (L-37) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{515}$).

a compound (L-37) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{516}$).

a compound (L-37) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{517}$).

a compound (L-37) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{518}$).

a compound (L-37) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{519}$).

a compound (L-37) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{520}$).

a compound (L-37) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{521}$).

a compound (L-37) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{522}$).

a compound (L-37) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{523}$).

a compound (L-37) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{524}$).

a compound (L-37) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{525}$).

a compound (L-37) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{526}$).

a compound (L-37) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{527}$).

a compound (L-37) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{528}$).

a compound (L-37) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{529}$).

a compound (L-37) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{530}$).

a compound (L-37) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{531}$).

a compound (L-37) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{532}$).

a compound (L-37) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{533}$).

a compound (L-37) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{534}$).

a compound (L-37) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{535}$).

a compound (L-37) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{536}$).

a compound (L-37) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{537}$).

a compound (L-37) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{538}$).

a compound (L-37) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{539}$).

a compound (L-37) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{540}$).

a compound represented by formula (L-38):

(L-38)

(hereinafter, referred to Compound (L-38)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{541}$).

a compound (L-38) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{542}$).

a compound (L-38) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{543}$).

a compound (L-38) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{544}$).

a compound (L-38) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{545}$).

a compound (L-38) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{546}$).

a compound (L-38) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{547}$).

a compound (L-38) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{548}$).

a compound (L-38) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{549}$).

a compound (L-38) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{550}$).

a compound (L-38) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{551}$).

a compound (L-38) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{552}$).

a compound (L-38) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{553}$).

a compound (L-38) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{554}$).

a compound (L-38) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{555}$).

a compound (L-38) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{556}$).

a compound (L-38) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{557}$).

a compound (L-38) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{558}$).

a compound (L-38) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{559}$).

a compound (L-38) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{560}$).

a compound (L-38) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{561}$).

a compound (L-38) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{562}$).

a compound (L-38) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{563}$).

a compound (L-38) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{564}$).

a compound (L-38) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{565}$).

a compound (L-38) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{566}$).

a compound (L-38) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{567}$).

a compound (L-38) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{568}$).

a compound represented by formula (L-39):

(L-39)

[Chemical structure of compound L-39]

(hereinafter, referred to Compound (L-39)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{569}$).

a compound (L-39) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{570}$).

a compound (L-39) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{571}$).

a compound (L-39) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{572}$).

a compound (L-39) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{573}$).

a compound (L-39) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{574}$).

a compound (L-39) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{575}$).

a compound (L-39) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{576}$).

a compound (L-39) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{577}$).

a compound (L-39) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{578}$).

a compound (L-39) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{579}$).

a compound (L-39) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{580}$).

a compound (L-39) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{581}$).

a compound (L-39) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{582}$).

a compound (L-39) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{583}$).

a compound (L-39) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{584}$).

a compound (L-39) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{585}$).

a compound (L-39) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{586}$).

a compound (L-39) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_5$).

a compound (L-39) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_5$).

a compound (L-39) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{589}$).

a compound (L-39) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{590}$).

a compound (L-39) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{591}$).

a compound (L-39) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{592}$).

a compound (L-39) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{593}$).

a compound (L-39) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{594}$).

a compound (L-39) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{595}$).

a compound (L-39) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{596}$).

a compound represented by formula (L-40):

(hereinafter, referred to Compound (L-40)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{597}$).

a compound (L-40) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{598}$).

a compound (L-40) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{599}$).

a compound (L-40) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{600}$).

a compound (L-40) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{601}$).

a compound (L-40) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{602}$).

a compound (L-40) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{603}$).

a compound (L-40) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{604}$).

a compound (L-40) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{605}$).

a compound (L-40) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{606}$).

a compound (L-40) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{607}$).

a compound (L-40) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{608}$).

a compound (L-40) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{609}$).

a compound (L-40) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{610}$).

a compound (L-40) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{611}$).

a compound (L-40) wherein $A^1$ represents a nitrogen atom, $R^{4a}$ represents a methyl group, $R^{4c}$ represents a hydrogen atom. $R^{3c}$ represents a hydrogen atom, and $R^{3b}$ represents any substituents indicated in Table 7 to Table 15 (hereinafter, referred to as Compound Class $SX_{612}$).

a compound (L-40) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{613}$).

a compound (L-40) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{614}$).

a compound (L-40) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{615}$).

a compound (L-40) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{616}$).

a compound (L-40) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{617}$).

a compound (L-40) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{618}$).

a compound (L-40) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{619}$).

a compound (L-40) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{620}$).

a compound (L-40) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{621}$).

a compound (L-40) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{622}$).

a compound (L-40) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{623}$).

a compound (L-40) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{624}$).

a compound represented by formula (L-41):

(L-41)

(hereinafter, referred to Compound (L-41)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{625}$).

a compound (L-41) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{626}$).

a compound (L-41) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{62}7$).

a compound (L-41) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{628}$).

a compound (L-41) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{629}$).

a compound (L-41) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{630}$).

a compound (L-41) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{631}$).

a compound (L-41) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{632}$).

a compound (L-41) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{633}$).

a compound (L-41) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{634}$).

a compound (L-41) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{635}$).

a compound (L-41) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{636}$).

a compound (L-41) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{637}$).

a compound (L-41) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{638}$).

a compound (L-41) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{639}$).

a compound (L-41) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{640}$).

a compound (L-41) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{641}$).

a compound (L-41) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{642}$).

a compound (L-41) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{643}$).

a compound (L-41) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{644}$).

a compound (L-41) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{645}$).

a compound (L-41) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{646}$).

a compound (L-41) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{647}$).

a compound (L-41) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{648}$).

a compound (L-41) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{649}$).

a compound (L-41) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{650}$).

a compound (L-41) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{651}$).

a compound (L-41) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{652}$).

a compound represented by formula (L-42):

(L-42)

(hereinafter, referred to Compound (L-42)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{653}$).

a compound (L-42) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{654}$).

a compound (L-42) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{655}$).

a compound (L-42) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{656}$).

a compound (L-42) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{657}$).

a compound (L-42) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{658}$).

a compound (L-42) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{659}$).

a compound (L-42) wherein $A^1$ represents a nitrogen atom, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{660}$).

a compound (L-42) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{661}$).

a compound (L-42) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{662}$).

a compound (L-42) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{663}$).

a compound (L-42) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{664}$).

a compound (L-42) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{665}$).

a compound (L-42) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{666}$).

a compound (L-42) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{667}$).

a compound (L-42) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{668}$).

a compound (L-42) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{669}$).

a compound (L-42) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{670}$).

a compound (L-42) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{671}$).

a compound (L-42) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{672}$).

a compound (L-42) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{673}$).

a compound (L-42) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{674}$).

a compound (L-42) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{675}$).

a compound (L-42) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{676}$).

a compound (L-42) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{677}$).

a compound (L-42) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{678}$).

a compound (L-42) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{679}$).

a compound (L-42) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{680}$).

a compound represented by formula (L-43):

$$\text{(L-43)}$$

(hereinafter, referred to Compound (L-43)) wherein $A^1$ represents a CH, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{681}$).

a compound (L-43) wherein $A^1$ represents a CH, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{682}$).

a compound (L-43) wherein $A^1$ represents a nitrogen atom, $R^{4a}$ represents a hydrogen atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{683}$).

a compound (L-43) wherein $A^1$ represents a nitrogen atom, $R^{4a}$ represents a hydrogen atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{684}$).

a compound (L-43) wherein $A^1$ represents a CH, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{685}$).

a compound (L-43) wherein $A^1$ represents a CH, $R^{4a}$ represents a chlorine atom, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{686}$).

a compound (L-43) wherein $A^1$ represents a nitrogen atom, $R^{4a}$ represents a chlorine atom, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{687}$).

a compound (L-43) wherein $A^1$ represents a nitrogen atom, $R^{4a}$ represents a chlorine atom, $R^{4c}$ represents a hydrogen atom. $R^{3c}$ represents a hydrogen atom, and $R^{3b}$ represents any substituents indicated in Table 7 to Table 15 (hereinafter, referred to as Compound Class $SX_{688}$).

a compound (L-43) wherein $A^1$ represents a CH, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{689}$).

a compound (L-43) wherein $A^1$ represents a CH, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{690}$).

a compound (L-43) wherein $A^1$ represents a nitrogen atom, $R^{4a}$ represents a hydrogen atom, $R^{4c}$ represents a chlorine atom, $R^{3b}$ represents a hydrogen atom, and $R^{3c}$ represents any substituents indicated in Table 7 to Table 15 (hereinafter, referred to as Compound Class $SX_{691}$).

a compound (L-43) wherein $A^1$ represents a nitrogen atom, $R^{4a}$ represents a hydrogen atom, $R^{4c}$ represents a chlorine atom, $R^{3c}$ represents a hydrogen atom, and $R^{3b}$ represents any substituents indicated in Table 7 to Table 15 (hereinafter, referred to as Compound Class $SX_{692}$).

a compound (L-43) wherein $A^1$ represents a CH, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{693}$).

a compound (L-43) wherein $A^1$ represents a CH, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{694}$).

a compound (L-43) wherein $A^1$ represents a nitrogen atom, $R^{4a}$ represents a methyl group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{695}$).

a compound (L-43) wherein $A^1$ represents a nitrogen atom, $R^{4a}$ represents a methyl group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{696}$).

a compound (L-43) wherein $A^1$ represents a CH, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{697}$).

a compound (L-43) wherein $A^1$ represents a CH, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{698}$).

a compound (L-43) wherein $A^1$ represents a nitrogen atom, $R^{4a}$ represents a hydrogen atom, $R^{4c}$ represents a methyl group, $R^{3b}$ represents a hydrogen atom, and $R^{3c}$ represents any substituents indicated in Table 7 to Table 15 (hereinafter, referred to as Compound Class $SX_{699}$).

a compound (L-43) wherein $A^1$ represents a nitrogen atom, $R^{4a}$ represents a hydrogen atom, $R^{4c}$ represents a methyl group, $R^{3c}$ represents a hydrogen atom, and $R^{3b}$ represents any substituents indicated in Table 7 to Table 15 (hereinafter, referred to as Compound Class $SX_{700}$).

a compound (L-43) wherein $A^1$ represents a CH, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{701}$).

a compound (L-43) wherein $A^1$ represents a CH, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{702}$).

a compound (L-43) wherein $A^1$ represents a nitrogen atom, $R^{4a}$ represents a methoxy group, $R^{4c}$ represents a hydrogen atom, $R^{3b}$ represents a hydrogen atom, and $R^{3c}$ represents any substituents indicated in Table 7 to Table 15 (hereinafter, referred to as Compound Class $SX_{703}$).

a compound (L-43) wherein $A^1$ represents a nitrogen atom, $R^{4a}$ represents a methoxy group, $R^{4c}$ represents a hydrogen atom, $R^{3c}$ represents a hydrogen atom, and $R^{3b}$ represents any substituents indicated in Table 7 to Table 15 (hereinafter, referred to as Compound Class $SX_{704}$).

a compound (L-43) wherein $A^1$ represents a CH, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{705}$.

a compound (L-43) wherein $A^1$ represents a CH, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{706}$.

a compound (L-43) wherein $A^1$ represents a nitrogen atom, $R^{4a}$ represents a hydrogen atom, $R^{4c}$ represents a methoxy group, $R^{3b}$ represents a hydrogen atom, and $R^{3c}$ represents any substituents indicated in Table 7 to Table 15 (hereinafter, referred to as Compound Class $SX_{707}$.

a compound (L-43) wherein $A^1$ represents a nitrogen atom, $R^{4a}$ represents a hydrogen atom, $R^{4c}$ represents a methoxy group, $R^{3c}$ represents a hydrogen atom, and $R^{3b}$ represents any substituents indicated in Table 7 to Table 15 (hereinafter, referred to as Compound Class $SX_{708}$.

The compound of the present invention may be mixed or combined with one or more kinds of agrochemical active ingredients selected from a group consisting of the following Group (a), Group (b), Group (c), and Group (d) (hereinafter, referred to as Present active ingredient).

Group (a) represents an insecticidal ingredient group, a miticidal ingredient group, or a nematicidal ingredient group, which is selected from the group consisting of the following sub group a-1 to sub group a-10.
Sub group a-1: Carbamate acetylcholinesterase (AChE) inhibitors
Sub group a-2: Organophosphorus acetylcholinesterase (AChE) inhibitors
Sub group a-3: GABA-gated chloride channel blockers
Sub group a-4: GABA-gated chloride channel allosteric modulators
Sub group a-5: Sodium channel modulators
Sub group a-6: Nicotinic acetylcholine receptor (nAChR) competitive modulators
Sub group a-7: Ryanodine receptor modulators
Sub group a-8: Microbial materials
Sub group a-9: Nematicidal ingredients
Sub group a-10: The other group as insecticides and miticides Group (b) represents a fungicidal active ingredient group selected from the group consisting of the following sub group b-1 to sub group b-18.
Sub group b-1: PA fungicides (Phenyl amide)
Sub group b-2: MBC fungicides (methyl benzimidazole carbamate)
Sub group b-3: Thiazole carboxamides
Sub group b-4: SDHI (Succinate dehydrogenase inhibitors)
Sub group b-5: QoI fungicides (Qo Inhibitors)
Sub group b-6: QiI fungicides (Qi Inhibitors)
Sub group b-7: Thiophene carboxamides
Sub group b-8: AP fungicides (Anilinopyrimidine)
Sub group b-9: PP fungicides (Phenylpyrrole)
Sub group b-10: AH fungicides (Aromatic hydrocarbons)
Sub group b-11: DMI fungicides (Demethylation inhibitors)
Sub group b-12: CCA fungicides (Carboxylic acid amide)
Sub group b-13: Piperidinyl thiazole isoxazoline
Sub group b-14: Tetrazolyl oxime
Sub group b-15: Dithiocarbamate
Sub group b-16: Phthalimide
Sub group b-17: Microbial fungicides
Sub group b-18: Other fungicides Group (c) represents a plant growth modulating ingredients group selected from the group consisting of the following sub group c-1, sub group c-2, and sub group c-3.
Sub group c-1: Plant growth modulating compounds
Sub group c-2: Mycorrhizal fungi group
Sub group c-3: Root nodule bacteria group Group (D) represents a phytotoxicity-reducing ingredient group.

Examples of the combination of the Present active ingredient and the Present compound are described below. The symbol of "SX" represents any one of the Present compound selected from the Compound Class $SX_1$ to the Compound Class $SX_{708}$. Also, all of the below-mentioned present active ingredient are known active ingredients, and are commercially available or may be produced by the known method. If the present active ingredient is a bacteria, it is available from the bacterial authority depository. The numerical number in bracket represents a CAS register number.

Examples of the combination of the Present active ingredient of the above sub group a-1 and the Present compound:
alanycarb+SX, aldicarb+SX, bendiocarb+SX, benfuracarb+SX, butocarboxim+SX, butoxycarboxim+SX, carbaryl: NAC+SX, carbofuran+SX, carbosulfan+SX, ethiofencarb+SX, fenobucarb: BPMC+SX, formetanate+SX, furathiocarb+SX, isoprocarb: MIPC+SX, methiocarb+SX, methomyl+SX, metolcarb+SX, oxamyl+SX, pirimicarb+SX, propoxur: PHC+SX, thiodicarb+SX, thiofanox+SX, triazamate+SX, trimethacarb+SX, XMC+SX, xylylcarb+SX.

Examples of the combination of the Present active ingredient of the above sub group a-2 and the Present compound:
acephate+SX, azamethiphos+SX, azinphos-ethyl+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos: CYAP+SX, demeton-S-methyl+SX, diazinon+SX, dichlorvos: DDVP+SX, dicrotophos+SX, dimethoate+SX, dimethylvinphos+SX, disulfoton+SX, EPN+SX, ethion+SX, ethoprophos+SX, famphur+SX, fenamiphos+SX, fenitrothion: MEP+SX, fenthion: MPP+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion: DMTP+SX, mevinphos+SX, monocrotophos+SX, naled: BRP+SX, omethoate+SX, oxydemetonmethyl+SX, parathion+SX, parathion-methyl+SX, phenthoate: PAP+SX, phorate+SX, phosalone+SX, phosmet: PMP+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon: DEP+SX, vamidothion+SX.

Examples of the combination of the Present active ingredient of the above sub group a-3 and the Present compound:
ethiprole+SX, fipronil+SX, flufiprole+SX, chlordane+SX, endosulfan+SX, alpha-endosulfan+SX.

Examples of the combination of the Present active ingredient of the above sub group a-4 and the Present compound:
afoxolaner+SX, fluralaner+SX, broflanilide+SX, fluxametamide+SX.

Examples of the combination of the Present active ingredient of the above sub group a-5 and the Present compound:
acrinathrin+SX, allethrin+SX, bifenthrin+SX, kappa-bifenthrin+SX, bioallethrin+SX, bioresmethrin+SX, cycloprothrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, betacypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silafluofen+SX, tefluthrin+SX, kappa-tefluthrin+SX, tetramethrin+SX, tetramethylfluthrin+SX, tralomethrin+SX, transfluthrin+SX, benfluthrin+SX, flufenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX.

Examples of the combination of the Present active ingredient of the above sub group a-6 and the Present compound:
acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, (E)-N-{1-[(6-chloropyridin-3-yl)methyl]pyridine-2(1H)-ylidene}-2,2,2-trifluoroacetamide (1689566-03-7, hereinafter referred to as insecticidal compound α1)+SX.

Examples of the combination of the Present active ingredient of the above sub group a-7 and the Present compound:
chlorantraniliprole+SX, cyantraniliprole+SX, cyclonilliprole+SX, flubendiamide+SX, tetraniliprole+SX, cyhalodiamide+SX, 3-bromo-N-[2,4-dichloro-6-(methylcarbamoyl)phenyl]-1-(3,5-dichloropyridin-2-yl)-1H-pyrazole-5-carboxamide (1104384-14-6)+SX.

Examples of the combination of the Present active ingredient of the above sub group a-8 and the Present compound:
*Beauveria bassiana*+SX, *Beauveria brongniartii*+SX, *Paecilomyces fumosoroseus*+SX, *Paecilomyces lilacinus*+SX, *Paecilomyces tenuipes*+SX, *Verticillium lecani*+SX, *Arthrobotrys dactyloides*+SX, *Bacillus thuringiensis*+SX, *Bacillus firmus* strain I-1582+SX, *Bacillus firmus* GB-126+SX, *Bacillus megaterium*+SX, *Hirsutella rhossiliensis*+SX, *Hirsutella minnesotensis*+SX, *Monacrosporium phymatopagus*+SX, *Pasteuria nishizawae*+SX, *Pasteuria penetrans*+SX, *Pasteuria usgae*+SX, *Verticillium chlamydosporium*+SX.

Examples of the combination of the Present active ingredient of the above sub group a-9 and the Present compound:
abamectin+SX, fluazaindolizine+SX, fluensulfone+SX, fluopyram+SX, tioxazafen+SX.

Examples of the combination of the Present active ingredient of the above sub group a-10 and the Present compound:
spinetoram+SX, spinosad+SX, emamectin-benzoate+SX, lepimectin+SX, milbemectin+SX, ivermectin+SX, milbemycin oxime+SX, moxidectin+SX, doramectin+SX, selamectin+SX, eprinomectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetradifon+SX, chlorfenapyr+SX, DNOC (2-methyl-4,6-dinitrophenol)+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromafenozide+SX, halofenozide+SX, methoxyfenozide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX,
N-[3-chloro-1-(pyridin-3-yl)-1H-pyrazol-4-yl]-N-ethyl-3-(3,3,3-trifluoropropylsulfanyl)propanamide (1477919-27-9)+SX,
N-[3-chloro-1-(pyridin-3-yl)-1H-pyrazol-4-yl]-N-ethyl-3-(3,3,3-trifluoropropanesulfinyl)propanamide (1477923-37-7)+SX, benzpyrimoxan+SX, acynonapyr+SX, spiropidion+SX, 2-[3-(ethanesulfonyl)pyridin-2-yl]-5-(trifluoromethanesulfonyl)benzoxazole (1616678-32-0)+SX,
4-[5-(3,5-dichlorophenyl)-5-(trifluoromethyl)-4,5-dihydro-1,2-oxazol-3-yl]-2-methyl-N-(1-oxothiethan-3-yl)benzamide (1241050-20-3)+SX,
3-methoxy-N-(5-{5-(trifluoromethyl)-5-[3-(trifluoromethyl)phenyl]-4,5-dihydro-1,2-oxazol-3-yl}indan-1-yl)propanamide (1118626-57-5)+SX,
N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX,
N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX,
N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX,
1-{2-fluoro-4-methyl-5-[(2,2,2-trifluoroethyl)sulfinyl]phenyl}-3-(trifluoromethyl)-1H-1,2,4-triazole-5-amine (885026-50-6)+SX.

Examples of the combination of the Present active ingredient of the above sub group b-1 and the Present compound:
benalaxyl+SX, benalaxyl-M+SX, furalaxyl+SX, metalaxyl+SX, metalaxyl-M+SX, oxadixyl+SX, ofurace+SX.

Examples of the combination of the Present active ingredient of the above sub group b-2 and the Present compound:
benomyl+SX, carbendazim+SX, fuberidazole+SX, thiabendazole+SX, thiophanate+SX, thiophanate-methyl+SX.

Examples of the combination of the Present active ingredient of the above sub group b-3 and the Present compound:
ethaboxam+SX.

Examples of the combination of the Present active ingredient of the above sub group b-4 and the Present compound:
benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, fluxapyroxad+SX, furametpyr+SX, isopyrazam+SX, penflufen+SX, penthiopyrad+SX, sedaxane+SX, pydiflumetofen+SX, boscalid+SX, pyraziflumid+SX, 3-difluoromethyl-N-methoxy-1-methyl-N-[(1R)-1-methyl-2-(2,4,6-trichlorophenyl)ethyl]pyrazol-4-carboxamide (1639015-48-7)+SX, 3-difluoromethyl-N-methoxy-1-methyl-N-[(1S)-1-methyl-2-(2,4,6-trichlorophenyl)ethyl]pyrazol-4-carboxamide (1639015-49-8)+SX, N-cyclopropyl-3-(difluoromethyl)-5-fluoro-N-(5-chloro-2-isopropylbenzyl)-1-methyl-1H-pyrazole-4-carboxamide (1255734-28-1)+SX, 3-difluoromethyl-1-methyl-N-(1,1,3-trimethylindan-4-yl) pyrazole-4-carboxamide (141573-94-6; hereinafter, referred to as fungicide compound β1)+SX, inpyrfluxam+SX, 3-difluoromethyl-N-(7-fluoro-1,1,3-trimethylindan-4-yl)-1-methylpyazole-4-carboxamide (1383809-87-7)+SX, 3-difluoromethyl-N-[(3R)-7-fluoro-1,1,3-trimethylindan-4-yl]-1-methylpyrazole-4-carboxamide (1513466-73-3)+SX.

Examples of the combination of the Present active ingredient of the above sub group b-5 and the Present compound:

azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxystrobin+SX, fenaminstrobin+SX, metominostrobin+SX, orysastrobin+SX, famoxadone+SX, fluoxastrobin+SX, fenamidone+SX, pyribencarb+SX.

Examples of the combination of the Present active ingredient of the above sub group b-6 and the Present compound:

cyazofamid+SX, amisulbrom+SX, binapacryl+SX, meptyldinocap+SX, dinocap+SX, fluazinam+SX.

Examples of the combination of the Present active ingredient of the above sub group b-7 and the Present compound:

silthiofam+SX.

Examples of the combination of the Present active ingredient of the above sub group b-8 and the Present compound:

cyprodinil+SX, mepanipyrim+SX, pyrimethanil+SX.

Examples of the combination of the Present active ingredient of the above sub group b-9 and the Present compound:

fenpiclonil+SX, fludioxonil+SX.

Examples of the combination of the Present active ingredient of the above sub group b-10 and the Present compound:

biphenyl+SX, chloroneb+SX, dicloran+SX, quintozene+SX, tecnazene+SX, tolclofos-methyl+SX.

Examples of the combination of the Present active ingredient of the above sub group b-11 and the Present compound:

azaconazole+SX, bitertanol+SX, bromuconazole+SX, cyproconazole+SX, difenoconazole+SX, diniconazole+SX, diniconazole-M+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentrifluconazole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SX, oxpoconazole fumarate+SX, pefurazoate+SX, prochloraz+SX, triflumizole+SX.

Examples of the combination of the Present active ingredient of the above sub group b-12 and the Present compound:

dimethomorph+SX, flumorph+SX, pyrimorph+SX, benthiavalicarb+SX, benthivalicarb-isopropyl+SX, iprovalicarb+SX, valifenalate+SX, mandipropamid+SX.

Examples of the combination of the Present active ingredient of the above sub group b-13 and the Present compound:

oxathiapiprolin+SX.

Examples of the combination of the Present active ingredient of the above sub group b-14 and the Present compound:

picarbutrazox+SX.

Examples of the combination of the Present active ingredient of the above sub group b-15 and the Present compound:

ferbam+SX, mancozeb+SX, maneb+SX, metiram+SX, propineb+SX, thiram+SX, zineb+SX, ziram+SX.

Examples of the combination of the Present active ingredient of the above sub group b-16 and the Present compound:

captan+SX, captafol+SX, folpet+SX.

Examples of the combination of the Present active ingredient of the above sub group b-17 and the Present compound:

*Agrobacterium* radiobactor strains (such as its 84 strain)+SX, *Bacillus amyloliquefaciens*+SX, *Bacillus amyloliquefaciens* strain QST713+SX, *Bacillus amyloliquefaciens* strain FZB24+SX, *Bacillus amyloliquefaciens* strain MBI600+SX, *Bacillus amyloliquefaciens* strain D747+SX, *Bacillus amyloliquefaciens* strain AT332+SX, *Bacillus amyloliquefaciens* strain PTA4838+SX, *Bacillus pumilus*+SX, *Bacillus simplex* CGF2856 strains (such as its CGF2856 strain)+SX, *Bacillus subtilis*+SX, *Bacillus subtilis* strain QST713+SX, *Bacillus subtilis* strain HAI0404+SX, *Bacillus subtilis* strain $Y^{1336}$+SX, *Variovorax paradoxus* strains (such as its CGF4526 strain)+SX, *Erwinia carotovora* strains (such as its CGE234M403 strain)+SX, *Pseudomonas fluorescens* strains (such as its G7090 strain)+SX, *Talaromyces flavus* strains (such as its SAY-Y-94-01 strain)+SX, *Trichoderma atroviride* strains (such as its SKT-1 strain), *Trichoderma harzianum* strains+SX, Hairpin protein+SX.

Examples of the combination of the Present active ingredient of the above sub group b-18 and the Present compound:

bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, diflumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinclozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, piperalin+SX, spiroxamine+SX, tridemorph+SX, fenhexamid+SX, fenpyrazamine+SX, pyributicarb+SX, naftifine+SX, terbinafine+SX, polyoxins+SX, phthalide+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cymoxanil+SX, fosetyl+SX, teclofthalam+SX, triazoxide+SX, flusulfamide+SX, diclomezine+SX, methasulfocarb+

SX, cyflufenamid+SX, metrafenone+SX, pyriofenone+SX, dodine+SX, flutianil+SX, ferimzone+SX, tebufloquin+SX, validamycin+SX, basic copper chloride+SX, copper(II) hydroxide+SX, basic copper sulphate+SX, Dodecylbenzenesulphonic acid bisethylenediamine copper [II] salt (DBEDC)+SX, organocopper+SX, sulfur+SX, chlorothalonil+SX, dichlofluanid+SX, tolylfluanid+SX, guazatine+SX, iminoctadine+SX, anilazine+SX, dithianon+SX, chinomethionat+SX, fluoroimide+SX, dipymetitrone+SX, quinofumelin+SX, dichlobentiazox+SX, aminopyrifen+SX, 3-chloro-5-phenyl-6-methyl-4-(2,6-difluorophenyl) pyridazine (1358061-55-8)+SX, fenpicoxamid+SX, N'-[4-({3-[(4-chlorophenyl)methyl]-1,2,4-thiadiazol-5-yl}oxy-2,5-dimethylphenyl]-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazole-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl] quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidine-2(1H)-one (1616664-98-2)+SX, N'-(2,5-dimethyl-4-phenoxyphenyl)-N-ethyl-N-methyl-methaneimidamide (1052688-31-9)+SX, N'-{4-[(4,5-dichlorothiazol-2-yl)oxy]-2,5-dimethylphenyl}-N-ethyl-N-methyl-methaneimidamide (929908-57-6)+SX, ethyl (2Z)-3-amino-2-cyano-3-phenylacrylate (39491-78-6)+SX, N-{(2-chlorothiazol-5-yl)methyl}-N-ethyl-6-methoxy-3-nitropyridine-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX.

Examples of the combination of the Present active ingredient of the above sub group c-1 and the Present compound: ethephon+SX, chlormequat+SX, chlormequat-chloride+SX, mepiquat+SX, mepiquat-chloride+SX, Gibberellin A3+SX, abscisic acid+SX, Kinetin+SX, benzyladenine+SX, forchlorfenuron+SX, thidiazuron+SX.

Examples of the combination of the Present active ingredient of the above sub group c-2 and the Present compound:

Glomus spp.+SX, Glomus intraradices+SX, Glomus mosseae+SX, Glomus aggregatum+SX, Glomus etunicatum+SX.

Examples of the combination of the Present active ingredient of the above sub group c-3 and the Present compound:

Bradyrhizobium elkani+SX, Bradyrhizobium japonicum+SX, Bradyrhizobium lupini+SX, Rhizobium leguminosarum bv. trifolii+SX, Rhizobium leguminosarum bv. phaseoli+SX, Rhizobium leguminosarum bv. viciae+SX, Sinorhizobium meiloti+SX, Rhizobium spp.+SX.

Examples of the combination of the Present active ingredient of the above sub group d and the Present compound:

benoxacor+SX, cloquintocet-mexyl+SX, cyometrinil+SX, dichlormid+SX, fenchlorazole-ethyl+SX, fenclorim+SX, flurazole+SX, furilazole+SX, mefenpyr-diethyl+SX, MG191 (2-(dichloromethyl)-2-methyl-1,3-dioxolane)+SX, oxabetrinil+SX, allidochlor+SX, isoxadifen-ethyl+SX, cyprosulfamide+SX, fluxofenim+SX, 1,8-naphthalic anhydride+SX, AD-67 4-(dichloroacetyl)-1-oxa-4-azaspiro [4.5]decane)+SX.

In the composition of the present invention, the weight ratio of the Present compound to the Present active ingredient includes, usually within a range of 100:1 to 1:100, and preferably within a range of 10:1 to 1:10, when the Present active ingredient is selected from the above-mentioned Group (a), Group (c) or Group (d). When the Present active ingredient is selected from the above-mentioned Group (b), the weight ratio of the Present compound to the Present active ingredient includes, usually within a range of 10000:1 to 1:100, and preferably within a range of 1000:1 to 1:10.

Examples of the pests on which the composition of the present invention has efficacies include harmful arthropods, harmful nematodes, plant pathogens and insect-mediated viruses. Examples of harmful arthropods on which the compound of the present invention and/or the composition of the present invention has/have efficacies include harmful insects and harmful mites. Specific examples of harmful arthropods include the followings.

Hemiptera Pests:

Delphacidae (for example, *Laodelphax striatellus, Nilaparvata lugens, Sogatella furcifera, Peregrinus maidis, Javesella pellucida, Perkinsiella saccharicida,* or *Tagosodes orizicolus*);

Cicadellidae (for example, *Nephotettix cincticeps, Nephotettix virescens, Nephotettix nigropictus, Recilia dorsalis, Empoasca onukii, Empoasca fabae, Dalbulus maidis,* or *Cofana spectra*);

Cercopidae (for example, *Mahanarva posticata,* or *Mahanarva fimbriolata*);

Aphididae (for example, *Aphis fabae, Aphis glycines, Aphis gossypii, Aphis pomi, Aphis spiraecola, Myzus persicae, Brachycaudus helichrysi, Brevicoryne brassicae,* Rosy apple aphid (*Dysaphis plantaginea*), *Lipaphis erysimi, Macrosiphum euphorbiae, Aulacorthum solani, Nasonovia ribisnigri, Rhopalosiphum padi, Rhopalosiphum maidis, Toxoptera citricidus, Hyalopterus pruni, Melanaphis sacchari, Tetraneura nigriabdominalis, Ceratovacuna lanigera,* or *Eriosoma lanigerum*);

Phylloxeridae (for example, *Daktulosphaira vitifoliae,* Pecan phylloxera (*Phylloxera devastatrix*), Pecan leaf phylloxera (*Phylloxera notabilis*), or Southern pecan leaf phylloxera (*Phylloxera russellae*));

Adelgidae (for example, *Adelges tsugae, Adelges piceae,* or *Aphrastasia pectinatae*);

Pentatomidae (for example, *Scotinophara lurida,* Malayan rice black bug (*Scotinophara coarctata*), *Nezara antennata, Eysarcoris aeneus, Eysarcoris lewisi, Eysarcoris ventralis, Eysarcoris annamita, Halyomorpha halys, Nezara viridula,* Brown stink bug (*Euschistus heros*), Red banded stink bug (*Piezodorus guildinii*), *Oebalus pugnax, Dichelops melacanthus*);

Cydnidae (for example, Burrower brown bug (*Scaptocoris castanea*));

Alydidae (for example, *Riptortus pedestris, Leptocorisa chinensis,* or *Leptocorisa acuta*);

Coreidae (for example, *Cletus punctiger,* or *Leptoglossus australis*);

Lygaeidae (for example, *Caverelius saccharivorus, Togo hemipterus,* or *Blissus leucopterus*);

Miridae (for example, *Trigonotylus caelestialium, Stenotus rubrovittatus, Stenodema calcarata,* or *Lygus lineolaris*);

Aleyrodidae (for example, *Trialeurodes vaporariorum, Bemisia tabaci, Dialeurodes citri, Aleurocanthus spiniferus, Aleurocanthus camelliae,* or *Pealius euryae*);

Diaspididae (for example, *Abgrallaspis cyanophylli*, *Aonidiella aurantii*, *Diaspidiotus perniciosus*, *Pseudaulacaspis pentagona*, *Unaspis yanonensis*, or *Unaspis citri*);
Coccidae (for example, *Ceroplastes rubens*);
Margarodidae (for example, *Icerya purchasi*, or *Icerya seychellarum*);
Pseudococcidae (for example, *Phenacoccus solani*, *Phenacoccus solenopsis*, *Planococcus kraunhiae*, *Planococcus comstocki*, *Planococcus citri*, *Pseudococcus calceolariae*, *Pseudococcus longispinus*, or *Brevennia rehi*);
Psyllidae (for example, *Diaphorina citri*, *Trioza erytreae*, *Cacopsylla pyrisuga*, *Cacopsylla chinensis*, *Bactericera cockerelli*, or Pear psylla (*Cacopsylla pyricola*));
Tingidae (for example, *Corythucha ciliata*, *Corythucha marmorata*, *Stephanitis nashi*, or *Stephanitis pyrioides*);
Cimicidae (for example, *Cimex lectularius*); and
Cicadidae (for example, Giant Cicada (*Quesada gigas*)).
Lepidoptera
Crambidae (for example, *Chilo suppressalis*, Darkheaded stem borer (*Chilo polychrysus*), White stem borer (*Scirpophaga innotata*), *Scirpophaga incertulas*, *Rupela albina*, *Cnaphalocrocis medinalis*, *Marasmia patnalis*, *Marasmia exigua*, *Notarcha derogata*, *Ostrinia furnacalis*, European corn borer (*Ostrinia nubilalis*), *Hellula undalis*, *Herpetogramma luctuosale*, *Pediasia teterrellus*, *Nymphula depunctalis*, Sugarcane borer (*Diatraea saccharalis*));
Pyralidae (for example, *Elasmopalpus lignosellus* or *Plodia interpunctella*);
Noctuidae (for example, *Spodoptera litura*, *Spodoptera exigua*, *Mythimna separata*, *Mamestra brassicae*, *Sesamia inferens*, *Spodoptera mauritia*, *Naranga aenescens*, *Spodoptera frugiperda*, *Spodoptera exempta*, *Agrotis ipsilon*, *Autographa nigrisigna*, *Plusia festucae*, Soybean looper (*Chrysodeixis includens*), *Trichoplusia* spp., *Heliothis* spp. (for example, *Heliothis virescens*), *Helicoverpa armigera*, *Helicoverpa* spp. (for example, *Helicoverpa zea*), Velvetbean caterpillar (*Anticarsia gemmatalis*), Cotton leafworm (*Alabama argillacea*), Hop vine borer (*Hydraecia immanis*)),
Pieridae (for example, *Pieris rapae*);
Tortricidae (for example, *Grapholita molesta*, *Grapholita dimorpha*, *Leguminivora glycinivorella*, *Matsumuraeses azukivora*, *Adoxophyes orana fasciata*, *Adoxophyes honmai*, *Homona magnanima*, *Archips fuscocupreanus*, *Cydia pomonella*, *Tetramoera schistaceana*, Bean Shoot Borer (*Epinotia aporema*), or Citrus fruit borer (*Ecdytolopha aurantiana*));
Gracillariidae (for example, *Caloptilia theivora*, or *Phyllonorycter ringoniella*);
Carposinidae (for example, *Carposina sasakii*);
Lyonetiidae (for example, Coffee Leaf miner (*Leucoptera coffeela*), *Lyonetia clerkella*, or *Lyonetia prunfoliella*);
Lymantriidae (for example, *Lymantria* spp. (for example, *Lymantria dispar*), or *Euproctis* spp. (for example, *Euproctis pseudoconspersa*));
Plutellidae (for example, *Plutella xylostella*);
Gelechiidae (for example, *Anarsia lineatella*, *Helcystogramma triannulellum*, *Pectinophora gossypiella*, *Phthorimaea operculella*, or *Tuta absolut*);
Arctiidae (for example, *Hyphantria cunea*);
Castniidae (for example, Giant Sugarcane borer (*Telchin licus*));
Cossidae (for example, *Cosus insularis*);
Geometridae (for example, *Ascotis selenaria*);
Limacodidae (for example, *Parasa lepida*);
Stathmopodidae (for example, *Stathmopoda masinissa*);
Sphingidae (for example, *Acherontia lachesis*);
Sesiidae (for example, *Nokona feralis*);
Hesperiidae (for example, *Parnara guttata*).

Thysanoptera
Thripidae (for example, *Frankliniella occidentalis*, *Thrips palmi*, *Scirtothrips dorsalis*, *Thrips tabaci*, *Frankliniella intonsa*, *Stenchaetothrips biformis*, or *Echinothrips americanus*);
Phlaeothripidae (for example, *Haplothrips aculeatus*).
Diptera
Anthomyiidae (for example, *Delia platura* or *Delia antiqua*);
Ulidiidae (for example, *Tetanops myopaeformis*);
Agromyzidae (for example, *Agromyza oryzae*, *Liriomyza sativae*, *Liriomyza trifolii*, or *Chromatomyia horticola*);
Chloropidae (for example, *Chlorops oryzae*);
Tephritidae (for example, *Bactrocera cucurbitae*, *Bactrocera dorsalis*, *Bactrocera latifrons*, *Bactrocera oleae*, *Bactrocera tryoni*, or *Ceratitis capitata*);
Ephydridae (for example, *Hydrellia griseola*, *Hydrellia philippina*, *Hydrellia sasakii*, or Ephydridae);
Drosophilidae (for example, *Drosophila suzukii*);
Phoridae (for example, *Megaselia spiracularis*);
Psychodidae (for example, *Clogmia albipunctata*);
Sciaridae (for example, *Bradysia difformis*);
Cecidomyiidae (for example, *Mayetiola destructor*, or *Orseolia oryzae*);
Diopsidae (for example, *Diopsis macrophthalma*);
Tipulidae (for example, *Tipula aino*, Common cranefly (*Tipula oleracea*), or European cranefly (*Tipula paludosa*)).
Coleoptera
Chrysomelidae (for example, *Diabrotica virgifera virgifera*, *Diabrotica undecimpunctata howardi*, *Diabrotica barberi*, *Diabrotica virgifera zeae*, *Diabrotica balteata*, Cucurbit Beetle (*Diabrotica speciosa*), *Cerotoma trifurcata*, *Oulema melanopus*, *Aulacophora femoralis*, *Phyllotreta striolata*, *Leptinotarsa decemlineata*, *Oulema oryzae*, *Colaspis brunnea*, *Chaetocnema pulicaria*, *Chaetocnema confi*, *Epitrix cucumeris*, *Dicladispa armigera*, Grape Colaspis (*Colaspis brunnea*), southern corn leaf beetle (*Myochrous denticollis*), *Laccoptera quadrimacu*, or *Epitrix hirtipennis*);
Carabidae (for example, Seedcorn beetle (*Stenolophus lecontei*), or Slender seedcorn beetle (*Clivina impressifrons*));
Scarabaeidae (for example, *Anomala cuprea*, *Anomala rufocuprea*, *Anomala albopilosa*, *Popillia japonica*, *Heptophylla picea*, European Chafer (*Rhizotrogus majalis*), *Tomarus gibbosus*, *Holotrichia* spp., or *Phyllophaga* spp. (for example, *Phyllophaga crinita*));
Curculionidae (for example, *Araecerus coffeae*, *Cylas formicarius*, *Euscepes postfasciatus*, *Hypera postica*, *Sitophilus zeamais*, *Echinocnemus squameus*, *Lissorhoptrus oryzophilus*, *Rhabdoscelus lineatocollis*, *Anthonomus grandis*, *Sphenophorus venatus*, Southern Corn Billbug (*Sphenophorus callosus*), Soybean stalk weevil (*Sternechus subsignatus*), Sugarcane weevil (*Sphenophorus levis*), *Scepticus griseus*, *Scepticus uniformis*, *Zabrotes subfasciatus*, *Tomicus piniperda*, or Coffee Berry Borer (*Hypothenemus hampei*));
Tenebrionidae (for example, *Tribolium castaneum*, or *Tribolium confusum*);
Coccinellidae (for example, *Epilachna vigintioctopunctata*);
Bostrychidae (for example, *Lyctus brunneus*);
Ptinidae;
Cerambycidae (for example, *Anoplophora malasiaca*, or *Migdolus fryanus*);

*Agriotes* sp., *Aelous* sp., *Anchastus* sp., *Melanotus* sp., *Limonius* sp., *Conoderus* sp., *Ctenicera* sp. (for example, *Melanotus okinawensis, Agriotes fuscicollis,* or *Melanotus legatus*);

Staphylinidae (for example, *Paederus fuscipes*).

Orthoptera

Acrididae (for example, *Locusta migratoria, Dociostaurus maroccanus, Chortoicetes terminifera, Nomadacris septemfasciata,* Brown Locust (*Locustana pardalina*), Tree Locust (*Anacridium melanorhodon*), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (*Camnula pellucida*), *Schistocerca gregaria*, Yellow-winged locust (*Gastrimargus musicus*), Spur-throated locust (*Austracris guttulosa*), *Oxya yezoensis, Oxya japonica,* or *Patanga succincta*);

Gryllotalpidae (for example, *Gryllotalpa africana*);

Gryllidae (for example, *Acheta domesticus,* or *Teleogryllus emma*);

Tettigoniidae (for example, Mormon cricket (*Anabrus simplex*).

Hymenoptera

*Solenopsis* spp.;

Formicidae (for example, Brown leaf-cutting ant (*Atta capiguara*)).

Blattodea

Blattellidae (for example, *Blattella germanica*);

Blattidae (for example, *Periplaneta fuliginosa, Periplaneta americana, Periplaneta brunnea,* or *Blatta orientalis*);

Termitidae (for example, *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae,* or *Cornitermes cumulans*).

Acari

Tetranychidae (for example, *Tetranychus urticae, Tetranychus kanzawai, Tetranychus evansi, Panonychus citri, Panonychus ulmi,* or *Oligonychus* spp.);

Eriophyidae (for example, *Aculops pelekassi, Phyllocoptruta citri, Aculops lycopersici, Calacarus carinatus, Acaphylla theavagrans, Eriophyes chibaensis, Aculus schlechtendali, Aceria diospyri, Aceria tosichella,* or *Shevtchenkella* sp.);

Tarsonemidae (for example, *Polyphagotarsonemus latus*);

Tenuipalpidae (for example, *Brevipalpus phoenicis*);

Tuckerellidae;

Ixodidae (for example, *Haemaphysalis longicornis, Haemaphysalis flava, Dermacentor taiwanensis, Dermacentor variabilis, Ixodes ovatus, Ixodes persulcatus, Ixodes scapularis, Amblyomma americanum, Boophilus microplus,* or *Rhipicephalus sanguineus*);

Acaridae (for example, *Tyrophagus putrescentiae,* or *Tyrophagus similis*);

Pyroglyphidae (for example, *Dermatophagoides farinae,* or *Dermatophagoides pteronyssinus*);

Cheyletidae (for example, *Cheyletus eruditus, Cheyletus malaccensis, Cheyletus moorei,* or *Cheyletiella yasguri*);

Sarcoptidae (for example, *Otodectes cynotis,* or *Sarcoptes scabiei*);

Demodicidae (for example, *Demodex canis*);

Listrophoridae;

Haplochthoniidae;

Macronyssidae (for example, *Ornithonyssus bacoti,* or *Ornithonyssus sylviarum*);

Dermanyssidae (for example, *Dermanyssus gallinae*);

Trombiculidae (for example, *Leptotrombidium akamushi*).

Araneae (for example, *Chiracanthium japonicum,* or *Latrodectus hasseltii*);

Chilopoda (for example, *Thereuonema hilgendorfi,* or *Scolopendra subspinipes*).

For example, the composition of the present invention may be used to control harmful nematodes in the case where the Present active ingredient is a nematicidal ingredient, or may be used to control plant pathogens in the case where the Present active ingredient is a bactericidal ingredient. Examples of the harmful nematodes and the plant pathogens include the followings.

Harmful Nematodes

*Aphelenchoides* sp. (for example, *Aphelenchoides basseyi*), *Pratylenchus* sp. (for example, *Pratylenchus coffeae, Pratylenchus brachyurus,* or *Pratylenchus neglectus*), *Pratylenchus* sp. (for example, *Pratylenchus coffeae, Pratylenchus brachyurus,* or *Pratylenchus neglectus*), *Meloidogyne* sp. (for example, *Meloidogyne javanica, Meloidogyne incognita,* or *Meloidogyne hapla*), *Heterodera* sp. (for example, *Heterodera glycines*), *Globodera* sp. (for example, *Globodera rostochiensis*), *Rotylenchulus reniformis, Nothotylenchus acris, Radopholus similis, Ditylenchus dipsaci, Tylenchulus semipenetrans, Longidorus* sp., *Xiphinema* sp., *Trichodorus* sp., *Bursaphelenchus* sp. (for example, *Bursaphelenchus xylophilus*).

Plant Pathogens

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (*Sclerophthora macrospora*);

Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale, M. majus*), typhulasnow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), and take-all disease (*Gaeumannomyces graminis*);

Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and rhizoctonia seeding blight (*Rhizoctonia solani*);

Corn diseases: rust (*Puccinia sorghi*), southern rust (*Puccinia polysora*), northern leaf blight (*Setosphaeria turcica*), tropical rust (*Physopella zeae*), southern leaf blight (*Cochliobolus heterostrophus*), anthracnose (*Colletotrichum gfaminicola*), gray leaf spot (*Cercospora zeae-maydis*), eyespot (*Kabatiella zeae*), phaeosphaeria leaf spot (*Phaeosphaeria maydis*), diplomat over Deer disease (*Stenocarpella maydis, Stenocarpella macrospora*), Stalk Rot (*Fusarium*

*graminearum, Fusarium verticilioides; Colletotrichum graminicola*), corn smut (*Ustilago maydis*), Cotton diseases: anthracnose (*Colletotrichum gossypii*), grey mildew (*Ramuraria areola*), alternaria leaf spot (*Alternaria macrospora, A. gossypii*), Black root rot due to *Thielaviopsis* spp. (*Thielaviopsis basicola*);

Coffee diseases: rust (*Hemileia vastatrix*), leaf spot (*Cercospora coffeicola*);

Rape seed diseases: sclerotinia rot (*Sclerotinia sclerotiorum*), black spot (*Alternaria brassicae*), and black leg (*Phoma lingam*);

Sugarcane diseases: rust (*Puccinia melanocephela, Puccinia kuehnii*), and smut (*Ustilago scitaminea*);

Sunflower diseases: rust (*Puccinia helianthi*), and downy mildew (*Plasmopara halstedii*);

Citrus diseases: melanose (*Diaporthe citri*), scab (*Elsinoe fawcetti*), fruit rot (*Penicillium digitatum, P. italicum*), and epidemics (*Phytophthora parasitica, Phytophthora citrophthora*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), anthracnose (*Glomerella cingulata*), brown spot (*Diplocarpon mali*), ring spot (*Botryosphaeria berengeriana*), and epidemics (*Phytophtora cactorum*);

Pear diseases: scab (*Venturia nashicola, V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), epidemics (*Phytophthora* sp.) and damping-off (*Pythium* sp.);

Tomato diseases: early blight (*Alternaria solani*), leaf mold (*Cladosporium fulvum*), leaf mold (*Pseudocercospora fuligena*), late blight (*Phytophthora infestans*), and powdery mildew (*Leveillula taurica*);

Eggplant disease: brown spot (*Phomopsis vexans*) and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora parasitica*), downy mildew (*Peronospora parasitica*);

Welsh onion diseases: rust (*Puccinia allii*);

Soybean diseases: purple stain (*Cercospora kikuchii*), sphaceloma scad (*Elsinoe glycines*), pod and stem blight (*Diaporthe phaseolorum* var. *sojae*), rust (*Phakopsora pachyrhizi*), target spot (*Corynespora cassiicola*), anthracnose (*Colletotrichum glycines, C. truncatum*), Rhizoctonia aerial blight (*Rhizoctonia solani*), septoria brown spot (*Septoria glycines*), frog eye leaf spot (*Cercospora sojina*), sclerotal disease (*Sclerotinia sclerotiorum*), Powdery mildew (*Microsphaera diffusa*), Stem plague (*Phytophthora sojae*), downy mildew (*Peronospora manshurica*), sudden death (*Fusarium virguliforme*);

Kidney bean diseases: Crown rot (*Sclerotinia sclerotiorum*), rust (*Uromyces appendiculatus*), angular leaf spot (*Phaeoisariopsis griseola*), and anthracnose (*Colletotrichum lindemthianum*);

Peanut diseases: early leaf spot (*Cercospora personata*), late leaf spot (*Cercospora arachidicola*) and southern blight (*Sclerotium rolfsii*);

Garden pea diseases: powdery mildew (*Erysiphe pisi*);

Potato diseases: early blight (*Alternaria solani*), late blight (*Phytophthora infestans*), Pink rot (*Phytophthora erythroseptica*), powdery scab (*Spongospora subterranean* f. sp. *subterranea*), and *verticillium* wilt (*Verticillium alboatrum, V. dahliae, V nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Tabaco diseases: brown spot (*Alternaria longipes*), anthracnose (*Colletotrichum tabacum*), downy mildew (*Peronospora tabacina*), and epidemics (*Phytophthora nicotianae*);

Sugar beet diseases: cercospora leaf spot (*Cercospora beticola*), leaf blight (*Thanatephorus cucumeris*), root rot (*Thanatephorus cucumeris*) and aphanomyces root rot (*Aphanomyces cochioides*);

Rose diseases: black spot (*Diplocarpon rosae*) and powdery mildew (*Sphaerotheca pannosa*);

Diseases of Chrysanthemum: leaf blight (*Septoria chrysanthemi-indici*) and white rust (*Puccinia horiana*);

Onion diseases: botrytis leaf blight (*Botrytis cinerea, B. byssoidea, B. squamosa*), gray-mold neck rot (*Botrytis alli*), and small sclerotial rot (*Botrytis squamosa*);

Various crops diseases: gray mold (*Botrytis cinerea*), and sclerotinia rot (*Sclerotinia sclerotiorum*);

Diseases of Japanese radish: alternaria leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola*).

Seed diseases or diseases in the early stages of the growth of various plants caused by bacteria of *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., and *Diplodia* spp.; and Viral diseases of various plants mediated by *Polymixa* genus or *Olpidium* genus.

*Burkholderia plantarii* of rice (*Burkholderia plantarii*); Angular Leaf Spot of Cucumber (*Pseudomonas syringae* pv. *Lachrymans*); wilt disease of eggplant (*Ralstonia solanacearum*); Citrus Canker (*Xanthomonas citiri*); and Sof rot of white cabbage (*Erwinia carotovora*).

The harmful arthropods, harmful nematodes and phytopathogenic fungus may be harmful arthropods, harmful nematodes or phytopathogenic fungus whose the sensitivity to any of the present active ingredient is lowered or whose the resistance against the present active ingredient is developed.

The compound of the present invention or the composition of the present invention can be used to protect plants from the plant diseases caused by insect-mediated viruses.

Examples of the plant diseases caused by the insect-mediated viruses on which the compound of the present invention or the composition of the present invention has a control efficacy include as follows.

Rice dwarf disease (Rice waika virus), Rice tungro disease (Rice tungro spherical virus, Rice tungro bacilliform virus), Rice grassy stunt disease (Rice grassy stunt virus), Rice ragged stunt disease (Rice ragged stunt virus), Rice stripe disease (Rice stripe virus), Rice black streaked dwarf disease (Rice black streaked dwarf virus), Southern rice black-streaked dwarf disease (Southern rice black-streaked dwarf virus), Rice gall dwarf disease (Rice gall dwarf virus), Rice hoja blanca disease (Rice hoja blanca virus), White leaf disease of rice (Rice white leaf virus), Yellow dwarf disease (Yellow dwarf virus), Red disease (Rice penyakit merah virus), Rice yellow stunt disease (Rice yellow stunt virus), Rice transitory yellowing disease (Rice transitory yellowing virus), Rice Yellow Mottle disease (Rice Yellow Mottle Virus), Rice necrosis mosaic disease (Rice necrosis mosaic virus), Rice dwarf stunt disease (Rice dwarf stunt virus);

Wheat northern cereal mosaic disease (Northern Cereal Mosaic Virus), Barley Yellow Dwarf disease (Barley Yellow Dwarf Virus), Wheat yellow dwarf disease (Wheat yellow dwarf virus), Oat sterile dwarf disease (Oat sterile dwarf virus), Wheat streak mosaic disease (Wheat streak mosaic virus);

Maize dwarf mosaic disease (Maize dwarf mosaic virus), Maize stripe disease (maize stripe tenuivirus), Maize chlorotic dwarf disease (Maize chlorotic dwarf virus), Maize chlorotic mottle disease (maize chlorotic mottle virus), Maize rayado fino disease (maize rayado fino marafivirus), Corn stunt disease (Corn stunt spiroplasma), Maize bushy stunt disease (Maize bushy stunt phytoplasma);

Sugarcane mosaic disease (Sugarcane mosaic virus);

Soybean mild mosaic disease (Soybean mild mosaic virus), Mosaic disease (Alfalfa Mosaic Virus, Bean yellow-spot mosaic virus, Soybean mosaic virus, Bean yellow mosaic virus, Cowpea severe mosaic virus), bean virus disease (Broad bean wilt virus, Bean common mosaic virus, Peanut stunt virus, Southern bean mosaic virus), Soybean dwarf disease (Soybean dwarf luteovirus, Milk-vetch dwarf luteovirus), Bean-pod mottle disease (Bean-pod mottle virus), Brazilian bud blight disease (Tobacco streak virus), Cowpea chlorotic mottle disease (Cowpea chlorotic mottle), Mung bean yellow mosaic disease (Mung bean yellow mosaic virus), Peanut stripe disease (Peanut stripe mottle), Soybean crinkle leaf disease (Soybean crinkle leaf virus), Soybean severe stunt disease (Soybean severe stunt virus);

Tomato yellow leaf disease (Tomato chlorosis virus), Tomato spotted wilt disease (Tomato spotted wilt virus), Tomato yellow leaf curl disease (Tomato yellow leaf curl virus), Melon spotted wilt disease (Melon yellow spot virus), Watermelon mosaic disease (Watermelon mosaic virus),
Cucumber Dwarf disease (Cucumber mosaic virus), Zucchini yellow mosaic disease (Zucchini yellow mosaic virus), Turnip mosaic disease (Turnip mosaic virus), Cucurbit chlorotic yellow disease (Cucurbit chlorotic yellows virus), Capsicum chlorosis disease (Capsicum chlorosis virus), Beet pseudo yellow disease (Beet pseudo yellows virus);

chrysanthemum stem necrosis disease (chrysanthemum stem necrosis virus), Impatiens necrotic spot disease (Impatiens necrotic spot virus), Iris yellow spot disease (Iris yellow spot virus);

Sweet potato mottle mosaic disease (Sweet potato internal cork virus), Sweet potato shukuyo mosaic disease (Sweet potato shukuyo mosaic virus); and Mosaic virus diseases of various plants mediated by *Polymixa* spp. or *Olpidium* spp.

The composition for controlling harmful arthropods of the present invention comprises the compound of the present invention and an inert active carrier. The composition for controlling harmful arthropods is usually prepared by mixing the compound of the present invention with an inert active carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, microcapsules, aerosols, smoking agents, poison baits, resin formulations, shampoo formulations, paste-like formulations, foams, carbon dioxide formulations and tablets and the others. Such formulations may be processed into mosquito repellent coils, electric mosquito repellent mats, liquid mosquito formulations, smoking agents, fumigants, sheet formulations, spot-on formulations or formulations for oral treatment. Also, the composition for controlling harmful arthropods of the present invention may be mixed with other pesticides, miticides, nematicides, fungicides, plant growth regulators, herbicides, and synergists.

The composition for controlling harmful arthropods of the present invention comprises usually 0.01 to 95% by weight of the compound of the present invention.

Examples of the solid carrier to be used in the formulation include fine powders or granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate or hydrated silica) or chemical fertilizers (for example, ammonium sulfate, ammonium phosphate, ammonium nitrate, urea or ammonium chloride) and the others; as well as synthetic resins (for Example, polyester resins such as polypropylene, polyacrylonitrile, polymethylmethacrylate and polyethylene terephthalate; nylon resins (for Example, nylon-6, nylon-11 and nylon-66); polyamide resins; polyvinyl chloride, polyvinylidene chloride, vinyl chloride-propylene copolymers, and the others).

Examples of the above-mentioned liquid carriers include water; alcohols (for example, methanol, ethanol, isopropyl alcohol, butanol, hexanol, benzyl alcohol, ethylene glycol, propylene glycol or phenoxy ethanol); ketones (for Example, acetone, methyl ethyl ketone or cyclohexanone); aromatic hydrocarbons (for example, toluene, xylene, ethyl benzene, dodecyl benzene, phenyl xylyl ethane or methylnaphthalene); aliphatic hydrocarbons (for example, hexane, cyclohexane, kerosene or light oil); esters (for example, ethyl acetate, butyl acetate, isopropyl myristate, ethyl oleate, diisopropyl adipate, diisobutyl adipate or propylene glycol monomethyl ether acetate); nitriles (for Example, acetonitrile or isobutyronitrile); ethers (for example, diisopropyl ether, 1,4-dioxane, ethyleneglycol dimethyl ether, diethyleneglycol dimethyl ether, diethylene glycol monomethyl ether, propylene glycol monomethyl ether, dipropylene glycol monomethyl ether or 3-methoxy-3-methyl-1-butanol); amides (for example, dimethylformamide (DMF) or dimethylacetamide); sulfoxides (for example, dimethyl sulfoxide (DMSO)); propylene carbonate; and vegetable oils (for example, soybean oil or cottonseed oil).

Examples of the above-mentioned gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol.

Examples of base material of the resin formulation include polyvinyl chloride polymers, polyurethane and the others, and a plasticizer such as phthalate esters (for example, dimethyl phthalate, dioctyl phthalate), adipic acid esters and stearic acid may be added to these base materials, if necessary. The resin formulation can be prepared by mixing the compound of the present invention with the above-mentioned base material, kneading the mixture, followed by molding it by injection molding, extrusion molding or pressure molding and the like. The resultant resin formulation can be subjected to further molding or cutting procedure and the like, if necessary, to be processed into shapes such as a plate, film, tape, net or string shape. These resin formulations can be processed into animal collars, animal ear tags, sheet products, trap strings, gardening supports and other products.

Examples of a base material for the poison baits include bait ingredients such as grain powder, vegetable oil, saccharide and crystalline cellulose, and if necessary, with addition of antioxidants such as dibutylhydroxytoluene and nordihydroguaiaretic acid, preservatives such as dehydroacetic acid, accidental ingestion inhibitors for children and pets such as a chili powder, insect attraction fragrances such as cheese flavor, onion flavor and peanut oil.

The method for controlling harmful arthropods of the present invention is conducted by applying an effective amount of the compound of the present invention to a harmful arthropod directly and/or a habitat thereof (for example, plant bodies, soil, an interior of a house, animal bodies). In the method for controlling harmful arthropods of the present invention, the Present compound is usually used in the form of a harmful arthropod controlling composition.

When a composition for controlling harmful arthropods of the present invention is used for controlling harmful arthropods in an agricultural field, the application dose as an amount of the compound of the present invention is usually within a range from 1 to 10,000 g per 10,000 $m^2$.

The emulsifiable concentrate, the wettable powder, or the flowable formulation etc. of a composition for controlling harmful arthropods of the present invention is usually applied by diluting it with water in such a way that a concentration of the compound of the present invention is within a range from 0.01 to 10,000 ppm. The granular formulation, or the dust formulation etc., is usually applied as itself without diluting it.

These formulations or a aqueous dilution thereof can be sparged directly to harmful arthropods or plants (such as crops) to be protected from harmful arthropods, and also may be applied to the soil of crop land in order to control harmful arthropods which live there.

The resin preparation which is processed into a sheet or a string may be applied by winding a crop with a sheet or a string of the resin preparation, putting a string of the resin preparation around a crop so that the crop is surrounded by the string, or laying a sheet of the resin preparation on the soil surface near the root of a crop.

When the composition for controlling harmful arthropods of the present invention is used to control harmful arthropods that live inside a house, the application dose as an amount of the Present compound is usually within a range from 0.01 to 1,000 mg per 1 $m^2$ of an area to be treated, in the case of using it on a planar area. In the case of using it spatially, the application dose as an amount of the Present compound is usually within a range from 0.01 to 500 mg per 1 $m^3$ of the space to be treated. When the agent for controlling harmful arthropods of the present invention is formulated into emulsifiable concentrates, wettable powders, flowables or the others, such formulations are usually applied after diluting it with water in such a way that a concentration of the active ingredient is within a range from 0.1 to 10,000 ppm, and then sparging it. In the case of being formulated into oil solutions, aerosols, smoking agents, poison baits and the others, such formulations are used as itself without diluting it.

When the composition for controlling harmful arthropods of the present invention is sued for controlling external parasites of livestock such as cows, horses, pigs, sheep, goats and chickens and small animals such as dogs, cats, rats and mice, the pest control agent of the present invention can be applied to the animals by a known method in the veterinary field. Specifically, when systemic control is intended, the pest control agent of the present invention is administered to the animals as a tablet, a mixture with feed or a suppository, or by injection (including intramuscular, subcutaneous, intravenous and intraperitoneal injections). On the other hand, when non-systemic control is intended, the pest control agent of the present invention is applied to the animals by means of spraying of the oil solution or aqueous solution, pour-on or spot-on treatment, or washing of the animal with a shampoo formulation, or by putting a collar or ear tag made of the resin formulations to the animal. In the case of administering to an animal body, the dose of the Present compound is usually within a range from 0.1 to 1,000 mg per 1 kg of an animal body weight.

The method for controlling harmful arthropods of the present invention is carried out by applying an effective amount of the compound of the present invention or the composition of the present invention directly to harmful arthropods, and/or habitats of harmful arthropods. Examples of the habitats of harmful arthropods include plants, soils for cultivating plants, houses, and animals.

Examples of applying an effective amount of the compound of the present invention or the composition of the present invention to plant or soils for cultivating plants include a method of applying an effective amount of the compound of the present invention or the composition of the present invention to a stem and leaf, a flower, a seedling, an ear of a plant; a method of applying an effective amount of the compound of the present invention or the composition of the present invention to a seed or a bulb such as seed tuber (for example, a seed disinfection, a seed soaking, or a seed coating), or a method of applying an effective amount of the compound of the present invention or the composition of the present invention to soils before planting plants or soils after planting plants.

Specific examples of applying an effective amount of the compound of the present invention or the composition of the present invention to a stem and leaf, a flower, a seedling, an ear of a plant include a method for applying an effective amount of the compound of the present invention or the composition of the present invention to a surface of a plant (for example, foliage application, and trunk application), a method for applying an effective amount of the compound of the present invention or the composition of the present invention to a flower or a whole plant at flowering times including before flowering, during flowering, and after flowering, and a method for applying an effective amount of the compound of the present invention or the composition of the present invention to an ear or a whole grain at sprouting season of grain.

Examples of a method of controlling harmful arthropods by applying an effective amount of the compound of the present invention or the composition of the present invention soils before planting plants or after planting plants include a method of applying an effective amount of a composition of the present invention to a root part of a crop to be protected from damage such as ingestion by harmful arthropods, and a method of controlling harmful arthropods that ingest a plant by permeating and transferring an effective amount of the composition of the present invention from a root into the interior of the plant body.

Examples of the method of applying an effective amount of the compound of the present invention or the composition of the present invention to soils before planting plants or after planting plants include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering soil, and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

In a step of applying to a seed or a bulb, a seed described herein represents a seed of a plant at the state before seeding to a soil or a culture medium for cultivating a seed, and a bulb described herein represents discoid stems, corms, rhizomes, tubers, tuberous, seed tubers, and tuberous roots of a plant at the state before planting in a soil or a culture medium for cultivating. A method for controlling harmful arthropods by applying an effective amount of the compound of the present invention or the composition of the present invention into a seed or a bulb include a method of applying an effective amount of the compound of the present invention or the composition of the present invention directly into a seed or a bulb of a plant to be protected from damage such as ingestion by harmful arthropods; and a method for controlling harmful arthropods that ingest a seed by applying an effective amount of the compound of the present invention or the composition of the present invention in the vicinity of a seed or a bulb; and a method for controlling harmful arthropods that ingest a plant by permeating and transferring an effective amount of the compound of the present invention or the composition of the present invention from a seed or a bulb into the interior of the plant body. Examples of a method of applying an effective amount of the compound of the present invention or the composition of the present invention to a seed or a bulb include spraying treatment, spray coating treatment, immersion treatment, impregnation treatment, coating treatment, film coating treatment, and pellet coating treatment, and these methods can provide a preparation of a seed or a bulb that retain an effective amount of the composition of the present invention or the composition of the present invention on the surface and/or into the interior thereof.

When the compound of the present invention or the composition of the present invention are applied to a seed or a bulb, an effective amount of the compound of the present invention is usually within a range of 0.001 to 100 g, preferably within a range of 0.02 to 20 g, based on 1 kg of the seed or the bulb. Also an effective amount of the composition of the present invention is usually within a range of 0.000001 to 50 g, preferably within a range of 0.0001 to 30 g of a total amount of the compound of the present invention and the active ingredient of the present invention, based on 1 kg of the seed or the bulb.

The plants to which the compound of the present invention and the composition of the present invention can be applied include the followings.

Crops:

corn, rice, wheat, barley, rye, triticale, oat, sorghum, cotton, soybean, peanut, arachis, common bean (kidney bean), lima bean, adzuki bean, cowpea, mung bean, urd bean, scarlet runner bean, rice bean, moth bean, tepary bean, broad bean, pea, chick pea, lentils, lupin, pigeon pea, alfalfa, buckwheat, beet, rape, sunflower, sugarcane, tobacco, and the others;

Vegetables:

solanaceous vegetables (for example, eggplant, tomato, pimento, pepper, bell pepper and potato), cucurbitaceous vegetables (for example, cucumber, pumpkin, zucchini, water melon, melon, and squash), cruciferous vegetables (for example, Japanese radish, white turnip, horseradish, kohlrabi, Chinese cabbage, cabbage, leaf mustard, broccoli and cauliflower), asteraceous vegetables (for example, burdock, crown daisy, artichoke and lettuce), liliaceous vegetables (for example, green onion, onion, garlic and asparagus), ammiaceous vegetables (for example, carrot, parsley, celery and parsnip), chenopodiaceous vegetables (for example, spinach and Swiss chard), lamiaceous vegetables (for example, *Perilla frutescens*, mint, basil, and lavender), strawberry, sweet potato, *Dioscorea japonica, colocasia,*
and the others;
Fruits:
pomaceous fruits (for example, apple, pear, Japanese pear, Chinese quince and quince), stone fleshy fruits (for example, peach, plum, nectarine, *Prunus mume*, cherry fruit, apricot and prune),
citrus fruits (for example, Citrus unshiu, orange, lemon, lime and grapefruit),
nuts (for example, chestnut, walnuts, hazelnuts, almond, pistachio, cashew nuts and macadamia nuts),
berry fruits (for example, blueberry, cranberry, blackberry and raspberry), grape, kaki persimmon, olive, Japanese plum, banana, coffee, date palm, coconuts,
and the others;
tea, mulberry,
flowering plant,
roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus* cuspidate),
flowers,
ornamental foliage plants,
sods, and
grasses.

The plants described above are not limited specifically, as long as they are breeds that are usually cultivated.

The plant described above may be plants that are bred by a hybrid technology.

That is, the plants that are bred by a hybrid technology is a first-generation hybrid that is produced by breeding two kinds of different lines of breed variety, and generally speaking, are plants having a heterosis having superior characters to those of both parents breeds (in general, for example, it leads to enhancement of yield potential and improvement of resistance to biological and abiotic stress factors).

The plants described above may include genetically-modified crop.

For example, the genetically-modified crop described above include also plants having resistance to herbicides including HPPD (that is, 4-hydroxyphenylpyruvate dioxygenase) inhibitors such as isoxaflutole; ALS (that is, acetoacetate synthase) inhibitors such as imazethapyr and thifensulfuron methyl; EPSP (that is, 5-enolpyruvoylshikimate-3-phosphate synthase) inhibitors; glutamine synthetase inhibitors; PPO (that is, protoporphyrinogen oxidase) inhibitors; bromoxynil; dicamba, and the like, which resistance has been imparted by a classical breeding method or gene recombination technology.

The plants described above may include plants that have become capable of synthesizing selective toxins and the like (for example, genus *Bacillus* such as *Bacillus thuringiensis*) produced by using a gene recombination technology; and the plants being capable of synthesizing a gene segment that match partially an endogenous gene derived from a harmful insect and also impart with specific insecticidal activity by inducing a gene silencing (RNAi; RNA interference) in a target harmful insect.

In addition, the plants described above include lines having two or more types of characters related to herbicide resistance, pest resistance, disease resistance, and the like as described above, which characters are imparted using a classical breeding technology or gene recombination technology, and lines having two or more types of properties possessed by parent lines, which properties are imparted by crossing genetically-engineered plants having the same or different types of properties. Examples of such plants include Smart stax (registered trademark).

EXAMPLES

Hereinafter, the present invention is explained in more detail by using Preparation example, Formulation example, and Test example and the like, however, the present invention should not be limited to these examples.

First, the preparation example of the present invention is shown.

Reference Preparation Example 1

To a mixture of tetramethylpiperidine 17.5 mL and THF 150 mL was added dropwise 1.6 M butyl lithium-hexane solution 64.4 mL at −78° C. To the reaction mixtures was added dropwise 2-fluoropyridine 10 g at −78° C. After the mixtures were stirred for 30 minutes, thereto was added dropwise dimethyl disulfide 12.7 ml. The reaction mixtures were stirred at −78° C. for 1 hour. To the resulting reaction mixtures was added saturated aqueous ammonium chloride solution under ice-cooling, and the mixtures were raised to room temperature, and extracted with ethyl acetate. The resulting organic layers were washed with saturated brine, dried over anhydrous sodium sulfate, and concentrated under reduced pressure. The obtained residue was subjected to a silica gel column chromatography to obtain the intermediate compound 1-1 below 14.23 g.

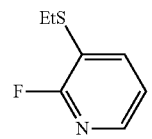

Intermediate compound 1-1: $^1$H-NMR (CDCl$_3$) δ: 8.03 (1H, td), 7.74-7.69 (1H, m), 7.14 (1H, ddd), 2.97 (2H, q), 1.33 (3H, t).

Reference Preparation Example 2

To a mixture of sodium hydride (in oil, 60%) 0.26 g, 2-bromo-3-fluoropyridine 1.0 g and DMF 20 mL was added dropwise ethanethiol 0.5 mL under ice-cooling. The reaction mixtures were stirred at room temperature for 2 hours. To the resulting reaction mixtures was added saturated aqueous ammonium chloride solution, and the mixtures were extracted with ethyl acetate. The resulting organic layers were dried over anhydrous sodium sulfate, and concentrated under reduced pressure. The obtained residue was subjected to a silica gel column chromatography to obtain the intermediate compound 1-2 below 0.72 g.

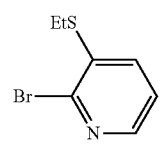

Intermediate compound 1-2 ¹H-NMR (CDCl₃) δ: 8.14 (1H, dd), 7.46 (1H, dd), 7.23 (1H, dd), 2.96 (2H, q), 1.40 (3H, t).

Reference Preparation Example 3

To a mixture of sodium hydride (in oil, 60%) 0.3 g, 2,3-dichloro-5-(trifluoromethyl)pyridine 0.5 mL and DMF 5 mL was added dropwise ethanethiol 0.54 mL under ice-cooling. The reaction mixtures were stirred at 40° C. for 12 hours. To the reaction mixtures was added saturated aqueous ammonium chloride solution, and the mixtures were extracted with ethyl acetate. The resulting organic layers were dried over anhydrous sodium sulfate, and concentrated under reduced pressure. The obtained residue was subjected to a silica gel column chromatography to obtain the intermediate compound 1-3 below 0.61 g.

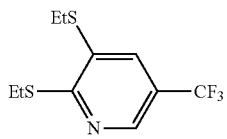

Intermediate compound 1-3: ¹H-NMR (CDCl₃) δ: 8.50 (1H, dd), 7.59 (1H, d), 3.24 (2H, q), 2.99 (2H, q), 1.39 (3H, t), 1.36 (3H, t).

Reference Preparation Example 4

To a mixture of the intermediate compound 1-1 8.9 g, and chloroform 100 mL was added 70% CPBA 28.0 g under ice-cooling, and the mixtures were stirred at room temperature for 12 hours. To the reaction mixtures were added saturated aqueous sodium hydrocarbonate solution and aqueous sodium thiosulfate solution, and the mixtures were extracted with chloroform. The resulting organic layers were dried over anhydrous sodium sulfate, and concentrated under reduced pressure. The obtained residue was subjected to a silica gel column chromatography to obtain the intermediate compound 1-4 below 11.99 g.

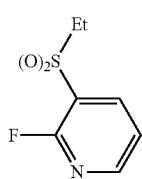

Intermediate compound 1-4: ¹H-NMR (CDCl₃) δ: 8.50 (1H, d), 8.43-8.38 (1H, m), 7.47-7.43 (1H, m), 3.38 (2H, q), 1.34 (3H, t).

Reference Preparation Example 5

The compounds that were prepared according to the similar method to the Reference Preparation Example 4, and their physical property values are shown below.

a compound of formula (A-1):

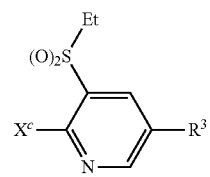

(A-1)

wherein a combination of R³ and X^c represent any combination indicated in Table 16.

[Table 6]

TABLE 16

| Intermediate compound | R³ | X^c |
|---|---|---|
| 1-5 | H | Br |
| 1-6 | CF₃ | S(O)₂Et |
| 1-14 | Br | Cl |
| 1-15 | 1-CN—c-Pr | Cl |
| 1-16 | 1-CN—c-Bu | Cl |
| 1-17 | 1-CN—c-Pen | Cl |
| 1-18 | 1-CN—c-Hex | Cl |

Intermediate compound 1-5: ¹H-NMR (CDCl₃) δ: 8.61 (1H, dd), 8.45 (1H, dd), 7.53 (1H, dd), 3.56 (2H, q), 1.31 (3H, t).

Intermediate compound 1-6: ¹H-NMR (CDCl₃) δ: 9.17 (1H, s), 8.84 (1H, s), 3.81-3.79 (2H, m), 3.71-3.67 (2H, m), 1.46-1.43 (3H, m), 1.41-1.36 (3H, m).

Intermediate compound 1-14: ¹H-NMR (CDCl₃) δ: 8.69 (1H, d), 8.56 (1H, d), 3.51 (2H, q), 1.33 (3H, t).

Intermediate compound 1-15: ¹H-NMR (CDCl₃) δ: 8.71 (1H, d), 8.18 (1H, d), 3.51 (2H, q), 1.94-1.93 (2H, m), 1.55-1.53 (2H, m), 1.33 (3H, t).

Intermediate compound 1-16: ¹H-NMR (CDCl₃) δ: 8.71 (1H, d), 8.44 (1H, d), 3.53 (2H, q), 2.98-2.91 (2H, m), 2.64-2.57 (3H, m), 2.23-2.13 (1H, m), 1.35 (3H, t).

Intermediate compound 1-17: ¹H-NMR (CDCl₃) δ: 8.78 (1H, d), 8.42 (1H, d), 3.52 (2H, q), 2.61-2.58 (2H, m), 2.12-2.03 (6H, m), 1.34 (3H, t).

Intermediate compound 1-18: ¹H-NMR (CDCl₃) δ: 8.82 (1H, d), 8.45 (1H, d), 3.52 (2H, q), 2.23-2.20 (2H, m), 1.90-1.81 (7H, m), 1.34 (4H, t).

Also, physical property values of the intermediate compound 1-19 below are shown below.

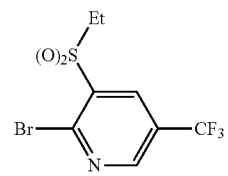

Intermediate compound 1-19: ¹H-NMR (CDCl₃) δ: 1.30 (3H, t), 3.48 (2H, q), 7.71 (1H, d), 7.91 (1H, d), 8.40 (1H, s).

Reference Preparation Example 6

To a mixture of 4-chloropyridine-1-oxide 5.0 g, and sodium hydride (in oil, 60%) 1.8 g and THF 70 mL was added dropwise 2,2,3,3,3-pentafluoro-1-propanol 6.9 g under ice-cooling. The reaction mixtures were heated under reflux with stirring for 14 hours. The resulting reaction mixtures were cooled to room temperature, and thereto was added tert-butanol 10 mL, and the mixtures were stirred for 30 minutes and filtered through Celite (registered trademark). The obtained filtrates were concentrated under reduced pressure, and the obtained residue was subjected to a silica gel column chromatography to obtain the intermediate compound 2-1 below 5.19 g.

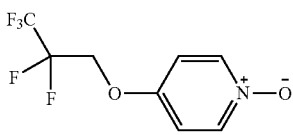 [SMILES: [O-][n+]1ccc(OCC(F)(F)C(F)(F)F)cc1]

Intermediate compound 2-1: $^1$H-NMR (CDCl$_3$) δ: 8.18 (2H, d), 6.88 (2H, d), 4.46 (2H, t).

Reference Preparation Example 7

A mixture of the intermediate compound 2-1 5.19 g, and acetic anhydride 50 mL was heated under reflux with stirring for 12 hours. The resulting reaction mixtures were cooled to room temperature, and concentrated under reduced pressure. To the obtained residue were added concentrated hydrochloric acid 5 mL and methanol 50 mL under ice-cooling, and the mixtures were heated under reflux with stirring for 5 hours. The resulting reaction mixtures were cooled to room temperature, and concentrated under reduced pressure. To the obtained residue was added saturated aqueous sodium hydrocarbonate solution to adjust pH 4, and the mixtures were extracted with ethyl acetate. The obtained organic layers were washed with saturated brine, dried over anhydrous sodium sulfate, and concentrated under reduced pressure. The obtained solids were washed with a mixed solvents of hexane:ethyl acetate=9:1 to obtain the intermediate compound 2-2 below 3.95 g.

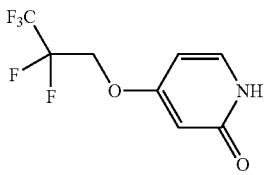

Intermediate compound 2-2: $^1$H-NMR (CDCl$_3$) δ: 7.30 (1H, d), 6.07 (1H, dd), 5.87 (1H, d), 4.38 (2H, t).

Reference Preparation Example 8

A mixture of the intermediate compound 1-4 2.0 g, 4-chloropyridine-2-(1H)-one 1.36 g, cesium carbonate 4.1 g and NMP 10 mL was stirred at room temperature for 3 hours. To the resulting reaction mixtures were added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 2-3 below 0.9 g.

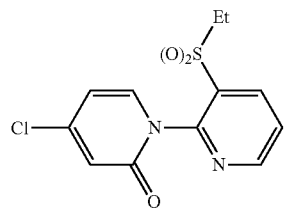

Intermediate compound 2-3: $^1$H-NMR (CDCl$_3$) δ: 8.86 (1H, dd), 8.47 (1H, dd), 7.70 (1H, dd), 7.27 (1H, d), 6.68 (1H, d), 6.38 (1H, dd), 3.50-3.33 (2H, m), 1.33 (3H, t).

Reference Preparation Example 9

A mixture of 3-(trifluoromethyl)pyrazole 1.5 g, 4-chloropyridine-2(H)-one 1.0 g, cesium carbonate 3.8 g, and NMP 5 mL was heated at 110° C. for 24 hours. To the resulting reaction mixtures was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 2-4 below 0.65 g.

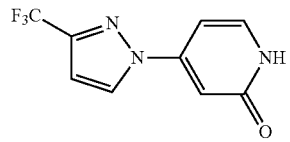

Intermediate compound 2-4: $^1$H-NMR (CDCl$_3$) δ: 12.01 (1H, s), 8.02-8.02 (1H, m), 7.48 (1H, d), 6.96 (1H, dd), 6.79-6.78 (2H, m).

Reference Preparation Example 10

To a mixture of the intermediate compound 1-1 3.0 g, and ethanol 15 mL was added dropwise hydrazine monohydrate 4.6 mL. The reaction mixtures were heated under reflux with stirring for 8 hours. The reaction mixtures were cooled to room temperature and concentrated under reduced pressure. To the obtained residue was added water, and the mixtures were extracted with MTBE, and the obtained organic layers were washed with saturated brine, dried over anhydrous sodium sulfate, and concentrated under reduced pressure. The obtained residue was subjected to a silica gel column chromatography to obtain the intermediate compound 2-5 below 3.13 g.

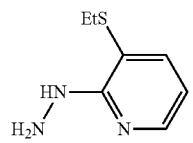

Intermediate compound 2-5: $^1$H-NMR (CDCl$_3$) δ: 8.13 (1H, dd), 7.57 (1H, dd), 6.73 (1H, s), 6.64 (1H, dd), 3.97 (2H, s), 2.76 (2H, q), 1.22 (3H, t).

Reference Preparation Example 11

To a mixture of the intermediate compound 2-5 2.0 g, mucochloric acid 2.0 g and ethanol 60 mL was added dropwise concentrated hydrochloric acid 1.0 mL. The reaction mixtures were heated under reflux with stirring for 1.5 hours. The resulting reaction mixtures were cooled to room temperature, and concentrated under reduced pressure. To the obtained residue was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 2-6 below 2.02 g.

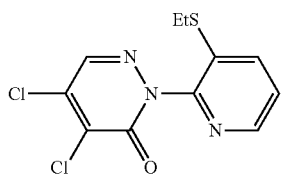

Intermediate compound 2-6: $^1$H-NMR (CDCl$_3$) δ: 8.44 (1H, dd), 7.94 (1H, s), 7.85 (1H, dd), 7.43 (1H, dd), 2.94 (2H, q), 1.29 (3H, t).

Reference Preparation Example 12

The intermediate compound 2-7 below was prepared by using the intermediate compound 2-6 instead of the intermediate compound 1-1 according to the similar method to the Reference Preparation Example 4.

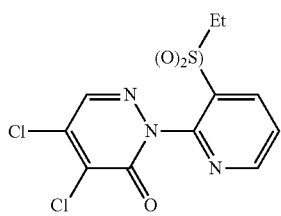

Intermediate compound 2-7: $^1$H-NMR (CDCl$_3$) δ: 8.90 (1H, dd), 8.46 (1H, dd), 7.95 (1H, s), 7.74 (1H, dd), 3.35 (2H, q), 1.33 (3H, t).

Reference Preparation Example 13

To a mixture of 4-chloro-6-methoxypyrimidine 1.5 g, 2,2,3,3,3-pentafluoro-1-propanol 1.2 mL and DMF 10 mL was added dropwise sodium hydride (in oil, 60%) 0.5 g under ice-cooling. The resulting mixtures were stirred at 80° C. for 5 hours. To the resulting reaction mixtures was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 2-8 below 1.78 g.

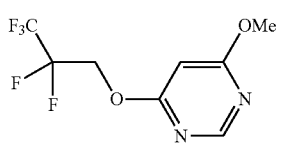 [SMILES: COc1cc(OCC(F)(F)C(F)(F)F)ncn1]

Intermediate compound 2-8: $^1$H-NMR (CDCl$_3$) δ: 8.45 (1H, s), 6.19 (1H, d), 4.87 (2H, td), 3.97 (3H, s).

Reference Preparation Example 14

A mixture of the intermediate compound 2-8 1.78 g, 6M hydrochloric acid 15 mL and methanol 18 mL was stirred at 75° C. for 10 hours. The reaction mixtures were concentrated under reduced pressure, and to the obtained residues was added saturated aqueous sodium hydrocarbonate solution to adjust pH 4, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 2-9 below 0.54 g.

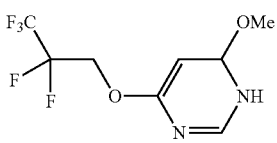 [SMILES: COC1C=C(OCC(F)(F)C(F)(F)F)N=CN1]

Intermediate compound 2-9: $^1$H-NMR (CDCl$_3$) δ: 8.04 (1H, s), 5.88 (1H, d), 4.84 (2H, td), 1.58 (1H, s).

Reference Preparation Example 15

To a mixture of the intermediate compound 1-4 1.24 g, sodium hydride (in oil, 60%) 0.31 g and NMP 5 mL was added 4-methoxypyrimidine-2(1H)-one 0.83 g and under ice-cooling, and the mixtures were stirred at 120° C. for 7 hours. The reaction mixtures were cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 2-10 below 0.75 g and the intermediate compound 2-11 below 0.34 g.

Intermediate Compound 2-10

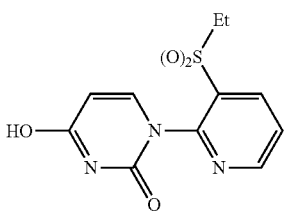

Intermediate compound 2-10: $^1$H-NMR (CDCl$_3$) δ: 9.80 (1H, s), 8.85 (1H, dd), 8.44 (1H, dd), 7.71 (1H, dd), 7.34 (1H, d), 5.90 (1H, d), 3.43 (2H, q), 1.37 (3H, t).

Intermediate Compound 2-11

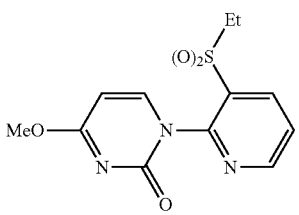

Intermediate compound 2-11: ¹H-NMR (CDCl₃) δ: 8.84 (1H, dd), 8.44 (1H, dd), 7.70 (1H, dd), 7.29 (1H, d), 5.94 (1H, d), 3.43-3.40 (2H, m), 3.39 (3H, s), 1.37 (3H, t).

Reference Preparation Example 16

The intermediate compound 1-7 was prepared by using 5-bromo-2-chloro-3-fluoropyridine according to the similar method to the Reference Preparation Example 2.

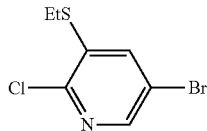

Intermediate compound 1-7: ¹H-NMR (CDCl₃) δ: 8.19 (1H, d), 7.57 (1H, d), 2.97 (2H, q), 1.42 (3H, t).

Reference Preparation Example 17

A mixture of the intermediate compound 1-15 5.0 g, (trimethylsilyl)acetonitrile 5.4 mL, zinc fluoride 1.2 g and 4,5-bis(diphenylphosphino)-9,9-dimethylxanthene 1.14 g, tris(dibenzylideneacetone)dipalladium(0) 0.9 g and DMF 10 mL was stirred at 100° C. for 5 hours. The reaction mixtures were cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 1-8 below 2.63 g.

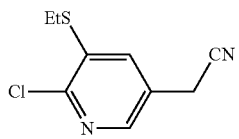

Intermediate compound 1-8: ¹H-NMR (CDCl₃) δ: 8.08 (1H, d), 7.49 (1H, d), 3.76 (2H, s), 3.00 (2H, q), 1.42 (3H, t).

Reference Preparation Example 18

A mixture of the intermediate compound 1-16 3.27 g, 1,2-dibromoethane 1.6 mL, sodium hydride (in oil, 60%) 1.29 g, and THF 30 mL was stirred at room temperature for 3 hours. To the reaction mixtures was added water, and the mixtures were extracted with ethyl acetate. The obtained organic layers were dried over anhydrous sodium sulfate, and concentrated under reduced pressure. The obtained residue was subjected to a silica gel column chromatography to obtain the intermediate compound 1-9 below 2.17 g.

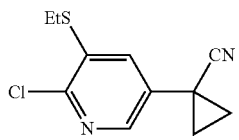

Intermediate compound 1-9: ¹H-NMR (CDCl₃) δ: 7.97 (1H, d), 7.51 (1H, d), 3.01 (2H, q), 1.83 (2H, m), 1.46 (2H, m), 1.42 (3H, t).

Reference Preparation Example 19

The compounds that were prepared according to the similar method to the Reference Preparation Example 18, and their physical property values are shown below.

a compound of formula (A-2):

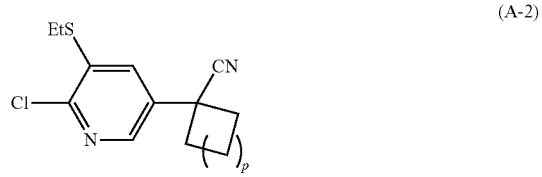

wherein p is any one of the number indicated in Table 17.

[Table 7]

TABLE 17

| Intermediate compound | p |
|---|---|
| 1-10 | 1 |
| 1-11 | 2 |
| 1-12 | 3 |

Intermediate compound 1-10: ¹H-NMR (CDCl₃) δ: 8.22 (1H, d), 7.50 (1H, d), 3.00 (2H, q), 2.92-2.86 (2H, m), 2.65-2.61 (2H, m), 2.55-2.43 (1H, m), 2.20-2.10 (1H, m), 1.42 (3H, t).

Intermediate compound 1-11: ¹H-NMR (CDCl₃) δ: 8.19 (1H, d), 7.59 (1H, d), 3.01 (2H, q), 2.53-2.51 (2H, m), 2.08-2.05 (4H, m), 2.00-1.98 (2H, m), 1.41 (3H, t).

Intermediate compound 1-12: ¹H-NMR (CDCl₃) δ: 8.22 (1H, d), 7.64 (1H, d), 3.01 (2H, q), 2.19-2.16 (2H, m), 1.87-1.60 (7H, m), 1.42 (3H, t), 1.34-1.27 (1H, m).

Reference Preparation Example 20

A mixture of 1.09 g of the intermediate compound 1-9, 1.2 g of cesium fluoride and 10 mL of DMSO was stirred at 70° C. for 11 hours. To the reaction mixtures was added water, and the mixtures were extracted with ethyl acetate. The resulting organic layers were dried over anhydrous sodium sulfate, and concentrated under reduced pressure. The obtained residue was subjected to a silica gel column chromatography to obtain the intermediate compound 1-21 below 0.85 g.

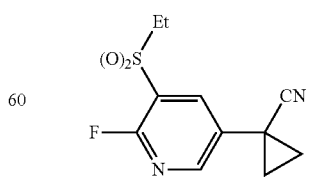

Intermediate compound 1-21: ¹H-NMR (CDCl₃) S: 8.54 (1H, dd), 8.17 (1H, dd), 3.38 (2H, q), 1.92-1.90 (2H, m), 1.55-1.53 (2H, m), 1.35 (3H, t).

Reference Preparation Example 21

The compounds that were prepared according to the similar method to the Reference preparation Example 20, and their physical property values are shown below.
a compound represented by formula (A-3):

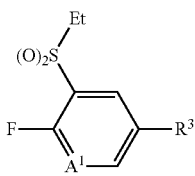

(A-3)

wherein a combination of R³ and A¹ represent any one of the combinations indicated in Table 18.
[Table 8]

TABLE 18

| Intermediate compound | R³ | A¹ |
|---|---|---|
| 1-20 | Br | N |
| 1-22 | 1-CN—c-Bu | N |
| 1-23 | 1-CN—c-Pen | N |
| 1-24 | 1-CN—c-Hex | N |
| 1-25 | CF₃ | CH |

Intermediate compound 1-20: ¹H-NMR (CDCl₃) δ: 8.53 (1H, dd), 8.48 (1H, dd), 3.38 (2H, q), 1.36 (3H, t).
Intermediate compound 1-22: ¹H-NMR (CDCl₃) δ: 8.55 (1H, dd), 8.39 (1H, dd), 3.40 (2H, q), 2.98-2.91 (2H, m), 2.70-2.51 (3H, m), 2.22-2.14 (1H, m), 1.38 (3H, t).
Intermediate compound 1-23: ¹H-NMR (CDCl₃) δ: 8.62 (1H, dd), 8.37 (1H, dd), 3.40 (2H, q), 2.62-2.59 (2H, m), 2.08 (6H, tdd), 1.37 (3H, t).
Intermediate compound 1-24] ¹H-NMR (CDCl₃) δ: 8.67 (1H, dd), 8.40 (1H, dd), 3.39 (2H, q), 2.22 (2H, d), 1.90-1.81 (7H, m), 1.35-1.29 (4H, m).
Intermediate compound 1-25: ¹H-NMR (CDCl₃) δ: 1.33 (3H, t), 3.35 (2H), 7.39 (1H, t), 7.92 (1H, br s), 8.24 (1H, d).

Reference Preparation Example 22

A mixture of 1.0 g of the intermediate compound 1-20, 0.67 g of methylboronic acid, 0.13 g of [1,1'-bis(diphenylphosphino)ferrocene] palladium dichloride, 2.3 g of tripotassium phosphate, 0.5 mL of water, and 5 mL of DME was stirred at 80° C. for 4 hours. The reaction mixtures were cooled to room temperature, and thereto was added water, and the mixtures were extracted with ethyl acetate. The obtained organic layers were washed with saturated brine and dried over anhydrous sodium sulfate, and concentrated under reduced pressure. The obtained residue was subjected to a silica gel column chromatography to obtain the intermediate compound 1-26 below 0.27 g.

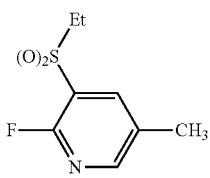

Intermediate compound 1-26: ¹H-NMR (CDCl₃) δ: 8.27 (1H, s), 8.18 (1H, dd), 3.36 (2H, q), 2.44 (3H, s), 1.33 (3H, t).

Reference Preparation Example 23

The compounds as below-mentioned were prepared according to the similar method to the Reference Preparation Example 22.

Intermediate Compound 1-27

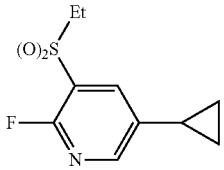

Intermediate compound 1-27: ¹H-NMR (CDCl₃) δ: 8.24 (1H, s), 7.95 (1H, dd), 3.35 (2H, q), 2.03-1.96 (1H, m), 1.33 (3H, t), 1.15-1.12 (2H, m), 0.80-0.77 (2H, m).

Intermediate Compound 1-28

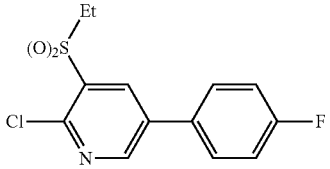

Intermediate compound 1-28: ¹H-NMR (CDCl₃) δ: 8.79 (1H, d), 8.57 (1H, d), 7.61-7.59 (2H, m), 7.24-7.22 (2H, m), 3.55 (2H, q), 1.35 (3H, t).

Intermediate Compound 1-29

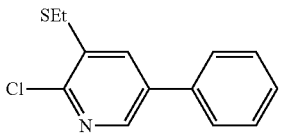

Intermediate compound 1-29: ¹H-NMR (CDCl₃) δ: 8.35 (1H, d), 7.67 (1H, d), 7.56-7.43 (5H, m), 3.03 (2H, q), 1.42 (3H, t).

Intermediate Compound 1-30

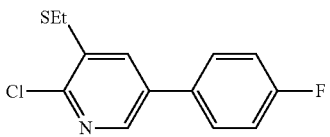

Intermediate compound 1-30: ¹H-NMR (CDCl₃) δ: 8.30 (1H, d), 7.62 (1H, d), 7.52-7.49 (2H, m), 7.19-7.17 (2H, m), 3.03 (2H, q), 1.42 (3H, t).

Reference Preparation Example 24

To a mixture of 5.0 g of 2-bromo-5-(trifluoromethyl) aniline, 2.77 mL of isoamyl nitrite and 50 mL of acetonitrile was added dropwise 2.6 mL of dimethyl disulfide under ice-cooling. The mixtures were stirred at 50° C. for 6 hours. The reaction mixtures were cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography to obtain the intermediate compound 1-13 below 4.5 g.

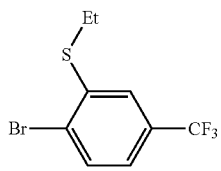

Intermediate compound 1-13: $^1$H-NMR (CDCl$_3$) δ: 1.40 (3H, t), 2.99 (2H, q), 7.23 (1H, d), 7.37 (1H, s), 7.63 (1H, d).

Reference Preparation Example 25

To a mixture of 5.0 g of 4,6-dichloropyrimidine, 3.3 g of sodium hydride (in oil, 60%) and 50 mL of THF was added dropwise benzyl alcohol 3.5 mL. The reaction mixtures were stirred at room temperature for 16 hours. To the reaction mixtures was added aqueous ammonium chloride solution, and the mixtures were extracted with ethyl acetate. The obtained organic layers were washed with saturated brine, dried over anhydrous sodium sulfate, and concentrated under reduced pressure to obtain the intermediate compound 2-12 below 6.1 g.

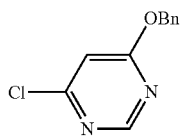 [SMILES: Clc1cc(OCc2ccccc2)ncn1]

intermediate compound 2-12: $^1$H-NMR (CDCl$_3$) δ: 8.60 (1H, s), 7.44-7.35 (5H, m), 6.82 (1H, d, J=0.9 Hz), 5.45 (2H, s).

Reference Preparation Example 25-1

The compounds that were prepared according to the similar method to the Reference Preparation Example 25 and their physical property values are shown below.

Intermediate Compound 2-26

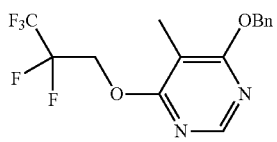 [SMILES: Cc1c(OCc2ccccc2)ncnc1OCC(F)(F)C(F)(F)F]

Intermediate compound 2-26: $^1$H-NMR (CDCl$_3$) δ: 8.31 (1H, d), 7.41-7.37 (5H, m), 5.45 (2H, s), 4.86 (2H, td), 2.07 (3H, d).

Intermediate Compound 2-29

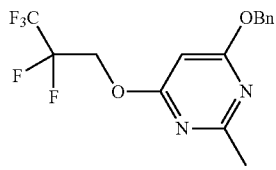 [SMILES: Cc1nc(OCc2ccccc2)cc(OCC(F)(F)C(F)(F)F)n1]

Intermediate compound 2-29: $^1$H-NMR (CDCl$_3$) δ: 7.44-7.33 (5H, m), 6.03 (1H, s), 5.39 (2H, s), 4.85 (2H, t), 2.53 (3H, s).

Intermediate Compound 2-32

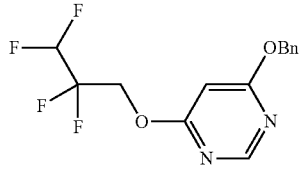 [SMILES: FC(F)C(F)(F)COc1cc(OCc2ccccc2)ncn1]

Intermediate compound 2-32: $^1$H-NMR (CDCl$_3$) δ: 8.46 (1H, d), 7.44-7.34 (5H, m), 6.21 (1H, d), 5.97 (1H, tt), 5.42 (2H, s), 4.78 (2H, tt).

Intermediate Compound 2-35

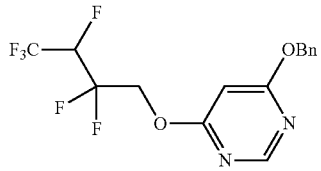 [SMILES: FC(C(F)(F)F)C(F)(F)COc1cc(OCc2ccccc2)ncn1]

Intermediate compound 2-35: $^1$H-NMR (CDCl$_3$) δ: 8.46 (1H, d), 7.44-7.33 (5H, m), 6.21 (1H, d), 5.43 (2H, s), 5.12-5.02 (1H, m), 4.81-4.76 (2H, m).

Reference Preparation Example 26

The compounds that were prepared according to the similar method to the Reference Preparation Example 13, and their physical property values are shown below.

Intermediate Compound 2-13

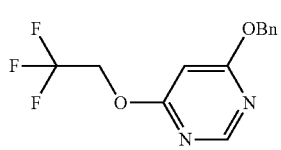 [SMILES: FC(F)(F)COc1cc(OCc2ccccc2)ncn1]

Intermediate compound 2-13: $^1$H-NMR (CDCl$_3$) δ: 4.78 (2H, q), 5.41 (2H, s), 6.22 (1H, s), 7.32-7.42 (5H, m), 8.44 (1H, s).

Intermediate Compound 2-14

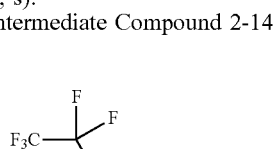

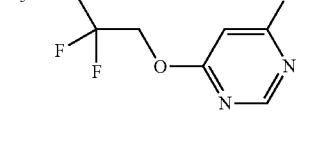

Intermediate compound 2-14: $^1$H-NMR (CDCl$_3$) δ: 4.90 (2H, t), 5.41 (2H, s), 6.22 (1H, s), 7.32-7.42 (5H, m), 8.44 (1H, s).

Intermediate Compound 2-25

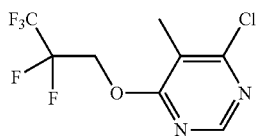 [SMILES: Cc1c(Cl)ncnc1OCC(F)(F)C(F)(F)F]

Intermediate compound 2-25: $^1$H-NMR (CDCl$_3$) δ: 8.45 (1H, d), 4.89 (2H, d), 2.28 (3H, d).

Intermediate Compound 2-28

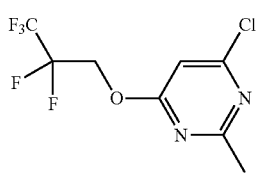 [SMILES: Cc1nc(Cl)cc(OCC(F)(F)C(F)(F)F)n1]

Intermediate compound 2-28: $^1$H-NMR (CDCl$_3$) δ: 6.74 (1H, d), 4.88 (2H, td), 2.62 (3H, d).

Intermediate Compound 2-31

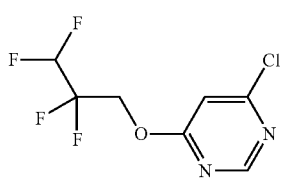 [SMILES: FC(F)C(F)(F)COc1cc(Cl)ncn1]

Intermediate compound 2-31: $^1$H-NMR (CDCl$_3$) δ: 8.63 (1H, d), 6.92 (1H, d), 5.96 (1H, tt), 4.83 (2H, tt).

Intermediate Compound 2-34

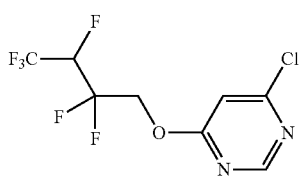 [SMILES: FC(C(F)(F)F)C(F)(F)COc1cc(Cl)ncn1]

Intermediate compound 2-34: $^1$H-NMR (CDCl$_3$) δ: 8.63 (1H, d), 6.92 (1H, d), 5.15-4.97 (1H, m), 4.83-4.80 (2H, m).

Reference Preparation Example 27

A mixture of 1.0 g of the intermediate compound 2-13, 37 mg of 10% palladium/carbon, and 15 mL of ethyl acetate was stirred under hydrogen atmosphere for 3 hours. The reaction mixtures were filtered through Celite (registered trademark) and concentrated under reduced pressure to obtain the intermediate compound 2-15 below 0.63 g.

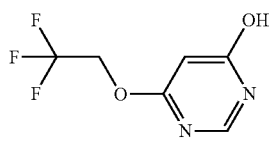 [SMILES: Oc1cc(OCC(F)(F)F)ncn1]

Intermediate compound 2-15: $^1$H-NMR (CDCl$_3$) δ: 4.73 (2H, q), 5.85 (1H, s), 8.00 (1H, s), 13.23 (1H, br s).

Reference Preparation Example 28

The intermediate compound 2-16 below was prepared according to the similar method to the Reference preparation Example 27.

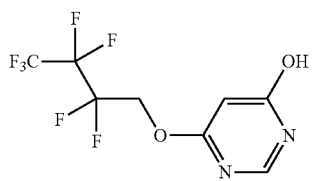 [SMILES: Oc1cc(OCC(F)(F)C(F)(F)C(F)(F)F)ncn1]

Intermediate compound 2-16: $^1$H-NMR (CDCl$_3$) δ: 4.87 (2H, t), 5.87 (1H, s), 8.03 (1H, s), 13.38 (1H, br s).

Intermediate Compound 2-27

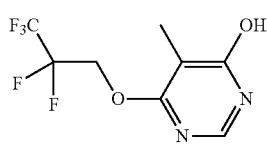 [SMILES: Cc1c(O)ncnc1OCC(F)(F)C(F)(F)F]

Intermediate compound 2-27: $^1$H-NMR (CDCl$_3$) δ: 7.97 (1H, s), 4.84 (2H, dd), 2.00 (3H, s).

Intermediate Compound 2-30

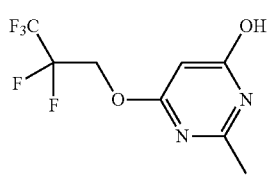 [SMILES: Cc1nc(O)cc(OCC(F)(F)C(F)(F)F)n1]

Intermediate compound 2-30: $^1$H-NMR (CDCl$_3$) δ: 5.71 (1H, s), 4.82 (2H, t), 2.47 (3H, s).

Intermediate Compound 2-33

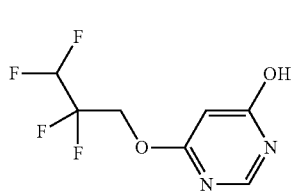 [SMILES: Oc1cc(OCC(F)(F)C(F)F)ncn1]

Intermediate compound 2-33: $^1$H-NMR (CDCl$_3$) δ: 8.04 (1H, d), 6.11-5.82 (1H, m), 5.85 (1H, d), 4.78-4.71 (2H, m).

Intermediate Compound 2-36

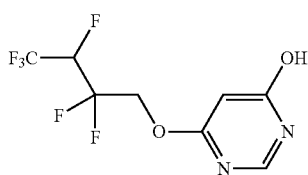 [SMILES: Oc1cc(OCC(F)(F)C(F)C(F)(F)F)ncn1]

Intermediate compound 2-36: ¹H-NMR (CDCl₃) δ: 8.05 (1H, d), 5.86 (1H, d), 5.16-4.97 (1H, m), 4.76-4.67 (2H, m).

Reference Preparation Example 29

The compounds that were prepared according to the similar method to the Reference Preparation Example 8, and their physical property values are shown below.

a compound represented by formula (A-4):

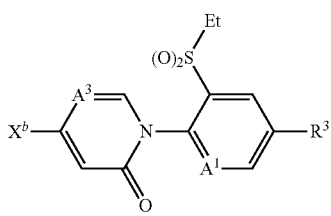

wherein, a combination of $R^3$, $A^1$, $A^3$ and $X^b$ represent any one of the combination indicated in Table 19.
[Table 9]

TABLE 19

| Intermediate compound | $R^3$ | $A^1$ | $A^3$ | $X^b$ |
|---|---|---|---|---|
| 2-17 | H | N | CH | I |
| 2-18 | CF₃ | CH | CH | Cl |
| 2-19 | CF₃ | CH | N | Cl |
| 2-20 | Br | N | CH | Cl |
| 2-21 | Br | N | N | Cl |
| 2-22 | H | N | N | Cl |

Intermediate compound 2-17: ¹H-NMR (CDCl₃) δ: 1.31 (3H, t), 3.31-3.48 (2H, m), 6.63-6.65 (1H, m), 6.98-7.00 (1H, m), 7.16 (1H, s), 7.65-7.69 (1H, m), 8.44 (1H, d), 8.84 (1H, d).

Intermediate compound 2-18: ¹H-NMR (CDCl₃) δ: 1.28 (3H, t), 3.26 (2H, q), 6.35-6.39 (1H, m), 6.68 (1H, s), 7.18 (1H, d), 7.50 (1H, d), 8.04 (1H, d), 8.40 (1H, s).

Intermediate compound 2-19: ¹H-NMR (CDCl₃) δ: 1.31 (3H, t), 3.15-3.24 (2H, m), 6.63 (1H, s), 7.55 (1H, d), 7.97 (1H, s), 8.08-8.10 (1H, m), 8.42 (1H, d).

Intermediate compound 2-20: ¹H-NMR (CDCl₃) δ: 1.33 (3H, t), 3.34-3.39 (2H, m), 6.35-6.37 (1H, m), 6.65 (1H, d), 7.19-7.24 (1H, m), 8.54 (1H, d), 8.87 (1H, d).

Intermediate compound 2-21: ¹H NMR (400 MHz, CDCl₃) δ: 1.35 (3H, t), 3.33-3.38 (2H, m), 6.60 (1H, s), 8.0 (1H, s), 8.55 (1H, d), 8.90 (1H, d).

Intermediate compound 2-22: ¹H-NMR (CDCl₃) δ: 1.33 (3H, t), 3.32-3.37 (2H, m), 6.61 (1H, s), 7.73-7.77 (1H, m), 8.04 (1H, s), 8.47 (1H, dd), 8.89 (1H, dd).

Reference Preparation Example 30

Under argon atmosphere, a mixture of 100 mg of the compound A-36 of the present invention, 56 mg of bis (pinacolato)diboron, 5 mg of [1,1'-bis(diphenylphosphino) ferrocene]palladium dichloride, 59 mg of potassium acetate and 3 mL of toluene was stirred at 80° C. for 4 hours. The reaction mixtures were cooled to room temperature, and thereto was added saturated brine, and the mixtures were extracted with ethyl acetate. The resulting organic layers were dried over anhydrous sodium sulfate, and concentrated under reduced pressure to obtain the intermediate compound 3-1 as crude product below 154 mg.

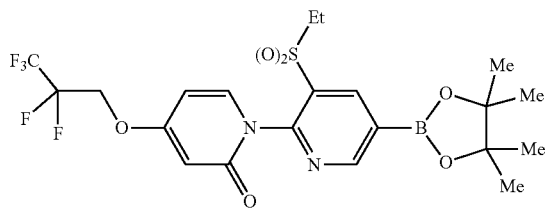

Intermediate compound 3-1: ¹H-NMR (CDCl₃) δ: 9.11 (1H, d), 8.78 (1H, d), 7.28-7.24 (1H, m), 6.15 (1H, dd), 5.89 (1H, d), 4.40 (2H, t), 3.45 (2H, q), 1.36 (3H, t), 1.27 (12H, s).

Reference Preparation Example 31

The intermediate compound 3-2 was prepared by using the compound C-23 of the present invention instead of the compound A-36 of the present invention according to the similar method to the Reference preparation example 30.

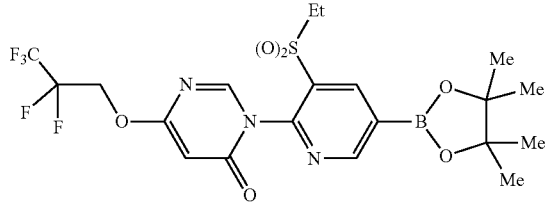

Intermediate compound 3-2: ¹H-NMR (CDCl₃) δ: 9.15 (1H, d), 8.80 (1H, d), 8.03 (1H, s), 5.93 (1H, s), 4.97 (1H, q), 4.75 (1H, q), 3.43-3.33 (2H, m), 1.42-1.21 (15H, m).

Reference Preparation Example 32

The intermediate compound 2-23 was prepared by using the intermediate compound 1-20 instead of the intermediate compound 1-1 according to the Reference Preparation Example 10.

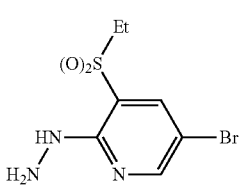

Intermediate compound 2-23: ¹H-NMR (CDCl₃) δ: 8.42 (1H, d), 8.04 (1H, d), 7.60 (1H, s), 3.97 (2H, s), 3.17 (2H, q), 1.30 (3H, t).

Reference Preparation Example 33

The intermediate compound 2-24 below was prepared by using the intermediate compound 2-23 instead of the intermediate compound 2-5 according to the similar method to the Reference preparation example 11.

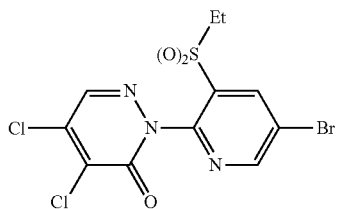

Intermediate compound 2-24: ¹H-NMR (CDCl₃) δ: 8.92 (1H, d), 8.56 (1H, d), 7.94 (1H, s), 3.36 (2H, q), 1.35 (3H, t).

Reference Preparation Example 34

A mixture of 5 mL of ethyl 2-cyano-2-methylpropionate, 3.85 g of potassium tert-butoxide, 10 mL of water, and 20 mL of ethanol was stirred at 60° C. for 4 hours. The reaction mixtures were cooled to room temperature, and concentrated under reduced pressure. The precipitated solids were washed with MTBE to obtain the intermediate compound 4-1 below 4.7 g.

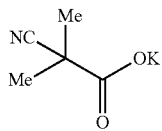

Intermediate compound 4-1: ¹H-NMR (CDCl₃) δ: 1.51 (6H, s).

Preparation Example 1

The compound A-1 of the present invention was prepared by using 4-(trifluoromethyl)pyridine-2(1H)-one instead of 4-chloropyridine-2(1H)-one according to the similar method to the Reference preparation example 8.

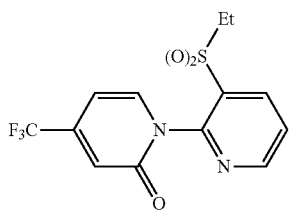

Compound A-1 of the present invention: ¹H-NMR (CDCl₃) δ: 8.88 (1H, dd), 8.48 (1H, dd), 7.72 (1H, dd), 7.46 (1H, d), 6.91 (1H, s), 6.47 (1H, dd), 3.50-3.33 (2H, m), 1.34 (3H, t).

Preparation Example 2

The compounds that were prepared according to the similar method to the Preparation example 1, and their physical property values are shown below.

a compound represented by formula (I-A):

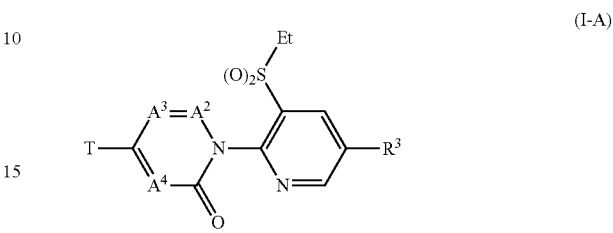

wherein, a combination of T, A², A³, A⁴ and R² represents any one of the combinations indicated in Table 20.

[Table 10]

TABLE 20

| Present compound | T | A² | A³ | A⁴ | R³ |
|---|---|---|---|---|---|
| A-36 | OCH₂CF₂CF₃ | CH | CH | CH | Br |
| A-45 | OCH₂CF₂CF₃ | CH | CH | CH | 1-CN—c-Pr |
| A-48 | CF₃ | CH | CH | CH | CF₃ |
| A-59 | OCH₂CF₂CF₃ | CH | CH | CH | 1-CN—c-Pen |
| A-60 | OCH₂CF₂CF₃ | CH | CH | CH | 1-CN—c-Hex |
| C-1 | OCH₂CF₂CF₃ | CH | N | CH | H |
| C-2 | OCH₂CF₂CF₂CF₃ | CH | N | CH | H |
| C-3 | OCH₂CF₂CF₃ | CH | N | CH | CF₃ |
| C-14 | CF₃ | CH | N | CH | H |
| C-21 | OCH₂CF₃ | CH | N | CH | H |
| C-22 | OCH₂CF₂CF₃ | CH | N | CH | CH₃ |
| C-23 | OCH₂CF₂CF₃ | CH | N | CH | Br |
| C-25 | OCH₂CF₂CF₃ | CH | N | CH | c-Pr |
| C-30 | OCH₂CF₂CF₃ | CH | N | CH | 1-CN—c-Bu |
| C-32 | OCH₂CF₂CF₃ | CH | N | CH | 1-CN—c-Pr |
| C-33 | CF₃ | CH | N | CH | CF₃ |
| C-34 | OCH₂CF₂CF₃ | CH | N | CH | 1-CN—c-Pen |
| C-35 | OCH₂CF₂CF₃ | CH | N | CH | 1-CN—c-Hex |
| C-40 | OCH₂CF₂CF₃ | CMe | N | CH | c-Pr |
| C-41 | OCH₂CF₂CF₃ | CH | N | CMe | c-Pr |
| C-42 | OCH₂CF₂CHF₂ | CH | N | CH | c-Pr |
| C-43 | OCH₂CF₂CHFCF₃ | CH | N | CH | c-Pr |

Compound A-36 of the present invention: ¹H-NMR (CDCl₃) δ: 8.88 (1H, d), 8.55 (1H, d), 7.24 (1H, d), 6.16 (1H, dd), 5.89 (1H, d), 4.41 (2H, t), 3.51-3.39 (2H, m), 1.36 (3H, t).

Compound A-45 of the present invention: ¹H-NMR (CDCl₃) δ: 8.84 (1H, d), 8.21 (1H, d), 7.24 (1H, d), 6.17 (1H, dd), 5.89 (1H, d), 4.41 (2H, t), 3.43 (2H, q), 2.00-1.99 (2H, m), 1.66-1.58 (2H, m), 1.34 (3H, t).

Compound A-48 of the present invention: ¹H-NMR (CDCl₃) δ: 9.12 (1H, s), 8.68 (1H, d), 7.46 (1H, d), 6.92 (1H, s), 6.51 (1H, dd), 3.50-3.46 (2H, m), 1.38 (3H, t).

Compound A-59 of the present invention: ¹H-NMR (CDCl₃) δ: 8.96 (1H, d), 8.43 (1H, d), 7.25 (1H, d), 6.18 (1H, dd), 5.90 (1H, d), 4.41 (2H, t), 3.48-3.42 (2H, m), 2.65-2.62 (2H, m), 2.05-2.01 (6H, m), 1.35 (3H, t).

Compound A-60 of the present invention: ¹H-NMR (CDCl₃) δ: ¹H-NMR (CDCl₃) δ: 9.00 (1H, d), 8.46 (1H, d), 7.26 (1H, d), 6.18 (1H, dd), 5.91 (1H, d), 4.42 (2H, t), 3.48-3.41 (2H, m), 2.29-2.26 (2H, m), 1.92-1.81 (7H, m), 1.35 (4H, t).

Compound C-1 of the present invention: $^{1}$H-NMR (CDCl$_3$) δ: 8.89 (1H, d), 8.49 (1H, d), 8.05 (1H, d), 7.75 (1H, dd), 5.93 (1H, s), 4.97 (1H, q), 4.77 (1H, q), 3.39-3.34 (2H, m), 1.32 (3H, t).

Compound C-2 of the present invention: $^{1}$H-NMR (CDCl$_3$) δ: 1.31 (3H, t), 3.31-3.39 (2H, m), 4.74-4.84 (1H, m), 4.96-5.06 (1H, m), 5.92 (1H, s), 7.72-7.75 (1H, m), 8.02 (1H, s), 8.47-8.49 (1H, m), 8.87-8.88 (1H, m).

Compound C-3 of the present invention: $^{1}$H-NMR (CDCl$_3$) δ: 9.14 (1H, dd), 8.70 (1H, d), 8.05 (1H, d), 5.95 (1H, d), 5.01-4.94 (1H, m), 4.82-4.76 (1H, m), 3.45 (2H, q), 1.37 (3H, t).

Compound C-14 of the present invention: $^{1}$H-NMR (CDCl$_3$) δ: 1.34 (3H, t), 3.32-3.37 (2H, m), 6.91 (1H, s), 7.76-7.79 (1H, m), 8.21 (1H, s), 8.48 (1H, d), 8.89 (1H, d).

Compound C-21 of the present invention: $^{1}$H-NMR (CDCl$_3$) δ: 1.28 (3H, t), 3.27-3.41 (2H, m), 4.60-4.88 (2H, m), 7.25 (1H, s), 7.73 (1H, dd), 8.02 (1H, s), 8.48 (1H, dd), 8.88 (1H, dd).

Compound C-22 of the present invention: $^{1}$H-NMR (CDCl$_3$) δ: 8.68 (1H, s), 8.27 (1H, s), 8.02 (1H, d), 5.92 (1H, d), 4.97 (1H, q), 4.76 (1H, q), 3.34 (2H, q), 2.56 (3H, s), 1.32 (3H, t).

Compound C-23 of the present invention: $^{1}$H-NMR (CDCl$_3$) δ: 8.92 (1H, d), 8.59 (1H, d), 8.01 (1H, s), 5.92 (1H, s), 4.96-4.77 (2H, m), 3.39 (2H, q), 1.35 (3H, t).

Compound C-25 of the present invention: $^{1}$H-NMR (CDCl$_3$) δ: 8.61 (1H, d), 8.02 (1H, d), 8.00 (1H, d), 5.92 (1H, d), 5.00-4.93 (1H, m), 4.78-4.72 (1H, m), 3.32 (2H, q), 2.13-2.06 (1H, m), 1.31 (3H, t), 1.32-1.19 (2H, m), 0.99-0.85 (2H, m).

Compound C-30 of the present invention: $^{1}$H-NMR (CDCl$_3$) δ: 8.96 (1H, d), 8.47 (1H, d), 8.03 (1H, d), 5.94 (1H, d), 4.97-4.78 (2H, m), 3.40 (2H, t), 3.03-2.97 (2H, m), 2.80-2.57 (3H, m), 2.27-2.20 (1H, m), 1.36 (3H, t).

Compound C-32 of the present invention: $^{1}$H-NMR (CDCl$_3$) δ: 8.87 (1H, d), 8.23 (1H, d), 8.01 (1H, s), 5.93 (1H, s), 4.87 (2H, dq), 3.39-3.35 (2H, m), 2.06-1.99 (2H, m), 1.68-1.59 (2H, m), 1.34 (3H, t).

Compound C-33 of the present invention: $^{1}$H-NMR (CDCl$_3$) δ: 9.16 (1H, s), 8.70 (1H, s), 8.23 (1H, s), 6.94 (1H, s), 3.46-3.41 (2H, m), 1.40 (3H, t).

Compound C-34 of the present invention: $^{1}$H-NMR (CDCl$_3$) δ: 9.00 (1H, d), 8.46 (1H, d), 8.03 (1H, s), 5.94 (1H, s), 4.97 (1H, q), 4.77 (1H, q), 3.39 (2H, q), 2.68-2.65 (2H, m), 2.16-2.10 (6H, m), 1.34 (3H, t).

Compound C-35 of the present invention: $^{1}$H-NMR (CDCl$_3$) δ: 9.04 (1H, d), 8.49 (1H, d), 8.03 (1H, s), 5.94 (1H, s), 4.97 (1H, q), 4.77 (1H, q), 3.39 (2H, q), 2.29-2.26 (2H, m), 1.96-1.83 (6H, m), 1.58-1.55 (1H, m), 1.34 (4H, t).

Compound C-40 of the present invention: $^{1}$H-NMR (CDCl$_3$) δ: 8.31 (1H, d), 8.00 (1H, d), 6.31 (1H, s), 4.87 (2H, t), 3.42 (2H, q), 2.52 (3H, s), 2.01-1.99 (1H, m), 1.31 (3H, t), 1.16-1.11 (2H, m), 0.83-0.81 (2H, m).

Compound C-41 of the present invention: $^{1}$H-NMR (CDCl$_3$) δ: 8.60 (1H, d), 8.02 (1H, d), 7.89 (1H, s), 4.86 (2H, dq), 3.36-3.26 (2H, m), 2.11-2.08 (1H, m), 2.05 (3H, s), 1.32-1.24 (5H, m), 0.96-0.87 (2H, m).

Compound C-42 of the present invention: $^{1}$H-NMR (CDCl$_3$) δ: 8.61 (1H, d), 8.02 (1H, d), 8.00 (1H, d), 6.13-5.85 (1H, m), 5.89 (1H, d), 4.76 (2H, dq), 3.33 (2H, q), 2.11-2.08 (1H, m), 1.30-1.27 (5H, m), 0.94-0.90 (2H, m).

Compound C-43 of the present invention: $^{1}$H-NMR (CDCl$_3$) δ: 8.61 (1H, d), 8.02 (1H, d), 8.00 (1H, d), 5.89 (1H, d), 5.19-5.00 (1H, m), 4.87-4.61 (2H, m), 3.35-3.31 (2H, m), 2.10-2.08 (1H, m), 1.31 (3H, t), 1.27-1.26 (2H, m), 0.98-0.87 (2H, m).

Preparation Example 3

To a mixture of 0.3 g of the intermediate compound 2-7, 0.1 mL of 2,2,3,3,3-pentafluoro-1-propanol and 3 mL of NMP was added 0.04 g of sodium sulfate (in oil, 60%) under ice-cooling. The reaction mixtures were stirred under ice-cooling for 1.5 hours. To the reaction mixtures was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane: ethyl acetate=1:2) to obtain the compound B-1 of the present invention below 0.37 g.

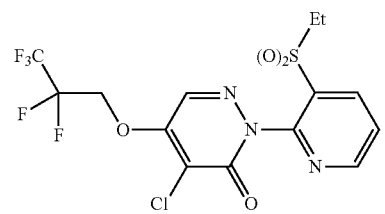

Compound B-1 of the present invention: $^{1}$H-NMR (CDCl$_3$) δ: 8.90 (1H, dd), 8.46 (1H, dd), 7.90 (1H, s), 7.74 (1H, dd), 4.76 (2H, t), 3.37 (2H, q), 1.33 (3H, t).

Preparation Example 4

The compounds that were prepared according to the similar method to the Preparation Example 3, and their physical property values are shown below.

a compound represented by formula (I-A)

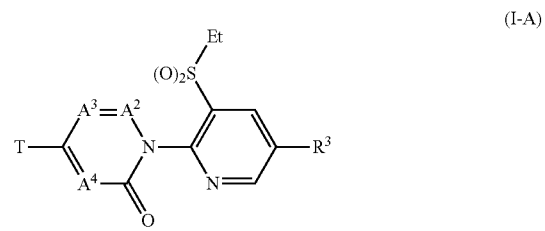

(I-A)

wherein a combination of T, $A^2$, $A^3$, $A^4$ and $R^3$ represents any one of the combinations indicated in Table 21.

[Table 11]

TABLE 21

| Present compound | T | $A^2$ | $A^3$ | $A^4$ | $R^3$ |
| --- | --- | --- | --- | --- | --- |
| A-2 | OCH$_2$CF$_2$CF$_3$ | CH | CH | CH | H |
| A-3 | OCH$_2$CF$_2$CHF$_2$ | CH | CH | CH | H |
| A-4 | OCH$_2$CF$_3$ | CH | CH | CH | H |
| A-5 | OCH(Me)CF$_3$ | CH | CH | CH | H |
| A-6 | F$_3$C-pyrazolyl | CH | CH | CH | H |
| A-7 | OCH$_2$CF$_2$CF$_3$ | CH | CH | CH | CF$_3$ |
| A-10 | OCH$_2$CF$_2$CF$_2$CF$_3$ | CH | CH | CH | H |
| A-11 | OCH$_2$CF$_2$CF$_2$CF$_2$CF$_3$ | CH | CH | CH | H |

TABLE 21-continued

| Present compound | T | $A^2$ | $A^3$ | $A^4$ | $R^3$ |
|---|---|---|---|---|---|
| A-23 | OCH$_2$CF$_2$CHFCF$_3$ | CH | CH | CH | H |
| B-2 | OCH$_2$CF$_2$CHF$_2$ | N | CH | CCl | H |
| B-3 | OCH$_2$CF$_2$CHFCF$_3$ | N | CH | CCl | H |
| B-4 | OCH$_2$CF$_3$ | N | CH | CCl | H |
| B-6 | OCH$_2$CF$_2$CF$_3$ | N | CH | CCl | Br |
| C-4 | F$_3$C-pyrazole | CH | N | CH | H |
| C-5 | F$_3$C-pyrazole | CH | N | CH | H |
| C-15 | F$_3$C-imidazole | CH | N | CH | H |
| C-16 | F$_3$C-triazole | CH | N | CH | H |

Compound A-2 of the present invention: $^1$H-NMR (CDCl$_3$) δ: 8.86 (1H, dd), 8.46 (1H, dd), 7.68 (1H, dd), 7.27 (1H, s), 6.17 (1H, dd), 5.90 (1H, d), 4.41 (2H, t), 3.49-3.39 (2H, m), 1.33 (3H, t).

Compound A-3 of the present invention: $^1$H-NMR (CDCl$_3$) δ: 8.86 (1H, dd), 8.46 (1H, dd), 7.68 (1H, dd), 7.27 (1H, d), 6.14 (1H, dd), 6.09-5.96 (1H, m), 5.92 (1H, d), 4.36 (2H, t), 3.48-3.39 (2H, m), 1.33 (3H, t).

Compound A-4 of the present invention: $^1$H-NMR (CDCl$_3$) δ: 8.85 (1H, dd), 8.46 (1H, dd), 7.68 (1H, dd), 7.27 (1H, d), 6.17 (1H, dd), 5.89 (1H, d), 4.35 (2H, q), 3.51-3.36 (2H, m), 1.32 (3H, t).

Compound A-5 of the present invention: $^1$H-NMR (CDCl$_3$) δ: 8.85 (1H, d), 8.48-8.45 (1H, m), 7.67 (1H, dd), 7.26 (1H, dd), 6.13 (1H, dd), 5.92 (1H, dd), 4.73-4.69 (1H, m), 3.48-3.38 (2H, m), 1.56 (3H, t), 1.33 (3H, t).

Compound A-6 of the present invention: $^1$H-NMR (CDCl$_3$) δ: 8.89 (1H, dd), 8.49 (1H, dd), 8.05 (1H, d), 7.72 (1H, dd), 7.48 (1H, d), 7.02 (1H, dd), 6.86 (1H, d), 6.80 (1H, d), 3.54-3.36 (2H, m), 1.35 (3H, t).

Compound A-7 of the present invention: $^1$H-NMR (CDCl$_3$) δ: 9.09 (1H, dd), 8.66 (1H, d), 7.28 (1H, d), 6.20 (1H, dd), 5.91 (1H, d), 4.42 (2H, t), 3.54-3.49 (2H, m), 1.38 (3H, t).

Compound A-10 of the present invention: $^1$H-NMR (CDCl$_3$) δ: 1.32 (3H, t), 3.33-3.51 (2H, m), 4.43 (2H, t), 5.88 (1H, d), 6.13-6.16 (1H, m), 7.27 (1H, s), 7.64-7.67 (1H, m), 8.43-8.46 (1H, dd), 8.83-8.84 (1H, m).

Compound A-11 of the present invention: $^1$H-NMR (CDCl$_3$) δ: 1.32 (3H, t), 3.37-3.48 (2H, m), 4.45 (2H, d), 5.89 (1H, s), 6.14-6.15 (1H, m), 7.25 (1H, m), 7.66 (1H, t), 8.45 (1H, d), 8.83 (1H, d).

Compound A-23 of the present invention: $^1$H-NMR (CDCl$_3$) δ: 1.32 (3H, t), 3.35-3.50 (2H, m), 4.27-4.44 (2H, m), 5.03-5.18 (1H, m), 5.90 (1H, d), 6.12 (1H, dd), 7.27 (1H, s), 7.65-7.68 (1H, m), 8.45 (1H, dd), 8.84 (1H, dd).

Compound B-2 of the present invention: $^1$H-NMR (CDCl$_3$) δ: 8.90 (1H, d), 8.46 (1H, d), 7.91 (1H, s), 7.74 (1H, dd), 6.09 (1H, t), 4.70 (2H, t), 3.37 (2H, q), 1.33 (3H, t).

Compound B-3 of the present invention: $^1$H-NMR (CDCl$_3$) δ: 8.90 (1H, dd), 8.46 (1H, dd), 7.91 (1H, s), 7.74 (1H, dd), 5.30-5.10 (1H, m), 4.77-4.58 (2H, m), 3.37 (2H, q), 1.33 (3H, t).

Compound B-4 of the present invention: $^1$H-NMR (CDCl$_3$) δ: 8.89 (1H, dd), 8.45 (1H, dd), 7.91 (1H, s), 7.73 (1H, dd), 4.69 (2H, q), 3.36 (2H, q), 1.32 (3H, t).

Compound B-6 of the present invention: $^1$H-NMR (CDCl$_3$) δ: 8.92 (1H, d), 8.55 (1H, d), 7.90 (1H, s), 4.76 (2H, t), 3.38 (2H, q), 1.35 (3H, t).

Compound C-4 of the present invention: $^1$H-NMR (CDCl$_3$) δ: 1.33 (3H, t), 3.33-3.39 (2H, m), 6.72 (1H, d), 7.14 (1H, s), 7.74-7.78 (1H, m), 8.13 (1H, s), 8.49-8.51 (1H, m), 8.53 (1H, d), 8.90-8.91 (1H, m).

Compound C-5 of the present invention: $^1$H-NMR (CDCl$_3$) δ: 1.33 (3H, t), 3.33-3.38 (2H, m), 7.11 (1H, s), 7.75-7.78 (1H, m), 7.95 (1H, s), 8.13 (1H, s), 8.49-8.51 (1H, m), 8.78 (1H, s), 8.90-8.91 (1H, m).

Compound C-15 of the present invention: $^1$H-NMR (CDCl$_3$) δ: 1.34 (3H, t), 3.33-3.39 (2H, m), 6.51 (1H, s), 7.77-7.80 (1H, m), 7.90 (1H, s), 8.18 (1H, s), 8.38 (1H, s), 8.50 (1H, d), 8.91-8.92 (1H, m).

Compound C-16 of the present invention: $^1$H-NMR (CDCl$_3$) δ: 1.34 (3H, t), 3.32-3.37 (2H, m), 7.10 (1H, s), 7.77-7.80 (1H, m), 8.17 (1H, s), 8.50 (1H, d), 8.91 (1H, d), 9.17 (1H, s).

Preparation Example 5

0.31 g of the compound B-1 of the present invention was added to a mixture of 0.31 g of 10% palladium/carbon, 0.2 mL of triethylamine, 5 mL of ethanol and 5 mL of ethyl acetate. The reaction mixtures were stirred vigorously at 40° C. under hydrogen atmosphere for 1 hour. The reaction mixtures were filtered through Celite (registered trademark), and the filtrates were concentrated under reduced pressure. The obtained residue was subjected to a silica gel column chromatography (hexane:ethyl acetate: 1:2) to obtain the compound B-5 of the present invention below 0.23 g.

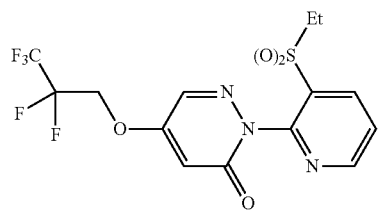

Compound B-5 of the present invention: $^1$H-NMR (CDCl$_3$) δ: 8.89 (1H, dd), 8.45 (1H, dd), 7.81 (1H, d), 7.70 (1H, dd), 6.28 (1H, d), 4.45 (2H, t), 3.36 (2H, q), 1.32 (3H, t).

Preparation Example 6

To a mixture of 0.35 g of the intermediate compound 2-10, 0.05 g of sodium hydride (in oil, 60%) and DMF was added dropwise 0.44 g of 2,2,3,3,3-pentafluoropropyl trifluoro methanesulfonate under ice-cooling. The reaction mixtures were stirred at room temperature for 3 hours, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane:ethyl acetate=1:9) to obtain the compound D-1 of the present invention below 0.28 g.

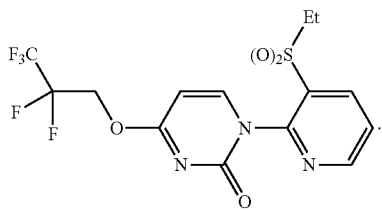

Compound D-1 of the present invention: $^1$H-NMR (CDCl$_3$) δ: 8.85 (1H, dd), 8.46 (1H, dd), 7.72 (1H, dd), 7.33 (1H, d), 5.99 (1H, d), 4.75-4.68 (2H, m), 3.42-3.32 (2H, m), 1.36 (3H, t).

Preparation Example 7

To a mixture of 0.8 g of the intermediate compound 2-3, 0.36 g of 4-(trifluoromethyl)imidazole and toluene were added 0.74 g of potassium carbonate, 0.26 mL of trans-N, N'-dimethylcyclohexane-1,2-diamine and 0.15 g of copper iodide. The reaction mixtures were stirred at 120° C. for 24 hours, and cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane:ethyl acetate=3:2) to obtain the compound A-12 of the present invention 0.32 g.

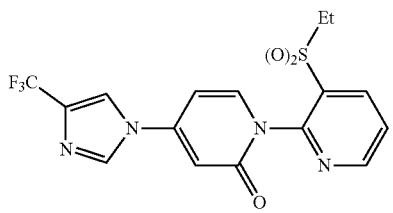

Compound A-12 of the present invention: $^1$H-NMR (CDCl$_3$) δ: 1.37 (3H, t), 3.41-3.49 (2H, m), 6.49 (1H, d), 6.66 (1H, s), 7.54 (1H, d), 7.70-7.76 (2H, m), 8.04 (1H, s), 8.50 (1H, d), 8.90 (1H, d).

Preparation Example 8

The compounds that were prepared according to the similar method to the Preparation Example 7, and their physical property values are shown below.

a compound represented by formula (I-B):

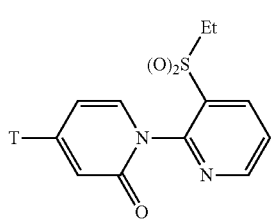

wherein T represents any one of groups indicated in Table 22.

[Table 12]

TABLE 22

| Present compound | T |
|---|---|
| A-13 | F$_3$C-pyrazole |
| A-14 | F$_3$C-triazole |
| A-26 | F$_3$C-pyridinone |

Compound A-13 of the present invention: $^1$H-NMR (CDCl$_3$) δ: 1.33 (3H, t), 3.38-3.50 (2H, m), 6.86 (1H, s), 6.92 (1H, d), 7.46 (1H, d), 7.68-7.71 (1H, m), 7.96 (1H, s), 8.25 (1H, s), 8.47 (1H, d), 8.86 (1H, d).

Compound A-14 of the present invention: $^1$H-NMR (CDCl$_3$) δ: 1.37 (3H, t), 3.39-3.51 (2H, m), 6.87-6.90 (1H, m), 6.98 (1H, d), 7.56 (1H, d), 7.73-7.77 (1H, m), 8.49-8.51 (1H, m), 8.75 (1H, s), 8.90-8.91 (1H, m).

Compound A-26 of the present invention: $^1$H-NMR (CDCl$_3$) δ: 1.34 (3H, t), 3.37-3.54 (2H, m), 6.42 (1H, d), 6.55 (1H, dd), 6.60 (1H, d), 6.93 (1H, s), 7.43 (1H, d), 7.52 (1H, d), 7.68-7.72 (1H, m), 8.46 (1H, d), 8.87 (1H, d).

Preparation Example 9

To a mixture of 0.6 g of the intermediate compound 2-22, 0.57 g of [5-(trifluoromethyl)pyridin-3-yl]boronic acid, 2 mL of water and 10 mL were added 0.63 g of sodium carbonate and 147 mg of [1,1'-bis(diphenylphosphino)ferrocene]palladium dichloride. The reaction mixtures were stirred at 100° C. for 16 hours, and then cooled to room temperature, and filtered. To the filtrates was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane:ethyl acetate=7:3) to obtain the compound C-6 of the present invention below 0.35 g.

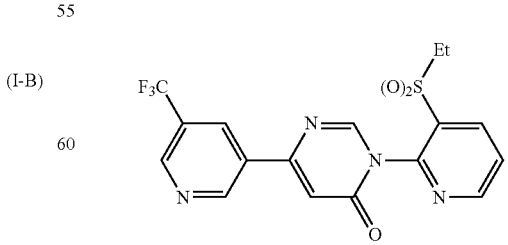

Compound C-6 of the present invention: $^1$H-NMR (CDCl$_3$) δ: 1.34 (3H, t), 3.35-3.42 (2H, m), 7.04 (1H, s), 7.75-7.78 (1H, m), 8.25 (1H, s), 8.50 (1H, dd), 8.62 (1H, s), 8.91-8.91 (1H, m), 8.98 (1H, s), 9.39 (1H, d).

Preparation Example 10

The compounds that were prepared according to the similar method to the Preparation Example 9, and their physical property values are shown below.

a compound represented by formula (I-C):

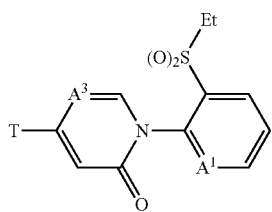

(I-C)

wherein a combination of $A^1$, $A^3$ and T represents any one of the combinations indicated in Table 23.

[Table 13]

TABLE 23

| Present compound | $A^1$ | $A^3$ | T |
|---|---|---|---|
| C-7 | N | N | F₃C-pyridine-methyl |
| C-8 | N | N | F₃C-phenyl |
| C-9 | N | N | F₃C-phenyl (para) |
| C-10 | N | N | 3,5-bis(F₃C)-phenyl |
| C-11 | N | N | F₃C-pyridine |
| C-12 | N | N | F,F-benzodioxole-methyl |
| C-13 | N | N | F,F-benzodioxole-methyl |
| A-15 | N | CH | F₃C-pyridine |
| A-16 | N | CH | F₃C-pyridine |
| A-17 | N | CH | F₃C-phenyl |
| A-18 | N | CH | F₃C-phenyl (para) |
| A-19 | N | CH | 3,5-bis(F₃C)-phenyl |
| A-20 | N | CH | F₃C-pyridine |
| A-21 | N | CH | F,F-benzodioxole-methyl |
| A-22 | N | CH | F,F-benzodioxole-methyl |

[Table 14]

Compound C-7 of the present invention: $^1$H-NMR (CDCl$_3$) δ: 1.35 (3H, t), 3.35-3.43 (2H, m), 7.04 (1H, s), 7.75-7.83 (2H, m), 8.25 (1H, s), 8.52 (2H, t), 8.92 (1H, d), 9.31 (1H, s).

Compound C-8 of the present invention: $^1$H-NMR (CDCl$_3$) δ: 1.34 (3H, t), 3.37-3.41 (2H, m), 6.98 (1H, s), 7.62-7.64 (1H, m), 7.75-7.76 (2H, m), 8.18-8.22 (2H, m), 8.33 (1H, s), 8.50 (1H, d), 8.92 (1H, d).

Compound C-9 of the present invention: ¹H-NMR (CDCl₃) δ: 1.34 (3H, t), 3.36-3.43 (2H, m), 6.98 (1H, s), 7.74-7.77 (3H, m), 8.13-8.15 (2H, m), 8.22 (1H, s), 8.50 (1H, dd), 8.91 (1H, dd).

Compound C-10 of the present invention: ¹H-NMR (CDCl₃) δ: 1.34 (3H, t), 3.37-3.40 (2H, m), 7.03 (1H, s), 7.75-7.78 (1H, m), 7.99 (1H, s), 8.25 (1H, m), 8.49 (3H, s), 8.92-8.93 (1H, m).

Compound C-11 of the present invention: ¹H-NMR (CDCl₃) δ: 1.32 (3H, t), 3.33-3.42 (2H, m), 7.60-7.62 (1H, m), 7.68 (1H, s), 7.74-7.77 (1H, m), 8.23 (1H, s), 8.50-8.51 (1H, m), 8.62 (1H, s), 8.88-8.92 (2H, m).

Compound C-12 of the present invention: ¹H-NMR (CDCl₃) δ: 1.34 (3H, t), 3.36-3.43 (2H, m), 7.17-7.25 (3H, m), 7.73-7.76 (1H, m), 8.03 (1H, dd), 8.20 (1H, s), 8.50 (1H, dd), 8.90-8.91 (1H, m).

Compound C-13 of the present invention: ¹H-NMR (CDCl₃) δ: 1.33 (3H, t), 3.35-3.49 (2H, m), 6.86 (1H, s), 7.16 (1H, d), 7.73-7.82 (3H, m), 8.18 (1H, s), 8.49 (1H, d), 8.90 (1H, d).

Compound A-15 of the present invention: ¹H-NMR (CDCl₃) δ: 1.34 (3H, t), 3.36-3.53 (2H, m), 6.58 (1H, dd), 6.85 (1H, s), 7.48 (1H, d), 7.69-7.72 (1H, m), 8.15 (1H, s), 8.47-8.49 (1H, m), 8.88 (1H, d), 8.97 (1H, s), 9.07 (1H, s).

Compound A-16 of the present invention: ¹H-NMR (CDCl₃) δ: 1.34 (3H, t), 3.38-3.54 (2H, m), 6.56-6.58 (1H, m), 6.85 (1H, s), 7.47 (1H, d), 7.69-7.72 (1H, m), 7.81 (1H, d), 8.10 (1H, d), 8.48-8.49 (1H, m), 8.88 (1H, d), 8.99 (1H, s).

Compound A-17 of the present invention: ¹H-NMR (CDCl₃) δ: 1.34 (3H, t), 3.41-3.51 (2H, m), 6.59-6.61 (1H, m), 6.83 (1H, s), 7.42 (1H, d), 7.61-7.63 (1H, m), 7.68-7.73 (2H, m), 7.82 (1H, d), 7.88 (1H, s), 8.48 (1H, d), 8.87-8.88 (1H, m).

Compound A-18 of the present invention: ¹H-NMR (CDCl₃) δ: 1.33 (3H, t), 3.37-3.54 (2H, m), 6.59 (1H, d), 6.82 (1H, s), 7.42 (1H, d), 7.68-7.74 (5H, m), 8.48 (1H, d), 8.87 (1H, d).

Compound A-19 of the present invention: ¹H-NMR (CDCl₃) δ: 1.34 (3H, t), 3.38-3.53 (2H, m), 6.59 (1H, dd), 6.85 (1H, d), 7.47 (1H, d), 7.69-7.72 (1H, m), 7.97 (1H, s), 8.06 (2H, s), 8.48 (1H, dd), 8.88 (1H, dd).

Compound A-20 of the present invention: ¹H-NMR (CDCl₃) δ: 1.34 (3H, t), 3.35-3.55 (2H, m), 7.08-7.10 (1H, m), 7.25 (1H, m), 7.46 (1H, d), 7.57 (1H, d), 7.67-7.70 (1H, m), 7.98 (1H, s), 8.47-8.49 (1H, m), 8.87-8.93 (2H, m).

Compound A-21 of the present invention: ¹H-NMR (CDCl₃) δ: 1.33 (3H, t), 3.38-3.55 (2H, m), 6.70-6.72 (1H, s), 7.01 (1H, s), 7.13-7.21 (2H, m), 7.34 (1H, d), 7.41 (1H, d), 7.67-7.71 (1H, m), 8.47-8.49 (1H, d), 8.87-8.88 (1H, d).

Compound A-22 of the present invention: ¹H-NMR (CDCl₃) δ: 1.33 (3H, t), 3.37-3.54 (2H, m), 6.51-6.53 (1H, m), 6.73-6.74 (1H, m), 7.16 (1H, d), 7.33-7.40 (3H, m), 7.67-7.70 (1H, m), 8.47-8.49 (1H, m), 8.86-8.88 (1H, m).

Compound C-18 of the Present Invention

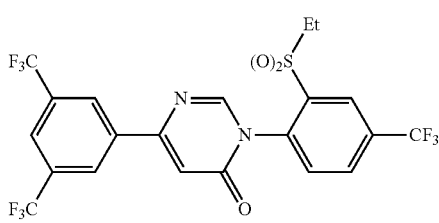

Compound C-18 of the present invention: ¹H-NMR (CDCl₃) δ: 1.28-1.35 (3H, m), 3.23-3.38 (2H, m), 7.06 (1H, s), 7.38 (1H, t), 7.62 (1H, d), 7.92-8.01 (1H, m), 8.11-8.25 (2H, m), 8.45-8.49 (2H, m).

Compound A-30 of the Present Invention

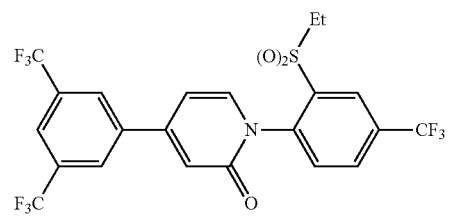

Compound A-30 of the present invention: ¹H-NMR (CDCl₃) δ: 1.30 (3H, t), 3.28-3.37 (2H, m), 6.57-6.60 (1H, m), 6.87 (1H, s), 7.39 (1H, d), 7.57 (1H, d), 7.98 (1H, s), 8.06-8.08 (3H, m), 8.43 (1H, s).

Preparation Example 11

The compounds that were prepared according to the similar method to the Preparation Example 9, and their physical property values are shown below.

a compound represented by formula (I-A):

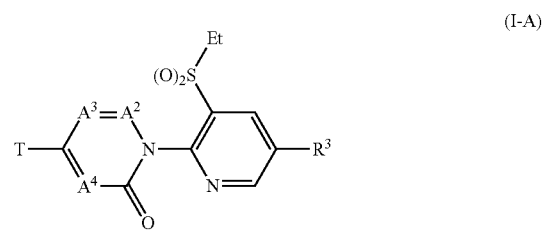

wherein a combination of R³, A², A³, A⁴ and T represents any one of the combinations indicated in Table 24. In the Table, Pm3 represents a 3-pyrimidinyl group.

[Table 15]

TABLE 24

| Present compound | R³ | A² | A³ | A⁴ | T |
|---|---|---|---|---|---|
| A-34 | CH=CH₂ | CH | CH | CH | OCH₂CF₂CF₃ |
| A-35 | 4-F—Ph | CH | CH | CH | OCH₂CF₂CF₃ |
| A-37 | Me | CH | CH | CH | OCH₂CF₂CF₃ |
| A-38 | c-Pr | CH | CH | CH | OCH₂CF₂CF₃ |
| A-43 | C(Me)=CH₂ | CH | CH | CH | OCH₂CF₂CF₃ |
| A-46 | 4-CN—Ph | CH | CH | CH | OCH₂CF₂CF₃ |
| A-47 | 4-Me—Ph | CH | CH | CH | OCH₂CF₂CF₃ |
| A-62 | NH—c-Pr | CH | CH | CH | OCH₂CF₂CF₃ |
| A-63 | Pm3 | CH | CH | CH | OCH₂CF₂CF₃ |
| A-68 | Py4 | CH | CH | CH | OCH₂CF₂CF₃ |
| B-7 | c-Pr | N | CH | CCl | OCH₂CF₂CF₃ |
| B-9 | 4-F—Ph | N | CH | CCl | OCH₂CF₂CF₃ |
| C-20 | 4-Cl—Ph | CH | N | CH | OCH₂CF₂CF₃ |
| C-24 | 4-F—Ph | CH | N | CH | OCH₂CF₂CF₃ |

Compound A-34 of the present invention: ¹H-NMR CDCl₃) δ: 8.79 (1H, d), 8.42 (1H, d), 7.26 (1H, d), 6.82 (1H, dd), 6.15 (1H, dd), 6.04 (1H, d), 5.90 (1H, d), 5.65 (1H, d), 4.41 (2H, t), 3.43 (2H, m), 1.34 (3H, t).

Compound A-35 of the present invention: ¹H-NMR (CDCl₃) δ: 8.98 (1H, d), 8.55 (1H, d), 7.66-7.62 (2H, m), 7.31 (1H, d), 7.28-7.24 (2H, m), 6.18 (1H, dd), 5.92 (1H, d), 4.42 (2H, t), 3.55-3.38 (2H, m), 1.36 (3H, t).

Compound A-37 of the present invention: $^1$H-NMR (CDCl$_3$) δ: 8.65 (1H, s), 8.25 (1H, s), 7.25 (1H, d), 6.14 (1H, dd), 5.90 (1H, d), 4.41 (2H, t), 3.44-3.37 (2H, m), 2.53 (3H, s), 1.33 (3H, t).

Compound A-38 of the present invention: $^1$H-NMR (CDCl$_3$) δ: 8.58 (1H, d), 8.00 (1H, d), 7.23 (1H, d), 6.14 (1H, dd), 5.89 (1H, d), 4.40 (2H, t), 3.46-3.31 (2H, m), 2.10-2.03 (1H, m), 1.31 (3H, t), 1.23-1.21 (2H, m), 0.93-0.85 (2H, m).

Compound A-43 of the present invention: $^1$H-NMR (CDCl$_3$) δ: 8.87 (1H, d), 8.42 (1H, d), 7.26 (1H, d), 6.16 (1H, dd), 5.90 (1H, d), 5.61 (1H, s), 5.41 (1H, s), 4.41 (2H, t), 3.47-3.39 (2H, m), 2.25 (3H, s), 1.34 (3H, t).

Compound A-46 of the present invention: $^1$H-NMR (CDCl$_3$) δ: 9.03 (1H, d), 8.60 (1H, d), 7.88-7.86 (2H, m), 7.78-7.77 (2H, m), 7.32 (1H, d), 6.20 (1H, dd), 5.93 (1H, d), 4.43 (2H, t), 3.52-3.45 (2H, m), 1.37 (3H, t).

Compound A-47 of the present invention: $^1$H-NMR (CDCl$_3$) δ: 9.00 (1H, d), 8.57 (1H, d), 7.55 (2H, d), 7.36 (2H, d), 7.31 (1H, d), 6.17 (1H, dd), 5.92 (1H, d), 4.42 (2H, t), 3.53-3.39 (2H, m), 2.45 (3H, s), 1.36 (3H, t).

Compound A-62 of the present invention: $^1$H-NMR (CDCl$_3$) δ: 8.25 (1H, d), 7.70 (1H, d), 7.24 (1H, d), 6.10 (1H, dd), 5.89 (1H, d), 4.72 (1H, s), 4.39 (2H, t), 3.40-3.31 (2H, m), 2.56-2.55 (1H, m), 1.32 (3H, t), 0.92-0.86 (2H, m), 0.66-0.57 (2H, m).

Compound A-63 of the present invention: $^1$H-NMR (CDCl$_3$) δ: 9.39 (1H, s), 9.06 (2H, s), 9.04 (1H, d), 8.63 (1H, d), 7.32 (1H, d), 6.21 (1H, dd), 5.93 (1H, d), 4.43 (2H, t), 3.53-3.47 (2H, m), 1.39 (3H, t).

Compound A-68 of the present invention: $^1$H-NMR (CDCl$_3$) δ: 9.06 (1H, d), 8.83 (2H, dd), 8.64 (1H, d), 7.59 (2H, dd), 7.32 (1H, d), 6.20 (1H, dd), 5.93 (1H, d), 4.43 (2H, t), 3.53-3.46 (2H, m), 1.38 (3H, t).

Compound B-7 of the present invention: $^1$H-NMR (CDCl$_3$) δ: 8.60 (1H, d), 7.99 (1H, d), 7.89 (1H, s), 4.75 (2H, t), 3.32 (2H, q), 2.10-2.06 (1H, m), 1.30 (3H, t), 1.25-1.23 (2H, m), 0.92-0.89 (2H, m).

Compound B-9 of the present invention: $^1$H-NMR (CDCl$_3$) δ: 9.02 (1H, d), 8.54 (1H, d), 7.92 (1H, s), 7.66-7.64 (2H, m), 7.28-7.24 (2H, m), 4.77 (2H, t), 3.40 (2H, q), 1.36 (3H, t).

Compound C-20 of the present invention: $^1$H-NMR (CDCl$_3$) δ: 1.34 (3H, t), 3.38-3.40 (2H, m), 4.75-4.78 (1H, m), 4.95-4.98 (1H, m), 5.94 (1H, s), 7.53-7.60 (4H, m), 8.06 (1H, s), 8.57 (1H, s), 9.01 (1H, s).

Compound C-24 of the present invention: $^1$H-NMR (CDCl$_3$) δ: 9.02 (1H, d), 8.57 (1H, d), 8.08 (1H, d), 7.67-7.64 (2H, m), 7.29-7.26 (2H, m), 5.96 (1H, d), 4.98-4.78 (2H, m), 3.42-3.38 (2H, m), 1.36 (3H, t).

The compounds that were prepared according to the similar method to the Preparation Example 4 and their physical property values are shown below.

a compound represented by formula (I-D):

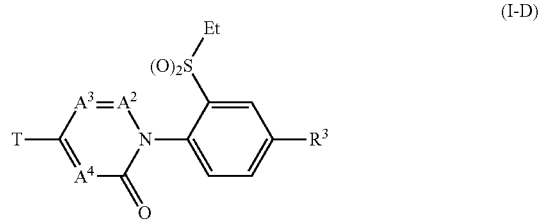

(I-D)

wherein a combination of T, A$^2$, A$^3$, A$^4$ and R$^3$ represents any one of the combinations indicated in Table 25.

[Table 16]

TABLE 25

| Present compound | T | A$^2$ | A$^3$ | A$^4$ | R$^3$ |
|---|---|---|---|---|---|
| A-27 | OCH$_2$CF$_2$CF$_3$ | CH | CH | CH | CF$_3$ |
| A-28 | OCH$_2$CF$_2$CF$_2$CF$_3$ | CH | CH | CH | CF$_3$ |
| A-29 | F$_3$C—pyrazolyl | CH | CH | CH | CF$_3$ |
| C-17 | F$_3$C—pyrazolyl | CH | N | CH | CF$_3$ |

Compound A-27 of the present invention: $^1$H-NMR (CDCl$_3$) δ: 1.28 (3H, t), 3.26-3.28 (2H, m), 4.40 (2H, t), 5.91 (1H, s), 6.14 (1H, d), 7.18 (1H, d), 7.48 (1H, d), 8.03 (1H, d), 8.40 (1H, s).

Compound A-28 of the present invention: $^1$H-NMR (CDCl$_3$) δ: 1.28 (3H, t), 3.24-3.30 (2H, m), 4.44 (2H, t), 5.92 (1H, s), 6.13-6.16 (1H, m), 7.18 (1H, d), 7.50 (1H, d), 8.03 (1H, d), 8.40 (1H, s).

Compound A-29 of the present invention: $^1$H-NMR (CDCl$_3$) δ: 1.29 (3H, t), 3.28-3.30 (2H, m), 6.79 (1H, d), 6.86 (1H, d), 6.99-7.01 (1H, m), 7.38 (1H, d), 7.56 (1H, d), 8.04-8.08 (2H, m), 8.42 (1H, s).

Compound C-17 of the present invention: $^1$H-NMR (CDCl$_3$) δ: 1.28 (3H, t), 3.20-3.26 (2H, m), 6.74 (1H, d), 7.16 (1H, s), 7.61 (1H, d), 8.08-8.12 (2H, m), 8.45 (1H, s), 8.53 (1H, s).

Preparation Example 13

To a mixture of 154 mg of the intermediate compound 3-1, 4 mL of THF and 2 mL of water were added 115 mg of sodium acetate and 1 mL of aqueous hydrogen peroxide solution (30%) under ice-cooling, and the mixtures were stirred at 0° C. for 3 hours. To the reaction mixtures was added saturated brine, and the mixtures were extracted with ethyl acetate. The resulting organic layers were dried over anhydrous sodium sulfate and concentrated under reduced pressure to obtain the compound A-44 of the present invention below as crude product 120 mg.

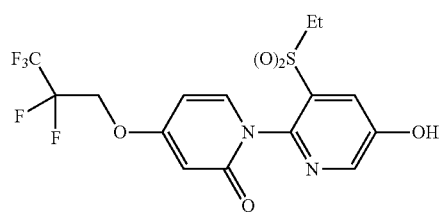

Compound A-44 of the present invention: $^1$H-NMR (CDCl$_3$) δ: 8.05 (1H, d), 7.71 (1H, d), 7.32 (1H, d), 6.26 (1H, dd), 6.02 (1H, d), 4.47 (2H, t), 3.35-3.15 (2H, m), 1.32 (3H, t).

Preparation Example 14

The compound C-31 of the present invention below was prepared by using the intermediate compound 3-2 instead of the intermediate compound 3-1 according to the similar method to the Preparation Example 13.

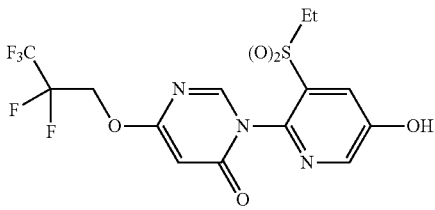

Compound C-31 of the present invention: $^1$H-NMR (CDCl$_3$) δ: 8.15 (1H, s), 8.07 (1H, s), 7.75 (1H, s), 6.02 (1H, s), 4.99 (1H, q), 4.80 (1H, q), 3.28-3.19 (2H, m), 1.33 (3H, t).

Preparation Example 15

A mixture of 120 mg of the compound A-44 of the present invention, 63 mg of ethyl iodide, 163 mg of cesium carbonate, and 3 ml of DMF was stirred at room temperature for 1 hour. To the mixtures was added saturated brine, and the mixtures were extracted with MTBE. The resulting organic layers were dried over anhydrous sodium sulfate and concentrated under reduced pressure. The obtained residue was subjected to a silica gel column chromatography (hexane:ethyl acetate=1:2) to obtain the compound A-39 of the present invention below 56 mg.

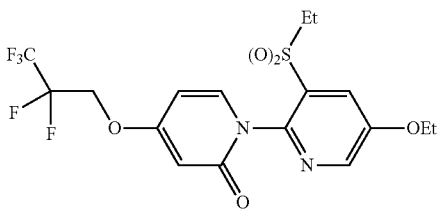

Compound A-39 of the present invention: $^1$H-NMR (CDCl$_3$) δ: 8.45 (1H, d), 7.87 (1H, d), 7.30-7.22 (1H, m), 6.13 (1H, dd), 5.89 (1H, d), 4.40 (2H, t), 4.26-4.18 (2H, m), 3.46-3.32 (2H, m), 1.51 (3H, t), 1.33 (3H, t).

Preparation Example 16

The compounds that were prepared according to the similar method to the Preparation Example 15, and their physical property values are shown below.
a compound represented by formula (I-E):

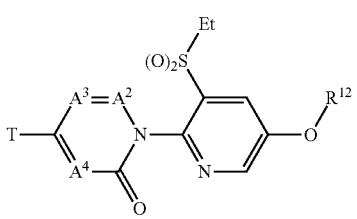

(I-E)

wherein a combination of T, A$^2$, A$^3$, A$^4$ and R$^{12}$ represents any one of the combinations indicated in Table 26.

[Table 17]

TABLE 26

| Present compound | T | A$^2$ | A$^3$ | A$^4$ | R$^{12}$ |
|---|---|---|---|---|---|
| A-40 | OCH$_2$CF$_2$CF$_3$ | CH | CH | CH | Pr |
| A-41 | OCH$_2$CF$_2$CF$_3$ | CH | CH | CH | i-Pr |
| A-42 | OCH$_2$CF$_2$CF$_3$ | CH | CH | CH | CH$_2$CF$_2$CF$_3$ |
| A-61 | OCH$_2$CF$_2$CF$_3$ | CH | CH | CH | Py2 |
| C-26 | OCH$_2$CF$_2$CF$_3$ | CH | N | CH | Et |
| C-27 | OCH$_2$CF$_2$CF$_3$ | CH | N | CH | Pr |
| C-28 | OCH$_2$CF$_2$CF$_3$ | CH | N | CH | CH$_2$CF$_2$CF$_3$ |
| C-29 | OCH$_2$CF$_2$CF$_3$ | CH | N | CH | i-Pr |
| C-39 | OCH$_2$CF$_2$CF$_3$ | CH | N | CH | Py2 |

Compound A-40 of the present invention: $^1$H-NMR (CDCl$_3$) δ: 8.45 (1H, d), 7.87 (1H, d), 7.23 (1H, d), 6.13 (1H, dd), 5.89 (1H, d), 4.40 (2H, t), 4.15-4.04 (2H, m), 3.46-3.32 (2H, m), 1.94-1.85 (2H, m), 1.33 (3H, t), 1.09 (3H, t).

Compound A-41 of the present invention: $^1$H-NMR (CDCl$_3$) δ: 8.41 (1H, d), 7.84 (1H, d), 7.23 (1H, d), 6.13 (1H, dd), 5.89 (1H, d), 4.76-4.68 (1H, m), 4.40 (2H, t), 3.48-3.29 (2H, m), 1.44 (3H, d), 1.42 (3H, d), 1.33 (3H, t).

Compound A-42 of the present invention: $^1$H-NMR (CDCl$_3$) δ: 8.55 (1H, d), 7.97 (1H, d), 7.23 (1H, d), 6.15 (1H, dd), 5.89 (1H, d), 4.61 (2H, t), 4.41 (2H, t), 3.48-3.36 (2H, m), 1.34 (3H, t).

Compound A-61 of the present invention: $^1$H-NMR (CDCl$_3$) δ: 8.72 (1H, d), 8.31 (1H, d), 8.17 (1H, ddd), 7.82 (1H, ddd), 7.30 (1H, d), 7.15 (1H, ddd), 7.10 (1H, ddd), 6.16 (1H, dd), 5.91 (1H, d), 4.41 (2H, t), 3.58-3.49 (1H, m), 3.42-3.33 (1H, m), 1.35 (3H, t).

Compound C-26 of the present invention: $^1$H-NMR (CDCl$_3$) δ: 8.48 (1H, d), 8.00 (1H, s), 7.88 (1H, d), 5.92 (1H, s), 4.96 (1H, q), 4.76 (1H, q), 4.28-4.19 (2H, m), 3.33 (2H, q), 1.52 (3H, t), 1.32 (3H, t).

Compound C-27 of the present invention: $^1$H-NMR (CDCl$_3$) δ: 8.48 (1H, d), 8.00 (1H, d), 7.88 (1H, d), 5.92 (1H, d), 4.96 (1H, ddd), 4.75 (1H, ddd), 4.18-4.05 (2H, m), 3.33 (2H, q), 1.96-1.86 (2H, m), 1.32 (3H, t), 1.09 (3H, t).

Compound C-28 of the present invention: $^1$H-NMR (CDCl$_3$) δ: 8.59 (1H, d), 8.01-7.97 (2H, m), 5.92 (1H, s), 4.96 (1H, q), 4.77 (1H, q), 4.63 (2H, t), 3.36 (2H, q), 1.34 (3H, t).

Compound C-29 of the present invention: $^1$H-NMR (CDCl$_3$) δ: 8.44 (1H, d), 8.00 (1H, d), 7.86 (1H, d), 5.92 (1H, d), 5.02-4.91 (1H, m), 4.82-4.69 (2H, m), 3.38-3.28 (2H, m), 1.46 (3H, d), 1.44 (3H, d), 1.32 (3H, t).

Compound C-39 of the present invention: $^1$H-NMR (CDCl$_3$) δ: 8.75 (1H, d), 8.34 (1H, d), 8.19 (1H, ddd), 8.07 (1H, d), 7.84 (1H, ddd), 7.17 (1H, ddd), 7.12 (1H, ddd), 5.94 (1H, d), 5.04-4.91 (1H, m), 4.83-4.70 (1H, m), 3.50-3.28 (2H, m), 1.34 (3H, t).

Preparation Example 17

To a mixture of 0.54 g of the intermediate compound 3-1, 0.28 g of 2-bromo-5-cyanopyridine, 1.28 g of tripotassium phosphate, and 0.15 g of [1,1'-bis(diphenylphosphino)ferrocene]palladium dichloride was added 10 mL of DME. The mixtures were stirred at 80° C. for 2 hours, then cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane:ethyl acetate=1:3) to obtain the compound A-52 of the present invention below 0.26 g.

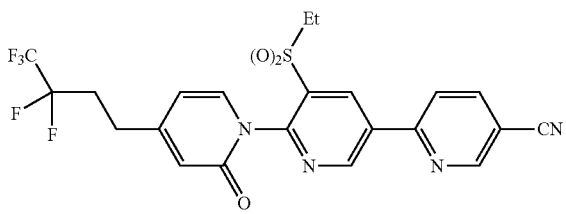

Compound A-52 of the present invention: ¹H-NMR (CDCl₃) δ: 9.47 (1H, d), 9.08 (1H, d), 9.05 (1H, dd), 8.17 (1H, dd), 8.01 (1H, dd), 7.32 (1H, d), 6.20 (1H, dd), 5.92 (1H, d), 4.43 (2H, t), 3.57-3.44 (2H, m), 1.39 (3H, t).

Preparation Example 18

The compounds that were prepared according to the similar method to the Preparation Example 17, and their physical property values are shown below.

a compound represented by formula (I-A):

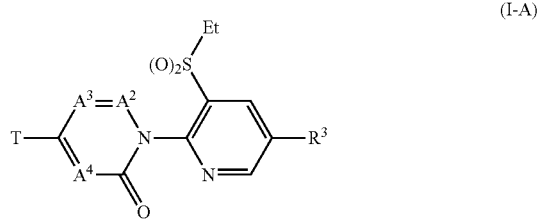

(I-A)

wherein a combination of R³, A², A³, A⁴ and T represents any one of the combinations indicated in Table 28. In the Table, Pm2 represents a 2-pyrimidinyl group and Prz represents a 2-pyrazinyl group.

[Table 18]

TABLE 28

| Present compound | R³ | A² | A³ | A⁴ | T |
|---|---|---|---|---|---|
| A-53 | Pm2 | CH | CH | CH | OCH₂CF₂CF₃ |
| A-55 | 5-F—Py2 | CH | CH | CH | OCH₂CF₂CF₃ |
| A-56 | 3,5-F₂—Py2 | CH | CH | CH | OCH₂CF₂CF₃ |
| A-65 | Py2 | CH | CH | CH | OCH₂CF₂CF₃ |
| A-66 | Py3 | CH | CH | CH | OCH₂CF₂CF₃ |
| A-67 | Prz | CH | CH | CH | OCH₂CF₂CF₃ |
| C-36 | 5-CN—Py2 | CH | N | CH | OCH₂CF₂CF₃ |
| C-37 | furyl | CH | N | CH | OCH₂CF₂CF₃ |
| C-38 | cyanothienyl | CH | N | CH | OCH₂CF₂CF₃ |

Compound A-53 of the present invention: ¹H-NMR (CDCl₃) δ: 9.83 (1H, d), 9.45 (1H, d), 8.90 (2H, d), 7.37 (1H, t), 7.34 (1H, d), 6.18 (1H, dd), 5.91 (1H, d), 4.42 (2H, t), 3.59-3.40 (2H, m), 1.40 (3H, t).

Compound A-55 of the present invention: ¹H-NMR (CDCl₃) δ: 9.38 (1H, d), 9.00 (1H, d), 8.64 (1H, d), 7.89 (1H, dd), 7.60 (1H, dt), 7.31 (1H, d), 6.18 (1H, dd), 5.91 (1H, d), 4.42 (2H, t), 3.55-3.43 (2H, m), 1.38 (3H, t).

Compound A-56 of the present invention: ¹H-NMR (CDCl₃) δ: 9.41 (1H, dd), 9.03 (1H, d), 8.55 (1H, d), 7.46-7.41 (1H, m), 7.33 (1H, d), 6.19 (1H, dd), 5.92 (1H, d), 4.42 (2H, t), 3.59-3.44 (2H, m), 1.39 (3H, t).

Compound A-65 of the present invention: ¹H-NMR (CDCl₃) δ: 9.43 (1H, d), 9.04 (1H, d), 8.79 (1H, td), 7.91-7.85 (2H, m), 7.42-7.40 (1H, m), 7.32 (1H, d), 6.18 (1H, dd), 5.92 (1H, d), 4.42 (2H, t), 3.53-3.46 (2H, m), 1.39 (3H, t).

Compound A-66 of the present invention: ¹H-NMR (CDCl₃) δ: 9.04 (1H, d), 8.94 (1H, dd), 8.78 (1H, dd), 8.61 (1H, d), 7.99-7.96 (1H, m), 7.53-7.50 (1H, m), 7.32 (1H, d), 6.20 (1H, dd), 5.93 (1H, d), 4.43 (2H, t), 3.52-3.45 (2H, m), 1.38 (3H, t).

Compound A-67 of the present invention: ¹H-NMR (CDCl₃) δ: 9.45 (1H, d), 9.18 (1H, d), 9.08 (1H, d), 8.76 (1H, dd), 8.71 (1H, d), 7.33 (1H, d), 6.20 (1H, dd), 5.92 (1H, d), 4.43 (2H, t), 3.58-3.45 (2H, m), 1.40 (3H, t).

Compound C-36 of the present invention: ¹H-NMR (CDCl₃) δ: 9.51 (1H, d), 9.12 (1H, d), 9.06 (1H, d), 8.19 (1H, dd), 8.09 (1H, s), 8.04 (1H, d), 5.96 (1H, s), 4.99 (1H, q), 4.78 (1H, q), 3.45 (2H, q), 1.39 (3H, t).

Compound C-37 of the present invention: ¹H-NMR (CDCl₃) δ: 8.96 (1H, d), 8.47 (1H, d), 8.05 (1H, d), 7.97 (1H, t), 7.62 (1H, t), 6.81 (1H, dd), 5.95 (1H, d), 4.98-4.77 (2H, m), 3.38 (2H, q), 1.35 (3H, t).

Compound C-38 of the present invention: ¹H-NMR (CDCl₃) δ: 9.04 (1H, d), 8.57 (1H, d), 8.06 (1H, d), 7.98 (1H, d), 7.97 (1H, d), 5.96 (1H, d), 4.98-4.78 (2H, m), 3.41 (2H, q), 1.36 (3H, t).

Preparation Example 19

The compounds that were prepared according to the similar method to the Preparation Example 5, and their physical property values are shown below.

Compound B-8 of the present invention

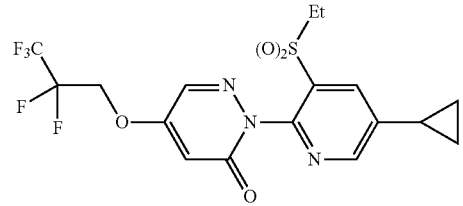

Compound B-8 of the present invention: ¹H-NMR (CDCl₃) δ: 8.61 (1H, d), 7.99 (1H, d), 7.79 (1H, d), 6.22 (1H, d), 4.43 (2H, t), 3.33 (2H, q), 2.11-2.05 (1H, m), 1.31 (3H, t), 1.24-1.21 (2H, m), 0.90-0.88 (2H, m).

Compound B-10 of the present invention

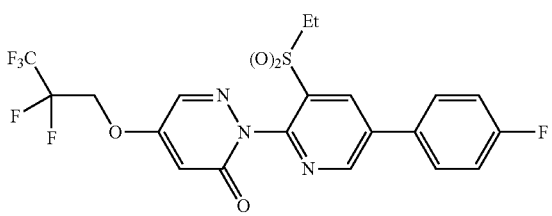

Compound B-10 of the present invention: ¹H-NMR (CDCl₃) δ: 9.02 (1H, d), 8.54 (1H, d), 7.83 (1H, d), 7.65-7.62 (2H, m), 7.26-7.24 (2H, m), 6.27 (1H, d), 4.46 (2H, t), 3.40 (2H, q), 1.35 (3H, t).

Preparation Example 20

To a mixture of 1.0 g of the compound A-36 of the present invention, 0.14 g of bis(triphenylphosphine)palladium(II) dichloride, 82 mg of 2-dicyclohexylphosphino-2',6'-dimethoxybiphenyl and 5 mL of THF was added 8.2 mL of cyclopentyl zinc bromide THF solution (0.5 M) and the mixtures were stirred at 60° C. for 2.5 hours. The mixtures were cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane:ethyl acetate=1:1) to obtain the compound A-49 of the present invention below 0.34 g.

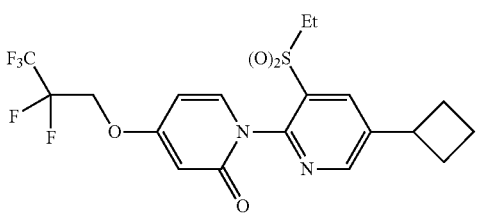

Compound A-49 of the present invention: ¹H-NMR (CDCl₃) δ: 8.64 (1H, d), 8.25 (1H, d), 7.24 (1H, d), 6.14 (1H, dd), 5.90 (1H, d), 4.40 (2H, t), 3.76-3.67 (1H, m), 3.44-3.38 (2H, m), 2.51-2.48 (2H, m), 2.30-2.10 (3H, m), 2.02-1.95 (1H, m), 1.33 (3H, t).

Preparation Example 21

The compounds that were prepared according to the similar method to the Preparation Example 20, and their physical property values are shown below.

Compound A-50 of the present invention

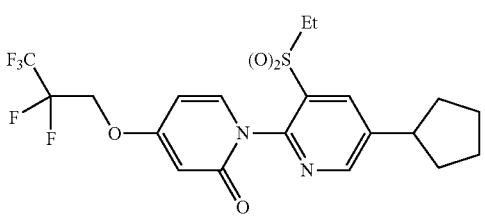

Compound A-50 of the present invention: ¹H-NMR (CDCl₃) δ: 8.68 (1H, d), 8.26 (1H, dd), 7.25 (1H, d), 6.14 (1H, dd), 5.90 (1H, d), 4.41 (2H, t), 3.48-3.32 (2H, m), 3.21-3.13 (1H, m), 2.26-2.17 (2H, m), 1.91-1.87 (2H, m), 1.84-1.73 (2H, m), 1.71-1.60 (2H, m), 1.32 (3H, t).

Compound A-51 of the Present Invention

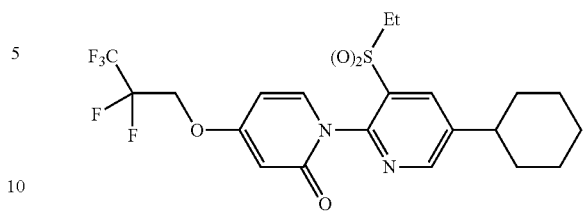

Compound A-51 of the present invention: ¹H-NMR (CDCl₃) δ: 8.66 (1H, d), 8.24 (1H, d), 7.25 (1H, d), 6.14 (1H, dd), 5.90 (1H, d), 4.41 (2H, t), 3.44-3.36 (2H, m), 2.76-2.71 (1H, m), 1.90-1.74 (5H, m), 1.44-1.34 (8H, m).

Preparation Example 22

Heptafluoro-3-iodopropane gas was browed into a mixture of 0.8 g of the intermediate compound 2-17, 0.39 g of copper powder and NMP for 2 minutes, and a sealed tube containing the mixtures was stirred at 140° C. for 16 hours. The mixtures were cooled to room temperature, and thereto was added 50 mL of ethyl acetate, and the mixtures were filtered through Celite (registered trade mark). The filtrates were extracted with ethyl acetate and water, and the obtained organic layers were washed with saturated brine, dried over anhydrous sodium sulfate, and concentrated under reduced pressure. The residue was subjected to a silica gel column chromatography (hexane:ethyl acetate=3:7) to obtain the compound A-24 of the present invention below 0.51 g.

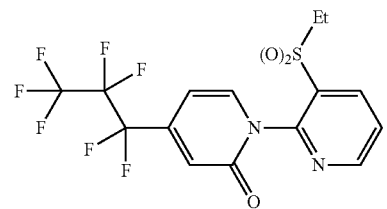

Compound A-24 of the present invention: ¹H-NMR (CDCl₃) δ: 1.32 (3H, t), 3.33-3.45 (2H, m), 6.43 (1H, d), 6.88 (1H, s), 7.44 (1H, d), 7.69-7.73 (1H, m), 8.47 (1H, d), 8.87 (1H, d).

Preparation Example 23

The compounds that were prepared according to the similar method to the Preparation Example 22, and their physical property values are shown below.

Compound A-25 of the present invention

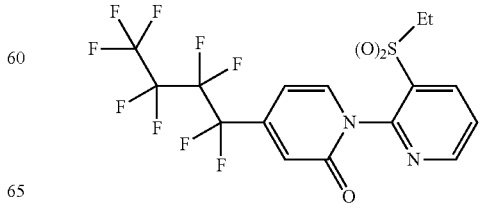

Compound A-25 of the present invention: $^1$H-NMR (CDCl$_3$) δ: 1.32 (3H, t), 3.31-3.47 (2H, m), 6.44 (1H, d), 6.88 (1H, s), 7.44 (1H, d), 7.70-7.73 (1H, m), 8.46-8.48 (1H, m), 8.86 (1H, t).

Preparation Example 24

A mixture of 1.0 g of the intermediate compound 2-17, 0.36 g of phenol, 155 mg of 5-(di-t-butylphosphino)-1',3',5'-triphenyl-1,4'-bi-1H-pyrazole, 0.43 g of potassium tert-butoxide, 0.54 mL of 2,2,3,3,3-pentafluoropropylamine, arylpalladium (II) chloride (dimer), and 20 mL of cyclopentylmethyl ether was stirred at 100° C. under nitrogen atmosphere for 4 hours. The mixtures were cooled to room temperature, and thereto was added 50 mL of ethyl acetate, and the mixtures were filtered through Celite (registered trade mark). The filtrates were extracted with ethyl acetate and water, and the obtained organic layers were washed with saturated brine, dried over anhydrous sodium sulfate, and concentrated under reduced pressure. The obtained residue was purified to obtain the compound A-32 of the present invention below 0.32 g.

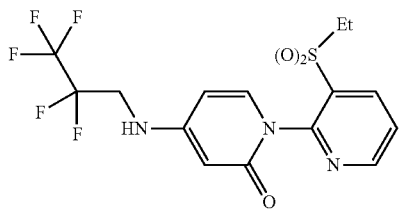

Compound A-32 of the present invention: $^1$H-NMR (CDCl$_3$) δ: 1.30 (3H, t), 3.35-3.40 (1H, m), 3.48-3.53 (1H, m), 3.81-3.82 (2H, m), 4.59 (1H, s), 5.64 (1H, s), 5.82 (1H, d), 7.13 (1H, d), 7.63 (1H, d), 8.44 (1H, d), 8.82 (1H, d).

Preparation Example 25

A compound C-19 of the present invention was prepared by using the intermediate compound 2-22 instead of the intermediate compound 2-17 according to the similar method to the preparation Example 24.

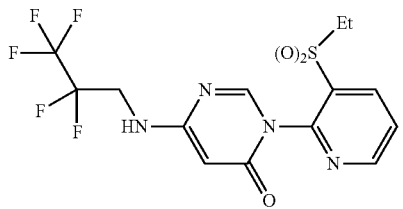

Compound C-19 of the present invention: $^1$H-NMR (CDCl$_3$) δ: 1.30 (3H, t), 3.32-3.45 (2H, m), 3.90-3.92 (1H, m), 3.94-3.96 (1H, m), 5.03 (1H, bs), 5.47 (1H, s), 7.67-7.71 (1H, m), 7.90 (1H, s), 8.45-8.47 (1H, m), 8.85-8.87 (1H, m).

Preparation Example 26

To a mixture of 0.3 g of the compound A-32 of the present invention and 10 mL of DMF was added 58 mg of sodium hydride (in oil, 60%), and the mixtures were stirred for 30 minutes. To the mixtures was added dropwise 0.09 mL of methyl iodide, and the mixtures were stirred at room temperature for 16 hours. To the mixtures was added water, and the mixtures were extracted with ethyl acetate. The obtained organic layers were washed with saturated brine, dried over anhydrous sodium sulfate, and concentrated under reduced pressure. The obtained residue was purified to obtain the compound A-33 of the present invention below 60 mg.

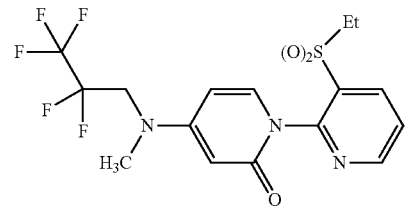

Compound A-33 of the present invention: $^1$H-NMR (CDCl$_3$) δ: 1.31 (3H, t), 3.13 (3H, s), 3.38-3.42 (1H, m), 3.51-3.55 (1H, m), 3.88-4.03 (2H, m), 5.70 (1H, s), 5.98-6.00 (1H, m), 7.19 (1H, d), 7.61-7.64 (1H, m), 8.43-8.45 (1H, m), 8.82-8.83 (1H, m).

Preparation Example 27

A mixture of 0.71 g of the compound A-34 of the present invention, 0.6 mL of (trifluoromethyl)trimethylsilane, 50 mg of sodium iodide and 10 mL of THF was stirred at 100° C. for 10 hours in a sealed tube. The mixtures were cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane:ethyl acetate=1:1) to obtain the compound A-64 of the present invention below 0.38 g

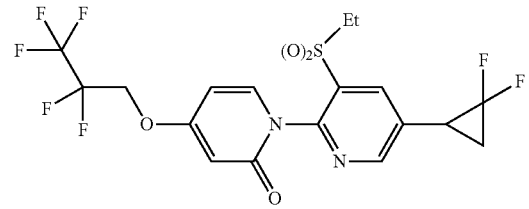

Compound A-64 of the present invention: $^1$H-NMR (CDCl$_3$) δ: 8.71 (1H, dd), 8.24 (1H, dd), 7.25 (1H, d), 6.16 (1H, dd), 5.90 (1H, d), 4.41 (2H, t), 3.51-3.35 (2H, m), 2.92-2.87 (1H, m), 2.12-2.08 (1H, m), 1.87-1.74 (1H, m), 1.33 (3H, td).

Preparation Example 28

The compounds of the present invention below were prepared by using the compound A-43 of the present invention instead of the intermediate compound 2-13 according to the similar method to the Reference Preparation Example 27.

Compound A-54 of the Present Invention

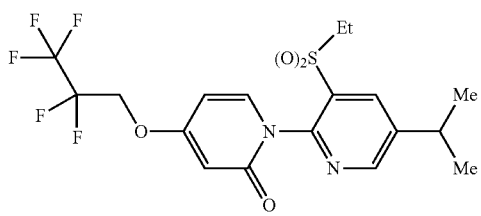

Compound A-54 of the present invention: $^1$H-NMR (CDCl$_3$) δ: 8.69 (1H, d), 8.26 (1H, d), 7.25 (1H, d), 6.14 (1H, dd), 5.90 (1H, d), 4.40 (2H, t), 3.44-3.37 (2H, m), 3.17-3.11 (1H, m), 1.39 (3H, s), 1.37 (3H, s), 1.32 (3H, t).

Compound A-58 of the Present Invention

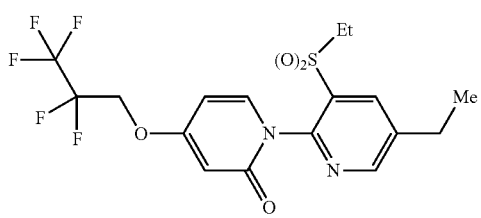

Compound A-58 of the present invention: $^1$H-NMR (CDCl$_3$) δ: 8.67 (1H, d), 8.25 (1H, d), 7.25 (1H, d), 6.14 (1H, dd), 5.90 (1H, d), 4.40 (2H, t), 3.49-3.33 (2H, m), 2.85 (2H, q), 1.38-1.31 (6H, m).

Preparation Example 29

A mixture of 1.0 g of the compound A-36 of the present invention, 0.61 g of the intermediate compound 4-1, 37 mg of arylpalladium (II) chloride (dimer), 0.12 g of 4,5'-bis(diphenylphosphino)-9,9'-dimethylxanthene, and 7 ml of xylene was stirred at 110° C. under nitrogen atmosphere for 7 hours. The mixtures were cooled to room temperature, and thereto was added water, and the mixtures were extracted with ethyl acetate. The obtained organic layers were washed with saturated brine, dried over anhydrous sodium sulfate, and concentrated under reduced pressure. The obtained residue was subjected to a silica gel column chromatography (hexane:ethyl acetate=1:6) to obtain the compound A-57 of the present invention below 0.53 g.

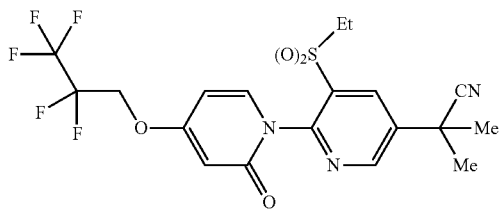

Compound A-57 of the present invention: $^1$H-NMR (CDCl$_3$) δ: 8.99 (1H, d), 8.46 (1H, d), 7.26 (1H, d), 6.18 (1H, dd), 5.91 (1H, d), 4.42 (2H, t), 3.48-3.43 (2H, m), 1.88 (3H, s), 1.86 (3H, s), 1.35 (3H, t).

Next, the formulation examples of the Present compound are shown below. The "parts" represents "part by weight" unless otherwise specified.

Formulation Example 1

Into a mixture of 35 parts of xylene and 35 parts of DMF, 10 parts of any one of the Present compounds A-1 to A-68, B-1 to B-10, C-1 to C-43 and D-1 is dissolved, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrated silicon oxide fine powder and 54 parts of diatomaceous earth are mixed, and further 20 parts of any one of the Present compounds A-1 to A-68, B-1 to B-10, C-1 to C-43 and D-1 is added, followed by mixing them to obtain each wettable powders.

Formulation Example 3

To 2 parts of any one of the Present compounds A-1 to A-68, B-1 to B-10, C-1 to C-43 and D-1, 1 part of synthetic hydrated silicon oxide fine powder, 2 parts of calcium lignin sulfonate, 30 parts of bentonite and 65 parts of kaolin clay are added, followed by mixing, granulation with a granulator and forced-air drying to obtain each granular formulation.

Formulation Example 4

Into an appropriate amount of acetone, 1 part of any one of the Present compounds A-1 to A-68, B-1 to B-10, C-1 to C-43 and D-1 is mixed, and then 5 parts of synthetic hydrous silicon oxide fine powder, 0.3 parts of isopropyl acid phosphate and 93.7 parts of kaolin clay are added, followed by mixing with stirring thoroughly and removal of acetone from the mixture by evaporation to obtain each of powder formulation.

Formulation Example 5

A mixture of 35 parts of polyoxyethylene alkyl ether sulfate ammonium salt and white carbon (weight ratio of 1:1), 20 parts of any one of the Present compounds A-1 to A-68, B-1 to B-10, C-1 to C-43 and D-1, and 45 parts of water are mixed, followed by finely grounding by a wet grinding method to obtain each flowable formulation.

Formulation Example 6

Into a mixture of 5 parts of xylene and 5 parts of trichloroethane, 0.1 parts of any one of the Present compounds A-1 to A-68, B-1 to B-10, C-1 to C-43 and D-1 is dissolved, and the resulting mixture is then mixed with 89.9 parts of kerosene to obtain each oil solution.

Formulation Example 7

Into 0.5 mL of acetone, 10 mg of any one of the Present compounds A-1 to A-68, B-1 to B-10, C-1 to C-43 and D-1 is dissolved and the solution is added dropwise to 5 g of a solid feed powder for an animal (solid feed powder for rearing and breeding CE-2, manufactured by CLEA Japan, Inc.), followed by mixing the resulting mixture uniformly, and then by drying them by evaporation of acetone to obtain each poison bait.

Formulation Example 8

Into an aerosol can, 0.1 part of any one of the Present compounds A-1 to A-68, B-1 to B-10, C-1 to C-43 and D-1 and 49.9 parts of Neothiozole (Chuo Kasei Co., Ltd.) are placed. After mounting an aerosol valve, 25 parts of dimethylether and 25 parts of LPG are filled, followed by shaking and further mounting an actuator to obtain an oily aerosol.

Formulation Example 9

A mixture of 0.6 part of any one of the Present compounds A-1 to A-68, B-1 to B-10, C-1 to C-43 and D-1, 0.01 part of BHT (2,6-di-tert-butyl-4-methylphenol), 5 parts of xylene, 3.39 parts of deodorized kerosine and 1 part of an emulsifier {Rheodol MO-60 (registered trademark of Kao Corporation)} and 50 parts of distilled water are filled into an aerosol container, and a valve part is attached. Then, 40 parts of a propellant (LPG) is filled therein through the valve under pressure to obtain an aqueous aerosol.

Formulation Example 10

0.1 parts of any one of the Present compounds A-1 to A-68, B-1 to B-10, C-1 to C-43 and D-1 are mixed into 2 mL of propylene glycol, and the resulting solution is impregnated into a ceramic plate having a size of 4.0 cm×4.0 cm and a thickness of 1.2 cm, to obtain thermal fumigants.

Formulation Example 11

5 parts of any one of the Present compounds A-1 to A-68, B-1 to B-10, C-1 to C-43 and D-1, and 95 parts of ethylene-methyl methacrylate copolymer (the ratio of the methyl methacrylate in the copolymer: 10 weight %), Acryft (registered by trademark) WD 301, manufactured by Sumitomo Chemical Co. Ltd.) are melted and kneaded with a closed type pressure kneader (manufactured by Moriyama Manufacturing Co. Ltd.), and the resulting kneaded product is extruded from an extrusion molding machine through a molding die to obtain a rod-shaped molded product having a length of 15 cm and a diameter of 3 mm.

Formulation Example 12

5 parts of any one of the Present compounds A-1 to A-68, B-1 to B-10, C-1 to C-43 and D-1, and 95 parts of plasticized polyvinyl chloride resin are melted and kneaded with a closed type pressure kneader (manufactured by Moriyama Manufacturing Co. Ltd.), and the resulting kneaded product is extruded from an extrusion molding machine through a molding die to obtain a rod-shaped molded product having a length of 15 cm and a diameter of 3 mm.

Formulation Example 13

100 mg of any one of the Present compounds A-1 to A-68, B-1 to B-10, C-1 to C-43 and D-1, 68.75 mg of lactose, 237.5 mg of corn starch, 43.75 mg of microcrystalline cellulose, 18.75 mg of polyvinylpyrrolidone, 28.75 mg of sodium carbomethyl starch and 2.5 mg of magnesium stearate are mixed, and the resulting mixture was compressed to an appropriate size to obtain a tablet.

Formulation Example 14

25 mg of any one of the Present compounds A-1 to A-68, B-1 to B-10, C-1 to C-43 and D-1, 60 mg of lactose, 25 mg of corn starch, 6 mg of carmellose calcium and an appropriate amount of 5% of hydroxypropyl methylcellulose are mixed, and the resulting mixture are filled into a hard shell gelatin capsule or a hydroxypropyl methylcellulose capsule to obtain capsules.

Formulation Example 15

To 100 mg of any one of the Present compounds A-1 to A-68, B-1 to B-10, C-1 to C-43 and D-1, 500 mg of fumaric acid, 2000 mg of sodium chloride, 150 mg of methyl paraben, 50 mg of propyl paraben, 25000 mg of granulated sugar, 13,000 mg of sorbitol (70% solution), 100 mg of Veegum K (manufactured by Vanderbilt Co.), 35 mg of perfume and 500 mg of coloring agent, a distilled water is added so that a final volume is set to be 100 mL, followed by mixing them to obtain a suspension for oral administration.

Formulation Example 16

Into a mixture of 5% by weight of an emulsifier, 3% by weight of benzyl alcohol and 30% by weight of propylene glycol, 5% by weight of any one of the Present compounds A-1 to A-68, B-1 to B-10, C-1 to C-43 and D-1 is dissolved, and phosphate buffer is added thereto so that a pH of the solution is set to be 6.0 to 6.5, and water is added as the rest parts to obtain the solution for oral administration.

Formulation Example 17

To a mixture of 57% by weight of fractional distillated palm oil and 3% by weight of polysorbate 85, 5% by weight of aluminum distearate is added, and heated to disperse it. The resulting mixture is cooled to room temperature, and 25% by weight of saccharin is dispersed in an oil vehicle. 10% by weight of any one of the Present compounds A-1 to A-68, B-1 to B-10, C-1 to C-43 and D-1 is divided thereto to obtain a paste for oral administration.

Formulation Example 18

5% by weight of any one of the Present compounds A-1 to A-68, B-1 to B-10, C-1 to C-43 and D-1 is mixed with 95% by weight of limestone filler, followed by a wet granulation of the resulting mixture to obtain a granule for oral administration.

Formulation Example 19

Into 80 parts of diethylene glycol monomethyl ether, 5 parts of any one of the Present compounds A-1 to A-68, B-1 to B-10, C-1 to C-43 and D-1 is dissolved, and 15 parts of propylene carbonate is added thereto, and the resulting mixture is mixed to obtain a spot-on solution.

Formulation Example 20

Into 70 parts of diethylene glycol monomethyl ether, 10 parts of any one of the Present compounds A-1 to A-68, B-1 to B-10, C-1 to C-43 and D-1 is dissolved, and 20 parts of 2-octyldodecanol is added thereto, and the resulting mixture is mixed to obtain a pour-on solution.

Formulation Example 21

To 0.5 parts of any one of the Present compounds A-1 to A-68, B-1 to B-10, C-1 to C-43 and D-1, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly, and 19.5 parts of water is then added thereto and the resulting mixture is further mixed with stirring thoroughly to obtain a hydrogenous solution of shampoo formulation.

Formulation Example 22

0.15% by weight of any one of the Present compounds A-1 to A-68, B-1 to B-10, C-1 to C-43 and D-1, 95% by weight of animal feed, as well as 4.85% by weight of a mixture of dibasic calcium phosphate, diatomaceous earth, aerosol and carbonate (or chalk) are mixed with stirring thoroughly to obtain a premix for animal feed.

Formulation Example 23

7.2 g of any one of the Present compounds A-1 to A-68, B-1 to B-10, C-1 to C-43 and D-1, and 92.8 g of Hosco (registered trademark) S-55 (manufactured by Maruishi Pharmaceuticals) are melted and mixed at 100° C., and the resulting mixture was poured into a suppository mold, followed by performing a cooling solidification to obtain a suppository.

Next, Test Examples are used to show an efficacy of the Present compound on controlling harmful arthropods.

The following test examples were carried out at 25° C.

Test Example 1

The test compounds was made to a formulation according to a similar method to that described in the Formulation Example 5, and thereto was added water containing 0.03 v/v % of a spreader to prepare a diluted solution containing a prescribed concentration of the test compound.

Cucumber (*Cucumis sativus*) seedling (on the developmental stage of the second true leaf) was planted in a container and approximately 30 of cotton aphid (*Aphis gossypii*) (all stages of life) were released onto the leaves of the cucumber. After 1 day, the diluted solutions were sprayed into the seedling in a ratio of 10 mL/seedling. After 5 days, the number of the surviving insects was examined and the controlling value was calculated by the following equation.

Controlling value (%)=$\{1-(Cb \times Tai)/(Cai \times Tb)\} \times 100$ wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the similar treatment procedure to that of the treated group except not using the test compound is done.

The test was conducted by making the prescribed concentration 500 ppm and using the below-mentioned Present compounds as a test compound according to the test example 1. As a result of the test, the treated group that was treated with the below-mentioned Present compounds showed 90% or greater as the controlling value.

Present compound number: Present compound A-1, A-2, A-3, A-4, A-5, A-6, A-7, A-10, A-12, A-13, A-14, A-15, A-16, A-17, A-18, A-19, A-20, A-21, A-23, A-24, A-25, A-26, A-27, A-28, A-29, A-32, A-33, A-34, A-36, A-37, A-38, A-43, A-44, A-45, A-46, A-47, A-49, A-50, A-51, A-52, A-53, A-54, A-55, A-56, A-57, A-58, A-59, A-60, A-62, A-64, B-5, B-7, B-8, B-10, C-1, C-2, C-4, C-5, C-6, C-7, C-8, C-9, C-11, C-12, C-15, C-16, C-17, C-19, C-20, C-22, C-23, C-24, C-25, C-30, C-31, C-32, C-34, C-36, C-37, C-38, and D-1.

The test was conducted by making the prescribed concentration 200 ppm and using the below-mentioned Present compounds as a test compound according to the test example 1. As a result of the test, the treated group that was treated with the below-mentioned Present compounds showed 90% or greater as the controlling value.

Present compound number: Present compound A-2, A-3, A-4, A-5, A-6, A-7, A-12, A-13, A-14, A-15, A-16, A-17, A-19, A-20, A-21, A-23, A-24, A-25, A-27, A-28, A-29, A-32, A-34, A-35, A-36, A-37, A-38, A-39, A-40, A-41, A-43, A-45, A-46, A-47, A-49, A-50, A-51, A-52, A-53, A-54, A-55, A-56, A-57, A-58, A-59, A-62, A-64, B-5, B-8, C-1, C-2, C-3, C-5, C-6, C-7, C-9, C-11, C-12, C-15, C-17, C-19, C-22, C-23, C-25, C-29, C-30, C-31, C-32, C-34, C-36, and C-37.

Test Example 2

The test compounds were made to a formulation according to a similar method to that described in the Formulation Example 5, and thereto was added water to prepare a diluted solution containing a prescribed concentration of the test compound.

Cucumber seedling (on the developmental stage of the second true leaf) is planted in a container, and the diluted solutions in the ratio on 5 mL/seedling were irrigated into the plant foot. After 7 days, approximately 30 of cotton aphid (all stages of life) were inoculated onto the cucumber leaves. After additional 6 days, the number of the surviving insects was examined, and the controlling value was calculated by the following equation.

Controlling value (%)=$\{1-(Cb \times Tai)/(Cai \times Tb)\} \times 100$ wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the similar treatment procedure to that of the treated group except not using the test compound is done.

The test was conducted by making the prescribed concentration 1000 ppm and using the below-mentioned Present compounds as a test compound according to the test example 2. As a result of the test, the treated group that was treated with the below-mentioned Present compounds showed 90% or greater as the controlling value.

Present compound number: Present compound A-2, A-3, A-4, A-5, A-6, A-7, A-12, A-13, A-14, A-15, A-16, A-17, A-20, A-21, A-23, A-27, A-28, A-29, A-32, A-34, A-35, A-36, A-37, A-38, A-39, A-40, A-41, A-42 A-43, A-44, A-45, A-46, A-49, A-50, A-51, A-52, A-53, A-54, A-55, A-56, A-57, A-58, A-59, A-62, A-64, B-5, B-8, C-1, C-2, C-3, C-4, C-5, C-6, C-7, C-8, C-11, C-12, C-15, C-16, C-19, C-22, C-23, C-25, C-29, C-30, C-32, C-34, C-36, and C-37.

Test Example 3

The test compounds were made to a formulation according to a similar method to that described in the Formulation Example 5, and thereto was added water containing 0.03 v/v % of a spreader to prepare a diluted solution containing a prescribed concentration of the test compound.

Rice (*Oryza sativa*) seedling (on the developmental stage of the second true leaf) was planted in a container, and the diluted solutions were sprayed into the seedling in a ratio of 10 mL/seedling. Thereafter, 20 of 3rd instar larvae of brown planthopper (*Nilaparvata lugens*) were released onto the rice leaves. After 6 days, the number of the surviving insects was examined, and the mortality was calculated by the following equation.

Mortality (%)={1−the number of the surviving insects/20}×100

The test was conducted by making the prescribed concentration 500 ppm and using the below-mentioned Present compounds as a test compound according to the test example 3. As a result of the test, the treated group that was treated with the below-mentioned Present compounds showed 90% or greater as the mortality.

Present compound number: Present compound A-2, A-3, A-10, A-12, A-15, A-17, A-20, A-23, A-24, A-25, A-38, A-45, A-52, A-53, A-55, A-56, A-57, C-1, C-2, C-7, C-12, C-25, and C-32.

Test Example 4

The test compounds were made to a formulation according to a similar method to that described in the Formulation Example 5, and thereto was added water to prepare a diluted solution containing a prescribed concentration of the test compound.

5 mL of the diluted solutions described above were added to a container, and therein was installed Rice seedling (on the developmental stage of the second true leaf) that had been planted in a container having a hole in the bottom. After 7 days, 20 of 3rd instar larvae of brown planthopper (*Nilaparvata lugens*) were released. After additional 6 days, the number of the surviving insects was examined, and the mortality was calculated by the following equation.

Mortality (%)={1−the number of the surviving insects/20}×100

The test was conducted by making the prescribed concentration 1000 ppm and using the below-mentioned Present compounds as a test compound according to the test example 4. As a result of the test, the treated group that was treated with the below-mentioned Present compounds showed 90% or greater as the mortality.

Present compound number: Present compound A-2, A-3, A-5, A-7, A-12, A-13, A-14, A-15, A-16, A-17, A-20, A-23, A-24, A-25, A-38, A-45, A-52, A-53, A-56, A-57, C-1, C-2, C-3 C-4, C-6, C-7, C-12, C-19, C-25, C-30, and C-32.

Test Example 5

The test compounds were made to a formulation according to a similar method to that described in the Formulation Example 5, and thereto was added water containing 0.03 v/v % of a spreader to prepare a diluted solution containing a prescribed concentration of the test compound.

The diluted solutions are sprayed into the cabbage (*Brassicae oleracea*) seedling (on the developmental stage of the second to third true leaf) that is planted in a container in a ratio of 20 mL/seedling. Thereafter, the stem and leaf thereof was cut out and then was installed into the container that was covered with the filter paper. Five of cabbage moth (*Plutella xylostella*) at the second instar larval stages were released into the cup. After 5 days, the number of surviving insects was counted, and the mortality of insects was calculated by the following equation.

Mortality (%)={1−the number of the surviving insects/5}×100

The test was conducted by making the prescribed concentration 500 ppm and using the below-mentioned Present compounds as a test compound according to the test example 6. As a result of the test, the treated group that was treated with the below-mentioned Present compounds showed 80% or greater as the mortality.

Present compound number: Present compound A-1, A-2, A-4, A-6, A-7, A-10, A-11, A-13, A-14, A-15, A-16, A-17, A-18, A-19, A-20, A-21, A-22, A-23, A-24, A-25, A-27, A-28, A-29, A-30, A-34, A-36, A-37, A-38, A-43, A-44, A-45, A-46, A-47, A-49, A-50, A-51, A-52, A-53, A-54, A-55, A-56, A-57, A-58, A-62, A-64, B-2, B-5, B-7, B-8, B-9, B-10, C-1, C-2, C-4, C-5, C-6, C-7, C-8, C-9, C-10, C-11, C-12, C-13, C-14, C-16, C-17, C-18, C-19, C-20, C-22, C-23, C-24, C-25, C-30, C-31, C-32, C-36, C-37, C-38, and D-1.

Test Example 6

The test compounds were made to a formulation according to a similar method to that described in the Formulation Example 5, and thereto was added water containing 0.03 v/v % of a spreader to prepare a diluted solution containing a prescribed concentration of the test compound.

The diluted solutions were sprayed into the cabbage seedling (on the developmental stage of the third to fourth true leaf) that was planted in a container in a ratio of 20 mL/seedling. Thereafter, 10 of cabbage moth (*Plutella xylostella*) at the third instar larval stages were released into the container. After 5 days, the surviving insects are counted, and the mortality of insects was calculated by the following equation.

Mortality (%)={1−the number of the surviving insects/10}×100

The test was conducted by making the prescribed concentration 200 ppm and using the below-mentioned Present compounds as a test compound according to the test example 7. As a result of the test, the treated group that was treated with the below-mentioned Present compounds showed 90% or greater as the mortality.

Present compound number: Present compound A-7, A-11, A-15, A-17, A-18, A-19, A-21, A-22, A-24, A-25, A-27, A-28, A-29, A-30, A-35, A-36, A-37, A-38, A-42, A-44, A-45, A-46, A-47, A-52, A-53, A-55, A-56, A-57, A-62, A-64, B-8, B-10, C-1, C-2, C-3, C-4, C-5, C-7, C-8, C-9, C-10, C-11, C-12, C-13, C-17, C-18, C-20, C-23, C-24, C-25, C-28, C-29, C-30, C-32, C-36, C-37, and C-38.

Test Example 7

The test compounds were dissolved into a mixed solution of polyoxyethylene sorbitan mono-cocoate and acetone (acetone and polyoxyethylene sorbitan mono-cocoate=5:95 (v/v ratio)) in a ratio of 50 μL of the mixed solution per 1 mg of the test compound. Thereto was added water containing 0.03% by volume of a spreader to prepare a diluted solution containing a prescribed concentration of the test compound.

The young seedling Corns (*Zea mays*) were immersed into the diluted solution for 30 seconds. Thereafter, two grains of the seedling were installed in a plastic petri dish (90 mm radius), and 10 of western corn rootworm (*Dia-* brotica virgifera virgifera) at the second instar larval stages were released onto the container. After 5 days, the number of the died insects was counted and the mortality of insects was calculated by the following equation.

Mortality (%)=(the number of the died insects/10)×100

The test was conducted by making the prescribed concentration 500 ppm and using the below-mentioned Present compounds as a test compound according to the test example 8. As a result of the test, the treated group that was treated with the below-mentioned Present compounds showed 80% or greater as the mortality.

Present compound number: Present compound A-2, A-3, A-7, A-11, A-14, A-16, A-17, A-18, A-19, A-20, A-23, A-24, A-25, A-27, A-28, A-29, A-30, A-35, A-36, A-38, A-42, A-43, A-46, A-52, A-53, A-57, B-8, B-10, C-2, C-7, C-8, C-9, C-10, C-20, C-23, C-25, C-26, C-29, and C-36.

Test Example 8

Each 1 mg of the Present compound was dissolved into a 10 µL of the mixed solution of xylene, dimethyl formamide and surfactants=4:4:1 (v/v ratio). Thereto was added water containing 0.02% by volume of a spreader to prepare a diluted solution containing a prescribed concentration of the test compound.

Thereafter, approximately 30 of cabbage aphids (Brevicoryne brassicae) (all stages of life) were released onto Cabbage seedling (on the developmental stage of the third to fourth true leaf) that was planted in a container. After 3 days, the diluted solutions are sprayed into the seedling in a ratio of 30 mL/seedling. After additional 7 days, the number of the surviving insects was examined and the controlling value was calculated by the following equation.

Controlling value (%)={1−($Cb$×$Tai$)/($Cai$×$Tb$)}×100 wherein the symbols in the formula represent the following descriptions.

Cb: Number of the test insects in untreated group;
Cai: Number of the surviving insects at the time of the investigation in untreated group;
Tb: Number of the test insects in treated group;
Tai: Number of the surviving insects at the time of the investigation in treated group;

Here the "untreated group" represents a group where the similar treatment procedure to that of the treated group except not using the test compound is done.

The test was conducted by making the prescribed concentration 50 ppm and using the below-mentioned Present compounds as a test compound according to the test example 8. As a result of the test, the treated group that was treated with the below-mentioned Present compounds showed 90% or greater as the controlling value.

Present compound number: Present compound A-2, A-35, A-37, A-38, A-39, A-40, A-41, A-45, A-46, A-47, A-52, A-53, A-55, B-8, C-23, C-25, C-26, C-27, C-29, C-30, and C-32.

Next, Test Examples are used to show an efficacy of the Present composition on controlling harmful arthropods.

Test Example 9

Each 1 mg of the Present compound was dissolved into a 10 µL of the mixed solution of xylene, DMF and surfactants (xylene, DMF and surfactants=4:4:1 (v/v ratio)). Thereto was added water containing 0.02% by volume of a spreader to prepare a diluted solution containing a prescribed concentration of the Present compound.

When the commercially available formulation of the present active ingredient was used, each of the commercially available formulation was diluted with water containing 0.02 v/v % of the spreader to prepare the prescribed concentration of the diluted solution of the present active ingredient.

Whereas, when the commercially available formulation of the present active ingredient was not used, each 1 mg of the present active ingredient was dissolved into a 10 µL of the mixed solution of xylene, DMF and surfactants (xylene, DMF and surfactants=4:4:1 (v/v ratio)). Thereto was added water containing 0.02% by volume of a spreader to prepare a diluted solution containing a prescribed concentration of the present active ingredient.

The above prepared diluted solution of the Present compound and the above prepared diluted solution of the present active ingredient were mixed to prepare the test chemical solution of the composition comprising the Present compound and the present active ingredient.

A leaf disk (length 1.5 cm) of the seed leaf of cucumber was placed into each well in a 24 well microplate, and 2 wingless adults of a cotton aphid (Aphis gossypii) and 8 nymphs of a cotton aphid were released per 1 well, and the test chemical solution was sprayed in a ratio of 20 µL per 1 well, which was referred to as a treated group.

Whereas, 20 µL water containing 0.02 v/v % of the spreader was sprayed into a well instead of the test chemical solution, which was referred to as an untreated group.

After the test chemical solution was dried, the upper part of a microplate is covered with a film sheet, and 5 days after the release, the number of the surviving insects of each well was examined.

The controlling value was calculated by the following equation.

Controlling value (%)={1−($Tai$)/($Cai$)}×100 wherein the symbols in the formula represent the following descriptions.

Cai: Number of the surviving insects at the time of the investigation in untreated group;
Tai: Number of the surviving insects at the time of the investigation in treated group;

The composition that was examined according to a method of Test example 9 is shown in Table 29. As a result, the composition described in Table 29 showed an excellent efficacy on controlling harmful arthropods.

In the Table 29, the Present compounds X represent Present compounds A-1 to A-68, B-1 to B-10, and C-1 to C-43 and D-1.

[Table 19]

TABLE 29

| Composition | Concentration (ppm) (Present compound + Present active ingredient) |
|---|---|
| any one kind of Present compounds X + Clothianidin | 200 + 2000 |
| any one kind of Present compounds X + Clothianidin | 200 + 200 |
| any one kind of Present compounds X + Clothianidin | 500 + 50 |
| any one kind of Present compounds X + Thiamethoxam | 200 + 2000 |
| any one kind of Present compounds X + Thiamethoxam | 200 + 200 |

TABLE 29-continued

| Composition | Concentration (ppm) (Present compound + Present active ingredient) |
|---|---|
| any one kind of Present compounds X + Thiamethoxam | 500 + 50 |
| any one kind of Present compounds X + Imidacloprid | 200 + 2000 |
| any one kind of Present compounds X + Imidacloprid | 200 + 200 |
| any one kind of Present compounds X + Imidacloprid | 500 + 50 |
| any one kind of Present compounds X + Thiacloprid | 200 + 2000 |
| any one kind of Present compounds X + Thiacloprid | 200 + 200 |
| any one kind of Present compounds X + Thiacloprid | 500 + 50 |
| any one kind of Present compounds X + Flupyradifurone | 200 + 2000 |
| any one kind of Present compounds X + Flupyradifurone | 200 + 200 |
| any one kind of Present compounds X + Flupyradifurone | 500 + 50 |
| any one kind of Present compounds X + Sulfoxaflor | 200 + 2000 |
| any one kind of Present compounds X + Sulfoxaflor | 200 + 200 |
| any one kind of Present compounds X + Sulfoxaflor | 500 + 50 |
| any one kind of Present compounds X + Triflumezopyrim | 200 + 2000 |
| any one kind of Present compounds X + Triflumezopyrim | 200 + 200 |
| any one kind of Present compounds X + Triflumezopyrim | 500 + 50 |
| any one kind of Present compounds X + Dicloromezotiaz | 200 + 2000 |
| any one kind of Present compounds X + Dicloromezotiaz | 200 + 200 |
| any one kind of Present compounds X + Dicloromezotiaz | 500 + 50 |
| any one kind of Present compounds X + Beta-cyfluthrin | 200 + 2000 |
| any one kind of Present compounds X + Beta-cyfluthrin | 200 + 200 |
| any one kind of Present compounds X + Beta-cyfluthrin | 500 + 50 |
| any one kind of Present compounds X + Tefluthrin | 200 + 2000 |
| any one kind of Present compounds X + Tefluthrin | 200 + 200 |
| any one kind of Present compounds X + Tefluthrin | 500 + 50 |
| any one kind of Present compounds X + Fipronil | 200 + 2000 |
| any one kind of Present compounds X + Fipronil | 200 + 200 |
| any one kind of Present compounds X + Fipronil | 500 + 50 |
| any one kind of Present compounds X + Chlorantraniliprole | 200 + 2000 |
| any one kind of Present compounds X + Chlorantraniliprole | 200 + 200 |
| any one kind of Present compounds X + Chlorantraniliprole | 500 + 50 |
| any one kind of Present compounds X + Cyantraniliprole | 200 + 2000 |
| any one kind of Present compounds X + Cyantraniliprole | 200 + 200 |
| any one kind of Present compounds X + Cyantraniliprole | 500 + 50 |
| any one kind of Present compounds X + Tetraniliprole | 200 + 2000 |
| any one kind of Present compounds X + Tetraniliprole | 200 + 200 |
| any one kind of Present compounds X + Tetraniliprole | 500 + 50 |
| any one kind of Present compounds X + Thiodicarb | 200 + 2000 |
| any one kind of Present compounds X + Thiodicarb | 200 + 200 |
| any one kind of Present compounds X + Thiodicarb | 500 + 50 |
| any one kind of Present compounds X + Carbofuran | 200 + 2000 |
| any one kind of Present compounds X + Carbofuran | 200 + 200 |
| any one kind of Present compounds X + Carbofuran | 500 + 50 |
| any one kind of Present compounds X + fluxametamide | 200 + 2000 |
| any one kind of Present compounds X + fluxametamide | 200 + 200 |
| any one kind of Present compounds X + fluxametamide | 500 + 50 |
| any one kind of Present compounds X + Afoxolaner | 200 + 2000 |
| any one kind of Present compounds X + Afoxolaner | 200 + 200 |
| any one kind of Present compounds X + Afoxolaner | 500 + 50 |
| any one kind of Present compounds X + fluralaner | 200 + 2000 |
| any one kind of Present compounds X + fluralaner | 200 + 200 |
| any one kind of Present compounds X + fluralaner | 500 + 50 |
| any one kind of Present compounds X + broflanilide | 200 + 2000 |
| any one kind of Present compounds X + broflanilide | 200 + 200 |
| any one kind of Present compounds X + broflanilide | 500 + 50 |
| any one kind of Present compounds X + Avermectin | 200 + 2000 |
| any one kind of Present compounds X + Avermectin | 200 + 200 |
| any one kind of Present compounds X + Avermectin | 500 + 5 |
| any one kind of Present compounds X + Fluopyram | 200 + 2000 |
| any one kind of Present compounds X + Fluopyram | 200 + 20 |
| any one kind of Present compounds X + Fluopyram | 500 + 0.5 |
| any one kind of Present compounds X + Fluensulfone | 200 + 2000 |
| any one kind of Present compounds X + Fluensulfone | 200 + 200 |
| any one kind of Present compounds X + Fluensulfone | 500 + 5 |
| any one kind of Present compounds X + Fluazaindolizine | 200 + 2000 |
| any one kind of Present compounds X + Fluazaindolizine | 200 + 200 |
| any one kind of Present compounds X + Fluazaindolizine | 500 + 5 |
| any one kind of Present compounds X + Tioxazafen | 200 + 2000 |
| any one kind of Present compounds X + Tioxazafen | 200 + 200 |
| any one kind of Present compounds X + Tioxazafen | 500 + 5 |
| any one kind of Present compounds X + Insecticide compound α1 | 200 + 2000 |
| any one kind of Present compounds X + Insecticide compound α1 | 200 + 200 |
| any one kind of Present compounds X + Insecticide compound α1 | 500 + 50 |
| any one kind of Present compounds X + Mycorrhizal fungi | 200 + 2000 |
| any one kind of Present compounds X + Mycorrhizal fungi | 200 + 200 |
| any one kind of Present compounds X + Mycorrhizal fungi | 500 + 5 |

TABLE 29-continued

| Composition | Concentration (ppm) (Present compound + Present active ingredient) |
|---|---|
| any one kind of Present compounds X + Bacillus firmus I- 1582 strain | 200 + 2000 |
| any one kind of Present compounds X + B Bacillus firmus I- 1582 strain | 200 + 200 |
| any one kind of Present compounds X + Bacillus firmus I- 1582 strain | 500 + 5 |
| any one kind of Present compounds X + Bacillus amyloliquefaciens | 200 + 2000 |
| any one kind of Present compounds X + Bacillus amyloliquefaciens | 200 + 200 |
| any one kind of Present compounds X + Bacillus amyloliquefaciens | 500 + 5 |
| any one kind of Present compounds X + Pasteuria nishizawae | 200 + 2000 |
| any one kind of Present compounds X + Pasteuria nishizawae | 200 + 200 |
| any one kind of Present compounds X + Pasteuria nishizawae | 500 + 5 |
| any one kind of Present compounds X + Pasteuria penetrans | 200 + 2000 |
| any one kind of Present compounds X + Pasteuria penetrans | 200 + 200 |
| any one kind of Present compounds X + Pasteuria penetrans | 500 + 5 |
| any one kind of Present compounds X + Tebuconazole | 200 + 2000 |
| any one kind of Present compounds X + Tebuconazole | 200 + 20 |
| any one kind of Present compounds X + Tebuconazole | 500 + 0.5 |
| any one kind of Present compounds X + Prothioconazole | 200 + 2000 |
| any one kind of Present compounds X + Prothioconazole | 200 + 20 |
| any one kind of Present compounds X + Prothioconazole | 500 + 0.5 |
| any one kind of Present compounds X + Metconazole | 200 + 2000 |
| any one kind of Present compounds X + Metconazole | 200 + 20 |
| any one kind of Present compounds X + Metconazole | 500 + 0.5 |
| any one kind of Present compounds X + Ipconazole | 200 + 2000 |
| any one kind of Present compounds X + Ipconazole | 200 + 20 |
| any one kind of Present compounds X + Ipconazole | 500 + 0.5 |
| any one kind of Present compounds X + Triticonazole | 200 + 2000 |
| any one kind of Present compounds X + Triticonazole | 200 + 20 |
| any one kind of Present compounds X + Triticonazole | 500 + 0.5 |
| any one kind of Present compounds X + Difenoconazole | 200 + 2000 |
| any one kind of Present compounds X + Difenoconazole | 200 + 20 |
| any one kind of Present compounds X + Difenoconazole | 500 + 0.5 |
| any one kind of Present compounds X + Imazalil | 200 + 2000 |
| any one kind of Present compounds X + Imazalil | 200 + 20 |
| any one kind of Present compounds X + Imazalil | 500 + 0.5 |
| any one kind of Present compounds X + Triadimenol | 200 + 2000 |
| any one kind of Present compounds X + Triadimenol | 200 + 20 |
| any one kind of Present compounds X + Triadimenol | 500 + 0.5 |
| any one kind of Present compounds X + Tetraconazole | 200 + 2000 |
| any one kind of Present compounds X + Tetraconazole | 200 + 20 |
| any one kind of Present compounds X + Tetraconazole | 500 + 0.5 |
| any one kind of Present compounds X + Flutriafol | 200 + 2000 |
| any one kind of Present compounds X + Flutriafol | 200 + 20 |
| any one kind of Present compounds X + Flutriafol | 500 + 0.5 |
| any one kind of Present compounds X + Mandestrobin | 200 + 2000 |
| any one kind of Present compounds X + Mandestrobin | 200 + 20 |
| any one kind of Present compounds X + Mandestrobin | 500 + 0.5 |
| any one kind of Present compounds X + Azoxystrobin | 200 + 2000 |
| any one kind of Present compounds X + Azoxystrobin | 200 + 20 |
| any one kind of Present compounds X + Azoxystrobin | 500 + 0.5 |
| any one kind of Present compounds X + Pyraclostrobin | 200 + 2000 |
| any one kind of Present compounds X + Pyraclostrobin | 200 + 20 |
| any one kind of Present compounds X + Pyraclostrobin | 500 + 0.5 |
| any one kind of Present compounds X + Trifloxystrobin | 200 + 2000 |
| any one kind of Present compounds X + Trifloxystrobin | 200 + 20 |
| any one kind of Present compounds X + Trifloxystrobin | 500 + 0.5 |
| any one kind of Present compounds X + Fluoxastrobin | 200 + 2000 |
| any one kind of Present compounds X + Fluoxastrobin | 200 + 20 |
| any one kind of Present compounds X + Fluoxastrobin | 500 + 0.5 |
| any one kind of Present compounds X + Picoxystrobin | 200 + 2000 |
| any one kind of Present compounds X + Picoxystrobin | 200 + 20 |
| any one kind of Present compounds X + Picoxystrobin | 500 + 0.5 |
| any one kind of Present compounds X + Fenamidone | 200 + 2000 |
| any one kind of Present compounds X + Fenamidone | 200 + 20 |
| any one kind of Present compounds X + Fenamidone | 500 + 0.5 |
| any one kind of Present compounds X + Metalaxyl | 200 + 2000 |
| any one kind of Present compounds X + Metalaxyl | 200 + 20 |
| any one kind of Present compounds X + Metalaxyl | 500 + 0.5 |
| any one kind of Present compounds X + Metalaxyl M | 200 + 2000 |
| any one kind of Present compounds X + Metalaxyl M | 200 + 20 |
| any one kind of Present compounds X + Metalaxyl M | 500 + 0.5 |
| any one kind of Present compounds X + Fludioxonil | 200 + 2000 |
| any one kind of Present compounds X + Fludioxonil | 200 + 20 |
| any one kind of Present compounds X + Fludioxonil | 500 + 0.5 |
| any one kind of Present compounds X + Sedaxane | 200 + 2000 |
| any one kind of Present compounds X + Sedaxane | 200 + 20 |
| any one kind of Present compounds X + Sedaxane | 500 + 0.5 |
| any one kind of Present compounds X + Penfurufen | 200 + 2000 |

TABLE 29-continued

| Composition | Concentration (ppm) (Present compound + Present active ingredient) |
|---|---|
| any one kind of Present compounds X + Penfurufen | 200 + 20 |
| any one kind of Present compounds X + Penfurufen | 500 + 0.5 |
| any one kind of Present compounds X + Fluxapyroxad | 200 + 2000 |
| any one kind of Present compounds X + Fluxapyroxad | 200 + 20 |
| any one kind of Present compounds X + Fluxapyroxad | 500 + 0.5 |
| any one kind of Present compounds X + Benzovindiflupyr | 200 + 2000 |
| any one kind of Present compounds X + Benzovindiflupyr | 200 + 20 |
| any one kind of Present compounds X + Benzovindiflupyr | 500 + 0.5 |
| any one kind of Present compounds X + Boscalid | 200 + 2000 |
| any one kind of Present compounds X + Boscalid | 200 + 20 |
| any one kind of Present compounds X + Boscalid | 500 + 0.5 |
| any one kind of Present compounds X + Carboxin | 200 + 2000 |
| any one kind of Present compounds X + Carboxin | 200 + 20 |
| any one kind of Present compounds X + Carboxin | 500 + 0.5 |
| any one kind of Present compounds X + Penthiopyrad | 200 + 2000 |
| any one kind of Present compounds X + Penthiopyrad | 200 + 20 |
| any one kind of Present compounds X + Penthiopyrad | 500 + 0.5 |
| any one kind of Present compounds X + Flutolanil | 200 + 2000 |
| any one kind of Present compounds X + Flutolanil | 200 + 20 |
| any one kind of Present compounds X + Flutolanil | 500 + 0.5 |
| any one kind of Present compounds X + Captan | 200 + 2000 |
| any one kind of Present compounds X + Captan | 200 + 20 |
| any one kind of Present compounds X + Captan | 500 + 0.5 |
| any one kind of Present compounds X + Thiuram | 200 + 2000 |
| any one kind of Present compounds X + Thiuram | 200 + 20 |
| any one kind of Present compounds X + Thiuram | 500 + 0.5 |
| any one kind of Present compounds X + Tolclofos-methyl | 200 + 2000 |
| any one kind of Present compounds X + Tolclofos-methyl | 200 + 20 |
| any one kind of Present compounds X + Tolclofos-methyl | 500 + 0.5 |
| any one kind of Present compounds X + Thiabendazole | 200 + 2000 |
| any one kind of Present compounds X + Thiabendazole | 200 + 20 |
| any one kind of Present compounds X + Thiabendazole | 500 + 0.5 |
| any one kind of Present compounds X + Ethaboxam | 200 + 2000 |
| any one kind of Present compounds X + Ethaboxam | 200 + 20 |
| any one kind of Present compounds X + Ethaboxam | 500 + 0.5 |
| any one kind of Present compounds X + Mancozeb | 200 + 2000 |
| any one kind of Present compounds X + Mancozeb | 200 + 20 |
| any one kind of Present compounds X + Mancozeb | 500 + 0.5 |
| any one kind of Present compounds X + Picarbutrazox | 200 + 2000 |
| any one kind of Present compounds X + Picarbutrazox | 200 + 20 |
| any one kind of Present compounds X + Picarbutrazox | 500 + 0.5 |
| any one kind of Present compounds X + Oxathiapiprolin | 200 + 2000 |
| any one kind of Present compounds X + Oxathiapiprolin | 200 + 20 |
| any one kind of Present compounds X + Oxathiapiprolin | 500 + 0.5 |
| any one kind of Present compounds X + Silthiofam | 200 + 2000 |
| any one kind of Present compounds X + Silthiofam | 200 + 20 |
| any one kind of Present compounds X + Silthiofam | 500 + 0.5 |
| any one kind of Present compounds X + Fungicide compound β1 | 200 + 2000 |
| any one kind of Present compounds X + Fungicide compound β1 | 200 + 20 |
| any one kind of Present compounds X + Fungicide compound β1 | 500 + 0.5 |
| any one kind of Present compounds X + Inpyrfluxam | 200 + 2000 |
| any one kind of Present compounds X + Inpyrfluxam | 200 + 20 |
| any one kind of Present compounds X + Inpyrfluxam | 500 + 0.5 |

[Table 20]
[Table 21]
[Table 22]
[Table 23]
[Table 24]
[Table 25]
[Table 26]
[Table 27]
[Table 28]
[Table 29]
[Table 30]
[Table 31]
[Table 32]

Test Example 10

Each 1 mg of the Present compound was dissolved into a 10 μL of the mixed solution of xylene, DMF and surfactants (xylene, DMF and surfactants=4:4:1 (v/v ratio)). Thereto was added water containing 0.02% by volume of a spreader to prepare a diluted solution containing a prescribed concentration of the Present compound.

When the commercially available formulation of the present active ingredient was used, each of the commercially available formulation is diluted with water containing 0.02 v/v % of the spreader to prepare the prescribed concentration of the diluted solution of the present active ingredient.

Whereas, when the commercially available formulation of the present active ingredient was not used, each 1 mg of the present active ingredient was dissolved into a 10 μL of the mixed solution of xylene, DMF and surfactants (xylene, DMF and surfactants=4:4:1 (v/v ratio)). Thereto was added water containing 0.02% by volume of a spreader to prepare a diluted solution containing a prescribed concentration of the present active ingredient.

The above prepared diluted solution of the Present compound and the above prepared diluted solution of the present active ingredient were mixed to prepare the test chemical solution of the composition comprising the Present compound and the present active ingredient.

A leaf disk (length 1.5 cm) of the seed leaf of cucumber was placed into each well in a 24 well microplate, and 2 wingless adults of a cotton aphid (*Aphis gossypii*) and 8 nymphs of a cotton aphid were released per 1 well, and the test chemical solution was sprayed in a ratio of 20 μL per 1 well, which was referred to as a treated group.

Whereas, 20 μL water containing 0.02 v/v % of the spreader is sprayed into a well instead of the test chemical solution, which is referred to as an untreated group.

After the test chemical solution was dried, the upper part of a microplate was covered with a film sheet, and 5 days after the release, the number of the surviving insects of each well was examined.

The controlling value was calculated by the following equation.

Controlling value (%)={1−(*Tai*)/(*Cai*)}×100 wherein the symbols in the formula represent the following descriptions.

Cai: Number of the surviving insects at the time of the investigation in untreated group;

Tai: Number of the surviving insects at the time of the investigation in treated group;

The results of the test that was conducted according to Test example 10 are shown below.

Any the present composition wherein the respective concentration of the Present compound and the Present active ingredient is indicated in the below-mentioned Tables 30 to 41 showed 90% or greater as a controlling value against harmful arthropods.

[Table 33]

TABLE 30

| Composition | Concentration (ppm) |
|---|---|
| Present compound A-2 + Clothianidin | 200 + 2000 |
| Present compound A-2 + Clothianidin | 500 + 50 |
| Present compound A-2 + Imidacloprid | 200 + 2000 |
| Present compound A-2 + Imidacloprid | 500 + 50 |
| Present compound A-2 + Thiamethoxam | 200 + 2000 |
| Present compound A-2 + Thiamethoxam | 500 + 50 |
| Present compound A-2 + Azoxystrobin | 200 + 200 |
| Present compound A-2 + Azoxystrobin | 500 + 0.5 |
| Present compound A-2 + Difenoconazole | 200 + 200 |
| Present compound A-2 + Difenoconazole | 500 + 0.5 |
| Present compound A-2 + Ethaboxam | 200 + 200 |
| Present compound A-2 + Ethaboxam | 500 + 0.5 |
| Present compound A-2 + Fludioxonil | 200 + 200 |
| Present compound A-2 + Fludioxonil | 500 + 0.5 |
| Present compound A-2 + Fluopyram | 200 + 2000 |
| Present compound A-2 + Fluopyram | 500 + 0.5 |
| Present compound A-2 + Fluoxastrobin | 200 + 200 |
| Present compound A-2 + Fluoxastrobin | 500 + 0.5 |
| Present compound A-2 + Flutolanil | 200 + 200 |
| Present compound A-2 + Flutolanil | 500 + 0.5 |
| Present compound A-2 + Flutriafol | 200 + 200 |
| Present compound A-2 + Flutriafol | 500 + 0.5 |
| Present compound A-2 + Fluxapyroxad | 200 + 200 |
| Present compound A-2 + Fluxapyroxad | 500 + 0.5 |
| Present compound A-2 + Ipconazole | 200 + 200 |
| Present compound A-2 + Ipconazole | 500 + 0.5 |
| Present compound A-2 + Mandestrobin | 200 + 200 |
| Present compound A-2 + Mandestrobin | 500 + 0.5 |
| Present compound A-2 + Metalaxyl M | 200 + 200 |
| Present compound A-2 + Metalaxyl M | 500 + 0.5 |
| Present compound A-2 + Metalaxyl | 200 + 200 |

TABLE 30-continued

| Composition | Concentration (ppm) |
|---|---|
| Present compound A-2 + Metalaxyl | 500 + 0.5 |
| Present compound A-2 + Metconazole | 200 + 200 |
| Present compound A-2 + Metconazole | 500 + 0.5 |
| Present compound A-2 + Oxathiapiprolin | 200 + 200 |
| Present compound A-2 + Oxathiapiprolin | 500 + 0.5 |
| Present compound A-2 + Penfurufen | 200 + 200 |
| Present compound A-2 + Penfurufen | 500 + 0.5 |
| Present compound A-2 + Penthiopyrad | 200 + 200 |
| Present compound A-2 + Penthiopyrad | 500 + 0.5 |
| Present compound A-2 + Picoxystrobin | 200 + 200 |
| Present compound A-2 + Picoxystrobin | 500 + 0.5 |
| Present compound A-2 + Prothioconazole | 200 + 200 |
| Present compound A-2 + Prothioconazole | 500 + 0.5 |
| Present compound A-2 + Pyraclostrobin | 200 + 200 |
| Present compound A-2 + Pyraclostrobin | 500 + 0.5 |
| Present compound A-2 + Inpyrfluxam | 200 + 200 |
| Present compound A-2 + Inpyrfluxam | 500 + 0.5 |
| Present compound A-2 + Sedaxane | 200 + 200 |
| Present compound A-2 + Sedaxane | 500 + 0.5 |
| Present compound A-2 + Tebuconazole | 200 + 200 |
| Present compound A-2 + Tebuconazole | 500 + 0.5 |
| Present compound A-2 + Triadimenol | 200 + 200 |
| Present compound A-2 + Triadimenol | 500 + 0.5 |
| Present compound A-2 + Trifloxystrobin | 200 + 200 |
| Present compound A-2 + Trifloxystrobin | 500 + 0.5 |
| Present compound A-2 + Triticonazole | 200 + 200 |
| Present compound A-2 + Triticonazole | 500 + 0.5 |

[Table 34]
[Table 35]
[Table 36]

TABLE 31

| Composition | Concentration (ppm) |
|---|---|
| Present compound A-12 + Clothianidin | 200 + 2000 |
| Present compound A-12 + Clothianidin | 500 + 50 |
| Present compound A-12 + Imidacloprid | 200 + 2000 |
| Present compound A-12 + Imidacloprid | 500 + 50 |
| Present compound A-12 + Thiamethoxam | 200 + 2000 |
| Present compound A-12 + Thiamethoxam | 500 + 50 |
| Present compound A-12 + Azoxystrobin | 200 + 200 |
| Present compound A-12 + Azoxystrobin | 500 + 0.5 |
| Present compound A-12 + Difenoconazole | 200 + 200 |
| Present compound A-12 + Difenoconazole | 500 + 0.5 |
| Present compound A-12 + Ethaboxam | 200 + 200 |
| Present compound A-12 + Ethaboxam | 500 + 0.5 |
| Present compound A-12 + Fludioxonil | 200 + 200 |
| Present compound A-12 + Fludioxonil | 500 + 0.5 |
| Present compound A-12 + Fluopyram | 200 + 2000 |
| Present compound A-12 + Fluopyram | 500 + 0.5 |
| Present compound A-12 + Fluoxastrobin | 200 + 200 |
| Present compound A-12 + Fluoxastrobin | 500 + 0.5 |
| Present compound A-12 + Flutolanil | 200 + 200 |
| Present compound A-12 + Flutolanil | 500 + 0.5 |
| Present compound A-12 + Flutriafol | 200 + 200 |
| Present compound A-12 + Flutriafol | 500 + 0.5 |
| Present compound A-12 + Fluxapyroxad | 200 + 200 |
| Present compound A-12 + Fluxapyroxad | 500 + 0.5 |
| Present compound A-12 + Ipconazole | 200 + 200 |
| Present compound A-12 + Ipconazole | 500 + 0.5 |
| Present compound A-12 + Mandestrobin | 200 + 200 |
| Present compound A-12 + Mandestrobin | 500 + 0.5 |
| Present compound A-12 + Metalaxyl M | 200 + 200 |
| Present compound A-12 + Metalaxyl M | 500 + 0.5 |
| Present compound A-12 + Metalaxyl | 200 + 200 |
| Present compound A-12 + Metalaxyl | 500 + 0.5 |
| Present compound A-12 + Metconazole | 200 + 200 |
| Present compound A-12 + Metconazole | 500 + 0.5 |
| Present compound A-12 + Oxathiapiprolin | 200 + 200 |
| Present compound A-12 + Oxathiapiprolin | 500 + 0.5 |
| Present compound A-12 + Penfurufen | 200 + 200 |
| Present compound A-12 + Penfurufen | 500 + 0.5 |

TABLE 31-continued

| Composition | Concentration (ppm) |
| --- | --- |
| Present compound A-12 + Penthiopyrad | 200 + 200 |
| Present compound A-12 + Penthiopyrad | 500 + 0.5 |
| Present compound A-12 + Picoxystrobin | 200 + 200 |
| Present compound A-12 + Picoxystrobin | 500 + 0.5 |
| Present compound A-12 + Prothioconazole | 200 + 200 |
| Present compound A-12 + Prothioconazole | 500 + 0.5 |
| Present compound A-12 + Pyraclostrobin | 200 + 200 |
| Present compound A-12 + Pyraclostrobin | 500 + 0.5 |
| Present compound A-12 + Inpyrfluxam | 200 + 200 |
| Present compound A-12 + Inpyrfluxam | 500 + 0.5 |
| Present compound A-12 + Sedaxane | 200 + 200 |
| Present compound A-12 + Sedaxane | 500 + 0.5 |
| Present compound A-12 + Tebuconazole | 200 + 200 |
| Present compound A-12 + Tebuconazole | 500 + 0.5 |
| Present compound A-12 + Triadimenol | 200 + 200 |
| Present compound A-12 + Triadimenol | 500 + 0.5 |
| Present compound A-12 + Trifloxystrobin | 200 + 200 |
| Present compound A-12 + Trifloxystrobin | 500 + 0.5 |
| Present compound A-12 + Triticonazole | 200 + 200 |
| Present compound A-12 + Triticonazole | 500 + 0.5 |

[Table 37]
[Table 38]
[Table 39]

TABLE 32

| Composition | Concentration (ppm) |
| --- | --- |
| Present compound A-17 + Clothianidin | 200 + 2000 |
| Present compound A-17 + Clothianidin | 500 + 50 |
| Present compound A-17 + Imidacloprid | 200 + 2000 |
| Present compound A-17 + Imidacloprid | 500 + 50 |
| Present compound A-17 + Thiamethoxam | 200 + 2000 |
| Present compound A-17 + Thiamethoxam | 500 + 50 |
| Present compound A-17 + Azoxystrobin | 200 + 200 |
| Present compound A-17 + Azoxystrobin | 500 + 0.5 |
| Present compound A-17 + Difenoconazole | 200 + 200 |
| Present compound A-17 + Difenoconazole | 500 + 0.5 |
| Present compound A-17 + Ethaboxam | 200 + 200 |
| Present compound A-17 + Ethaboxam | 500 + 0.5 |
| Present compound A-17 + Fludioxonil | 200 + 200 |
| Present compound A-17 + Fludioxonil | 500 + 0.5 |
| Present compound A-17 + Fluopyram | 200 + 2000 |
| Present compound A-17 + Fluopyram | 500 + 0.5 |
| Present compound A-17 + Fluoxastrobin | 200 + 200 |
| Present compound A-17 + Fluoxastrobin | 500 + 0.5 |
| Present compound A-17 + Flutolanil | 200 + 200 |
| Present compound A-17 + Flutolanil | 500 + 0.5 |
| Present compound A-17 + Flutriafol | 200 + 200 |
| Present compound A-17 + Flutriafol | 500 + 0.5 |
| Present compound A-17 + Fluxapyroxad | 200 + 200 |
| Present compound A-17 + Fluxapyroxad | 500 + 0.5 |
| Present compound A-17 + Ipconazole | 200 + 200 |
| Present compound A-17 + Ipconazole | 500 + 0.5 |
| Present compound A-17 + Mandestrobin | 200 + 200 |
| Present compound A-17 + Mandestrobin | 500 + 0.5 |
| Present compound A-17 + Metalaxyl M | 200 + 200 |
| Present compound A-17 + Metalaxyl M | 500 + 0.5 |
| Present compound A-17 + Metalaxyl | 200 + 200 |
| Present compound A-17 + Metalaxyl | 500 + 0.5 |
| Present compound A-17 + Metconazole | 200 + 200 |
| Present compound A-17 + Metconazole | 500 + 0.5 |
| Present compound A-17 + Oxathiapiprolin | 200 + 200 |
| Present compound A-17 + Oxathiapiprolin | 500 + 0.5 |
| Present compound A-17 + Penfurufen | 200 + 200 |
| Present compound A-17 + Penfurufen | 500 + 0.5 |
| Present compound A-17 + Penthiopyrad | 200 + 200 |
| Present compound A-17 + Penthiopyrad | 500 + 0.5 |
| Present compound A-17 + Picoxystrobin | 200 + 200 |
| Present compound A-17 + Picoxystrobin | 500 + 0.5 |
| Present compound A-17 + Prothioconazole | 200 + 200 |
| Present compound A-17 + Prothioconazole | 500 + 0.5 |
| Present compound A-17 + Pyraclostrobin | 200 + 200 |

TABLE 32-continued

| Composition | Concentration (ppm) |
| --- | --- |
| Present compound A-17 + Pyraclostrobin | 500 + 0.5 |
| Present compound A-17 + Inpyrfluxam | 200 + 200 |
| Present compound A-17 + Inpyrfluxam | 500 + 0.5 |
| Present compound A-17 + Sedaxane | 200 + 200 |
| Present compound A-17 + Sedaxane | 500 + 0.5 |
| Present compound A-17 + Tebuconazole | 200 + 200 |
| Present compound A-17 + Tebuconazole | 500 + 0.5 |
| Present compound A-17 + Triadimenol | 200 + 200 |
| Present compound A-17 + Triadimenol | 500 + 0.5 |
| Present compound A-17 + Trifloxystrobin | 200 + 200 |
| Present compound A-17 + Trifloxystrobin | 500 + 0.5 |
| Present compound A-17 + Triticonazole | 200 + 200 |
| Present compound A-17 + Triticonazole | 500 + 0.5 |

[Table 40]
[Table 41]
[Table 42]

TABLE 33

| Composition | Concentration (ppm) |
| --- | --- |
| Present compound A-25 + Clothianidin | 200 + 2000 |
| Present compound A-25 + Clothianidin | 500 + 50 |
| Present compound A-25 + Imidacloprid | 200 + 2000 |
| Present compound A-25 + Imidacloprid | 500 + 50 |
| Present compound A-25 + Thiamethoxam | 200 + 2000 |
| Present compound A-25 + Thiamethoxam | 500 + 50 |
| Present compound A-25 + Azoxystrobin | 200 + 200 |
| Present compound A-25 + Azoxystrobin | 500 + 0.5 |
| Present compound A-25 + Difenoconazole | 200 + 200 |
| Present compound A-25 + Difenoconazole | 500 + 0.5 |
| Present compound A-25 + Ethaboxam | 200 + 200 |
| Present compound A-25 + Ethaboxam | 500 + 0.5 |
| Present compound A-25 + Fludioxonil | 200 + 200 |
| Present compound A-25 + Fludioxonil | 500 + 0.5 |
| Present compound A-25 + Fluopyram | 200 + 2000 |
| Present compound A-25 + Fluopyram | 500 + 0.5 |
| Present compound A-25 + Fluoxastrobin | 200 + 200 |
| Present compound A-25 + Fluoxastrobin | 500 + 0.5 |
| Present compound A-25 + Flutolanil | 200 + 200 |
| Present compound A-25 + Flutolanil | 500 + 0.5 |
| Present compound A-25 + Flutriafol | 200 + 200 |
| Present compound A-25 + Flutriafol | 500 + 0.5 |
| Present compound A-25 + Fluxapyroxad | 200 + 200 |
| Present compound A-25 + Fluxapyroxad | 500 + 0.5 |
| Present compound A-25 + Ipconazole | 200 + 200 |
| Present compound A-25 + Ipconazole | 500 + 0.5 |
| Present compound A-25 + Mandestrobin | 200 + 200 |
| Present compound A-25 + Mandestrobin | 500 + 0.5 |
| Present compound A-25 + Metalaxyl M | 200 + 200 |
| Present compound A-25 + Metalaxyl M | 500 + 0.5 |
| Present compound A-25 + Metalaxyl | 200 + 200 |
| Present compound A-25 + Metalaxyl | 500 + 0.5 |
| Present compound A-25 + Metconazole | 200 + 200 |
| Present compound A-25 + Metconazole | 500 + 0.5 |
| Present compound A-25 + Oxathiapiprolin | 200 + 200 |
| Present compound A-25 + Oxathiapiprolin | 500 + 0.5 |
| Present compound A-25 + Penfurufen | 200 + 200 |
| Present compound A-25 + Penfurufen | 500 + 0.5 |
| Present compound A-25 + Penthiopyrad | 200 + 200 |
| Present compound A-25 + Penthiopyrad | 500 + 0.5 |
| Present compound A-25 + Picoxystrobin | 200 + 200 |
| Present compound A-25 + Picoxystrobin | 500 + 0.5 |
| Present compound A-25 + Prothioconazole | 200 + 200 |
| Present compound A-25 + Prothioconazole | 500 + 0.5 |
| Present compound A-25 + Pyraclostrobin | 200 + 200 |
| Present compound A-25 + Pyraclostrobin | 500 + 0.5 |
| Present compound A-25 + Inpyrfluxam | 200 + 200 |
| Present compound A-25 + Inpyrfluxam | 500 + 0.5 |
| Present compound A-25 + Sedaxane | 200 + 200 |
| Present compound A-25 + Sedaxane | 500 + 0.5 |
| Present compound A-25 + Tebuconazole | 200 + 200 |
| Present compound A-25 + Tebuconazole | 500 + 0.5 |

TABLE 33-continued

| Composition | Concentration (ppm) |
|---|---|
| Present compound A-25 + Triadimenol | 200 + 200 |
| Present compound A-25 + Triadimenol | 500 + 0.5 |
| Present compound A-25 + Trifloxystrobin | 200 + 200 |
| Present compound A-25 + Trifloxystrobin | 500 + 0.5 |
| Present compound A-25 + Triticonazole | 200 + 200 |
| Present compound A-25 + Triticonazole | 500 + 0.5 |

[Table 43]
[Table 44]
[Table 45]

TABLE 34

| Composition | Concentration (ppm) |
|---|---|
| Present compound A-32 + Clothianidin | 200 + 2000 |
| Present compound A-32 + Clothianidin | 500 + 50 |
| Present compound A-32 + Imidacloprid | 200 + 2000 |
| Present compound A-32 + Imidacloprid | 500 + 50 |
| Present compound A-32 + Thiamethoxam | 200 + 2000 |
| Present compound A-32 + Thiamethoxam | 500 + 50 |
| Present compound A-32 + Azoxystrobin | 200 + 200 |
| Present compound A-32 + Azoxystrobin | 500 + 0.5 |
| Present compound A-32 + Difenoconazole | 200 + 200 |
| Present compound A-32 + Difenoconazole | 500 + 0.5 |
| Present compound A-32 + Ethaboxam | 200 + 200 |
| Present compound A-32 + Ethaboxam | 500 + 0.5 |
| Present compound A-32 + Fludioxonil | 200 + 200 |
| Present compound A-32 + Fludioxonil | 500 + 0.5 |
| Present compound A-32 + Fluopyram | 200 + 2000 |
| Present compound A-32 + Fluopyram | 500 + 0.5 |
| Present compound A-32 + Fluoxastrobin | 200 + 200 |
| Present compound A-32 + Fluoxastrobin | 500 + 0.5 |
| Present compound A-32 + Flutolanil | 200 + 200 |
| Present compound A-32 + Flutolanil | 500 + 0.5 |
| Present compound A-32 + Flutriafol | 200 + 200 |
| Present compound A-32 + Flutriafol | 500 + 0.5 |
| Present compound A-32 + Fluxapyroxad | 200 + 200 |
| Present compound A-32 + Fluxapyroxad | 500 + 0.5 |
| Present compound A-32 + Ipconazole | 200 + 200 |
| Present compound A-32 + Ipconazole | 500 + 0.5 |
| Present compound A-32 + Mandestrobin | 200 + 200 |
| Present compound A-32 + Mandestrobin | 500 + 0.5 |
| Present compound A-32 + Metalaxyl M | 200 + 200 |
| Present compound A-32 + Metalaxyl M | 500 + 0.5 |
| Present compound A-32 + Metalaxyl | 200 + 200 |
| Present compound A-32 + Metalaxyl | 500 + 0.5 |
| Present compound A-32 + Metconazole | 200 + 200 |
| Present compound A-25 + Metconazole | 500 + 0.5 |
| Present compound A-32 + Oxathiapiprolin | 200 + 200 |
| Present compound A-32 + Oxathiapiprolin | 500 + 0.5 |
| Present compound A-32 + Penfurufen | 200 + 200 |
| Present compound A-32 + Penfurufen | 500 + 0.5 |
| Present compound A-32 + Penthiopyrad | 200 + 200 |
| Present compound A-32 + Penthiopyrad | 500 + 0.5 |
| Present compound A-32 + Picoxystrobin | 200 + 200 |
| Present compound A-32 + Picoxystrobin | 500 + 0.5 |
| Present compound A-32 + Prothioconazole | 200 + 200 |
| Present compound A-32 + Prothioconazole | 500 + 0.5 |
| Present compound A-32 + Pyraclostrobin | 200 + 200 |
| Present compound A-32 + Pyraclostrobin | 500 + 0.5 |
| Present compound A-32 + Inpyrfluxam | 200 + 200 |
| Present compound A-32 + Inpyrfluxam | 500 + 0.5 |
| Present compound A-32 + Sedaxane | 200 + 200 |
| Present compound A-32 + Sedaxane | 500 + 0.5 |
| Present compound A-32 + Tebuconazole | 200 + 200 |
| Present compound A-32 + Tebuconazole | 500 + 0.5 |
| Present compound A-32 + Triadimenol | 200 + 200 |
| Present compound A-32 + Triadimenol | 500 + 0.5 |
| Present compound A-32 + Trifloxystrobin | 200 + 200 |
| Present compound A-32 + Trifloxystrobin | 500 + 0.5 |
| Present compound A-32 + Triticonazole | 200 + 200 |
| Present compound A-32 + Triticonazole | 500 + 0.5 |

[Table 46]
[Table 47]
[Table 48]

TABLE 35

| Composition | Concentration (ppm) |
|---|---|
| Present compound A-36 + Clothianidin | 200 + 2000 |
| Present compound A-36 + Clothianidin | 500 + 50 |
| Present compound A-36 + Imidacloprid | 200 + 2000 |
| Present compound A-36 + Imidacloprid | 500 + 50 |
| Present compound A-36 + Thiamethoxam | 200 + 2000 |
| Present compound A-36 + Thiamethoxam | 500 + 50 |
| Present compound A-36 + Azoxystrobin | 200 + 200 |
| Present compound A-36 + Azoxystrobin | 500 + 0.5 |
| Present compound A-36 + Difenoconazole | 200 + 200 |
| Present compound A-36 + Difenoconazole | 500 + 0.5 |
| Present compound A-36 + Ethaboxam | 200 + 200 |
| Present compound A-36 + Ethaboxam | 500 + 0.5 |
| Present compound A-36 + Fludioxonil | 200 + 200 |
| Present compound A-36 + Fludioxonil | 500 + 0.5 |
| Present compound A-36 + Fluopyram | 200 + 2000 |
| Present compound A-36 + Fluopyram | 500 + 0.5 |
| Present compound A-36 + Fluoxastrobin | 200 + 200 |
| Present compound A-36 + Fluoxastrobin | 500 + 0.5 |
| Present compound A-36 + Flutolanil | 200 + 200 |
| Present compound A-36 + Flutolanil | 500 + 0.5 |
| Present compound A-36 + Flutriafol | 200 + 200 |
| Present compound A-36 + Flutriafol | 500 + 0.5 |
| Present compound A-36 + Fluxapyroxad | 200 + 200 |
| Present compound A-36 + Fluxapyroxad | 500 + 0.5 |
| Present compound A-36 + Ipconazole | 200 + 200 |
| Present compound A-36 + Ipconazole | 500 + 0.5 |
| Present compound A-36 + Mandestrobin | 200 + 200 |
| Present compound A-36 + Mandestrobin | 500 + 0.5 |
| Present compound A-36 + Metalaxyl M | 200 + 200 |
| Present compound A-36 + Metalaxyl M | 500 + 0.5 |
| Present compound A-36 + Metalaxyl | 200 + 200 |
| Present compound A-36 + Metalaxyl | 500 + 0.5 |
| Present compound A-36 + Metconazole | 200 + 200 |
| Present compound A-36 + Metconazole | 500 + 0.5 |
| Present compound A-36 + Oxathiapiprolin | 200 + 200 |
| Present compound A-36 + Oxathiapiprolin | 500 + 0.5 |
| Present compound A-36 + Penfurufen | 200 + 200 |
| Present compound A-36 + Penfurufen | 500 + 0.5 |
| Present compound A-36 + Penthiopyrad | 200 + 200 |
| Present compound A-36 + Penthiopyrad | 500 + 0.5 |
| Present compound A-36 + Picoxystrobin | 200 + 200 |
| Present compound A-36 + Picoxystrobin | 500 + 0.5 |
| Present compound A-36 + Prothioconazole | 200 + 200 |
| Present compound A-36 + Prothioconazole | 500 + 0.5 |
| Present compound A-36 + Pyraclostrobin | 200 + 200 |
| Present compound A-36 + Pyraclostrobin | 500 + 0.5 |
| Present compound A-36 + Inpyrfluxam | 200 + 200 |
| Present compound A-36 + Inpyrfluxam | 500 + 0.5 |
| Present compound A-36 + Sedaxane | 200 + 200 |
| Present compound A-36 + Sedaxane | 500 + 0.5 |
| Present compound A-36 + Tebuconazole | 200 + 200 |
| Present compound A-36 + Tebuconazole | 500 + 0.5 |
| Present compound A-36 + Triadimenol | 200 + 200 |
| Present compound A-36 + Triadimenol | 500 + 0.5 |
| Present compound A-36 + Trifloxystrobin | 200 + 200 |
| Present compound A-36 + Trifloxystrobin | 500 + 0.5 |
| Present compound A-36 + Triticonazole | 200 + 200 |
| Present compound A-36 + Triticonazole | 500 + 0.5 |

[Table 49]
[Table 50]
[Table 51]

TABLE 36

| Composition | Concentration (ppm) |
|---|---|
| Present compound A-40 + Clothianidin | 200 + 2000 |
| Present compound A-40 + Clothianidin | 500 + 50 |

TABLE 36-continued

| Composition | Concentration (ppm) |
|---|---|
| Present compound A-40 + Imidacloprid | 200 + 2000 |
| Present compound A-40 + Imidacloprid | 500 + 50 |
| Present compound A-40 + Thiamethoxam | 200 + 2000 |
| Present compound A-40 + Thiamethoxam | 500 + 50 |
| Present compound A-40 + Azoxystrobin | 200 + 200 |
| Present compound A-40 + Azoxystrobin | 500 + 0.5 |
| Present compound A-40 + Difenoconazole | 200 + 200 |
| Present compound A-40 + Difenoconazole | 500 + 0.5 |
| Present compound A-40 + Ethaboxam | 200 + 200 |
| Present compound A-40 + Ethaboxam | 500 + 0.5 |
| Present compound A-40 + Fludioxonil | 200 + 200 |
| Present compound A-40 + Fludioxonil | 500 + 0.5 |
| Present compound A-40 + Fluopyram | 200 + 2000 |
| Present compound A-40 + Fluopyram | 500 + 0.5 |
| Present compound A-40 + Fluoxastrobin | 200 + 200 |
| Present compound A-40 + Fluoxastrobin | 500 + 0.5 |
| Present compound A-40 + Flutolanil | 200 + 200 |
| Present compound A-40 + Flutolanil | 500 + 0.5 |
| Present compound A-40 + Flutriafol | 200 + 200 |
| Present compound A-40 + Flutriafol | 500 + 0.5 |
| Present compound A-40 + Fluxapyroxad | 200 + 200 |
| Present compound A-40 + Fluxapyroxad | 500 + 0.5 |
| Present compound A-40 + Ipconazole | 200 + 200 |
| Present compound A-40 + Ipconazole | 500 + 0.5 |
| Present compound A-40 + Mandestrobin | 200 + 200 |
| Present compound A-40 + Mandestrobin | 500 + 0.5 |
| Present compound A-40 + Metalaxyl M | 200 + 200 |
| Present compound A-40 + Metalaxyl M | 500 + 0.5 |
| Present compound A-40 + Metalaxyl | 200 + 200 |
| Present compound A-40 + Metalaxyl | 500 + 0.5 |
| Present compound A-40 + Metconazole | 200 + 200 |
| Present compound A-40 + Metconazole | 500 + 0.5 |
| Present compound A-40 + Oxathiapiprolin | 200 + 200 |
| Present compound A-40 + Oxathiapiprolin | 500 + 0.5 |
| Present compound A-40 + Penfurufen | 200 + 200 |
| Present compound A-40 + Penfurufen | 500 + 0.5 |
| Present compound A-40 + Penthiopyrad | 200 + 200 |
| Present compound A-40 + Penthiopyrad | 500 + 0.5 |
| Present compound A-40 + Picoxystrobin | 200 + 200 |
| Present compound A-40 + Picoxystrobin | 500 + 0.5 |
| Present compound A-40 + Prothioconazole | 200 + 200 |
| Present compound A-40 + Prothioconazole | 500 + 0.5 |
| Present compound A-40 + Pyraclostrobin | 200 + 200 |
| Present compound A-40 + Pyraclostrobin | 500 + 0.5 |
| Present compound A-40 + Inpyrfluxam | 200 + 200 |
| Present compound A-40 + Inpyrfluxam | 500 + 0.5 |
| Present compound A-40 + Sedaxane | 200 + 200 |
| Present compound A-40 + Sedaxane | 500 + 0.5 |
| Present compound A-40 + Tebuconazole | 200 + 200 |
| Present compound A-40 + Tebuconazole | 500 + 0.5 |
| Present compound A-40 + Triadimenol | 200 + 200 |
| Present compound A-40 + Triadimenol | 500 + 0.5 |
| Present compound A-40 + Trifloxystrobin | 200 + 200 |
| Present compound A-40 + Trifloxystrobin | 500 + 0.5 |
| Present compound A-40 + Triticonazole | 200 + 200 |
| Present compound A-40 + Triticonazole | 500 + 0.5 |

[Table 52]
[Table 53]
[Table 54]

TABLE 37

| Composition | Concentration (ppm) |
|---|---|
| Present compound A-46 + Clothianidin | 200 + 2000 |
| Present compound A-46 + Clothianidin | 500 + 50 |
| Present compound A-46 + Imidacloprid | 200 + 2000 |
| Present compound A-46 + Imidacloprid | 500 + 50 |
| Present compound A-46 + Thiamethoxam | 200 + 2000 |
| Present compound A-46 + Thiamethoxam | 500 + 50 |
| Present compound A-46 + Azoxystrobin | 200 + 200 |
| Present compound A-46 + Azoxystrobin | 500 + 0.5 |
| Present compound A-46 + Difenoconazole | 200 + 200 |

TABLE 37-continued

| Composition | Concentration (ppm) |
|---|---|
| Present compound A-46 + Difenoconazole | 500 + 0.5 |
| Present compound A-46 + Ethaboxam | 200 + 200 |
| Present compound A-46 + Ethaboxam | 500 + 0.5 |
| Present compound A-46 + Fludioxonil | 200 + 200 |
| Present compound A-46 + Fludioxonil | 500 + 0.5 |
| Present compound A-46 + Fluopyram | 200 + 2000 |
| Present compound A-46 + Fluopyram | 500 + 0.5 |
| Present compound A-46 + Fluoxastrobin | 200 + 200 |
| Present compound A-46 + Fluoxastrobin | 500 + 0.5 |
| Present compound A-46 + Flutolanil | 200 + 200 |
| Present compound A-46 + Flutolanil | 500 + 0.5 |
| Present compound A-46 4 Flutriafol | 200 + 200 |
| Present compound A-46 + Flutriafol | 500 + 0.5 |
| Present compound A-46 + Fluxapyroxad | 200 + 200 |
| Present compound A-46 + Fluxapyroxad | 500 + 0.5 |
| Present compound A-46 + Ipconazole | 200 + 200 |
| Present compound A-46 + Ipconazole | 500 + 0.5 |
| Present compound A-46 + Mandestrobin | 200 + 200 |
| Present compound A-46 + Mandestrobin | 500 + 0.5 |
| Present compound A-46 + Metalaxyl M | 200 + 200 |
| Present compound A-46 + Metalaxyl M | 500 + 0.5 |
| Present compound A-46 + Metalaxyl | 200 + 200 |
| Present compound A-46 + Metalaxyl | 500 + 0.5 |
| Present compound A-46 + Metconazole | 200 + 200 |
| Present compound A-46 + Metconazole | 500 + 0.5 |
| Present compound A-46 + Oxathiapiprolin | 200 + 200 |
| Present compound A-46 + Oxathiapiprolin | 500 + 0.5 |
| Present compound A-46 + Penfurufen | 200 + 200 |
| Present compound A-46 + Penfurufen | 500 + 0.5 |
| Present compound A-46 + Penthiopyrad | 200 + 200 |
| Present compound A-46 + Penthiopyrad | 500 + 0.5 |
| Present compound A-46 + Picoxystrobin | 200 + 200 |
| Present compound A-46 + Picoxystrobin | 500 + 0.5 |
| Present compound A-46 + Prothioconazole | 200 + 200 |
| Present compound A-46 + Prothioconazole | 500 + 0.5 |
| Present compound A-46 + Pyraclostrobin | 200 + 200 |
| Present compound A-46 + Pyraclostrobin | 500 + 0.5 |
| Present compound A-46 + Inpyrfluxam | 200 + 200 |
| Present compound A-46 + Inpyrfluxam | 500 + 0.5 |
| Present compound A-46 + Sedaxane | 200 + 200 |
| Present compound A-46 + Sedaxane | 500 + 0.5 |
| Present compound A-46 + Tebuconazole | 200 + 200 |
| Present compound A-46 + Tebuconazole | 500 + 0.5 |
| Present compound A-46 + Triadimenol | 200 + 200 |
| Present compound A-46 + Triadimenol | 500 + 0.5 |
| Present compound A-46 + Trifloxystrobin | 200 + 200 |
| Present compound A-46 + Trifloxystrobin | 500 + 0.5 |
| Present compound A-46 + Triticonazole | 200 + 200 |
| Present compound A-46 + Triticonazole | 500 + 0.5 |

[Table 55]
[Table 56]
[Table 57]

TABLE 38

| Composition | Concentration (ppm) |
|---|---|
| Present compound B-5 + Clothianidin | 200 + 2000 |
| Present compound B-5 + Clothianidin | 500 + 50 |
| Present compound B-5 + Imidacloprid | 200 + 2000 |
| Present compound B-5 + Imidacloprid | 500 + 50 |
| Present compound B-5 + Thiamethoxam | 200 + 2000 |
| Present compound B-5 + Thiamethoxam | 500 + 50 |
| Present compound B-5 + Azoxystrobin | 200 + 200 |
| Present compound B-5 + Azoxystrobin | 500 + 0.5 |
| Present compound B-5 + Difenoconazole | 200 + 200 |
| Present compound B-5 + Difenoconazole | 500 + 0.5 |
| Present compound B-5 + Ethaboxam | 200 + 200 |
| Present compound B-5 + Ethaboxam | 500 + 0.5 |
| Present compound B-5 + Fludioxonil | 200 + 200 |
| Present compound B-5 + Fludioxonil | 500 + 0.5 |
| Present compound B-5 + Fluopyram | 200 + 2000 |
| Present compound B-5 + Fluopyram | 500 + 0.5 |

TABLE 38-continued

| Composition | Concentration (ppm) |
|---|---|
| Present compound B-5 + Fluoxastrobin | 200 + 200 |
| Present compound B-5 + Fluoxastrobin | 500 + 0.5 |
| Present compound B-5 + Flutolanil | 200 + 200 |
| Present compound B-5 + Flutolanil | 500 + 0.5 |
| Present compound B-5 + Flutriafol | 200 + 200 |
| Present compound B-5 + Flutriafol | 500 + 0.5 |
| Present compound B-5 + Fluxapyroxad | 200 + 200 |
| Present compound B-5 + Fluxapyroxad | 500 + 0.5 |
| Present compound B-5 + Ipconazole | 200 + 200 |
| Present compound B-5 + Ipconazole | 500 + 0.5 |
| Present compound B-5 + Mandestrobin | 200 + 200 |
| Present compound B-5 + Mandestrobin | 500 + 0.5 |
| Present compound B-5 + Metalaxyl M | 200 + 200 |
| Present compound B-5 + Metalaxyl M | 500 + 0.5 |
| Present compound B-5 + Metalaxyl | 200 + 200 |
| Present compound B-5 + Metalaxyl | 500 + 0.5 |
| Present compound B-5 + Metconazole | 200 + 200 |
| Present compound B-5 + Metconazole | 500 + 0.5 |
| Present compound B-5 + Oxathiapiprolin | 200 + 200 |
| Present compound B-5 + Oxathiapiprolin | 500 + 0.5 |
| Present compound B-5 + Penfurufen | 200 + 200 |
| Present compound B-5 + Penfurufen | 500 + 0.5 |
| Present compound B-5 + Penthiopyrad | 200 + 200 |
| Present compound B-5 + Penthiopyrad | 500 + 0.5 |
| Present compound B-5 + Picoxystrobin | 200 + 200 |
| Present compound B-5 + Picoxystrobin | 500 + 0.5 |
| Present compound B-5 + Prothioconazole | 200 + 200 |
| Present compound B-5 + Prothioconazole | 500 + 0.5 |
| Present compound B-5 + Pyraclostrobin | 200 + 200 |
| Present compound B-5 + Pyraclostrobin | 500 + 0.5 |
| Present compound B-5 + Inpyrfluxam | 200 + 200 |
| Present compound B-5 + Inpyrfluxam | 500 + 0.5 |
| Present compound B-5 + Sedaxane | 200 + 200 |
| Present compound B-5 + Sedaxane | 500 + 0.5 |
| Present compound B-5 + Tebuconazole | 200 + 200 |
| Present compound B-5 + Tebuconazole | 500 + 0.5 |
| Present compound B-5 + Triadimenol | 200 + 200 |
| Present compound B-5 + Triadimenol | 500 + 0.5 |
| Present compound B-5 + Trifloxystrobin | 200 + 200 |
| Present compound B-5 + Trifloxystrobin | 500 + 0.5 |
| Present compound B-5 + Triticonazole | 200 + 200 |
| Present compound B-5 + Triticonazole | 500 + 0.5 |

[Table 58]
[Table 59]
[Table 60]

TABLE 39

| Composition | Concentration (ppm) |
|---|---|
| Present compound C-1 + Clothianidin | 200 + 2000 |
| Present compound C-1 + Clothianidin | 500 + 50 |
| Present compound C-1 + Imidacloprid | 200 + 2000 |
| Present compound C-1 + Imidacloprid | 500 + 5.0 |
| Present compound C-1 + Thiamethoxam | 200 + 2000 |
| Present compound C-1 + Thiamethoxam | 500 + 50 |
| Present compound C-1 + Azoxystrobin | 200 + 200 |
| Present compound C-1 + Azoxystrobin | 500 + 0.5 |
| Present compound C-1 + Difenoconazole | 200 + 200 |
| Present compound C-1 + Difenoconazole | 500 + 0.5 |
| Present compound C-1 + Ethaboxam | 200 + 200 |
| Present compound C-1 + Ethaboxam | 500 + 0.5 |
| Present compound C-1 + Fludioxonil | 200 + 200 |
| Present compound C-1 + Fludioxonil | 500 + 0.5 |
| Present compound C-1 + Fluopyram | 200 + 2000 |
| Present compound C-1 + Fluopyram | 500 + 0.5 |
| Present compound C-1 + Fluoxastrobin | 200 + 200 |
| Present compound C-1 + Fluoxastrobin | 500 + 0.5 |
| Present compound C-1 + Flutolanil | 200 + 200 |
| Present compound C-1 + Flutolanil | 500 + 0.5 |
| Present compound C-1 + Flutriafol | 200 + 200 |
| Present compound C-1 + Flutriafol | 500 + 0.5 |
| Present compound C-1 + Fluxapyroxad | 200 + 200 |

TABLE 39-continued

| Composition | Concentration (ppm) |
|---|---|
| Present compound C-1 + Fluxapyroxad | 500 + 0.5 |
| Present compound C-1 + Ipconazole | 200 + 200 |
| Present compound C-1 + Ipconazole | 500 + 0.5 |
| Present compound C-1 + Mandestrobin | 200 + 200 |
| Present compound C-1 + Mandestrobin | 500 + 0.5 |
| Present compound C-1 + Metalaxyl M | 200 + 200 |
| Present compound C-1 + Metalaxyl M | 500 + 0.5 |
| Present compound C-1 + Metalaxyl | 200 + 200 |
| Present compound C-1 + Metalaxyl | 500 + 0.5 |
| Present compound C-1 + Metconazole | 200 + 200 |
| Present compound C-1 + Metconazole | 500 + 0.5 |
| Present compound C-1 + Oxathiapiprolin | 200 + 200 |
| Present compound C-1 + Oxathiapiprolin | 500 + 0.5 |
| Present compound C-1 + Penfurufen | 200 + 200 |
| Present compound C-1 + Penfurufen | 500 + 0.5 |
| Present compound C-1 + Penthiopyrad | 200 + 200 |
| Present compound C-1 + Penthiopyrad | 500 + 0.5 |
| Present compound C-1 + Picoxystrobin | 200 + 200 |
| Present compound C-1 + Picoxystrobin | 500 + 0.5 |
| Present compound C-1 + Prothioconazole | 200 + 200 |
| Present compound C-1 + Prothioconazole | 500 + 0.5 |
| Present compound C-1 + Pyraclostrobin | 200 + 200 |
| Present compound C-1 + Pyraclostrobin | 500 + 0.5 |
| Present compound C-1 + Inpyrfluxam | 200 + 200 |
| Present compound C-1 + Inpyrfluxam | 500 + 0.5 |
| Present compound C-1 + Sedaxane | 200 + 200 |
| Present compound C-1 + Sedaxane | 500 + 0.5 |
| Present compound C-1 + Tebuconazole | 200 + 200 |
| Present compound C-1 + Tebuconazole | 500 + 0.5 |
| Present compound C-1 + Triadimenol | 200 + 200 |
| Present compound C-1 + Triadimenol | 500 + 0.5 |
| Present compound C-1 + Trifloxystrobin | 200 + 200 |
| Present compound C-1 + Trifloxystrobin | 500 + 0.5 |
| Present compound C-1 + Triticonazole | 200 + 200 |
| Present compound C-1 + Triticonazole | 500 + 0.5 |

[Table 61]
[Table 62]
[Table 63]

TABLE 40

| Composition | Concentration (ppm) |
|---|---|
| Present compound C-25 + Clothianidin | 200 + 2000 |
| Present compound C-25 + Clothianidin | 500 + 50 |
| Present compound C-25 + Imidacloprid | 200 + 2000 |
| Present compound C-25 + Imidacloprid | 500 + 50 |
| Present compound C-25 + Thiamethoxam | 200 + 2000 |
| Present compound C-25 + Thiamethoxam | 500 + 50 |
| Present compound C-25 + Azoxystrobin | 200 + 200 |
| Present compound C-25 + Azoxystrobin | 500 + 0.5 |
| Present compound C-25 + Difenoconazole | 200 + 200 |
| Present compound C-25 + Difenoconazole | 500 + 0.5 |
| Present compound C-25 + Ethaboxam | 200 + 200 |
| Present compound C-25 + Ethaboxam | 500 + 0.5 |
| Present compound C-25 + Fludioxonil | 200 + 200 |
| Present compound C-25 + Fludioxonil | 500 + 0.5 |
| Present compound C-25 + Fluopyram | 200 + 2000 |
| Present compound C-25 + Fluopyram | 500 + 0.5 |
| Present compound C-25 + Fluoxastrobin | 200 + 200 |
| Present compound C-25 + Fluoxastrobin | 500 + 0.5 |
| Present compound C-25 + Flutolanil | 200 + 200 |
| Present compound C-25 + Flutolanil | 500 + 0.5 |
| Present compound C-25 + Flutriafol | 200 + 200 |
| Present compound C-25 + Flutriafol | 500 + 0.5 |
| Present compound C-25 + Fluxapyroxad | 200 + 200 |
| Present compound C-25 + Fluxapyroxad | 500 + 0.5 |
| Present compound C-25 + Ipconazole | 200 + 200 |
| Present compound C-25 + Ipconazole | 500 + 0.5 |
| Present compound C-25 + Mandestrobin | 200 + 200 |
| Present compound C-25 + Mandestrobin | 500 + 0.5 |
| Present compound C-25 + Metalaxyl M | 200 + 200 |
| Present compound C-25 + Metalaxyl M | 500 + 0.5 |

TABLE 40-continued

| Composition | Concentration (ppm) |
|---|---|
| Present compound C-25 + Metalaxyl | 200 + 200 |
| Present compound C-25 + Metalaxyl | 500 + 0.5 |
| Present compound C-25 + Metconazole | 200 + 200 |
| Present compound C-25 + Metconazole | 500 + 0.5 |
| Present compound C-25 + Oxathiapiprolin | 200 + 200 |
| Present compound C-25 + Oxathiapiprolin | 500 + 0.5 |
| Present compound C-25 + Penfurufen | 200 + 200 |
| Present compound C-25 + Penfurufen | 500 + 0.5 |
| Present compound C-25 + Penthiopyrad | 200 + 200 |
| Present compound C-25 + Penthiopyrad | 500 + 0.5 |
| Present compound C-25 + Picoxystrobin | 200 + 200 |
| Present compound C-25 + Picoxystrobin | 500 + 0.5 |
| Present compound C-25 + Prothioconazole | 200 + 200 |
| Present compound C-25 + Prothioconazole | 500 + 0.5 |
| Present compound C-25 + Pyraclostrobin | 200 + 200 |
| Present compound C-25 + Pyraclostrobin | 500 + 0.5 |
| Present compound C-25 + Inpyrfluxam | 200 + 200 |
| Present compound C-25 + Inpyrfluxam | 500 + 0.5 |
| Present compound C-25 + Sedaxane | 200 + 200 |
| Present compound C-25 + Sedaxane | 500 + 0.5 |
| Present compound C-25 + Tebuconazole | 200 + 200 |
| Present compound C-25 + Tebuconazole | 500 + 0.5 |
| Present compound C-25 + Triadimenol | 200 + 200 |
| Present compound C-25 + Triadimenol | 500 + 0.5 |
| Present compound C-25 + Trifloxystrobin | 200 + 200 |
| Present compound C-25 + Trifloxystrobin | 500 + 0.5 |
| Present compound C-25 + Triticonazole | 200 + 200 |
| Present compound C-25 + Triticonazole | 500 + 0.5 |

[Table 64]
[Table 65]
[Table 66]

TABLE 41

| Composition | Concentration (ppm) |
|---|---|
| Present compound C-32 + Clothianidin | 200 + 2000 |
| Present compound C-32 + Clothianidin | 500 + 50 |
| Present compound C-32 + Imidacloprid | 200 + 2000 |
| Present compound C-32 + Imidacloprid | 500 + 50 |
| Present compound C-32 + Thiamethoxam | 200 + 2000 |
| Present compound C-32 + Thiamethoxam | 500 + 50 |
| Present compound C-32 + Azoxystrobin | 200 + 200 |
| Present compound C-32 + Azoxystrobin | 500 + 0.5 |
| Present compound C-32 + Difenoconazole | 200 + 200 |
| Present compound C-32 + Difenoconazole | 500 + 0.5 |
| Present compound C-32 + Ethaboxam | 200 + 200 |
| Present compound C-32 + Ethaboxam | 500 + 0.5 |
| Present compound C-32 + Fludioxonil | 200 + 200 |
| Present compound C-32 + Fludioxonil | 500 + 0.5 |
| Present compound C-32 + Fluopyram | 200 + 2000 |
| Present compound C-32 + Fluopyram | 500 + 0.5 |
| Present compound C-32 + Fluoxastrobin | 200 + 200 |
| Present compound C-32 + Fluoxastrobin | 500 + 0.5 |
| Present compound C-32 + Flutolanil | 200 + 200 |
| Present compound C-32 + Flutolanil | 500 + 0.5 |
| Present compound C-32 + Flutriafol | 200 + 200 |
| Present compound C-32 + Flutriafol | 500 + 0.5 |
| Present compound C-32 + Fluxapyroxad | 200 + 200 |
| Present compound C-32 + Fluxapyroxad | 500 + 0.5 |
| Present compound C-32 + Ipconazole | 200 + 200 |
| Present compound C-32 + Ipconazole | 500 + 0.5 |
| Present compound C-32 + Mandestrobin | 200 + 200 |
| Present compound C-32 + Mandestrobin | 500 + 0.5 |
| Present compound C-32 + Metalaxyl M | 200 + 200 |
| Present compound C-32 + Metalaxyl M | 500 + 0.5 |
| Present compound C-32 + Metalaxyl | 200 + 200 |
| Present compound C-32 + Metalaxyl | 500 + 0.5 |
| Present compound C-32 + Metconazole | 200 + 200 |
| Present compound C-32 + Metconazole | 500 + 0.5 |
| Present compound C-32 + Oxathiapiprolin | 200 + 200 |
| Present compound C-32 + Oxathiapiprolin | 500 + 0.5 |
| Present compound C-32 + Penfurufen | 200 + 200 |

TABLE 41-continued

| Composition | Concentration (ppm) |
|---|---|
| Present compound C-32 + Penfurufen | 500 + 0.5 |
| Present compound C-32 + Penthiopyrad | 200 + 200 |
| Present compound C-32 + Penthiopyrad | 500 + 0.5 |
| Present compound C-32 + Picoxystrobin | 200 + 200 |
| Present compound C-32 + Picoxystrobin | 500 + 0.5 |
| Present compound C-32 + Prothioconazole | 200 + 200 |
| Present compound C-32 + Prothioconazole | 500 + 0.5 |
| Present compound C-32 + Pyraclostrobin | 200 + 200 |
| Present compound C-32 + Pyraclostrobin | 500 + 0.5 |
| Present compound C-32 + Inpyrfluxam | 200 + 200 |
| Present compound C-32 + Inpyrfluxam | 500 + 0.5 |
| Present compound C-32 + Sedaxane | 200 + 200 |
| Present compound C-32 + Sedaxane | 500 + 0.5 |
| Present compound C-32 + Tebuconazole | 200 + 200 |
| Present compound C-32 + Tebuconazole | 500 + 0.5 |
| Present compound C-32 + Triadimenol | 200 + 200 |
| Present compound C-32 + Triadimenol | 500 + 0.5 |
| Present compound C-32 + Trifloxystrobin | 200 + 200 |
| Present compound C-32 + Trifloxystrobin | 500 + 0.5 |
| Present compound C-32 + Triticonazole | 200 + 200 |
| Present compound C-32 + Triticonazole | 500 + 0.5 |

[Table 67]
[Table 68]

Test Example 11

Each 1 mg of the Present compound was dissolved into a mixed solution that was prepared by mixing a 10 μL of the mixed solution of xylene, DMF and surfactants (xylene, DMF and surfactants=4:4:1 (v/v ratio)) and a mixed solution of acetone: polyoxyethylene sorbitan mono-cocoate (acetone and polyoxyethylene sorbitan mono-cocoate=95:5 (v/v ratio)). Thereto was added water containing 0.02% by volume of a spreader to prepare a diluted solution containing a prescribed concentration of the Present compound. The tests were conducted according to the similar method of the Test example 9 except that the above mentioned diluted solution was used as a diluted solution of the Present compound.

The results of the test that was conducted according to Test example 11 are shown below.

Any the present composition wherein the respective concentration of the Present compound and the Present active ingredient is indicated in the below-mentioned Table 42 showed 90% or greater as a controlling value against harmful arthropods.

[Table 69]

TABLE 42

| Composition | Concentration (ppm) |
|---|---|
| Present compound A-7 + Clothianidin | 200 + 2000 |
| Present compound A-7 + Clothianidin | 500 + 50 |
| Present compound A-7 + Imidacloprid | 200 + 2000 |
| Present compound A-7 + Imidacloprid | 500 + 50 |
| Present compound A-7 + Thiamethoxam | 200 + 2000 |
| Present compound A-7 + Thiamethoxam | 500 + 50 |
| Present compound A-7 + Azoxystrobin | 200 + 200 |
| Present compound A-72 + Azoxystrobin | 500 + 0.5 |
| Present compound A-7 + Difenoconazole | 200 + 200 |
| Present compound A-7 + Difenoconazole | 500 + 0.5 |
| Present compound A-7 + Ethaboxam | 200 + 200 |
| Present compound A-7 + Ethaboxam | 500 + 0.5 |
| Present compound A-7 + Fludioxonil | 200 + 200 |
| Present compound A-7 + Fludioxonil | 500 + 0.5 |
| Present compound A-7 + Fluopyram | 200 + 2000 |

TABLE 42-continued

| Composition | Concentration (ppm) |
|---|---|
| Present compound A-7 + Fluopyram | 500 + 0.5 |
| Present compound A-7 + Fluoxastrobin | 200 + 200 |
| Present compound A-7 + Fluoxastrobin | 500 + 0.5 |
| Present compound A-7 + Flutolanil | 200 + 200 |
| Present compound A-7 + Flutolanil | 500 + 0.5 |
| Present compound A-7 + Flutriafol | 200 + 200 |
| Present compound A-7 + Flutriafol | 500 + 0.5 |
| Present compound A-7 + Fluxapyroxad | 200 + 200 |
| Present compound A-7 + Fluxapyroxad | 500 + 0.5 |
| Present compound A-7 + Ipconazole | 200 + 200 |
| Present compound A-7 + Ipconazole | 500 + 0.5 |
| Present compound A-7 + Mandestrobin | 200 + 200 |
| Present compound A-7 + Mandestrobin | 500 + 0.5 |
| Present compound A-7 + Metalaxyl M | 200 + 200 |
| Present compound A-7 + Metalaxyl M | 500 + 0.5 |
| Present compound A-7 + Metalaxyl | 200 + 200 |
| Present compound A-7 + Metalaxyl | 500 + 0.5 |
| Present compound A-7 + Metconazole | 200 + 200 |
| Present compound A-7 + Metconazole | 500 + 0.5 |
| Present compound A-7 + Oxathiapiprolin | 200 + 200 |
| Present compound A-7 + Oxathiapiprolin | 500 + 0.5 |
| Present compound A-7 + Penfurufen | 200 + 200 |
| Present compound A-7 + Penfurufen | 500 + 0.5 |
| Present compound A-7 + Penthiopyrad | 200 + 200 |
| Present compound A-7 + Penthiopyrad | 500 + 0.5 |
| Present compound A-7 + Picoxystrobin | 200 + 200 |
| Present compound A-7 + Picoxystrobin | 500 + 0.5 |
| Present compound A-7 + Prothioconazole | 200 + 200 |
| Present compound A-7 + Prothioconazole | 500 + 0.5 |
| Present compound A-7 + Pyraclostrobin | 200 + 200 |
| Present compound A-7 + Pyraclostrobin | 500 + 0.5 |
| Present compound A-7 + Inpyrfluxam | 200 + 200 |
| Present compound A-7 + Inpyrfluxam | 500 + 0.5 |
| Present compound A-7 + Sedaxane | 200 + 200 |
| Present compound A-7 + Sedaxane | 500 + 0.5 |
| Present compound A-7 + Tebuconazole | 200 + 200 |
| Present compound A-7 + Tebuconazole | 500 + 0.5 |
| Present compound A-7 + Triadimenol | 200 + 200 |
| Present compound A-7 + Triadimenol | 500 + 0.5 |
| Present compound A-7 + Trifloxystrobin | 200 + 200 |
| Present compound A-7 + Trifloxystrobin | 500 + 0.5 |
| Present compound A-7 + Triticonazole | 200 + 200 |
| Present compound A-7 + Triticonazole | 500 + 0.5 |

[Table 70]
[Table 71]
Comparative Test

The comparative tests were conducted by using the compound 1 which is described in Table I of JP S63-170362 A1 (hereinafter, referred to as Comparative compound 1), the compound 2 which is described in Table I of JP H02-088570 A1 (hereinafter, referred to as Comparative compound 2), the Present compound A-48 or the present compound C-33 as a test compound, according to the method of the above-mentioned Test example 8.

As a result, the Present compound A-48 and the Present compound C-33 showed superior controlling value to the Comparative compound 1 and the Comparative compound 2.

The test results are indicated in Table 43.

TABLE 43

| Test compound | Compound Structure | Controlling value at 500 ppm (%) |
|---|---|---|
| Present compound A-48 | 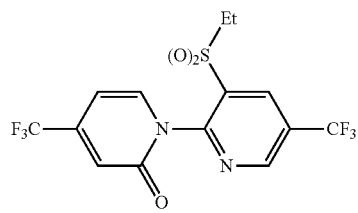 | 93% |
| Comparative compound 1 | 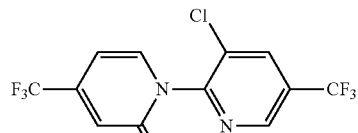 | 7% |
| Present compound C-33 | 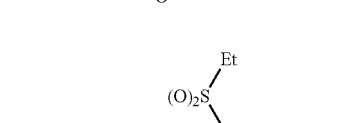 | 77% |

TABLE 43-continued

| Test compound | Compound Structure | Controlling value at 500 ppm (%) |
|---|---|---|
| Comparative compound 2 | 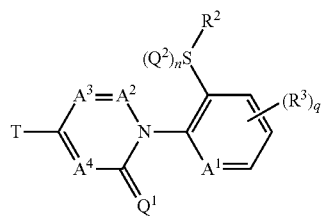 | 14% |

INDUSTRIAL APPLICABILITY

The Present compound shows an excellent control effect against a harmful arthropod. Also, the composition comprising the Present compound and one or more kinds of ingredients selected from the group consisting of Group (a), Group (b), Group (c) and Group (d) shows an excellent control effect against a harmful arthropod.

The invention claimed is:

1. A compound represented by formula (I):

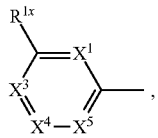

wherein
Q$^1$ represents an oxygen atom or a sulfur atom;
n is 1 or 2;
Q$^2$ represents an oxygen atom, a N—CN, a N—NO$_2$, a NR$^5$, a N—C(O)R$^5$ or a N—C(O)OR$^{15}$, and when n is 2, said two Q$^2$ may be independently identical to or different from each other;
R$^5$ represents a C1-C6 alkyl group optionally substituted with one or more halogen atoms, or a hydrogen atom;
A$^1$ represents a nitrogen atom or a CR$^6$;
A$^2$ represents a nitrogen atom or a CR$^{4a}$;
A$^3$ represents a nitrogen atom or a CR$^{4b}$;
A$^4$ represents a nitrogen atom or a CR$^{4c}$;
R$^{4a}$, R$^{4b}$ and R$^{4c}$ represent independently of each other a hydrogen atom, a C1-C6 chain hydrocarbon group optionally substituted with one or more halogen atoms, a nitro group, a OR$^{18}$, a NR$^{18}$R$^{19}$, a cyano group, or a halogen atom;
R$^6$ represents a hydrogen atom or a halogen atom;
T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl) C1-C3 alkyl group substituted with one or more substituents selected from Group G, a C3-C7 cycloalkyl group substituted with one or more substituents selected from Group G, a OR$^1$, a S(O)$_v$R$^1$, a OS(O)$_2$R$^1$, a CH$_2$OR$^1$, a NR$^1$R$^{29}$, a C(O)R$^1$, a C(O)NR$^1$R$^{29}$, a NR$^{29}$C(O)R$^1$, a N=CR$^1$R$^{30}$, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12,

T-1

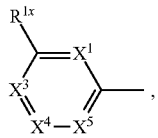

T-2

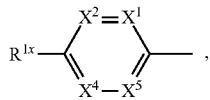

T-3

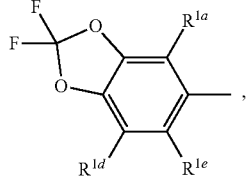

T-4

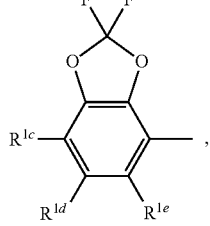

T-5

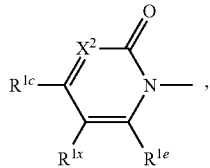

-continued

T-6
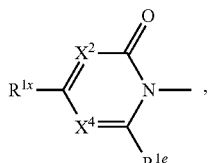

T-7
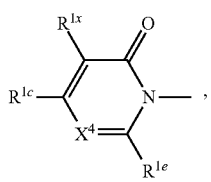

T-8
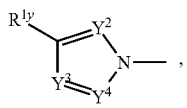

T-9
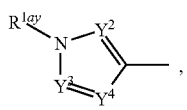

T-10
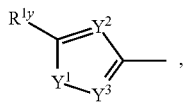

T-11
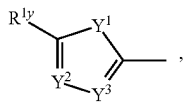

T-12
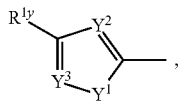

$X^1$ represents a nitrogen atom or a $CR^{1a}$;
$X^2$ represents a nitrogen atom or a $CR^{1b}$;
$X^3$ represents a nitrogen atom or a $CR^{1c}$;
$X^4$ represents a nitrogen atom or a $CR^{1d}$;
$X^5$ represents a nitrogen atom or a $CR^{1e}$;
$R^{1x}$ represents a $OR^7$, a $OS(O)_2R^7$, a $S(O)_mR^7$, a $NR^8S(O)_2R^7$, a C1-C5 chain hydrocarbon group substituted with one or more halogen atoms, or a halogen atom;
q is 0, 1, 2, or 3;
$R^{1a}$, $R^{1b}$, $R^{1c}$, $R^{1d}$, and $R^{1e}$ represent independently of each other a hydrogen atom, a C1-C6 chain hydrocarbon group optionally substituted with one or more halogen atoms, a C3-C6 cycloalkyl group optionally substituted with one or more halogen atoms, or a halogen atom;
$Y^1$ represents a $NR^{25}$, an oxygen atom or a sulfur atom;
$Y^2$ represents a nitrogen atom or a $CR^{26}$;
$Y^3$ represents a nitrogen atom or a $CR^{27}$;
$Y^4$ represents a nitrogen atom or a $CR^{28}$;
$R^{25}$, $R^{26}$, $R^{27}$, and $R^{28}$ represent independently of each other a hydrogen atom, a C1-C6 chain hydrocarbon group optionally substituted with one or more halogen atoms, a C3-C6 cycloalkyl group optionally substituted with one or more halogen atoms, or a halogen atom;

$R^{1y}$ represents a $OR^7$, a $OS(O)_2R^7$, a $S(O)_mR^7$, a $NR^8S(O)_2R^7$, a cyano group, a C1-C5 chain hydrocarbon group substituted with one or more halogen atoms, or a halogen atom;
$R^{1ay}$ and $R^7$ represent independently of each other a C1-C6 chain hydrocarbon group substituted with one or more halogen atoms;
$R^8$ represents a hydrogen atom, or a C1-C6 chain hydrocarbon group optionally substituted with one or more halogen atoms;
m and v are independently of each other 0, 1 or 2,
$R^1$ represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, or a C3-C7 cycloalkyl group substituted with one or more substituents selected from Group G;
$R^2$ represents a cyclopropyl group, a cyclopropylmethyl group, or a C1-C6 alkyl group optionally substituted with one or more halogen atoms;
$R^3$ represents a C1-C6 chain hydrocarbon group optionally substituted with one or more substituents selected from Group B, a C3-C7 cycloalkyl group optionally substituted with one or more substituents selected from Group E, a C3-C7 cycloalkenyl group optionally substituted with one or more substituents selected from Group J, a phenyl group optionally substituted with one or more substituents selected from Group H, a five or six membered aromatic heterocyclic group optionally substituted with one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15x}R^{16x}$, a $NR^{24}NR^{11}C(O)NR^{15x}R^{16x}$, a $N=CHNR^{15x}R^{16x}$, a $N=S(O)R^{15}R^{16}$, a $C(O)R^{17}$, a $C(O)OR^{17}$, a $C(O)NR^{15x}R^{16x}$, a $C(O)NR^{11}S(O)_2R^{23}$, a $CR^{24}=NOR^{17}$, a $NR^{11}CR^{24}=NOR^7$, a cyano group, a nitro group, or a halogen atom, and when q is 2 or 3, a plurality of $R^3$ may represent independently identical to or different from each other;
when two $R^3$ are adjacent to each other, said two $R^3$ may combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring, wherein the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, or the pyrazine ring may be optionally substituted with one or more substituents selected from Group H:
$R^{17}$ represent independently of each other a hydrogen atom, a C1-C6 chain hydrocarbon group optionally substituted with one or more substituents selected from Group F, or a C3-C7 cycloalkyl group optionally substituted with one or more substituents selected from Group J;

$R^{11}$, $R^{19}$, $R^{24}$, and $R^{29}$ represent independently of each other a hydrogen atom, or a C1-C6 chain hydrocarbon group optionally substituted with one or more halogen atoms;

$R^{30}$ represents a hydrogen atom, a halogen atom, a $OR^{35}$, a $NR^{36}R^{37}$, or a C1-C6 chain hydrocarbon group optionally substituted with one or more halogen atoms;

$R^{18}$ and $R^{35}$ represent independently of each other a C1-C6 chain hydrocarbon group substituted with one or more halogen atoms;

$R^{36}$ and $R^{37}$ represent independently of each other a hydrogen atom, or a C1-C6 chain hydrocarbon group optionally substituted with one or more halogen atoms;

$R^{12}$ represents a C1-C6 chain hydrocarbon group optionally substituted with one or more halogen atoms, a C1-C6 chain hydrocarbon group optionally substituted with one or more substituents selected from Group F, a C3-C7 cycloalkyl group optionally substituted with one or more substituents selected from Group J, a C3-C7 cycloalkenyl group optionally substituted with one or more substituents selected from Group J, a phenyl group, a six membered aromatic heterocyclic group, a hydrogen atom, or a $S(O)_2R^{23}$, wherein the phenyl group or the six membered aromatic heterocyclic group may be optionally substituted with one or more substituents selected from Group D;

$R^{23}$ represents a C1-C6 chain hydrocarbon group optionally substituted with one or more halogen atoms, a C3-C7 cycloalkyl group optionally substituted with one or more halogen atoms, or a phenyl group optionally substituted with one or more substituents selected from Group D;

$R^{11a}$ and $R^{12a}$ combine together with a nitrogen atom to which they are attached to form a three to seven membered nonaromatic heterocyclic group optionally substituted with one or more substituents selected from Group E, $R^{13}$ represents a hydrogen atom, a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, a phenyl group optionally substituted with one or more substituents selected from Group D, or a five or six membered aromatic heterocyclic group optionally substituted with one or more substituents selected from Group D;

$R^{14}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, or a phenyl C1-C3 alkyl group, wherein a phenyl moiety in the phenyl C1-C3 alkyl group may be optionally substituted with one or more substituents selected from group D;

$R^{15}$ and $R^{16}$ represent independently of each other a C1-C6 alkyl group optionally substituted with one or more halogen atoms;

$R^{15x}$ represents a C1-C6 alkyl group optionally substituted with one or more halogen atoms, or a hydrogen atom;

$R^{16x}$ represents a C1-C6 chain hydrocarbon group optionally substituted with one or more substituents selected from Group F, a C3-C7 cycloalkyl group optionally substituted with one or more substituents selected from Group J, or a hydrogen atom;

x is 0 or 1;

Group B is selected from the group consisting of a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, a C3-C6 cycloalkyl group optionally substituted with one or more halogen atoms, a cyano group, a hydroxy group and a halogen atom;

Group C is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, and a halogen atom;

Group D is selected from the group consisting of a C1-C6 chain hydrocarbon group optionally substituted with one or more halogen atoms, a hydroxy group, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a sulfanyl group, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom, wherein the $R^{21}$ and the $R^{22}$ represent independently of each other a C1-C6 alkyl group optionally substituted with one or more halogen atoms;

Group E is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a halogen atom, an oxo group, a hydroxy group, a cyano group, and a nitro group;

Group F is selected from the group consisting of a C1-C6 alkoxy group optionally substituted with one or more halogen atoms, an amino group, a $NHR^{21}$, a $NR^{21}R^{22}$, a cyano group, a phenyl group optionally substituted with one or more substituents selected from Group D, a five or six membered aromatic heterocyclic group optionally substituted with one or more substituents selected from Group D, a C3-C7 cycloalkyl group optionally substituted with one or more halogen atoms, and a three to seven membered nonaromatic heterocyclic group optionally substituted with one or more substituents selected from Group C, wherein the $R^{21}$ and the $R^{22}$ represent independently of each other a C1-C6 alkyl group optionally substituted with one or more halogen atoms;

Group G is selected from the group consisting of a halogen atom and a C1-C6 haloalkyl group;

Group H is selected from the group consisting of a halogen atom, a nitro group, a cyano group, an amino group, a five or six membered aromatic heterocyclic group, a C1-C6 alkyl group optionally substituted with one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$, wherein the $R^9$ represents a C1-C6 alkyl group optionally substituted with one or more halogen atoms or a C3-C6 cycloalkyl group optionally substituted with one or more halogen atoms, and the $R^{10}$ represents a hydrogen atom, a C1-C6 alkyl group optionally substituted with one or more halogen atoms, or a C3-C6 cycloalkyl group optionally substituted with one or more halogen atoms;

Group J is selected from the group consisting of a halogen atom, a cyano group, a triazolyl group, a C1-C6 alkyl group optionally substituted with one or more halogen atoms, and a $NR^{10}C(O)R^9$, wherein the $R^9$ represents a C1-C6 alkyl group optionally substituted with one or more halogen atoms or a C3-C6 cycloalkyl group optionally substituted with one or more halogen atoms, and the $R^{10}$ represents a hydrogen atom, a C1-C6 alkyl group optionally substituted with one or more halogen atoms, or a C3-C6 cycloalkyl group optionally substituted with one or more halogen atoms.

2. The compound according to claim 1 wherein:

$R^3$ represents a C1-C6 chain hydrocarbon group optionally substituted with one or more substituents selected from Group B, a C3-C7 cycloalkyl group optionally substituted with one or more substituents selected from Group E, a phenyl group optionally substituted with one or more substituents selected from Group H, a five or six membered aromatic heterocyclic group optionally substituted with one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a $N=CHNR^{15}R^{16}$, a $N=S(O)_xR^{15}R^{16}$, a $C(O)OR^{17}$, a cyano group, a nitro group, or a halogen atom, and when q is 2 or 3, a plurality of the $R^3$ may be identical to or different from each other;

when q is 2 and two $R^3$ are adjacent to each other, said two $R^3$ may combine with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring, wherein the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may be optionally substituted with one or more substituents selected from Group H;

$R^{17}$ represents a hydrogen atom, or a C1-C6 chain hydrocarbon group;

$R^{12}$ represents a hydrogen atom, a $S(O)_2R^{23}$, a C1-C6 chain hydrocarbon group optionally substituted with one or more halogen atoms, or a C1-C6 alkyl group substituted with one or more substituents selected from Group F;

$R^{23}$ represents a C1-C6 chain hydrocarbon group optionally substituted with one or more halogen atoms, or a phenyl group optionally substituted with one or more substituents selected from Group D.

3. The compound according to claim 1, wherein $A^1$ represents a CH.

4. The compound according to claim 1, wherein $A^1$ represents a nitrogen atom.

5. The compound according to claim 1, wherein $A^2$ represents a $CR^{4a}$, $A^3$ represents a $CR^{4b}$, and $A^4$ represents a $CR^{4c}$.

6. The compound according to claim 1, wherein $A^2$ represents a nitrogen atom, $A^3$ represents a $CR^{4b}$, and $A^4$ represents a $CR^{4c}$.

7. The compound according to claim 1, wherein $A^3$ represents a nitrogen atom, $A^2$ represents a $CR^{4a}$, and $A^4$ represents a $CR^{4c}$.

8. The compound according to claim 1, wherein $A^4$ represents a nitrogen atom, $A^2$ represents a $CR^{4a}$, and $A^3$ represents a $CR^{4b}$.

9. The compound according to claim 1, wherein $A^2$ and $A^4$ both represent a nitrogen atom, and $A^3$ represents a $CR^4$b.

10. The compound according to claim 1, wherein $Q^1$ represents an oxygen atom, and T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, a $OR^1$, a $S(O)_xR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9.

11. The compound according to claim 1, wherein T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, a $OR^1$, a $S(O)_xR^1$, a $OS(O)_2R^1$, or a $NR^1R^{29}$.

12. The compound according to claim 1, wherein T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9.

13. The compound according to claim 1, wherein $Q^1$ represents an oxygen atom, and T represents a C1-C5 chain hydrocarbon group substituted with one or more halogen atoms, a $OR^1$, a $S(O)_vR^1$, a $OS(O)_2R^1$, a $NR^1R^{29}$, a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, $R^1$, $R^{1x}$, $R^{1y}$, and $R^{ay}$ represent independently of each other a C1-C5 chain hydrocarbon group substituted with one or more halogen atoms, and q is 0 or 1.

14. The compound according to claim 1, wherein $Q^1$ represents an oxygen atom, T represents a C1-C5 chain hydrocarbon group substituted with one or more halogen atoms, a $OR^1$, a $S(O)_vR^1$, a $OS(O)_2R^1$, a $NR^1R^{29}$, $R^1$ represents a C1-C5 chain hydrocarbon group substituted with one or more halogen atoms, and q is 0 or 1.

15. The compound according to claim 1, wherein $Q^1$ represents an oxygen atom, T represents a group represented by the formula T-1, a group represented by the formula T-2, a group represented by the formula T-3, a group represented by the formula T-4, a group represented by the formula T-5, a group represented by the formula T-6, a group represented by the formula T-7, a group represented by the formula T-8, or a group represented by the formula T-9, $R^{1a}$, $R^{1y}$, and $R^{ay}$ represent independently of each other a C1-C5 chain hydrocarbon group substituted with one or more halogen atoms, and q is 0 or 1.

16. The compound according to claim 1, wherein $R^3$ represents a C1-C6 alkyl group optionally substituted with one or more halogen atoms, a phenyl group, a six membered aromatic heterocyclic group, a five membered aromatic heterocyclic group containing 1 to 4 nitrogen atoms, wherein the phenyl group, the a six membered aromatic heterocyclic group, and the five membered aromatic heterocyclic group containing 1 to 4 nitrogen atoms may be optionally substituted with one or more substituents selected from Group H, a $NR^{11}R^{12}$, a $NR^{11}C(O)OR^{14}$, or a halogen atom.

17. The compound according to claim 1, wherein $R^3$ represents a C1-C6 alkyl group optionally substituted with one or more halogen atoms, a phenyl group, a pyridyl group, a pyrimidinyl group, a pyrazolyl group, a triazolyl group, wherein the phenyl group, the pyridyl group, the pyrimidinyl group, the pyrazolyl group, and the triazolyl group may be optionally substituted with one or more substituents selected from Group H, an amino group, a $NR^{11}C(O)OR^{14}$, or a halogen atom.

18. The compound according to claim 1, wherein $R^2$ represents an ethyl group.

19. The compound according to claim 1, wherein $Q^2$ represents an oxygen atom.

20. A method for controlling a harmful arthropod which comprises applying an effective amount of the compound according to claim 1 to a harmful arthropod or a habitat where a harmful arthropod lives.

21. A method for controlling a harmful arthropod which comprises applying an effective amount of the compound according to claim 1 to a plant or soil where a plant grows.

22. A method for controlling a harmful arthropod which comprises applying an effective amount of the compound according to claim 1 to a seed or bulb.

23. A composition for controlling a harmful arthropod comprising the compound according to claim 1 and an inert carrier.

24. A composition comprising the compound according to claim 1 and one or more ingredients selected from the group consisting of the following Groups (a), (b), (c), and (d):

Group (a) is one or more ingredients selected from the group consisting of insecticidal ingredients, miticidal ingredients, and nematicidal ingredients;
Group (b) is fungicidal ingredients;
Group (c) is plant growth modulating ingredients; and
Group (d) is phytotoxicity-reducing ingredients.

25. A method for controlling a harmful arthropod which comprises applying an effective amount of the composition according to claim 24 to a harmful arthropod or a habitat where a harmful arthropod lives.

26. A method for controlling a harmful arthropod which comprises applying an effective amount of the composition according to claim 24 to a plant or soil where a plant grows.

27. A method for controlling a harmful arthropod which comprises applying an effective amount of the composition according to claim 24 to a seed or bulb.

28. A composition for controlling a harmful arthropod comprising the composition according to claim 24 and an inert carrier.

29. A seed or bulb carrying an effective amount of the compound according to claim 1.

30. A compound represented by formula (II):

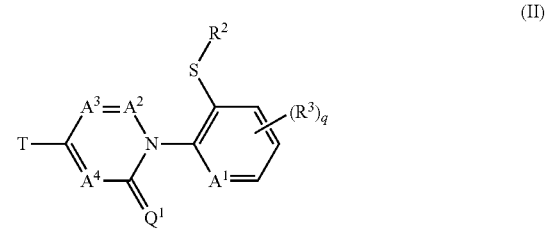

(II)

wherein,
$Q^1$ represents an oxygen atom or a sulfur atom;
$A^1$ represents a nitrogen atom or a $CR^6$;
$A^2$ represents a nitrogen atom or a $CR^{4a}$;
$A^3$ represents a nitrogen atom or a $CR^{4b}$;
$A^4$ represents a nitrogen atom or a $CR^{4c}$;
$R^{4a}$, $R^{4b}$ and $R^{4c}$ represent independently of each other a hydrogen atom, a C1-C6 chain hydrocarbon group optionally substituted with one or more halogen atoms, a nitro group, a $OR^{18}$, a $NR^{18}R^{19}$, a cyano group, or a halogen atom;
$R^6$ represents a hydrogen atom, or a halogen atom;
T represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl)C1-C3 alkyl group substituted with one or more substituents selected from Group G, a C3-C7 cycloalkyl group substituted with one or more substituents selected from Group G, a OR¹, a S(O)ᵥR¹, a OS(O)₂R¹, a CH₂OR¹, a NR¹R²⁹, a C(O)R¹, a C(O)NR¹R²⁹, a NR²⁹C(O)R¹, a N=CR¹R³⁰, a group represented by the following formula T-1, a group represented by the following formula T-2, a group represented by the following formula T-3, a group represented by the following formula T-4, a group represented by the following formula T-5, a group represented by the following formula T-6, a group represented by the following formula T-7, a group represented by the following formula T-8, a group represented by the following formula T-9, a group represented by the following formula T-10, a group represented by the following formula T-11, or a group represented by the following formula T-12:

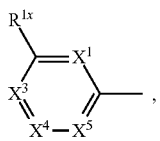

T-1

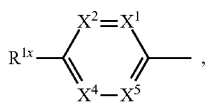

T-2

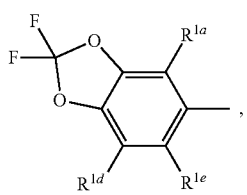

T-3

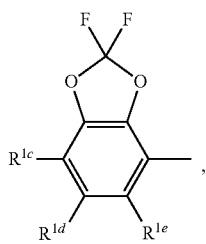

T-4

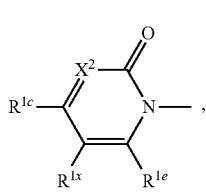

T-5

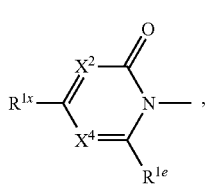

T-6

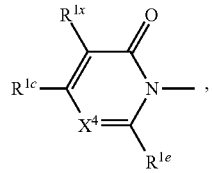

T-7

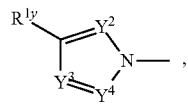

T-8

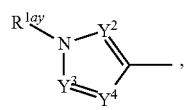

T-9

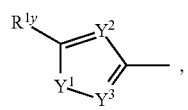

T-10

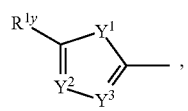

T-11

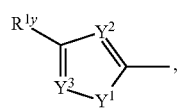

T-12

$X^1$ represents a nitrogen atom or a $CR^{1a}$;
$X^2$ represents a nitrogen atom or a $CR^{1b}$;
$X^3$ represents a nitrogen atom or a $CR^{1c}$;
$X^4$ represents a nitrogen atom or a $CR^{1d}$;
$X^5$ represents a nitrogen atom or a $CR^{1e}$;
$R^{1x}$ represents a $OR^7$, a $OS(O)_2R^7$, a $S(O)_mR^7$, a $NR^8S(O)_2R^7$, a C1-C5 chain hydrocarbon group substituted with one or more halogen atoms, or a halogen atom;
q is 0, 1, 2, or 3;
$R^{1a}$, $R^{1b}$, $R^{1c}$, $R^{1d}$, and $R^{1e}$ represent independently of each other a hydrogen atom, a C1-C6 chain hydrocarbon group optionally substituted with one or more halogen atoms, a C3-C6 cycloalkyl group optionally substituted with one or more halogen atoms, or a halogen atom;
$Y^1$ represents a $NR^{25}$, an oxygen atom, or a sulfur atom;
$Y^2$ represents a nitrogen atom or a $CR^{26}$;
$Y^3$ represents a nitrogen atom or a $CR^{27}$;
$Y^4$ represents a nitrogen atom or a $CR^{28}$;
$R^{25}$, $R^{26}$, $R^{27}$, and $R^{28}$ represent independently of each other a hydrogen atom, a C1-C6 chain hydrocarbon group optionally substituted with one or more halogen atoms, a C3-C6 cycloalkyl group optionally substituted with one or more halogen atoms, or a halogen atom;
$R^{1y}$ represents a $OR^7$, a $OS(O)_2R^7$, a $S(O)_mR^7$, a NR'S(O)₂R⁷, a cyano group, a C1-C5 chain hydrocarbon group substituted with one or more halogen atoms, or a halogen atom;
$R^{1ay}$ and $R^7$ represent independently of each other a C1-C6 chain hydrocarbon group substituted with one or more halogen atoms;

$R^8$ represents a hydrogen atom, or a C1-C6 chain hydrocarbon group optionally substituted with one or more halogen atoms;

m and v is independently of each other 0, 1 or 2;

$R^1$ represents a C1-C10 chain hydrocarbon group substituted with one or more halogen atoms, a (C1-C5 alkoxy)C2-C5 alkyl group substituted with one or more halogen atoms, a (C1-C5 alkylsulfanyl)C2-C5 alkyl group substituted with one or more halogen atoms, a (C1-C5 alkylsulfinyl)C2-C5 alkyl group substituted with one or more halogen atoms, a (C1-C5 alkylsulfonyl)C2-C5 alkyl group substituted with one or more halogen atoms, a (C3-C7 cycloalkyl) C1-C3 alkyl group substituted with one or more substituents selected from Group G, or a C3-C7 cycloalkyl group substituted with one or more substituents selected from Group G;

$R^2$ represents a cyclopropyl group, a cyclopropylmethyl group, or a C1-C6 alkyl group optionally substituted with one or more halogen atoms;

$R^3$ represents a C1-C6 chain hydrocarbon group optionally substituted with one or more substituents selected from Group B, a C3-C7 cycloalkyl group optionally substituted with one or more substituents selected from Group E, a phenyl group optionally substituted with one or more substituents selected from Group H, a five or six membered aromatic heterocyclic group optionally substituted with one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15}R^{16}$, a $NR^{24}NR^{11}C(O)NR^{15}R^{16}$, a N=$CHNR^{15}R^{16}$, a N=$S(O)_xR^{15}R^{16}$, a $C(O)OR^{17}$, a cyano group, a nitro group, or a halogen atom, and when q is 2 or 3, a plurality of the $R^3$ may be identical to or different from each other;

When q is 2 and two $R^3$ are adjacent to each other, said two $R^3$ may combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring, wherein the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may be optionally substituted with one or more substituents selected from Group H;

$R^{11}$, $R^{17}$, $R^{19}$, $R^{24}$, and $R^{29}$ represent independently of each other a hydrogen atom, or a C1-C6 chain hydrocarbon group optionally substituted with one or more halogen atoms;

$R^{30}$ represents a hydrogen atom, a halogen atom, a $OR^{35}$, a $NR^{36}R^{37}$, or a C1-C6 chain hydrocarbon group optionally substituted with one or more halogen atoms;

$R^{18}$ and $R^{35}$ represent independently of each other a C1-C6 chain hydrocarbon group optionally substituted with one or more halogen atoms;

$R^{36}$ and $R^{37}$ represent independently of each other a hydrogen atom, or a C1-C6 chain hydrocarbon group optionally substituted with one or more halogen atoms;

$R^{12}$ represents a hydrogen atom, a $S(O)_2R^{23}$, a C1-C6 chain hydrocarbon group optionally substituted with one or more halogen atoms, or a C1-C6 alkyl group substituted with one substituent selected from Group F;

$R^{23}$ represents a C1-C6 chain hydrocarbon group optionally substituted with one or more halogen atoms, or a phenyl group optionally substituted with one or more substituents selected from Group D;

$R^{11a}$ and $R^{12a}$ combine together with a nitrogen atom to which they are attached to form a three to seven membered nonaromatic heterocyclic group optionally substituted with one or more substituents selected from Group E;

$R^{13}$ represents a hydrogen atom, a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, a phenyl group optionally substituted with one or more substituents selected from Group D, or a five or six membered aromatic heterocyclic group optionally substituted with one or more substituents selected from Group D;

$R^{14}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, or a phenyl C1-C3 alkyl group, wherein a phenyl moiety in the phenyl C1-C3 alkyl group may be optionally substituted with one or more substituents selected from Group D;

$R^{15}$ and $R^{16}$ represent independently of each other a C1-C6 alkyl group optionally substituted with one or more halogen atoms; and x is 0 or 1;

Group B is selected from the group consisting of a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, a C3-C6 cycloalkyl group optionally substituted with one or more halogen atoms, a cyano group, a hydroxy group, and a halogen atom;

Group C is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, and a halogen atom;

Group D is selected from the group consisting of a C1-C6 chain hydrocarbon group optionally substituted with one or more halogen atoms, a hydroxy group, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a sulfanyl group, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom, wherein the $R^{21}$ and the $R^{22}$ represent independently of each other a C1-C6 alkyl group optionally substituted with one or more halogen atoms;

Group E is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a halogen atom, an oxo group, a hydroxy group, a cyano group, and a nitro group;

Group F is selected from the group consisting of a C1-C6 alkoxy group optionally substituted with one or more halogen atoms, an amino group, a $NHR^{21}$, a $NR^{21}R^{22}$, a cyano group, a phenyl group optionally substituted with one or more substituents selected from Group D, a five or six membered aromatic heterocyclic group optionally substituted with one or more substituents selected from Group D, a C3-C7 cycloalkyl group optionally substituted with one or more halogen atoms, and a three to seven membered nonaromatic heterocyclic group optionally substituted with one or more substituents selected from Group C, wherein the $R^{21}$ and the $R^{22}$ represent independently of each other a C1-C6 alkyl group optionally substituted with one or more halogen atoms;

Group G is selected from the group consisting of a halogen atom and a C1-C6 haloalkyl group;

Group H is selected from the group consisting of a halogen atom, a nitro group, a cyano group, an amino group, a five or six membered aromatic heterocyclic group, a C1-C6 alkyl group optionally substituted with one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$, wherein the $R^9$ represents a C1-C6 alkyl group optionally substituted with one or more halogen atoms, or a C3-C6 cycloalkyl group optionally substituted with one or more halogen atoms, and the $R^{10}$ represents a hydrogen atom, a C1-C6 alkyl group optionally substituted with one or more halogen atoms, or a C3-C6 cycloalkyl group optionally substituted with one or more halogen atoms.

31. A compound represented by formula (II-1):

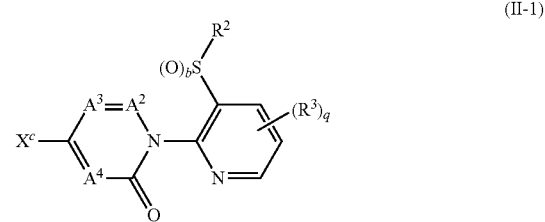

wherein,
$X^c$ represents a halogen atom;
b is 0, 1 or 2;
$A^2$ represents a nitrogen atom or a $CR^{4a}$;
$A^3$ represents a nitrogen atom or a $CR^{4b}$;
$A^4$ represents a nitrogen atom or a $CR^{4c}$;
$R^{4a}$, $R^{4b}$ and $R^{4c}$ represent independently of each other a hydrogen atom, a C1-C6 chain hydrocarbon group optionally substituted with one or more halogen atoms, a nitro group, a $OR^{18}$, a $NR^{18}R^{19}$, a cyano group, or a halogen atom;
$R^2$ represents a cyclopropyl group, a cyclopropylmethyl group, or a C1-C6 alkyl group optionally substituted with one or more halogen atoms;
q is 0, 1, 2, or 3;
$R^3$ represents a C1-C6 chain hydrocarbon group optionally substituted with one or more substituents selected from Group B, a C3-C7 cycloalkyl group optionally substituted with one or more substituents selected from Group E, a C3-C7 cycloalkenyl group optionally substituted with one or more substituents selected from Group J, a phenyl group optionally substituted with one or more substituents selected from Group H, a five or six membered aromatic heterocyclic group optionally substituted with one or more substituents selected from Group H, a $OR^{12}$, a $NR^{11}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15x}R^{16x}$, a $NR^{24}NR^{11}C(O)NR^{15x}R^{16x}$, a N=$CHNR^{15x}R^{16x}$, a N=$S(O)R^{15}R^{16}$, a $C(O)R^{17}$, a $C(O)OR^{17}$, a $C(O)NR^{15x}R^{16x}$, a $C(O)NR^{11}S(O)_2R^{23}$, a $CR^{24}$=$NOR^{17}$, a $NR^{11}CR^{24}$=$NOR^{17}$, a cyano group, a nitro group, or a halogen atom, and when q is 2 or 3, a plurality of $R^3$ may be identical to or different from each other;

when two $R^3$ are adjacent to each other, said two $R^3$ combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring, wherein the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may be optionally substituted with one or more substituents selected from Group H;

$R^{17}$ represents independently of each other a hydrogen atom, a C1-C6 chain hydrocarbon group optionally substituted with one or more substituents selected from Group F, or a C3-C7 cycloalkyl group optionally substituted with one or more substituents selected from Group J;

$R^{11}$, $R^{19}$, $R^{24}$, and $R^{29}$ represent independently of each other a hydrogen atom, or a C1-C6 chain hydrocarbon group optionally substituted with one or more halogen atoms;

$R^{30}$ represents a hydrogen atom, a halogen atom, a $OR^{35}$, a $NR^{36}R^{37}$, or a C1-C6 chain hydrocarbon group optionally substituted with one or more halogen atoms;

$R^{18}$ and $R^{35}$ represent independently of each other a C1-C6 chain hydrocarbon group optionally substituted with one or more halogen atoms;

$R^{36}$ and $R^{37}$ represent independently of each other a hydrogen atom, or a C1-C6 chain hydrocarbon group optionally substituted with one or more halogen atoms;

$R^{12}$ represents a C1-C6 chain hydrocarbon group optionally substituted with one or more halogen atoms, a C1-C6 chain hydrocarbon group optionally substituted with one or more substituents selected from Group F, a C3-C7 aliphatic hydrocarbon group optionally substituted with one or more substituents selected from Group J, a phenyl group, a six membered aromatic heterocyclic group, a hydrogen atom, or a $S(O)_2R^{23}$, wherein the phenyl group or the six membered aromatic heterocyclic group may be optionally substituted with one or more substituents selected from Group D;

$R^{23}$ represents a C1-C6 chain hydrocarbon group optionally substituted with one or more halogen atoms, a C3-C7 cycloalkyl group optionally substituted with one or more halogen atoms, or a phenyl group optionally substituted with one or more substituents selected from Group D;

$R^{11a}$ and $R^{12a}$ combine together a nitrogen atom to which they are attached to form a three to seven membered nonaromatic heterocyclic group optionally substituted with one or more substituents selected from Group E;

$R^{13}$ represents a hydrogen atom, a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, a phenyl group optionally substituted with one or more substituents selected from Group D, or a five or six membered aromatic heterocyclic group optionally substituted with one or more substituents selected from Group D;

$R^{14}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, or a phenyl C1-C3 alkyl group, wherein the phenyl moiety in the phenyl C1-C3 alkyl group may be optionally substituted with one or more substituents selected from Group D;

$R^{15}$ and $R^{16}$ represent independently of each other a C1-C6 alkyl group optionally substituted with one or more halogen atoms;

$R^{15x}$ represents a C1-C6 alkyl group optionally substituted with one or more halogen atoms, or a hydrogen atom;

$R^{16x}$ represents a C1-C6 chain hydrocarbon group optionally substituted with one or more substituents selected from Group F, a C3-C7 cycloalkyl group optionally substituted with one or more substituents selected from Group J, or a hydrogen atom; and x is 0 or 1;

Group B is selected from the group consisting of a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, a C3-C6 cycloalkyl group optionally substituted with one or more halogen atoms, a cyano group, a hydroxy group, and a halogen atom;

Group C is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, and a halogen atom;

Group D is selected from the group consisting of a C1-C6 chain hydrocarbon group optionally substituted with one or more halogen atoms, a hydroxy group, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a sulfanyl group, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, an amino group, a $NHR^{21}$, a $NR^{21}R^{22}$, a $C(O)R^{21}$, a $OC(O)R^{21}$, a $C(O)OR^{21}$, a cyano group, a nitro group, and a halogen atom, wherein the $R^{21}$ and the $R^{22}$ represent independently of each other a C1-C6 alkyl group optionally substituted with one or more halogen atoms;

Group E is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a halogen atom, an oxo group, a hydroxy group, a cyano group, and a nitro group;

Group F is selected from the group consisting of a C1-C6 alkoxy group optionally substituted with one or more halogen atoms, an amino group, a $NHR^{21}$, a $NR^{21}R^{22}$, a cyano group, a phenyl group optionally substituted with one or more substituents selected from Group D, a five or six membered aromatic heterocyclic group optionally substituted with one or more substituents selected from Group D, a C3-C7 cycloalkyl group optionally substituted with one or more halogen atoms, and a three to seven membered nonaromatic heterocyclic group optionally substituted with one or more substituents selected from Group C, wherein the $R^{21}$ and the $R^{22}$ represent independently of each other a C1-C6 alkyl group optionally substituted with one or more halogen atoms;

Group H is selected from the group consisting of a halogen atom, a nitro group, a cyano group, an amino group, a five or six membered aromatic heterocyclic group, a C1-C6 alkyl group optionally substituted with one or more halogen atoms, a $OR^{10}$, a $NR^9R^{10}$, a $C(O)R^{10}$, a $C(O)NR^9R^{10}$, a $OC(O)R^9$, a $OC(O)OR^9$, a $NR^{10}C(O)R^9$, a $NR^{10}C(O)OR^9$, and a $C(O)OR^{10}$, wherein the $R^9$ represents a C1-C6 alkyl group optionally substituted with one or more halogen atoms or a C3-C6 cycloalkyl group optionally substituted with one or more halogen atoms, and the $R^{10}$ represents a hydrogen atom, a C1-C6 alkyl group optionally substituted with one or more halogen atoms, or a C3-C6 cycloalkyl group optionally substituted with one or more halogen atoms;

Group J is selected from the group consisting of a halogen atom, a cyano group, a triazolyl group, a C1-C6 alkyl group optionally substituted with one or more halogen atoms, and a $NR^{10}C(O)R^9$, wherein the $R^9$ represents a C1-C6 alkyl group optionally substituted with one or more halogen atoms, or a C3-C6 cycloalkyl group optionally substituted with one or more halogen atoms, and the $R^{10}$ represents a hydrogen atom, a C1-C6 alkyl group optionally substituted with one or more halogen atoms, or a C3-C6 cycloalkyl group optionally substituted with one or more halogen atoms.

32. A compound represented by formula (II-2):

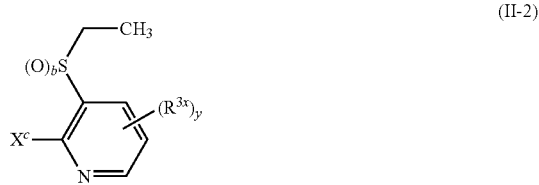

(II-2)

wherein,
$X^c$ represents a halogen atom;
b is 0, 1, or 2;
y is 1, 2, or 3;
$R^{3x}$ represents a C1-C6 chain hydrocarbon group optionally substituted with one or more substituents selected from group K, a C3-C7 cycloalkyl group optionally substituted with one or more substituents selected from Group E, a C3-C7 cycloalkenyl group optionally substituted with one or more substituents selected from Group J, a five or six membered aromatic heterocyclic group optionally substituted with one or more substituents selected from Group H, a $OR^{12}$, a $NR^{11b}R^{12}$, a $NR^{11a}R^{12a}$, a $NR^{29}NR^{11}R^{12}$, a $NR^{29}OR^{11}$, a $NR^{11}C(O)R^{13}$, a $NR^{29}NR^{11}C(O)R^{13}$, a $NR^{11}C(O)OR^{14}$, a $NR^{29}NR^{11}C(O)OR^{14}$, a $NR^{11}C(O)NR^{15x}R^{16x}$, a $NR^{24}NR^{11}C(O)NR^{15x}R^{16x}$, a $N=CHNR^{15x}R^{16x}$, a $N=S(O)_xR^{15}R^{16}$, a $C(O)R^{17}$, a $C(O)OR^{17a}$, a $C(O)NR^{15x}R^{16x}$, a $C(O)NR^{11}S(O)_2R^{23}$, a $CR^{24}=NOR^{17}$, a $NR^{11}CR^{24}=NOR^{17}$, a cyano group, or a nitro group, and when y is 2 or 3, a plurality of $R^{3x}$ may be identical to or different from each other;

when two $R^{3x}$ are adjacent to each other, said two $R^{3x}$ combine together with a carbon atom to which they are attached to form a benzene ring, a pyrrole ring, a furan ring, a thiophene ring, a pyrazole ring, an imidazole ring, a triazole ring, an oxazole ring, an isoxazole ring, a thiazole ring, an oxadiazole ring, a thiadiazole ring, a pyridine ring, a pyridazine ring, a pyrimidine ring, or a pyrazine ring, wherein the benzene ring, the pyrrole ring, the furan ring, the thiophene ring, the pyrazole ring, the imidazole ring, the triazole ring, the oxazole ring, the isoxazole ring, the thiazole ring, the oxadiazole ring, the thiadiazole ring, the pyridine ring, the pyridazine ring, the pyrimidine ring, and the pyrazine ring may be optionally substituted with one or more substituents selected from Group H;

$R^{17}$ represents independently of each other a C1-C6 chain hydrocarbon group optionally substituted with one or more substituents selected from Group F, or a C3-C7 cycloalkyl group optionally substituted with one or more substituents selected from Group J;

$R^{17a}$ represents independently of each other a C1-C6 chain hydrocarbon group optionally substituted with one or more substituents selected from Group F, or a C3-C7 cycloalkyl group optionally substituted with one or more substituents selected from Group J;

$R^{11}$, $R^{19}$, $R^{24}$, and $R^{29}$ represent independently of each other a hydrogen atom, or a C1-C6 chain hydrocarbon group optionally substituted with one or more halogen atoms;

$R^{11b}$ represents a C1-C6 chain hydrocarbon group optionally substituted with one or more halogen atoms;

$R^{30}$ represents a hydrogen atom, a halogen atom, a $OR^{35}$, a $NR^{36}R^{37}$, or a C1-C6 chain hydrocarbon group optionally substituted with one or more halogen atoms;

$R^{18}$ and $R^{35}$ represent independently of each other a C1-C6 chain hydrocarbon group optionally substituted with one or more halogen atoms;

$R^{36}$ and $R^{37}$ represent independently of each other a hydrogen atom, or a C1-C6 chain hydrocarbon group optionally substituted with one or more halogen atoms;

$R^{12}$ represents a C1-C6 chain hydrocarbon group optionally substituted with one or more halogen atoms, a C1-C6 chain hydrocarbon group optionally substituted with one or more substituents selected from Group F, a C3-C7 cycloalkyl group optionally substituted with one or more substituents selected from Group J, a C3-C7 cycloalkenyl group optionally substituted with one or more substituents selected from Group J, a phenyl group, a six membered aromatic heterocyclic group, a hydrogen atom, or a $S(O)_2R^{23}$, wherein the phenyl group or the six membered aromatic heterocyclic group may be optionally substituted with one or more substituents selected from Group D;

$R^{12b}$ represents a C1-C6 chain hydrocarbon group optionally substituted with one or more halogen atoms, a C1-C6 chain hydrocarbon group optionally substituted with one or more substituents selected from Group F, a C3-C7 aliphatic hydrocarbon group optionally substituted with one or more substituents selected from Group J, a phenyl group, a six membered aromatic heterocyclic group, wherein the phenyl group or the six membered aromatic heterocyclic group may be optionally substituted with one or more substituents selected from Group D, or a S(O)$_2$R$^{23}$;

$R^{23}$ represents a C1-C6 chain hydrocarbon group optionally substituted with one or more halogen atoms, a C3-C7 cycloalkyl group optionally substituted with one or more halogen atoms, or a phenyl group optionally substituted with one or more substituents selected from Group D;

$R^{11a}$ and $R^{12a}$ combine together with a nitrogen atom to which they are attached to form a three to seven membered nonaromatic heterocyclic group optionally substituted with one or more substituents selected from Group E;

$R^{13}$ represents a hydrogen atom, a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, a phenyl group optionally substituted with one or more substituents selected from Group D, or a five or six membered aromatic heterocyclic group optionally substituted with one or more substituents selected from Group D;

$R^{14}$ represents a C1-C6 chain hydrocarbon group optionally substituted with one or more halogen atoms, a C3-C7 cycloalkyl group optionally substituted with one or more halogen atoms, a (C3-C6 cycloalkyl)C1-C3 alkyl group optionally substituted with one or more halogen atoms, or a phenyl C1-C3 alkyl group, wherein the phenyl moiety in the phenyl C1-C3 alkyl group may be optionally substituted with one or more substituents selected from Group D;

$R^{15}$ and $R^{16}$ represent independently of each other a C1-C6 alkyl group optionally substituted with one or more halogen atoms;

$R^{15x}$ represents a C1-C6 alkyl group optionally substituted with one or more halogen atoms, or a hydrogen atom;

$R^{16x}$ represents a C1-C6 chain hydrocarbon group optionally substituted with one or more substituents selected from Group F, a C3-C7 cycloalkyl group optionally substituted with one or more substituents selected from Group J, or a hydrogen atom; and x is 0 or 1;

Group C is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, and a halogen atom;

Group D is selected from the group consisting of a C1-C6 chain hydrocarbon group optionally substituted with one or more halogen atoms, a hydroxy group, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a sulfanyl group, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, an amino group, a NHR$^{21}$, a NR$^{21}$R$^{22}$, a C(O)R$^{21}$, a OC(O)R$^{21}$, a C(O)OR$^{21}$, a cyano group, a nitro group, and a halogen atom, wherein the R$^{21}$ and the R$^{22}$ represent independently of each other a C1-C6 alkyl group optionally substituted with one or more halogen atoms;

Group E is selected from the group consisting of a C1-C6 chain hydrocarbon group optionally substituted with one or more halogen atoms, a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a halogen atom, an oxo group, a hydroxy group, a cyano group, and a nitro group;

Group F is selected from the group consisting of a C1-C6 alkoxy group optionally substituted with one or more halogen atoms, an amino group, a NHR$^{21}$, a NR$^{21}$R$^{22}$, a cyano group, a phenyl group optionally substituted with one or more substituents selected from Group D, a five or six membered aromatic heterocyclic group optionally substituted with one or more substituents selected from Group D, a C3-C7 cycloalkyl group optionally substituted with one or more halogen atoms, and a three to seven membered nonaromatic heterocyclic group optionally substituted with one or more substituents selected from Group C, wherein the R$^{21}$ and the R$^{22}$ represent independently of each other a C1-C6 alkyl group optionally substituted with one or more halogen atoms;

Group H is selected from the group consisting of a halogen atom, a nitro group, a cyano group, an amino group, a five or six membered aromatic heterocyclic group, a C1-C6 alkyl group optionally substituted with one or more halogen atoms, a OR$^{10}$, a NR$^9$R$^{10}$, a C(O)R$^{10}$, a C(O)NR$^9$R$^{10}$, a OC(O)R$^9$, a OC(O)OR$^9$, a NR$^{10}$C(O)R$^9$, a NR$^{10}$C(O)OR$^9$, and a C(O)OR$^{10}$, wherein the R$^9$ represents a C1-C6 alkyl group optionally substituted with one or more halogen atoms, or a C3-C6 cycloalkyl group optionally substituted with one or more halogen atoms, and the R$^{10}$ represents a hydrogen atom, a C1-C6 alkyl group optionally substituted with one or more halogen atoms, or a C3-C6 cycloalkyl group optionally substituted with one or more halogen atoms;

Group J is selected from the group consisting of a halogen atom, a cyano group, a triazolyl group, a C1-C6 alkyl group optionally substituted with one or more halogen atoms, and a NR$^{10}$C(O)R$^9$, wherein the R$^9$ represents a C1-C6 alkyl group optionally substituted with one or more halogen atoms, or a C3-C6 cycloalkyl group optionally substituted with one or more halogen atoms, and the R$^{10}$ represents a hydrogen atom, a C1-C6 alkyl group optionally substituted with one or more halogen atoms, or a C3-C6 cycloalkyl group optionally substituted with one or more halogen atoms;

Group K is selected from the group consisting of a C1-C6 alkoxy group optionally substituted with one or more halogen atoms, a C3-C6 alkenyloxy group optionally substituted with one or more halogen atoms, a C3-C6 alkynyloxy group optionally substituted with one or more halogen atoms, a C1-C6 alkylsulfanyl group optionally substituted with one or more halogen atoms, a C1-C6 alkylsulfinyl group optionally substituted with one or more halogen atoms, a C1-C6 alkylsulfonyl group optionally substituted with one or more halogen atoms, a C3-C6 cycloalkyl group optionally substituted with one or more halogen atoms, a cyano group, and a hydroxy group.

33. A seed or bulb carrying an effective amount of the composition according to claim 24.

* * * * *